(12) United States Patent
Momose et al.

(10) Patent No.: US 7,022,725 B2
(45) Date of Patent: Apr. 4, 2006

(54) ISOXAZOLE DERIVATIVES

(75) Inventors: Yu Momose, Takarazuka (JP); Tsuyoshi Maekawa, Nara (JP); Tomoko Asakawa, Takatsuki (JP); Nozomu Sakai, Kobe (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 96 days.

(21) Appl. No.: 10/416,658

(22) PCT Filed: Nov. 16, 2001

(86) PCT No.: PCT/JP01/10001

§ 371 (c)(1),
(2), (4) Date: May 14, 2003

(87) PCT Pub. No.: WO02/40458

PCT Pub. Date: May 23, 2002

(65) Prior Publication Data

US 2004/0048908 A1 Mar. 11, 2004

(30) Foreign Application Priority Data

Nov. 17, 2000 (JP) .............................. 2000-350869

(51) Int. Cl.
*A61K 31/42* (2006.01)
*C07F 261/02* (2006.01)
*A61P 3/00* (2006.01)

(52) U.S. Cl. ...................... 514/378; 514/380; 548/240; 548/243

(58) Field of Classification Search ................ 514/378, 514/380; 548/240, 243
See application file for complete search history.

(56) References Cited

U.S. PATENT DOCUMENTS

| 3,752,818 | A | 8/1973 | Plumpe et al. ............... 260/287 |
| 5,814,627 | A | 9/1998 | Schwab et al. .......... 514/236.8 |
| 6,060,494 | A | * | 5/2000 | Faasch et al. ................ 514/378 |

FOREIGN PATENT DOCUMENTS

| EP | 0208040 | | 1/1987 |
| EP | 0903345 | A1 | 3/1999 |
| JP | 69029656 | B | 2/1969 |
| JP | 54044665 | A | 4/1979 |
| WO | WP 98/28282 | | 7/1998 |
| WO | WO 00/08001 | | 2/2000 |
| WO | WO 00/38666 | | 7/2000 |

OTHER PUBLICATIONS

Fossa. et al. "5-Substituted 4-Isoxazoleacetic Acids with Analgesic Activity" IL FARMACO 49(1):41-44 (1994).

* cited by examiner

*Primary Examiner*—Taofiq Solola
*Assistant Examiner*—Robert Shiao
(74) *Attorney, Agent, or Firm*—Elaine M. Ramesh; Mark Chao

(57) ABSTRACT

A compound represented by the formula (I)

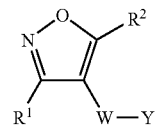

wherein one of $R^1$ and $R^2$ is a hydrogen atom or a substituent and the other is an optionally substituted cyclic group; W is a bond or a divalent aliphatic hydrocarbon group; Y is a group of the formula: —$OR^3$ (wherein $R^3$ is a hydrogen atom, an optionally substituted hydrocarbon group, an optionally substituted heterocyclic group or an optionally substituted acyl group) or an optionally esterified or amidated carboxyl group, or a salt thereof or a prodrug thereof has a superior insulin secretion promoting action and a hypoglycemic action and shows low toxicity. Therefore, the compound is useful as a pharmaceutical agent, particularly as an agent for the prophylaxis or treatment of diabetes and diabetic complications, and the like.

14 Claims, No Drawings

ISOXAZOLE DERIVATIVES

TECHNICAL FIELD

The present invention relates to an agent for the prophylaxis or treatment of diabetes, impaired glucose tolerance or diabetic complications, which comprises an isoxazole derivative.

In addition, the present invention relates to an insulin secretagogue comprising an isoxazole derivative.

Moreover, the present invention relates to a novel isoxazole derivative having a superior hypoglycemic action and useful as an agent for the prophylaxis or treatment of diabetes, impaired glucose tolerance, diabetic complications and the like, and a method for the prophylaxis or treatment of diabetes or diabetic complications, which comprises administration of said novel isoxazole derivative to a mammal, as well as to use of said novel isoxazole derivative for the production of an agent for the prophylaxis or treatment of diabetes or an agent for the prophylaxis or treatment of diabetic complications.

BACKGROUND ART

At present, a sulfonylurea, a biguanide, an α-glucosidase inhibitor and the like have been used as agents for treating diabetes. While a sulfonylurea produces a potent hypoglycemic action, it sometimes causes serious hypoglycemia and requires attention during use. A biguanide easily causes relatively serious lactic acidosis as a side effect. An α-glucosidase inhibitor delays digestion and absorption of glucose in the gastrointestinal tract and suppresses increase in the blood glucose level after meal, but side effects of sense of distension, diarrhea and the like are problematic (JOSLIN'S DIABETES MELLITUS 13Th Edition 521–522).

As isoxazole derivatives, for example, the following compounds are known.

(1) JP-B-44-29656 describes that a compound represented by the formula

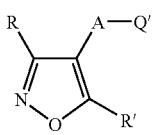

wherein R is a phenyl group, R' is a hydrogen or a lower alkyl group, A is a straight-chain or branched divalent hydrocarbon group having 2 to 5 carbon atoms, and Q' is a hydroxy group, an amino group or an acylamino group, has an analgesic action, an antitussive action, an antipyretic action and an anti-inflammatory action.

(2) Japanese Patent Application under PCT laid-open under kohyo No. 9-509951 describes that a compound represented by the formula

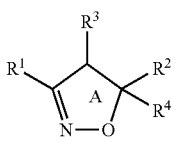

wherein one of $R^1$ and $R^2$ is 3,5-dimethyl-4-hydroxyphenyl and the other $R^1$ or $R^2$ is pyridyl etc.; A is a double bond etc.; $R^4$ is a hydrogen atom etc.; and $R^3$ is a hydrogen atom, $(C_1-C_4)$-alkyl or hydroxy-$(C_1-C_4)$-alkyl, is useful for the treatment of inflammation, asthma, rheumatic disease and autoimmune disease.

(3) WO00/08001 describes that a compound represented by the formula

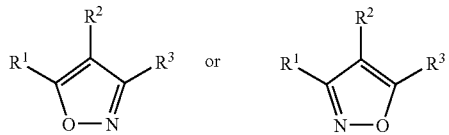

wherein $R^1$ and $R^3$ are each an optionally substituted lower alkyl, aryl etc., and $R^2$ is a hydrogen atom etc., is useful as an estrogen receptor modulator.

(4) WO98/28282 describes that a compound represented by the formula

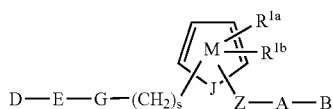

wherein ring M may contain 0 to 2 N-atoms besides J; J is O or S; D is CN etc.; E is phenyl etc.; G is absent or $NHCH_2$ etc.; Z is $C_{1-4}$ alkylene etc.; $R^{1a}$ and $R^{1b}$ are independently absent or $-(CH_2)_r-R1'$ (r is 0, 1, 2 or 3, R1' is hydrogen atom etc.) etc.; A is $C_{3-10}$ carbocyclic residue etc.; B is $C_{3-10}$ carbocycle residue etc.; s is 0, 1 or 2, is useful as a Xa factor inhibitor.

However, it is not known that the above-mentioned isoxazole derivatives are useful as agents for the prophylaxis or treatment of diabetes or impaired glucose tolerance, insulin secretagogues and the like.

DISCLOSURE OF THE INVENTION

The present inventors have first found that a compound represented by the formula (Ia)

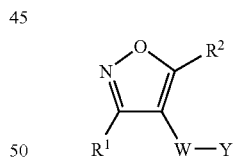

wherein one of $R^1$ and $R^2$ is a hydrogen atom or a substituent and the other is an optionally substituted cyclic group; W designates a bond or a divalent aliphatic hydrocarbon group; and Y represents the formula: $-OR^3$ ($R^3$ is a hydrogen atom, an optionally substituted hydrocarbon group, an optionally substituted heterocyclic group or an optionally substituted acyl group) or an optionally esterified or amidated carboxyl group, provided that when $R^1$ or $R^2$ is 3,5-di-tert-butyl-4-hydroxyphenyl and W is $C_{1-4}$ alkylene, Y should not be OH, which is structurally characterized in that a group represented by the formula: $-W-Y$ [W and Y are as defined above] is bonded at the 4-position of the isoxazole ring, unexpectedly has a superior insulin secretion promoting action and a hypoglycemic action based on the characteristic chemical structure, and is useful as an agent for the prophylaxis or treatment of diabetes, impaired glucose tolerance, diabetic complications and the like, based on which finding, they have completed the present invention.

Accordingly, the present invention relates to 1) an agent for the prophylaxis or treatment of diabetes, which comprises a compound represented by the formula (Ia) or a salt thereof or a prodrug thereof;
2) an agent for the prophylaxis or treatment of impaired glucose tolerance, which comprises a compound represented by the formula (I)

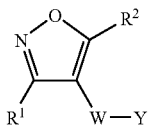

wherein one of $R^1$ and $R^2$ is a hydrogen atom or a substituent and the other is an optionally substituted cyclic group;
W is a bond or a divalent aliphatic hydrocarbon group;
Y is a group of the formula: —$OR^3$ (wherein $R^3$ is a hydrogen atom, an optionally substituted hydrocarbon group, an optionally substituted heterocyclic group or an optionally substituted acyl group) or an optionally esterified or amidated carboxyl group, or a salt thereof or a prodrug thereof;
3) an insulin secretagogue comprising a compound represented by the formula (I) or a salt thereof or a prodrug thereof;
4) an agent for the prophylaxis or treatment of diabetic complications, which comprises a compound represented by the formula (I) or a salt thereof or a prodrug thereof;
5) the agent of the aforementioned 4), wherein the diabetic complication is neuropathy;
6) a compound represented by the formula (II)

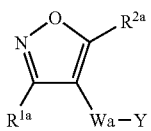

wherein one of $R^{1a}$ and $R^{2a}$ is a hydrogen atom and the other is an optionally substituted cyclic group;
Wa is a divalent aliphatic hydrocarbon group;
Y is a group of the formula: —$OR^3$ (wherein $R^3$ is a hydrogen atom, an optionally substituted hydrocarbon group, an optionally substituted heterocyclic group or an optionally substituted acyl group) or an optionally esterified or amidated carboxyl group, provided that when Wa is $C_{1-3}$ alkylene and Y is a group of the formula: —$OR^3$ (wherein $R^3$ is as defined above) or an optionally methylesterified carboxyl group, $R^{1a}$ should be a hydrogen atom and $R^{2a}$ should be an optionally substituted cyclic group, except 5-phenyl-4-isoxazolylmethanol and 5-phenyl-4-isoxazolylacetic acid, or a salt thereof;
7) the compound of the aforementioned 6), wherein the optionally substituted cyclic group represented by $R^{1a}$ or $R^{2a}$ is an optionally substituted aromatic group;
8) the compound of the aforementioned 6), wherein $R^{1a}$ is a hydrogen atom and $R^{2a}$ is an optionally substituted cyclic group;
9) the compound of the aforementioned 8), wherein $R^{2a}$ is an optionally substituted aromatic group;
10) the compound of the aforementioned 6), wherein Wa is a divalent aliphatic hydrocarbon group having 1 to 4 carbon atoms;
11) the compound of the aforementioned 6), wherein Y is an optionally amidated carboxyl group;
12) a prodrug of the compound of the aforementioned 6);
13) the compound of the aforementioned 6), which is
3-[5-(3,4-dichlorophenyl)-4-isoxazolyl]propan-1-ol;
3-[5-(3,4-dichlorophenyl)-4-isoxazolyl]propionic acid or a salt thereof;
3-[5-(4-chlorophenyl)-4-isoxazolyl]propan-1-ol;
3-[5-(4-chlorophenyl)-4-isoxazolyl]propionic acid or a salt thereof;
3-[5-(3,4-difluorophenyl)-4-isoxazolyl]propan-1-ol;
3-[5-(3,4-difluorophenyl)-4-isoxazolyl]propionic acid or a salt thereof;
N-[4-(diethylphosphonomethyl)phenyl]-3-(5-phenyl-4-isoxazolyl)propionamide;
N-[4-(diethylphosphonomethyl)phenyl]-3-[5-(4-fluorophenyl)-4-isoxazolyl]propionamide;
N-[4-(dimethylphosphonomethyl)phenyl]-3-(5-phenyl-4-isoxazolyl)propionamide;
N-{4-[(2-oxide-1,3,2-dioxaphosphinan-2-yl)methyl]phenyl}-3-(5-phenyl-4-isoxazolyl)propionamide;
N-benzyl-N-[2-(dimethylamino)ethyl]-3-[5-(4-fluorophenyl)-4-isoxazolyl]propionamide; or
N-benzyl-N-(1-benzyl-3-pyrrolidinyl)-3-[5-(4-fluorophenyl)-4-isoxazolyl]propionamide;
14) a pharmaceutical agent comprising the compound of the aforementioned 6) or a prodrug thereof;
15) a glucose-dependent insulin secretagogue comprising an isoxazole derivative;
16) a method for the prophylaxis or treatment of diabetes in a mammal, which comprises administering to said mammal an effective amount of a compound represented by the formula (Ia) or a salt thereof or a prodrug thereof;
17) a method for the prophylaxis or treatment of diabetic complication in a mammal, which comprises administering to said mammal an effective amount of a compound represented by the formula (I) or a salt thereof or a prodrug thereof;
18) a method for the prophylaxis or treatment of impaired glucose tolerance in a mammal, which comprises administering to said mammal an effective amount of a compound represented by the formula (I) or a salt thereof or a prodrug thereof;
19) a method for promoting an insulin secretion in a mammal, which comprises administering to said mammal an effective amount of a compound represented by the formula (I) or a salt thereof or a prodrug thereof;
20) use of a compound represented by the formula (Ia) or a salt thereof or a prodrug thereof for the production of an agent for the prophylaxis or treatment of diabetes;
21) use of a compound represented by the formula (I) or a salt thereof or a prodrug thereof for the production of an agent for the prophylaxis or treatment of diabetic complications;
22) use of a compound represented by the formula (I) or a salt thereof or a prodrug thereof for the production of an agent for the prophylaxis or treatment of impaired glucose tolerance;
23) use of a compound represented by the formula (I) or a salt thereof or a prodrug thereof for the production of an insulin secretagogue;
24) a commercial package comprising the agent for the prophylaxis or treatment of diabetes according to the aforementioned 1) and written matter associated therewith, the written matter stating that the agent can or should be used for the prophylaxis or treatment of diabetes;

25) a commercial package comprising the agent for the prophylaxis or treatment of impaired glucose tolerance according to the aforementioned 2) and written matter associated therewith, the written matter stating that the agent can or should be used for the prophylaxis or treatment of impaired glucose tolerance;

26) a commercial package comprising the insulin secretagogue of the aforementioned 3) and written matter associated therewith, the written matter stating that the agent can or should be used for promoting insulin secretion;

27) a commercial package comprising the agent for the prophylaxis or treatment of diabetic complications according to the aforementioned 4) and written matter associated therewith, the written matter stating that the agent can or should be used for the prophylaxis or treatment of diabetic complications; and the like.

DETAILED DESCRIPTION OF THE INVENTION

The compound represented by the formula (I), (Ia) or (II) is described in detail in the following.

(1) Definition of $R^1$ and $R^2$

In the formulas (I) and (Ia), the "cyclic group" of the "optionally substituted cyclic group" represented by $R^1$ or $R^2$ is exemplified by alicyclic hydrocarbon group, aromatic hydrocarbon group, aromatic heterocyclic group, non-aromatic heterocyclic group and the like.

Said alicyclic hydrocarbon groups include saturated or unsaturated alicyclic hydrocarbon groups containing 3 to 12 carbon atoms, such as cycloalkyl groups, cycloalkenyl groups and cycloalkadienyl groups.

Preferable examples of the cycloalkyl groups are $C_{3-10}$ cycloalkyl groups such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl.

Preferable examples of the cycloalkenyl groups are $C_{3-10}$ cycloalkenyl groups such as 2-cyclopenten-1-yl, 3-cyclopenten-1-yl, 2-cyclohexen-1-yl and 3-cyclohexen-1-yl.

Preferable examples of the cycloalkadienyl groups are $C_{4-10}$-cycloalkadienyl groups such as 2,4-cyclopentadien-1-yl, 2,4-cyclohexadien-1-yl and 2,5-cyclohexadien-1-yl.

As the aromatic hydrocarbon group, an aromatic hydrocarbon group having 6 to 14 carbon atoms (e.g., aryl group etc.) is exemplified. Preferable examples of the aromatic hydrocarbon group include phenyl, naphthyl, anthryl, phenanthryl, acenaphthylenyl, biphenylyl, indenyl and the like, with preference given to phenyl, 1-naphthyl, 2-naphthyl and the like. The aromatic hydrocarbon group may be partially saturated, and examples of the partially saturated aromatic hydrocarbon group (aryl group having 6 to 14 carbon atoms) include dihydroindenyl and the like.

As the non-aromatic heterocyclic group, a 5 to 7-membered monocyclic non-aromatic heterocyclic group containing, besides carbon atom, 1 to 4 hetero atoms selected from oxygen atom, sulfur atom and nitrogen atom, as a ring constituting atom, or non-aromatic fused heterocyclic group is exemplified. Examples of the non-aromatic fused heterocyclic group include a group obtained by condensation of these 5 to 7-membered monocyclic non-aromatic heterocyclic groups with a 6-membered ring containing 1 or 2 nitrogen atoms, benzene ring or a 5-membered ring containing one sulfur atom, and the like.

Preferable examples of the non-aromatic heterocyclic group include pyrrolidinyl (e.g., 1-pyrrolidinyl), piperidinyl (e.g., piperidino), morpholinyl (e.g., morpholino), thiomorpholinyl (e.g., thiomorpholino), piperazinyl (e.g., 1-piperazinyl), hexamethyleneiminyl (e.g., hexamethyleneimin-1-yl), oxazolidinyl (e.g., oxazolidin-3-yl), thiazolidinyl (e.g., thiazolidin-3-yl), imidazolidinyl (e.g., imidazolidin-3-yl), oxoimidazolidinyl (e.g., 2-oxoimidazolidin-1-yl), dioxoimidazolidinyl (e.g., 2,4-dioxoimidazolidin-3-yl), dioxooxazolidinyl (e.g., 2,4-dioxooxazolidin-3-yl), dioxothiazolidinyl (e.g., 2,4-dioxothiazolidin-3-yl), tetrahydrofuranyl, azepanyl, tetrahydropyridinyl (e.g., 1,2,3,6-tetrahydropyridin-1-yl) and the like.

As the aromatic heterocyclic group, a 5 to 7-membered monocyclic aromatic heterocyclic group containing, besides carbon atom, 1 to 4 hetero atoms selected from oxygen atom, sulfur atom and nitrogen atom, as a ring constituting atom, or fused aromatic heterocyclic group is exemplified. As the fused aromatic heterocyclic group, a group obtained by condensation of these 5 to 7-membered monocyclic aromatic heterocyclic groups with a 6-membered ring containing 1 or 2 nitrogen atoms, benzene ring or a 5-membered ring containing one sulfur atom, and the like Specific examples of the aromatic heterocyclic group include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), isoxazolyl, isothiazolyl, thiazolyl (e.g., 2-thiazolyl, 4-thiazolyl, 5-thiazolyl), oxazolyl (e.g., 2-oxazolyl, 4-oxazolyl, 5-oxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), quinolyl (e.g., 2-quinolyl, 3-quinolyl, 4-quinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl), benzimidazoyl (e.g., benzimidazol-1-yl, benzimidazol-2-yl), indolyl (e.g., indol-1-yl, indol-3-yl), 1H-indazolyl (e.g., 1H-indazol-3-yl), 1H-pyrrolo[2,3-b]pyrazinyl (e.g., 1H-pyrrolo[2,3-b]pyrazin-2-yl), 1H-pyrrolopyridinyl (e.g., 1H-pyrrolo[2,3-b]pyridin-6-yl), 1H-imidazopyridinyl (e.g., 1H-imidazo[4,5-b]pyridin-2-yl, 1H-imidazo[4,5-c]pyridin-2-yl), 1H-imidazopyrazinyl (e.g., 1H-imidazo[4,5-b]pyrazin-2-yl), triazinyl, isoquinolyl, benzothiadiazolyl and the like.

The aromatic heterocyclic group is preferably a 5 or 6-membered aromatic heterocyclic group optionally condensed with a benzene ring (preferably furyl, thienyl, pyridyl, pyrimidinyl, pyrazinyl, oxazolyl, thiazolyl, oxadiazolyl, benzoxazolyl, benzothiazolyl, quinolyl) and the like. The "cyclic group" is preferably an aromatic group such as aromatic hydrocarbon group, aromatic heterocyclic group and the like, more preferably aromatic hydrocarbon group having 6 to 14 carbon atoms (e.g., aryl group etc.). Particularly, phenyl is preferable.

In the formulas (I) and (Ia), the "cyclic group" represented by $R^1$ or $R^2$ optionally has 1 to 5, preferably 1 to 3, substituents at a substitutable position(s) on the cyclic group. Examples of such substituent include "halogen atom", "nitro group", "cyano group", "$C_{1-3}$ alkylenedioxy group", "optionally substituted aliphatic hydrocarbon group", "optionally substituted alicyclic hydrocarbon group", "optionally substituted aromatic hydrocarbon group", "optionally substituted heterocyclic group", "optionally substituted acyl group", "optionally substituted amino group", "optionally substituted hydroxy group", "optionally substituted thiol group", "optionally esterified or amidated carboxyl group" and the like.

As the "halogen atom", fluorine, chlorine, bromine and iodine are exemplified. Of these, fluorine and chlorine are preferable.

As the "$C_{1-3}$ alkylenedioxy group", methylenedioxy and ethylenedioxy are exemplified.

Said aliphatic hydrocarbon groups in the "optionally substituted aliphatic hydrocarbon group" include straight-chain or branched aliphatic hydrocarbon groups containing 1 to 15 carbon atoms, such as alkyl groups, alkenyl groups, alkynyl groups, and the like.

Preferable examples of the alkyl groups are $C_{1-10}$ alkyl groups such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2,-dimethylbutyl, 3,3-dimethylbutyl, 2-ethylbutyl, heptyl, octyl, nonyl and decyl.

Preferable examples of the alkenyl groups are $C_{2-10}$ alkenyl groups such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Preferable examples of the alkynyl groups are $C_{2-10}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-exynyl, 5-hexynyl, 1-heptynyl, 1-octynyl and the like.

As the substituent of the "optionally substituted aliphatic hydrocarbon group", for example, cycloalkyl group having 3 to 10 carbon atoms, aryl group having 6 to 14 carbon atoms (e.g., phenyl, naphthyl and the like), aromatic heterocyclic group (e.g., thienyl, furyl, pyridyl, oxazolyl, thiazolyl and the like), non-aromatic heterocyclic group (e.g., tetrahydrofuryl, morpholino, thiomorpholino, piperidino, pyrrolidinyl, piperazinyl and the like), aralkyl group having 7 to 13 carbon atoms, amino group, amino group mono- or di-substituted by alkyl having 1 to 4 carbon atoms or acyl group having 2 to 8 carbon atoms (e.g., alkanoyl group and the like), amidino group, acyl group having 2 to 8 carbon atoms (e.g., alkanoyl group and the like), carbamoyl group, carbamoyl group mono- or di-substituted by alkyl having 1 to 4 carbon atoms, sulfamoyl group, sulfamoyl group mono- or di-substituted by alkyl having 1 to 4 carbon atoms, carboxyl group, alkoxycarbonyl group having 2 to 8 carbon atoms, hydroxy group, alkoxy group having 1 to 6 carbon atoms which is optionally substituted by 1 to 3 halogen atoms (e.g., fluorine, chlorine, bromine, iodine and the like), alkenyloxy group having 2 to 5 carbon atoms which is optionally substituted by 1 to 3 halogen atoms (e.g., fluorine, chlorine, bromine, iodine and the like), cycloalkyloxy group having 3 to 7 carbon atoms, aralkyloxy group having 7 to 13 carbon atoms, aryloxy group having 6 to 14 carbon atoms (e.g., phenyloxy, naphthyloxy and the like), thiol group, alkylthio group having 1 to 6 carbon atoms which is optionally substituted by 1 to 3 halogen atoms (e.g., fluorine, chlorine, bromine, iodine and the like), aralkylthio group having 7 to 13 carbon atoms, arylthio group having 6 to 14 carbon atoms (e.g., phenylthio, naphthylthio and the like), sulfo group, cyano group, azide group, nitro group, nitroso group, halogen atom (e.g., fluorine, chlorine, bromine, iodine) and the like. The number of the substituent is, for example, 1 to 3.

Examples of the alicyclic hydrocarbon group and aromatic hydrocarbon group of the "optionally substituted alicyclic hydrocarbon group" and "optionally substituted aromatic hydrocarbon group" respectively include those exemplified as the "cyclic group" represented by $R^1$ or $R^2$.

As the heterocyclic group of the "optionally substituted heterocyclic group", the aromatic heterocyclic group and non-aromatic heterocyclic group exemplified as the "cyclic group" represented by $R^1$ or $R^2$ are exemplified.

As the substituent of the aforementioned "optionally substituted alicyclic hydrocarbon group", "optionally substituted aromatic hydrocarbon group" and "optionally substituted heterocyclic group", alkyl group having 1 to 6 carbon atoms which is optionally substituted by 1 to 3 halogen atoms (e.g., fluorine, chlorine, bromine, iodine and the like), alkenyl group having 2 to 6 carbon atoms which is optionally substituted by 1 to 3 halogen atoms (e.g., fluorine, chlorine, bromine, iodine and the like), cycloalkyl group having 3 to 10 carbon atoms, aryl group having 6 to 14 carbon atoms (e.g., phenyl, naphthyl and the like), aromatic heterocyclic group (e.g., thienyl, furyl, pyridyl, oxazolyl, thiazolyl and the like), non-aromatic heterocyclic group (e.g., tetrahydrofuryl, morpholino, thiomorpholino, piperidino, pyrrolidinyl, piperazinyl and the like), aralkyl group having 7 to 13 carbon atoms, amino group, amino group mono- or di-substituted by alkyl having 1 to 4 carbon atoms or acyl group having 2 to 8 carbon atoms (e.g., alkanoyl group and the like), amidino group, acyl group having 2 to 8 carbon atoms (e.g., alkanoyl group and the like), carbamoyl group, carbamoyl group mono- or di-substituted by alkyl having 1 to 4 carbon atoms, sulfamoyl group, sulfamoyl group mono- or di-substituted by alkyl having 1 to 4 carbon atoms, carboxyl group, alkoxycarbonyl group having 2 to 8 carbon atoms, hydroxy group, alkoxy group having 1 to 6 carbon atoms which is optionally substituted by 1 to 3 halogen atoms (e.g., fluorine, chlorine, bromine, iodine and the like), alkenyloxy group having 2 to 5 carbon atoms which is optionally substituted by 1 to 3 halogen atoms (e.g., fluorine, chlorine, bromine, iodine and the like), cycloalkyloxy group having 3 to 7 carbon atoms, aralkyloxy group having 7 to 13 carbon atoms, aryloxy group having 6 to 14 carbon atoms (e.g., phenyloxy, naphthyloxy and the like), thiol group, alkylthio group having 1 to 6 carbon atoms which is optionally substituted by 1 to 3 halogen atoms (e.g., fluorine, chlorine, bromine, iodine and the like), aralkylthio group having 7 to 13 carbon atoms, arylthio group having 6 to 14 carbon atoms (e.g., phenylthio, naphthylthio and the like), sulfo group, cyano group, azide group, nitro group, nitroso group, halogen atom (e.g., fluorine, chlorine, bromine, iodine) and the like. The number of the substituent is, for example, 1 to 3.

The acyl group of the "optionally substituted acyl group" is an acyl group having 1 to 13 carbon atoms, which is specifically formyl, a group represented by the formula: —$COR^4$, —$SO_2R^4$, —$SOR^4$ or —$PO_3R^4R^5$, wherein $R^4$ and $R^5$ are the same or different and each is hydrocarbon group or aromatic heterocyclic group, and $R^4$ and $R^5$ may form a heterocycle together with the adjacent oxo-substituted phosphorus atom and two oxygen atoms, and the like.

The hydrocarbon group represented by $R^4$ or $R^5$ is exemplified by aliphatic hydrocarbon group, alicyclic hydrocarbon group, aromatic hydrocarbon group, aromatic aliphatic hydrocarbon group and the like.

The aliphatic hydrocarbon group is exemplified by the "aliphatic hydrocarbon group" of the "optionally substituted aliphatic hydrocarbon group" exemplified as a substituent for the "cyclic group" represented by $R^1$ or $R^2$.

The alicyclic hydrocarbon group and aromatic hydrocarbon group are respectively exemplified by those exemplified as "cyclic group" represented by $R^1$ or $R^2$.

The aromatic aliphatic hydrocarbon group is exemplified by aromatic aliphatic hydrocarbon group having 7 to 13 carbon atoms, such as aralkyl group, arylalkenyl group and the like.

Preferable examples of the aralkyl group include aralkyl group having 7 to 13 carbon atoms, such as benzyl, phenethyl, naphthylmethyl, benzhydryl and the like.

Preferable examples of the arylalkenyl group include arylalkenyl group having 8 to 13 carbon atoms, such as styryl and the like.

The hydrocarbon group is preferably alkyl group having 1 to 10 carbon atoms, alkenyl group having 2 to 10 carbon atoms, cycloalkyl group having 3 to 10 carbon atoms, cycloalkenyl group having 3 to 10 carbon atoms, aryl group having 6 to 12 carbon atoms, aralkyl group having 7 to 13 carbon atoms and the like.

The aromatic heterocyclic group represented by $R^4$ or $R^5$ is exemplified by those exemplified as the "cyclic group" represented by $R^1$ or $R^2$. Of those, for example, thienyl, furyl, pyridyl and the like are preferable.

The heterocycle formed by $R^4$ and $R^5$ with the adjacent oxo-substituted phosphorus atom and two oxygen atoms is exemplified by a 4 to 7-membered heterocycle containing, besides carbon atom, oxo-substituted phosphorus atom and two oxygen atoms, and optionally further having 1 or 2 hetero atoms selected from oxygen atom, nitrogen atom and sulfur atom, as ring constituting atom, and the like. Specific examples of the heterocycle include 2-oxide-1,3,2-dioxaphosphinane; 2-oxide-1,3,2-dioxaphophorane and the like.

Preferable examples of the acyl group include alkanoyl group having 2 to 10 carbon atoms (e.g., acetyl, propionyl, butyryl, isobutyryl, valeryl, isovaleryl, pivaloyl, hexanoyl, heptanoyl, octanoyl), alkenoyl group having 3 to 10 carbon atoms (e.g., crotonyl), cycloalkanoyl group having 4 to 10 carbon atoms (e.g., cyclobutanecarbonyl, cyclopentanecarbonyl, cyclohexanecarbonyl, cycloheptanecarbonyl), cycloalkenoyl group having 4 to 10 carbon atoms (e.g., 2-cyclohexenecarbonyl), arylcarbonyl group having 7 to 13 carbon atoms (e.g., benzoyl), aromatic heterocyclic carbonyl (e.g., nicotinoyl, isonicotinoyl), alkylsulfinyl group having 1 to 10 carbon atoms (e.g., methylsulfinyl, ethylsulfinyl), alkylsulfonyl group having 1 to 10 carbon atoms (e.g., methylsulfonyl, ethylsulfonyl), (mono- or di(C1–C10)alkyl) phosphono group which may form a ring (e.g., dimethylphosphono; diethylphosphono; diisopropylphosphono; dibutylphosphono; 2-oxide-1,3,2-dioxaphosphinanyl) and the like.

The acyl group may have 1 to 3 substituents at a substitutable position(s). Examples of the substituent include $C_{1-6}$ alkyl group (e.g., methyl, ethyl and the like) optionally substituted by 1 to 3 halogen atoms (e.g., fluorine, chlorine, iodine and the like), $C_{1-6}$ alkoxy group (e.g., methoxy, ethoxy and the like) optionally substituted by 1 to 3 halogen atoms (e.g., fluorine, chlorine, bromine, iodine and the like), halogen atom (e.g., fluorine, chlorine, bromine, iodine and the like), nitro, hydroxy, amino and the like.

The "optionally substituted amino group" is exemplified by amino group optionally mono- or di-substituted by alkyl group having 1 to 10 carbon atoms, alkenyl group having 2 to 10 carbon atoms, cycloalkyl group having 3 to 10 carbon atoms, cycloalkenyl group having 3 to 10 carbon atoms, aryl group having 6 to 14 carbon atoms, acyl group having 1 to 13 carbon atoms and the like.

The alkyl group having 1 to 10 carbon atoms and alkenyl group having 2 to 10 carbon atoms are respectively exemplified by those exemplified as the substituents of "cyclic group" represented by $R^1$ or $R^2$.

The cycloalkyl group having 3 to 10 carbon atoms, cycloalkenyl group having 3 to 10 carbon atoms and aryl group having 6 to 14 carbon atoms are respectively exemplified by those exemplified as "cyclic group" represented by $R^1$ or $R^2$.

The acyl group having 1 to 13 carbon atoms is exemplified by those exemplified as acyl group of the aforementioned "optionally substituted acyl group", preferably alkanoyl group having 2 to 10 carbon atoms, arylcarbonyl group having 7 to 13 carbon atoms and the like.

The substituted amino group is exemplified by mono- or di-$C_{1-10}$ alkylamino (e.g., methylamino, dimethylamino, ethylamino, diethylamino, ethylmethylamino, propylamino, dibutylamino), mono- or di-$C_{2-10}$ alkenylamino (e.g., diallylamino), mono- or di-$C_{3-10}$ cycloalkylamino (e.g., cyclohexylamino), mono- or di-$C_{2-10}$ alkanoylamino (e.g., acetylamino, propionylamino), arylcarbonylamino group having 7 to 13 carbon atoms (e.g., benzoylamino), arylamino having 6 to 14 carbon atoms (e.g., phenylamino), N—$C_{1-10}$ alkyl-N—$C_{6-14}$ arylamino (e.g., N-methyl-N-phenylamino) and the like.

The "optionally substituted hydroxy group" is exemplified by hydroxy group optionally substituted by "alkyl group having 1 to 10 carbon atoms", "alkenyl group having 2 to 10 carbon atoms", "cycloalkyl group having 3 to 10 carbon atoms", "cycloalkenyl group having 3 to 10 carbon atoms", "aryl group having 6 to 14 carbon atoms", "aralkyl having 7 to 13 carbon atoms", "acyl group having 1 to 13 carbon atoms" or "heteroaryl group", each being optionally substituted.

As used herein, the "alkyl group having 1 to 10 carbon atoms", "alkenyl group having 2 to 10 carbon atoms" and "acyl group having 1 to 13 carbon atoms" are respectively exemplified by those exemplified as the substituent of the "cyclic group" represented by $R^1$ or $R^2$.

Examples of the "cycloalkyl group having 3 to 10 carbon atoms", "cycloalkenyl group having 3 to 10 carbon atoms" and "aryl group having 6 to 14 carbon atoms" include those exemplified as "cyclic group" represented by $R^1$ or $R^2$.

The "aralkyl having 7 to 13 carbon atoms" is exemplified by benzyl, phenethyl, naphthylmethyl, naphthylethyl and the like.

These "alkyl group having 1 to 10 carbon atoms", "alkenyl group having 2 to 10 carbon atoms", "cycloalkyl group having 3 to 10 carbon atoms", "cycloalkenyl group having 3 to 10 carbon atoms", "aryl group having 6 to 14 carbon atoms", "aralkyl having 7 to 13 carbon atoms" and "acyl group having 1 to 13 carbon atoms" may have 1 or 2 substituents at a substitutable position(s), wherein the substituent is exemplified by halogen atom (e.g., fluorine, chlorine, bromine, iodine and the like), alkoxy group having 1 to 3 carbon atoms (e.g., methoxy, ethoxy and the like) and the like.

The "heteroaryl group" is exemplified by the aromatic heterocyclic group exemplified as the "optionally substituted cyclic group" represented by $R^1$ or $R^2$. Of those, pyridyl, imidazolyl, triazolyl and the like are preferable.

The substituted hydroxy group is exemplified by alkoxy group, alkenyloxy group, cycloalkyloxy group, cycloalkenyloxy group, aryloxy group, aralkyloxy group, acyloxy group, heteroaryloxy group, each being optionally substituted, and the like.

Preferable examples of the alkoxy groups are $C_{1-10}$ alkoxy groups such as methoxy, ethoxy, propoxy, isopropoxy, butoxy, isobutoxy, sec-butoxy, t-butoxy, pentyloxy, isopentyloxy, neopentyloxy, hexyloxy, heptyloxy, nonyloxy and the like.

Preferable examples of the alkenyloxy groups are $C_{2-10}$ alkenyloxy groups such as allyloxy, crotyloxy, 2-pentenyloxy, 3-hexenyloxy and the like.

Preferable examples of the cycloalkyloxy group include cycloalkyloxy group having 3 to 10 carbon atoms, such as cyclobutoxy, cyclopentyloxy, cyclohexyloxy and the like.

Preferable examples of the cycloalkenyloxy group include cycloalkenyloxy group having 3 to 10 carbon atoms, such as 2-cyclopentenyloxy, 2-cyclohexenyloxy and the like.

Preferable examples of the aryloxy group include aryloxy group having 6 to 14 carbon atoms, such as phenoxy, naphthyloxy and the like.

Preferable examples of the aralkyloxy group include aralkyloxy group having 7 to 13 carbon atoms, such as benzyloxy, phenethyloxy, naphthylmethyloxy and the like.

Preferable examples of the acyloxy groups are $C_{2-13}$ acyloxy groups, such as $C_{2-4}$ alkanoyloxy groups (e.g., acetyloxy, propionyloxy, butyryloxy, isobutyryloxy and the like) and the like.

Preferable examples of the heteroaryloxy group include a 5 to 7-membered monocyclic heteroaryloxy group, such as 2-pyridyloxy, 3-pyridyloxy, 2-imidazolyloxy, 1,2,4-triazol-5-yloxy and the like.

The above-mentioned alkoxy group, alkenyloxy group, cycloalkyloxy group, cycloalkenyloxy group, aryloxy group, aralkyloxy group, acyloxy group and heteroaryloxy group may have 1 or 2 substituents at a substitutable position(s). Examples of the substituent include halogen atom (e.g., fluorine, chlorine, bromine, iodine and the like), $C_{1-6}$ alkoxy group (e.g., methoxy, ethoxy and the like) optionally substituted by 1 to 3 halogen atoms (e.g., fluorine, chlorine, bromine, iodine and the like), hydroxy, nitro, amino and the like. For example, 4-chlorophenoxy, 2-methoxyphenoxy and the like are mentioned as substituted aryloxy group.

Examples of the optionally substituted thiol group include a thiol group optionally substituted by "alkyl group having 1 to 10 carbon atoms", "alkenyl group having 2 to 10 carbon atoms", "cycloalkyl group having 3 to 10 carbon atoms", "cycloalkenyl group having 3 to 10 carbon atoms", "aryl group having 6 to 14 carbon atoms", "aralkyl having 7 to 13 carbon atoms", "acyl group having 1 to 13 carbon atoms", "heteroaryl group" and the like.

As used herein, the "alkyl group having 1 to 10 carbon atoms", "alkenyl group having 2 to 10 carbon atoms", "cycloalkyl group having 3 to 10 carbon atoms", "cycloalkenyl group having 3 to 10 carbon atoms", "aryl group having 6 to 14 carbon atoms", "aralkyl having 7 to 13 carbon atoms", "acyl group having 1 to 13 carbon atoms" and "heteroaryl group" are exemplified by those exemplified for the aforementioned "optionally substituted hydroxy group".

The substituted thiol group is exemplified by alkylthio, alkenylthio, cycloalkylthio, cycloalkenylthio, arylthio, aralkylthio, acylthio, heteroarylthio and the like.

Preferable examples of the alkylthio group include alkylthio group having 1 to 10 carbon atoms, such as methylthio, ethylthio, propylthio, isopropylthio, butylthio, isobutylthio, sec-butylthio, t-butylthio, pentylthio, isopentylthio, neopentylthio, hexylthio, heptylthio, nonylthio and the like.

Preferable examples of the alkenylthio group include alkenylthio group having 2 to 10 carbon atoms, such as allylthio, crotylthio, 2-pentenylthio, 3-hexenylthio and the like.

Preferable examples of the cycloalkylthio group include cycloalkylthio group having 3 to 10 carbon atoms, such as cyclobutylthio, cyclopentylthio, cyclohexylthio and the like.

Preferable examples of the cycloalkenylthio group include cycloalkenylthio group having 3 to 10 carbon atoms, such as 2-cyclopentenylthio, 2-cyclohexenylthio and the like.

Preferable examples of the arylthio group include arylthio group having 6 to 14 carbon atoms, such as phenylthio, naphthylthio and the like.

Preferable examples of the aralkylthio group include aralkylthio group having 7 to 13 carbon atoms, such as benzylthio, phenethylthio, naphthylmethylthio and the like.

Preferable examples of the acylthio group include, acylthio group having 2 to 13 carbon atoms, such as alkanoylthio group having 2 to 4 carbon atoms (e.g., acetylthio, propionylthio, butyrylthio, isobutyrylthio and the like), and the like.

Preferable examples of the heteroarylthio group include 5 to 7-membered monocyclic heteroarylthio group, such as 2-pyridylthio, 3-pyridylthio, 2-imidazolylthio, 1,2,4-triazol-5-ylthio and the like.

In the optionally esterified carboxyl group, examples of the esterified carboxyl group include alkoxycarbonyl group having 2 to 5 carbon atoms (e.g., methoxycarbonyl, ethoxycarbonyl, propoxycarbonyl, butoxycarbonyl and the like), aralkyloxycarbonyl group having 8 to 14 carbon atoms (e.g., benzyloxycarbonyl and the like), aryloxycarbonyl group having 7 to 15 carbon atoms (e.g., phenoxycarbonyl, p-tolyloxycarbonyl and the like) optionally substituted by 1 or 2 alkyl group having 1 to 3 carbon atoms and the like.

In the optionally amidated carboxyl group, the amidated carboxyl group is, for example, a group of the formula: —CON($R^6$)($R^7$) wherein $R^6$ and $R^7$ are the same or different and each is a hydrogen atom, an optionally substituted hydrocarbon group or an optionally substituted heterocyclic group, or $R^6$ and $R^7$ may form, together with the adjacent nitrogen atom, an optionally substituted nitrogen-containing heterocycle.

Here, the hydrocarbon group of the "optionally substituted hydrocarbon group" represented by $R^6$ or $R^7$ is exemplified by the hydrocarbon group exemplified for the aforementioned $R^4$. The hydrocarbon group is preferably alkyl group having 1 to 10 carbon atoms (preferably methyl, ethyl, propyl, butyl, tert-butyl, pentyl, 1-ethylpropyl, 2,2-dimethylpropyl); alkynyl group having 2 to 10 carbon atoms (preferably 2-propynyl); cycloalkyl group having 3 to 10 carbon atoms (preferably cyclopropyl, cyclohexyl) optionally condensed with benzene ring; aryl group having 6 to 14 carbon atoms (preferably phenyl, dihydroindenyl, biphenylyl) optionally condensed with cycloalkane having 3 to 10 carbon atoms (preferably cyclopentane); aralkyl group having 7 to 13 carbon atoms (preferably benzyl, phenethyl, phenylpropyl, naphthylmethyl, benzhydryl) and the like.

The heterocyclic group of the "optionally substituted heterocyclic group" represented by $R^6$ and $R^7$ is exemplified by aromatic heterocyclic group and non-aromatic heterocyclic group exemplified for "cyclic group" represented by $R^1$ or $R^2$. The heterocyclic group is preferably thiazolyl, oxazolyl, isothiazolyl, isoxazolyl, pyrazolyl, pyridyl, pyrazinyl, triazinyl, benzoxazolyl, benzothiazolyl, benzothiadiazolyl, quinolyl, isoquinolyl, pyrrolidinyl, piperidinyl, piperazinyl, azepanyl and the like.

The hydrocarbon group and heterocyclic group may have 1 to 4 (preferably 1 to 3) substituents at a substitutable position(s), and examples of the substituent include halogen atom (e.g., fluorine, chlorine, bromine, iodine and the like); $C_{1-6}$ alkyl group (e.g., methyl, trifluoromethyl and the like) optionally substituted by 1 to 3 halogen atoms (e.g., fluorine, chlorine, bromine, iodine and the like); $C_{1-6}$ alkoxy group (e.g., methoxy, isopropoxy, trifluoromethoxy and the like) optionally substituted by 1 to 3 halogen atoms (e.g., fluorine, chlorine, bromine, iodine and the like); nitro; hydroxy; amino; carbamoyl group; (mono- or di-$C_{1-6}$ alkyl-phosphono optionally forming a ring)-$C_{1-6}$ alkyl group [e.g., dimethylphosphonomethyl, diethylphosphonomethyl, diisopropylphosphonomethyl, dibutylphosphonomethyl, diethylphosphonoethyl, (2-oxide-1,3,2-dioxaphosphinanyl)methyl, (methyl-2-oxide-1,3,2 dioxaphosphinanyl)methyl, (dimethyl-2-oxide-1,3,2-dioxaphosphinanyl)methyl, (diethyl-2-oxide-1,3,2-dioxaphosphinanyl)methyl, (5-butyl-5-ethyl-2-oxide-1,3,2-dioxaphosphinanyl)methyl, (5-ethyl-5-methyl-2-oxide-1,3,2-dioxaphosphinanyl)methyl and the like]; phosphono-$C_{1-6}$ alkyl group (e.g., phosphonomethyl and the like); $C_{2-5}$ alkoxycarbonyl group (e.g., methoxycarbonyl, ethoxycarbonyl and the like); $C_{2-5}$ alkoxycarbonyl-$C_{1-6}$ alkyl group (e.g., ethoxycarbonylmethyl and the like); $C_{6-10}$ aryl group (e.g., phenyl and the like) optionally substituted by 1 to 3 halogen atoms (e.g., fluorine, chlorine, bromine, iodine and the like), $C_{1-6}$ alkoxy group or carbamoyl group; heterocyclic group (e.g., indolyl, imidazolyl, pyridyl, morpholino, furyl, tetrahydrofuranyl, pyrrolidinyl, piperidinyl, piperazinyl and the like) optionally substituted by $C_{1-6}$ alkyl group (e.g., methyl and the like) or oxo group; $C_{1-6}$ alkyl-heterocyclic-$C_{1-6}$ alkoxy group (e.g., ethyltriazolylethoxy and the like); mono- or di-$C_{1-6}$ alkylamino group (e.g., dimethylamino, diethylamino, ethylmethylamino, diisopropylamino, N-methyl-N-phenylamino, di-hydroxyethyl-amino and the like) optionally substituted by hydroxy group, $C_{6-10}$ aryl group (e.g., phenyl and the like) or $C_{1-6}$ alkyl-$C_{6-10}$ aryl group (e.g., methylphenyl and the like); $C_{6-10}$ arylamino group (e.g., phenylamino and the like); $C_{3-10}$ cycloalkyl group (e.g., cyclohexyl and the like); $C_{1-3}$ alkylenedioxy group (e.g., methylenedioxy, ethylenedioxy and the like); $C_{1-6}$ alkylthio group (e.g., methylthio and the like) optionally substituted by 1 to 3 halogen atoms (e.g., fluorine, chlorine, bromine, iodine and the like); $C_{7-13}$ aralkyl group (e.g., benzyl and the like); aromatic heterocyclic amino group (e.g., pyridylamino and the like) optionally substituted by nitro group; $C_{6-10}$ aryloxy group (e.g., phenoxy and the like); mono- or di-$C_{1-6}$ alkyl-phosphono group (e.g., diethylphosphono and the like); mono- or di-(mono- or di-$C_{1-6}$ alkyl-phosphono)-$C_{2-6}$ alkenyl group [e.g., bis(diethylphosphono)ethenyl, 2-diethylphosphono-2-ethoxycarbonylethenyl and the like] optionally substituted by $C_{2-5}$ alkoxycarbonyl group (e.g., methoxycarbonyl, ethoxycarbonyl and the like); bis(mono- or di-$C_{1-6}$ alkylamino)-phosphoryl-$C_{1-6}$ alkyl group (e.g., bis(ethylamino) phosphorylmethyl and the like); oxo group and the like.

The nitrogen-containing heterocycle formed by $R^6$ and $R^7$ together with the adjacent nitrogen atom is exemplified by a 5 to 8-membered (preferably 5 to 7-membered) nitrogen-containing (preferably saturated) heterocyclic group containing, besides carbon atom, at least one nitrogen atom and optionally 1 or 2 hetero atoms selected from oxygen atom, sulfur atom and nitrogen atom, as ring constituting atom. Preferable examples of the nitrogen-containing heterocyclic group include 1-pyrrolidinyl, 1-imidazolidinyl, 1-pyrazolidinyl, 1-piperidinyl, 1-piperazinyl, 4-morpholinyl, 4-thiomorpholinyl, 1-azepanyl, 1-azocanyl and the like. The nitrogen-containing heterocyclic group may form a fused ring group with benzene ring or $C_{3-10}$ cycloalkane (e.g., cyclohexane), and examples of the fused ring group include tetrahydroisoquinolin-2-yl, decahydroisoquinolin-2-yl and the like.

The nitrogen-containing heterocyclic group may have 1 or 2 substituents at a substitutable position(s). Examples of such substituent include $C_{1-6}$ alkyl group (e.g., methyl, ethyl and the like) optionally substituted by 1 to 3 halogen atoms (e.g., fluorine, chlorine, bromine, iodine and the like), hydroxy group, $C_{2-7}$ alkoxycarbonyl group (e.g., ethoxycarbonyl) or 5 or 6-membered nitrogen-containing heterocyclic group (e.g., pyrrolidinyl and the like); $C_{7-14}$ aralkyl group (e.g., benzyl, diphenylmethyl, benzhydryl and the like) optionally substituted by $C_{1-3}$ alkylenedioxy group (e.g., methylenedioxy and the like); $C_{6-14}$ aryl group (e.g., phenyl and the like) optionally substituted by $C_{1-6}$ alkyl group (e.g., methyl, trifluoromethyl and the like) optionally substituted by 1 to 3 halogen atoms (e.g., fluorine, chlorine, bromine, iodine and the like), halogen atom (e.g., fluorine, chlorine, bromine, iodine and the like), $C_{1-6}$ alkoxy group (e.g., methoxy, ethoxy and the like) or $C_{2-10}$ alkanoyl group (e.g., acetyl and the like); $C_{6-14}$ aryl-$C_{2-6}$ alkenyl group (e.g., phenylpropenyl and the like); $C_{6-14}$ arylamino-$C_{1-6}$ alkyl group (e.g., phenylaminomethyl and the like) optionally substituted by $C_{1-6}$ alkyl group (e.g., methyl and the like); cyano group; oxo group; hydroxy group; mono- or di-$C_{2-10}$ alkanoylamino group (e.g., acetylamino, trifluoroacetylamino, propionylamino, N-acetyl-N-ethylamino and the like) optionally substituted by 1 to 3 halogen atoms (e.g., fluorine, chlorine, bromine, iodine and the like) or $C_{1-6}$ alkyl group (e.g., methyl, ethyl and the like); $C_{2-7}$ alkoxycarbonylamino group (e.g., tert-butoxycarbonylamino and the like); 5 or 6-membered nitrogen-containing heterocyclic group (e.g., pyridyl, piperidinyl, pyrimidinyl, pyrrolidinyl and the like); aromatic heterocyclic carbonyl group (e.g., furoyl and the like); carbamoyl group; $C_{2-10}$ alkanoyl group (e.g., acetyl and the like); $C_{2-7}$ alkoxycarbonyl group (e.g., methoxycarbonyl, ethoxycarbonyl and the like); and the like.

The "substituent" of the "optionally substituted cyclic group" represented by $R^1$ or $R^2$ is preferably
1) halogen atom (e.g., fluorine, chlorine, bromine, iodine and the like);
2) alkyl group having 1 to 6 carbon atoms (e.g., methyl, trifluoromethyl and the like) optionally substituted by 1 to 5 halogen atoms (e.g., fluorine, chlorine, bromine, iodine and the like);
3) alkoxy group having 1 to 6 carbon atoms (e.g., methoxy, trifluoromethoxy and the like) optionally substituted by 1 to 3 halogen atoms (e.g., fluorine, chlorine, bromine, iodine and the like);
4) alkylthio group having 1 to 6 carbon atoms (e.g., methylthio and the like) optionally substituted by 1 to 3 halogen atoms (e.g., fluorine, chlorine, bromine, iodine and the like);
5) nitro group;
6) cyano group;
7) $C_{1-3}$ alkylenedioxy group (e.g., methylenedioxy and the like);
8) aryl group having 6 to 14 carbon atoms (e.g., phenyl and the like);
9) alkylsulfinyl group having 1 to 6 carbon atoms (e.g., methylsulfinyl and the like);

10) alkylsulfonyl group having 1 to 6 carbon atoms (e.g., methylsulfonyl and the like); and the like. The number of the substituent is preferably 1 to 3, more preferably 1 or 2.

The "substituent" is more preferably 1 or 2 selected from
1) halogen atom (e.g., fluorine, chlorine, bromine, iodine and the like);
2) alkyl group having 1 to 6 carbon atoms (e.g., methyl, trifluoromethyl and the like) optionally substituted by 1 to 5 halogen atoms (e.g., fluorine, chlorine, bromine, iodine and the like);
3) alkoxy group having 1 to 6 carbon atoms (e.g., methoxy, trifluoromethoxy and the like) optionally substituted by 1 to 3 halogen atoms (e.g., fluorine, chlorine, bromine, iodine and the like);
4) nitro group;
5) cyano group; and the like.

The "optionally substituted cyclic group" represented by $R^1$ or $R^2$ is preferably an optionally substituted aromatic group, more preferably aromatic hydrocarbon group (preferably phenyl, naphthyl) or aromatic heterocyclic group (preferably furyl, thienyl, pyridyl, quinolyl, more preferably thienyl, pyridyl) optionally having 1 to 3 substituents selected from
1) halogen atom (e.g., fluorine, chlorine, bromine, iodine);
2) alkyl group having 1 to 6 carbon atoms (e.g., methyl, ethyl, trifluoromethyl) optionally substituted by 1 to 5 halogen atoms (e.g., fluorine, chlorine, bromine, iodine);
3) alkoxy group having 1 to 6 carbon atoms (e.g., methoxy, ethoxy, trifluoromethoxy) optionally substituted by 1 to 3 halogen atoms (e.g., fluorine, chlorine, bromine, iodine);
4) alkylthio group having 1 to 6 carbon atoms (e.g., methylthio) optionally substituted by 1 to 3 halogen atoms (e.g., fluorine, chlorine, bromine, iodine);
5) nitro group;
6) cyano group;
7) $C_{1-3}$ alkylenedioxy group (e.g., methylenedioxy);
8) aryl group having 6 to 14 carbon atoms (e.g., phenyl);
9) alkylsulfinyl group having 1 to 6 carbon atoms (e.g., methylsulfinyl); and
10) alkylsulfonyl group having 1 to 6 carbon atoms (e.g., methylsulfonyl).

The "optionally substituted cyclic group" represented by $R^1$ or $R^2$ is particularly preferably $C_{6-14}$ aryl group (preferably phenyl) optionally having 1 to 3 halogen atoms (preferably fluorine, chlorine, bromine).

In the formulas (I) and (Ia), the "substituent" represented by $R^1$ or $R^2$ is exemplified by those exemplified as the "substituent" of "optionally substituted cyclic group" represented by $R^1$ or $R^2$.

The substituent is preferably
1) alkyl group having 1 to 6 carbon atoms (e.g., methyl, ethyl, trifluoromethyl) optionally substituted by 1 to 5 halogen atoms (e.g., fluorine, chlorine, bromine, iodine);
2) hydroxy group;
3) aryl group having 6 to 14 carbon atoms (e.g., phenyl); and the like.

In the formulas (I) and (Ia), $R^1$ is preferably a hydrogen atom or a substituent and $R^2$ is preferably an optionally substituted cyclic group. It is more preferable that $R^1$ be a hydrogen atom, and $R^2$ be an optionally substituted cyclic group.

(2) Definition of $R^{1a}$ and $R^{2a}$

In the formula (II), the "optionally substituted cyclic group" represented by $R^{1a}$ or $R^{2a}$ is exemplified by those exemplified for $R^1$ or $R^2$ of the formulas (I) and (Ia).

In the formula (II), $R^{1a}$ is preferably a hydrogen atom and $R^{2a}$ is preferably an optionally substituted cyclic group. Moreover, $R^{2a}$ is preferably an optionally substituted aromatic group, particularly preferably $C_{6-14}$ aryl group (preferably phenyl) optionally having 1 to 3 halogen atoms (preferably fluorine, chlorine, bromine).

(3) Definition of W and Wa

In the formulas (I), (Ia) and (II), "divalent aliphatic hydrocarbon group" represented by W or Wa may be straight-chain or branched, and saturated or unsaturated.

The "divalent aliphatic hydrocarbon group" is preferably a divalent aliphatic hydrocarbon group having 1 to 8 carbon atoms, which is specifically exemplified by
(1) $C_{1-8}$ alkylene (e.g., $-CH_2-$, $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-CH(CH_3)-$, $-(CH(CH_3))_2-$, $-(CH_2)_2C(CH_3)_2-$, $-(CH_2)_3C(CH_3)_2-$ and the like);
(2) $C_{2-8}$ alkenylene (e.g., $-CH=CH-$, $-CH_2-CH=CH-$, $-C(CH_3)_2-CH=CH-$, $-CH_2-CH=CH-CH_2-$, $-CH_2-CH_2-CH=CH-$, $-CH=CH-CH=CH-$, $-CH=CH-CH_{2-CH2}-$ and the like) and the like.

The "divalent aliphatic hydrocarbon group" is preferably a divalent aliphatic hydrocarbon group having 1 to 4 carbon atoms, and it is more preferably saturated. Particularly, $-CH_2-$, $-(CH_2)_2-$, $-(CH_2)_3-$, $-(CH_2)_4-$ and the like are preferable, of which $-(CH_2)_2-$, $-(CH_2)_3-$, $-(CH_2)_4-$ and the like are preferable.

In the formulas (I) and (Ia), a compound wherein W is a "divalent aliphatic hydrocarbon group" has a superior hypoglycemic action as compared to a compound wherein W is a bond. Therefore, W is preferably a divalent aliphatic hydrocarbon group.

W and Wa are preferably a divalent aliphatic hydrocarbon group having 1 to 4 carbon atoms, more preferably $-CH_2-$, $-(CH_2)_2-$, $-(CH_2)_3-$ and $-(CH_2)_4-$. Of these, $-(CH_2)_2-$, $-(CH_2)_3-$, $-(CH_2)_4-$ and the like are preferable.

In the formulas (I), (Ia) and (II), when Y is a group represented by the formula: $-OR^3$ ($R^3$ is as defined above), W and Wa are particularly preferably $-(CH_2)_3-$.

In the formulas (I), (Ia) and (II), when Y is an optionally esterified or amidated carboxyl group, W and Wa are particularly preferably $-(CH_2)_2-$.

(4) Definition of Y

In the formulas (I), (Ia) and (II), Y is a group represented by the formula: $-OR^3$ ($R^3$ is hydrogen atom, optionally substituted hydrocarbon group, optionally substituted heterocyclic group or optionally substituted acyl group) or optionally esterified or amidated carboxyl group.

As used herein, the "optionally substituted heterocyclic group" and "optionally substituted acyl group" represented by $R^3$ are each exemplified by those exemplified as the "substituent" of the "optionally substituted cyclic group" represented by $R^1$ or $R^2$.

As used herein, the "optionally substituted hydrocarbon group" represented by $R^3$ is exemplified by the "optionally substituted aliphatic hydrocarbon group", "optionally substituted alicyclic hydrocarbon group" and "optionally substituted aromatic hydrocarbon group" exemplified as the "substituent" of the "optionally substituted cyclic group" represented by $R^1$ or $R^2$.

$R^3$ is preferably a hydrogen atom, an alkyl group having 1 to 10 carbon atoms and the like, particularly preferably a hydrogen atom.

The "optionally esterified or amidated carboxyl group" represented by Y is exemplified by those exemplified as the "substituent" of the "optionally substituted cyclic group" represented by $R^1$ or $R^2$.

Specific examples of the "optionally esterified or amidated carboxyl group" include
1) carboxyl group;
2) alkoxycarbonyl group having 2 to 5 carbon atoms (e.g., methoxycarbonyl, ethoxycarbonyl and the like);
3) carbamoyl group (e.g., carbamoyl, ethylcarbamoyl, indolylethylcarbamoyl, methylpyrazylmethylcarbamoyl and the like) optionally mono- or di-substituted by $C_{1-6}$ alkyl group optionally having 1 or 2 heterocyclic groups optionally substituted by $C_{1-6}$ alkyl group;
4) $C_{6-10}$ aryl-carbamoyl group (e.g., diethylphosphonomethylphenylcarbamoyl, methoxycarbonylphenylcarbamoyl, carbamoylphenylcarbamoyl, ethoxycarbonylmethylphenylcarbamoyl, imidazolylphenylcarbamoyl, morpholinophenylcarbamoyl, ethyltriazolylethoxyphenylcarbamoyl and the like) optionally having 1 or 2 substituents selected from (mono- or di-$C_{1-6}$ alkyl)-phosphono-$C_{1-6}$ alkyl group; $C_{2-5}$ alkoxycarbonyl group; carbamoyl group; $C_{2-5}$ alkoxycarbonyl-$C_{1-6}$ alkyl group; heterocyclic group; and heterocyclic $C_{1-6}$ alkoxy group optionally substituted by $C_{1-6}$ alkyl group;
5) $C_{7-13}$ aralkyl-carbamoyl group (e.g., trifluoromethylbenzylcarbamoyl, methoxyphenylethylcarbamoyl and the like) optionally having 1 or 2 substituents selected from $C_{1-6}$ alkyl group optionally substituted by 1 to 3 halogen atoms (e.g., fluorine, chlorine, bromine, iodine and the like) and $C_{1-6}$ alkoxy-$C_{7-13}$ aralkyl group;
6) heterocyclic carbamoyl group (e.g., 4-(4-chlorophenyl)thiazol-2-yl-carbamoyl, 5-methyl-3-phenylthiazol-2-yl-carbamoyl, quinolylcarbamoyl, pyridylcarbamoyl, (2-methyl-1-imidazolyl)pyridylcarbamoyl, pyrazylcarbamoyl, morpholinopyridylcarbamoyl and the like) optionally having 1 or 2 substituents selected from $C_{6-10}$ aryl group optionally substituted by 1 to 3 halogen atoms (e.g., fluorine, chlorine, bromine, iodine and the like); $C_{1-6}$ alkyl; and heterocyclic group optionally substituted by $C_{1-6}$ alkyl;
7) $C_{7-14}$ aralkyl-nitrogen-containing (preferably saturated) heterocyclic carbonyl group (e.g., 4-diphenylmethylpiperazin-1-ylcarbonyl and the like); and the like.

Of these, carboxyl group, alkoxycarbonyl group having 2 to 5 carbon atoms (e.g., methoxycarbonyl, ethoxycarbonyl and the like) and the like are preferable.

Y is preferably an "optionally amidated carboxyl group", more preferably an "amidated carboxyl group" of the following a) to g) and the like.
a) Carbamoyl group optionally mono- or di-substituted by $C_{1-6}$ aliphatic hydrocarbon group [e.g., alkyl group (e.g., methyl, ethyl, propyl, butyl, tert-butyl, 1-ethylpropyl, 2,2-dimethylpropyl and the like), $C_{2-6}$ alkynyl group (e.g., propynyl and the like)] optionally having 1 or 2 substituents selected from $C_{1-6}$ alkoxy group (e.g., methoxy, isopropoxy and the like); heterocyclic group (e.g., indolyl, imidazolyl, pyridyl, morpholino, furyl, tetrahydrofuranyl, pyrrolidinyl, piperidinyl, piperazinyl and the like) optionally substituted by $C_{1-6}$ alkyl group (e.g., methyl and the like) or oxo group; $C_{1-6}$ alkylthio group (e.g., methylthio and the like); mono- or di-$C_{1-6}$ alkylamino group (e.g., dimethylamino, diethylamino, ethylmethylamino, diisopropylamino, N-methyl-N-phenylamino, di-hydroxyethyl-amino and the like) optionally substituted by hydroxy group, $C_{6-10}$ aryl group (e.g., phenyl and the like) or $C_{1-6}$ alkyl-$C_{6-10}$ aryl group (e.g., methylphenyl and the like); $C_{6-10}$ arylamino group (e.g., phenylamino and the like); aromatic heterocyclic amino group (e.g., pyridylamino and the like) optionally substituted by nitro group; mono- or di-$C_{1-6}$ alkyl-phosphono group (e.g., diethylphosphono and the like).
b) $C_{6-14}$ Aryl-carbamoyl group (e.g., phenylcarbamoyl, naphthylcarbamoyl, dihydroindenylcarbamoyl, biphenylylcarbamoyl) optionally condensed with $C_{3-10}$ cycloalkane (e.g., cyclopentane) and optionally having 1 or 2 substituents selected from halogen atom (e.g., fluorine, chlorine, bromine, iodine and the like); $C_{1-6}$ alkyl group (e.g., methyl, trifluoromethyl) optionally substituted by 1 to 3 halogen atoms (e.g., fluorine, chlorine, bromine, iodine and the like); $C_{1-6}$ alkoxy group (e.g., methoxy, trifluoromethoxy) optionally substituted by 1 to 3 halogen atoms (e.g., fluorine, chlorine, bromine, iodine and the like); carbamoyl group; (mono- or di-$C_{1-6}$ alkyl-phosphono optionally forming a ring)-$C_{1-16}$ alkyl group [e.g., methylphosphonomethyl, ethylphosphonomethyl, dimethylphosphonomethyl, diethylphosphonomethyl, ethylmethylphosphonomethyl, diisopropylphosphonomethyl, dibutylphosphonomethyl, diethylphosphonoethyl, (2-oxide-1,3,2-dioxaphosphinanyl)methyl, (methyl-2-oxide-1,3,2-dioxaphosphinanyl)methyl, (dimethyl-2-oxide-1,3,2-dioxaphosphinanyl)methyl, (diethyl-2-oxide-1,3,2-dioxaphosphinanyl)methyl, (5-butyl-5-ethyl-2-oxide-1,3,2-dioxaphosphinanyl)methyl, (5-ethyl-5-methyl-2-oxide-1,3,2-dioxaphosphinanyl)methyl and the like]; phosphono-$C_{1-6}$ alkyl group (e.g., phosphonomethyl and the like); $C_{2-5}$ alkoxycarbonyl group (e.g., methoxycarbonyl, ethoxycarbonyl and the like); $C_{2-5}$ alkoxycarbonyl-$C_{1-6}$ alkyl group (e.g., ethoxycarbonylmethyl and the like); heterocyclic group (e.g., imidazolyl, morpholino); heterocyclic $C_{1-6}$ alkoxy group (e.g., triazolylethoxy) optionally substituted by $C_{1-6}$ alkyl group (e.g., methyl, ethyl); $C_{1-3}$ alkylenedioxy group (e.g., methylenedioxy, ethylenedioxy and the like); $C_{7-14}$ aralkyl group (e.g., benzyl); $C_{6-10}$ aryloxy group (e.g., phenoxy and the like); mono- or di-$C_{1-6}$ alkyl-phosphono group (e.g., diethylphosphono and the like); mono- or di-(mono- or di-$C_{1-6}$ alkyl-phosphono)-$C_{2-6}$ alkenyl group [e.g., bis(diethylphosphono)ethenyl, 2-diethylphosphono-2-ethoxycarbonylethenyl and the like] optionally substituted by $C_{2-5}$ alkoxycarbonyl group (e.g., methoxycarbonyl, ethoxycarbonyl and the like).
c) $C_{3-10}$ Cycloalkyl-carbamoyl group (e.g., cyclopropylcarbamoyl, cyclohexylcarbamoyl, dihydroindenylcarbamoyl) optionally substituted by 1 or 2 $C_{1-6}$ alkyl groups (e.g., methyl) and optionally condensed with benzene ring.
d) $C_{7-13}$ Aralkyl-carbamoyl group (e.g., benzylcarbamoyl, phenethylcarbamoyl, phenylpropylcarbamoyl, benzhydrylcarbamoyl) optionally having 1 or 2 substituents selected from $C_{1-6}$ alkyl group (e.g., methyl, trifluoromethyl, dimethylaminoethyl, diethylaminoethyl) optionally substituted by 1 to 3 halogen atoms (e.g., fluorine, chlorine, bromine, iodine and the like) or mono- or di-$C_{1-6}$ alkylamino; $C_{1-6}$ alkoxy group (e.g., methoxy); $C_{1-3}$ alkylenedioxy group (e.g., methylenedioxy and the like); $C_{6-14}$ aryl group (e.g., phenyl); and $C_{2-5}$ alkoxycarbonyl-$C_{1-6}$ alkyl group (e.g., ethoxycarbonylethyl).
e) $C_{3-10}$ cycloalkyl-$C_{1-6}$ alkyl-carbamoyl group (e.g., cyclohexylmethylcarbamoyl).
f) Heterocyclic carbamoyl group (e.g., piperidinylcarbamoyl, azepanylcarbamoyl, pyrrolidinylcarbamoyl, oxazolylcarbamoyl, thiazolylcarbamoyl, pyridylcarbamoyl, triazinylcarbamoyl, quinolylcarbamoyl, isoquinolylcarbamoyl, benzothiazolylcarbamoyl, pyrazolylcarbamoyl, piperazinylcarbamoyl, benzothiadiazolylcarbamoyl, pyrazinylcarbamoyl) optionally having 1 to 4 (preferably 1 or 2) substituents selected from $C_{6-10}$ aryl group (e.g., phenyl and the like) optionally substituted by 1 to 3 halogen atoms (e.g., fluorine, chlorine, bromine, iodine and the like); $C_{1-6}$ alkyl (e.g., methyl) optionally substituted by 1 to 3 halogen atoms (e.g., fluorine, chlorine, bromine, iodine and the like); heterocyclic group (e.g., imidazolyl, morpholino) optionally substituted by $C_{1-6}$ alkyl group (e.g., methyl); $C_{7-14}$ aralkyl group (e.g., benzyl); and oxo group.

g) Nitrogen-containing heterocyclic carbonyl group (e.g., piperidinylcarbonyl, pyrrolidinylcarbonyl, morpholinocarbonyl, thiomorpholinocarbonyl, piperazinylcarbonyl, tetrahydroisoquinolinecarbonyl, decahydroisoquinolinecarbonyl, azepanecarbonyl, azocanecarbonyl, 1,2,3,6-tetrahydropyridinecarbonyl and the like) optionally condensed with benzene ring or $C_{3-10}$ cycloalkane (e.g., cyclohexane and the like), and optionally having 1 or 2 substituents selected from $C_{1-6}$ alkyl (e.g., methyl, ethyl and the like) optionally substituted by 1 to 3 halogen atoms (e.g., fluorine, chlorine, bromine, iodine and the like), hydroxy group, $C_{2-7}$ alkoxycarbonyl group (e.g., ethoxycarbonyl) or 5 or 6-membered nitrogen-containing heterocyclic group (e.g., pyrrolidinyl and the like); $C_{7-14}$ aralkyl group (e.g., benzyl, benzhydryl and the like) optionally substituted by $C_{1-3}$ alkylenedioxy group (e.g., methylenedioxy and the like); $C_{6-14}$ aryl group (e.g., phenyl and the like) optionally substituted by $C_{1-6}$ alkyl group (e.g., methyl, trifluoromethyl and the like) optionally substituted by 1 to 3 halogen atoms (e.g., fluorine, chlorine, bromine, iodine and the like), halogen atom (e.g., fluorine, chlorine, bromine, iodine and the like), $C_{1-6}$ alkoxy group (e.g., methoxy, ethoxy and the like) or $C_{2-10}$ alkanoyl group (e.g., acetyl and the like); $C_{6-14}$ aryl-$C_{2-6}$ alkenyl group (e.g., phenylpropenyl and the like); $C_{6-14}$ arylamino-$C_{1-6}$ alkyl group (e.g., phenylaminomethyl and the like) optionally substituted by $C_{1-6}$ alkyl group (e.g., methyl and the like); cyano group; oxo group; hydroxy group; mono- or di-$C_{2-10}$ alkanoylamino group (e.g., acetylamino, trifluoroacetylamino, propionylamino, N-acetyl-N-ethylamino and the like) optionally substituted by 1 to 3 halogen atoms (e.g., fluorine, chlorine, bromine, iodine and the like) or $C_{1-6}$ alkyl group (e.g., methyl, ethyl and the like); $C_{2-7}$ alkoxycarbonylamino group (e.g., tert-butoxycarbonylamino and the like); 5 or 6-membered nitrogen-containing heterocyclic group (e.g., pyridyl, piperidinyl, pyrimidinyl, pyrrolidinyl and the like); aromatic heterocyclic carbonyl group (e.g., furoyl and the like); carbamoyl group; $C_{2-10}$ alkanoyl group (e.g., acetyl and the like); and $C_{2-7}$ alkoxycarbonyl group (e.g., methoxycarbonyl, ethoxycarbonyl and the like).

Of these, b), d) and f) are preferable. Particularly, $C_{6-14}$ aryl-carbamoyl group (preferably phenylcarbamoyl) optionally substituted by (mono- or di-$C_{1-6}$ alkyl-phosphono optionally forming a ring)-$C_{1-6}$ alkyl group [e.g., dimethylphosphonomethyl, diethylphosphonomethyl, diisopropylphosphonomethyl, dibutylphosphonomethyl, diethylphosphonoethyl, (2-oxide-1,3,2-dioxaphosphinanyl)methyl, (methyl-2-oxide-1,3,2-dioxaphosphinanyl)methyl, (dimethyl-2-oxide-1,3,2-dioxaphosphinanyl)methyl, (diethyl-2-oxide-1,3,2-dioxaphosphinanyl)methyl, (5-butyl-5-ethyl-2-oxide-1,3,2-dioxaphosphinanyl)methyl, (5-ethyl-5-methyl-2-oxide-1,3,2-dioxaphosphinanyl)methyl and the like] is preferable.

(5) Preferable Compound

Of the compounds represented by the formula (I) and a salt thereof, a compound represented by the formula (II) (except 5-phenyl-4-isoxazolylmethanol and 5-phenyl-4-isoxazolylacetic acid) and a salt thereof are novel compounds.

Preferable examples of a compound represented by the formula (II) include the following compounds (A), (B), (C) and the like.

Compound (A)
A compound wherein
$R^{1a}$ is a hydrogen atom;
$R^{2a}$ is an aromatic hydrocarbon group (preferably phenyl, naphthyl) or aromatic heterocyclic group (preferably furyl, thienyl, pyridyl, quinolyl, more preferably thienyl, pyridyl) optionally having 1 to 3 substituents selected from
1) a halogen atom (e.g., fluorine, chlorine, bromine, iodine);
2) an alkyl group having 1 to 6 carbon atoms (e.g., methyl, ethyl, trifluoromethyl) optionally substituted by 1 to 5 halogen atoms (e.g., fluorine, chlorine, bromine, iodine);
3) an alkoxy group having 1 to 6 carbon atoms (e.g., methoxy, ethoxy, trifluoromethoxy) optionally substituted by 1 to 3 halogen atoms (e.g., fluorine, chlorine, bromine, iodine);
4) an alkylthio group having 1 to 6 carbon atoms (e.g., methylthio) optionally substituted by 1 to 3 halogen atoms (e.g., fluorine, chlorine, bromine, iodine);
5) a nitro group;
6) a cyano group;
7) a $C_{1-3}$ alkylenedioxy group (e.g., methylenedioxy);
8) an aryl group having 6 to 14 carbon atoms (e.g., phenyl);
9) an alkylsulfinyl group having 1 to 6 carbon atoms (e.g., methylsulfinyl); and
10) alkylsulfonyl group having 1 to 6 carbon atoms (e.g., methylsulfonyl);
Wa is a divalent aliphatic hydrocarbon group having 1 to 4 carbon atoms (preferably —$CH_2$—, —$(CH_2)_2$—, —$(CH_2)_3$—, —$(CH_2)_4$—; more preferably —$(CH_2)_2$—, —$(CH_2)_3$—, —$(CH_2)_4$—; particularly preferably —$(CH_2)_3$—);
Y is a group represented by the formula: —$OR^3$, and
$R^3$ is a hydrogen atom or an alkyl group having 1 to 10 carbon atoms.

Compound (B)
A compound wherein
$R^{1a}$ is a hydrogen atom;
$R^{2a}$ is an aromatic hydrocarbon group (preferably phenyl, naphthyl) or aromatic heterocyclic group (preferably furyl, thienyl, pyridyl, quinolyl, more preferably thienyl, pyridyl) optionally having 1 to 3 substituents selected from
1) a halogen atom (e.g., fluorine, chlorine, bromine, iodine);
2) an alkyl group having 1 to 6 carbon atoms (e.g., methyl, ethyl, trifluoromethyl) optionally substituted by 1 to 5 halogen atoms (e.g., fluorine, chlorine, bromine, iodine);
3) an alkoxy group having 1 to 6 carbon atoms (e.g., methoxy, ethoxy, trifluoromethoxy) optionally substituted by 1 to 3 halogen atoms (e.g., fluorine, chlorine, bromine, iodine);
4) an alkylthio group having 1 to 6 carbon atoms (e.g., methylthio) optionally substituted by 1 to 3 halogen atoms (e.g., fluorine, chlorine, bromine, iodine);
5) a nitro group;
6) a cyano group;
7) a $C_{1-3}$ alkylenedioxy group (e.g., methylenedioxy);

8) an aryl group having 6 to 14 carbon atoms (e.g., phenyl);
9) an alkylsulfinyl group having 1 to 6 carbon atoms (e.g., methylsulfinyl); and
10) an alkylsulfonyl group having 1 to 6 carbon atoms (e.g., methylsulfonyl);

Wa is a divalent aliphatic hydrocarbon group having 1 to 4 carbon atoms (preferably —$CH_2$—, —$(CH_2)_2$—, —$(CH_2)_3$—, —$(CH_2)_4$—; more preferably —$(CH_2)_2$—, —$(CH_2)_3$—, —$(CH_2)_4$—; particularly preferably —$(CH_2)_2$—); and Y is a carboxyl group or alkoxycarbonyl group having 2 to 5 carbon atoms (e.g., methoxycarbonyl, ethoxycarbonyl and the like).

Compound (C)

A compound wherein $R^{1a}$ is a hydrogen atom;

$R^{2a}$ is an aromatic hydrocarbon group (preferably phenyl, naphthyl) or aromatic heterocyclic group (preferably furyl, thienyl, pyridyl, quinolyl, more preferably thienyl, pyridyl) optionally having 1 to 3 substituents selected from 1) a halogen atom (e.g., fluorine, chlorine, bromine, iodine);
2) an alkyl group having 1 to 6 carbon atoms (e.g., methyl, ethyl, trifluoromethyl) optionally substituted by 1 to 5 halogen atoms (e.g., fluorine, chlorine, bromine, iodine);
3) an alkoxy group having 1 to 6 carbon atoms (e.g., methoxy, ethoxy, trifluoromethoxy) optionally substituted by 1 to 3 halogen atoms (e.g., fluorine, chlorine, bromine, iodine);
4) an alkylthio group having 1 to 6 carbon atoms (e.g., methylthio) optionally substituted by 1 to 3 halogen atoms (e.g., fluorine, chlorine, bromine, iodine);
5) a nitro group;
6) a cyano group;
7) a $C_{1-3}$ alkylenedioxy group (e.g., methylenedioxy);
8) an aryl group having 6 to 14 carbon atoms (e.g., phenyl);
9) an alkylsulfinyl group having 1 to 6 carbon atoms (e.g., methylsulfinyl); and
10) an alkylsulfonyl group having 1 to 6 carbon atoms (e.g., methylsulfonyl);

Wa is a divalent aliphatic hydrocarbon group having 1 to 4 carbon atoms (preferably —$CH_2$—, —$(CH_2)_2$—, —$(CH_2)_3$—, —$(CH_2)_4$—; more preferably —$(CH_2)_2$—, —$(CH_2)_3$—, —$(CH_2)_4$—; particularly preferably —$(CH_2)_2$—);

Y is a) carbamoyl group optionally mono- or di-substituted by $C_{1-6}$ aliphatic hydrocarbon group [e.g., alkyl group (e.g., methyl, ethyl, propyl, butyl, tert-butyl, 1-ethylpropyl, 2,2-dimethylpropyl and the like), $C_{2-6}$ alkynyl group (e.g., propynyl and the like)] optionally having 1 or 2 substituents selected from $C_{1-6}$ alkoxy group (e.g., methoxy, isopropoxy and the like); heterocyclic group (e.g., indolyl, imidazolyl, pyridyl, morpholino, furyl, tetrahydrofuranyl, pyrrolidinyl, piperidinyl, piperazinyl and the like) optionally substituted by $C_{1-6}$ alkyl group (e.g., methyl and the like) or oxo group; $C_{1-6}$ alkylthio group (e.g., methylthio and the like); mono- or di-$C_{1-6}$ alkylamino group (e.g., dimethylamino, diethylamino, ethylmethylamino, diisopropylamino, N-methyl-N-phenylamino, di-hydroxyethyl-amino and the like) optionally substituted by hydroxy group, $C_{6-10}$ aryl group (e.g., phenyl and the like) or $C_{1-6}$ alkyl-$C_{6-10}$ aryl group (e.g., methylphenyl and the like); $C_{6-10}$ arylamino group (e.g., phenylamino and the like); aromatic heterocyclic amino group (e.g., pyridylamino and the like) optionally substituted by nitro group; mono- or di-$C_{1-6}$ alkyl-phosphono group (e.g., diethylphosphono and the like);

b) $C_{6-14}$ aryl-carbamoyl group (e.g., phenylcarbamoyl, naphthylcarbamoyl, dihydroindenylcarbamoyl, biphenylylcarbamoyl) optionally condensed with $C_{3-10}$ cycloalkane (e.g., cyclopentane) and optionally having 1 or 2 substituents selected from halogen atom (e.g., fluorine, chlorine, bromine, iodine and the like); $C_{1-6}$ alkyl group (e.g., methyl, trifluoromethyl) optionally substituted by 1 to 3 halogen atoms (e.g., fluorine, chlorine, bromine, iodine and the like); $C_{1-6}$ alkoxy group (e.g., methoxy, trifluoromethoxy) optionally substituted by 1 to 3 halogen atoms (e.g., fluorine, chlorine, bromine, iodine and the like); carbamoyl group; (mono- or di-$C_{1-6}$ alkyl-phosphono optionally forming a ring)-$C_{1-6}$ alkyl group [e.g., methylphosphonomethyl, ethylphosphonomethyl, dimethylphosphonomethyl, diethylphosphonomethyl, ethylmethylphosphonomethyl, diisopropylphosphonomethyl, dibutylphosphonomethyl, diethylphosphonoethyl, (2-oxide-1,3,2-dioxaphosphinanyl)methyl, (methyl-2-oxide-1,3,2-dioxaphosphinanyl)methyl, (dimethyl-2-oxide-1,3,2-dioxaphosphinanyl)methyl, (diethyl-2-oxide-1,3,2-dioxaphosphinanyl)methyl, (5-butyl-5-ethyl-2-oxide-1,3,2-dioxaphosphinanyl)methyl, (5-ethyl-5-methyl-2-oxide-1,3,2-dioxaphosphinanyl)methyl and the like]; $C_{2-5}$ alkoxycarbonyl group (e.g., methoxycarbonyl, ethoxycarbonyl and the like); $C_{2-5}$ alkoxycarbonyl-$C_{1-6}$ alkyl group (e.g., ethoxycarbonylmethyl and the like); phosphono-$C_{1-6}$ alkyl group (e.g., phosphonomethyl and the like); heterocyclic group (e.g., imidazolyl, morpholino); heterocyclic-$C_{1-6}$ alkoxy group (e.g., triazolylethoxy) optionally substituted by $C_{1-6}$ alkyl group (e.g., methyl, ethyl); $C_{1-3}$ alkylenedioxy group (e.g., methylenedioxy, ethylenedioxy and the like); $C_{7-14}$ aralkyl group (e.g., benzyl); $C_{6-10}$ aryloxy group (e.g., phenoxy and the like); mono- or di-$C_{1-6}$ alkyl-phosphono group (e.g., diethylphosphono and the like); and mono- or di-(mono- or di-$C_{1-6}$ alkyl-phosphono)-$C_{2-6}$ alkenyl group [e.g., bis(diethylphosphono)ethenyl, 2-diethylphosphono-2-ethoxycarbonylethenyl and the like] optionally substituted by $C_{2-5}$ alkoxycarbonyl group (e.g., methoxycarbonyl, ethoxycarbonyl and the like);

c) $C_{3-10}$ cycloalkyl-carbamoyl group (e.g., cyclopropylcarbamoyl, cyclohexylcarbamoyl, dihydroindenylcarbamoyl) optionally substituted by 1 or 2 $C_{1-6}$ alkyl groups (e.g., methyl) and optionally condensed with a benzene ring;

d) $C_{7-13}$ aralkyl-carbamoyl group (e.g., benzylcarbamoyl, phenethylcarbamoyl, phenylpropylcarbamoyl, benzhydrylcarbamoyl) optionally having 1 or 2 substituents selected from $C_{1-6}$ alkyl group (e.g., methyl, trifluoromethyl, dimethylaminoethyl, diethylaminoethyl) optionally substituted by 1 to 3 halogen atoms (e.g., fluorine, chlorine, bromine, iodine and the like) or mono- or di-$C_{1-6}$ alkylamino; $C_{1-6}$ alkoxy group (e.g., methoxy); $C_{1-3}$ alkylenedioxy group (e.g., methylenedioxy and the like); $C_{6-14}$ aryl group (e.g., phenyl); and $C_{2-5}$ alkoxycarbonyl-$C_{1-6}$ alkyl group (e.g., ethoxycarbonylethyl);

e) $C_{3-10}$ cycloalkyl-$C_{1-6}$ alkyl-carbamoyl group (e.g., cyclohexylmethylcarbamoyl);

f) heterocyclic carbamoyl group (e.g., piperidinylcarbamoyl, azepanylcarbamoyl, pyrrolidinylcarbamoyl, oxazolylcarbamoyl, thiazolylcarbamoyl, pyridylcarbamoyl, triazinylcarbamoyl, quinolylcarbamoyl, isoquinolylcarbamoyl, benzothiazolylcarbamoyl, pyrazolylcarbamoyl, piperazinylcarbamoyl, benzothiadiazolylcarbamoyl, pyrazinylcarbamoyl) optionally having 1 to 4 (preferably 1 or 2)

substituents selected from $C_{6-10}$ aryl group (e.g., phenyl and the like) optionally substituted by 1 to 3 halogen atoms (e.g., fluorine, chlorine, bromine, iodine and the like); $C_{1-6}$ alkyl (e.g., methyl) optionally substituted by 1 to 3 halogen atoms (e.g., fluorine, chlorine, bromine, iodine and the like); heterocyclic group (e.g., imidazolyl, morpholino) optionally substituted by $C_{1-6}$ alkyl group (e.g., methyl); $C_{7-14}$ aralkyl group (e.g., benzyl); and oxo group; or g) a nitrogen-containing heterocyclic carbonyl group (e.g., piperidinylcarbonyl, pyrrolidinylcarbonyl, morpholinocarbonyl, thiomorpholinocarbonyl, piperazinylcarbonyl, tetrahydroisoquinolinecarbonyl, decahydroisoquinolinecarbonyl, azepanecarbonyl, azocanecarbonyl, 1,2,3,6-tetrahydropyridinecarbonyl and the like) optionally condensed with benzene ring or $C_{3-10}$ cycloalkane (e.g., cyclohexane and the like), and optionally having 1 or 2 substituents selected from $C_{1-6}$ alkyl (e.g., methyl, ethyl and the like) optionally substituted by 1 to 3 halogen atoms (e.g., fluorine, chlorine, bromine, iodine and the like), hydroxy group, $C_{2-7}$ alkoxycarbonyl group (e.g., ethoxycarbonyl) or 5 or 6-membered nitrogen-containing heterocyclic group (e.g., pyrrolidinyl and the like); $C_{7-14}$ aralkyl group (e.g., benzyl, benzhydryl and the like) optionally substituted by $C_{1-3}$ alkylenedioxy group (e.g., methylenedioxy and the like); $C_{6-14}$ aryl group (e.g., phenyl and the like) optionally substituted by $C_{1-6}$ alkyl group (e.g., methyl, trifluoromethyl and the like) optionally substituted by 1 to 3 halogen atoms (e.g., fluorine, chlorine, bromine, iodine and the like), halogen atom (e.g., fluorine, chlorine, bromine, iodine and the like), $C_{1-6}$ alkoxy group (e.g., methoxy, ethoxy and the like) or $C_{2-10}$ alkanoyl group (e.g., acetyl and the like); $C_{6-14}$ aryl-$C_{2-6}$ alkenyl group (e.g., phenylpropenyl and the like); $C_{6-14}$ arylamino-$C_{1-6}$ alkyl group (e.g., phenylaminomethyl and the like) optionally substituted by $C_{1-6}$ alkyl group (e.g., methyl and the like); cyano group; oxo group; hydroxy group; mono- or di-$C_{2-10}$ alkanoylamino group (e.g., acetylamino, trifluoroacetylamino, propionylamino, N-acetyl-N-ethylamino and the like) optionally substituted by 1 to 3 halogen atoms (e.g., fluorine, chlorine, bromine, iodine and the like) or $C_{1-6}$ alkyl group (e.g., methyl, ethyl and the like); $C_{2-7}$ alkoxycarbonylamino group (e.g., tert-butoxycarbonylamino and the like); 5 or 6-membered nitrogen-containing heterocyclic group (e.g., pyridyl, piperidinyl, pyrimidinyl, pyrrolidinyl and the like); aromatic heterocyclic carbonyl group (e.g., furoyl and the like); carbamoyl group; $C_{2-10}$ alkanoyl group (e.g., acetyl and the like); $C_{2-7}$ alkoxycarbonyl group (e.g., methoxycarbonyl, ethoxycarbonyl and the like).

Of the aforementioned compounds (A), (B) and (C), the following compounds and the like are preferable:

3-[5-(3,4-dichlorophenyl)-4-isoxazolyl]propan-1-ol;
3-[5-(3,4-dichlorophenyl)-4-isoxazolyl]propionic acid;
3-[5-(4-chlorophenyl)-4-isoxazolyl]propan-1-ol;
3-[5-(4-chlorophenyl)-4-isoxazolyl]propionic acid;
3-[5-(3,4-difluorophenyl)-4-isoxazolyl]propan-1-ol;
3-[5-(3,4-difluorophenyl)-4-isoxazolyl]propionic acid;
N-[4-(diethylphosphonomethyl)phenyl]-3-(5-phenyl-4-isoxazolyl)propionamide;
N-[4-(diethylphosphonomethyl)phenyl]-3-[5-(4-fluorophenyl)-4-isoxazolyl]propionamide;
N-[4-(dimethylphosphonomethyl)phenyl]-3-(5-phenyl-4-isoxazolyl)propionamide;
N-{4-[(2-oxide-1,3,2-dioxaphosphinan-2-yl)methyl]phenyl}-3-(5-phenyl-4-isoxazolyl)propionamide;
N-benzyl-N-[2-(dimethylamino)ethyl]-3-[5-(4-fluorophenyl)-4-isoxazolyl]propionamide; and
N-benzyl-N-(1-benzyl-3-pyrrolidinyl)-3-[5-(4-fluorophenyl)-4-isoxazolyl]propionamide.

(6) Salt

The salt of compound represented by the formula (I), (Ia) or (II) (hereinafter sometimes to be abbreviated as compound (I), (Ia) or (II)) is preferably a pharmacologically acceptable one and may be, for example, a salt with an inorganic base, a salt with an organic base, a salt with an inorganic acid, a salt with an organic acid or a salt with a basic or acidic amino acid. Preferable examples of the salt with an inorganic base include alkali metal salts such as sodium salt and potassium salt; alkaline earth metal salts such as calcium salt and magnesium salt; and aluminum salt, ammonium salt and the like. Preferable examples of the salt with an organic base include salts with trimethylamine, triethylamine, pyridine, picoline, ethanolamine, diethanolamine, triethanolamine, dicyclohexylamine, N,N'-dibenzylethylenediamine, and the like. Preferable examples of the salt with an inorganic acid include salts with hydrochloric acid, hydrobromic acid, nitric acid, sulfuric acid, and phosphoric acid. Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like. Preferable examples of the salt with a basic amino acid include salts with arginine, lysine and ornithine. Preferable examples of the salt with an acidic amino acid include salts with aspartic acid, glutamic acid, and the like. Among these salts, a sodium salt and potassium salt are most preferred.

(7) Prodrug and the Like

The "prodrug of compound (I) means a compound that can be converted to compound (I) in vivo by the action of an enzyme or gastric juice under physiological conditions, namely a compound capable of being converted to compound (I) upon enzymatic oxidation, reduction or hydrolysis, among others, or a compound capable of being converted to compound (I) upon hydrolysis by gastric juice. The prodrug of compound (I) includes compounds derived by acylation, alkylation or phosphorylation of the amino group of compound (I) (e.g., compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of compound (I)), compounds derived by acylation, alkylation, phosphorylation or boration of the hydroxy group of compound (I) (e.g., compounds derived by acetylation, palmitoylation, propanoylation, pivaloylation, succinylation, fumarylation, alanylation or dimethylaminomethylcarbonylation of the hydroxy group of compound (I)), and compounds derived by esterification or amidation of the carboxyl group of compound (I) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of compound (I)), among others. These compounds can be produced from compound (I) by a method known per se.

The prodrug of compound (I) may be one that can be converted to compound (I) under physiological conditions, as described in "Iyakuhin no Kaihatsu (Development of Drugs)", vol 7, Molecular Designing, published by Hirokawa Shoten, 1990, pages 163–198.

As the prodrug of compound (Ia) or (II), those similar to the prodrug of the aforementioned compound (I) are exemplified.

The compounds (I), (Ia) and compound (II) may be labeled with isotope (e.g., $^3H$, $^{14}C$, $^{35}S$, $^{125}I$ and the like) and the like.

The compounds (I), (Ia) and compound (II) may be an anhydride or a hydrate.

(8) Formulation

The compounds (I), (Ia), (II) and a salt thereof (hereinafter sometimes to be simply referred to as the compound of the present invention) show low toxicity and can be used, as they are or by admixing with a pharmacologically acceptable carrier and the like to give a pharmaceutical composition, as agents for the prophylaxis or treatment of various diseases to be mentioned later for mammals (e.g., human, mouse, rat, rabbit, dog, cat, cattle, horse, swine, simian and the like).

The above-mentioned pharmacologically acceptable carrier includes various organic or inorganic carrier substances which are conventionally used as pharmaceutical preparation materials. They are incorporated as excipients, lubricants, binders, disintegrants or the like in solid preparations; as solvents, solubilizers, suspending agents, isotonizing agents, buffers, analgesics or the like in liquid preparations. Where necessary, additives such as preservatives, antioxidants, coloring agents and sweeteners may be used.

Preferable examples of the excipient include lactose, sucrose, D-mannitol, D-sorbitol, starch, gelatinized starch, dextrin, crystalline cellulose, low-substituted hydroxypropylcellulose, carboxymethylcellulose sodium, gum arabic, dextrin, pullulan, light silicic anhydride, synthetic aluminum silicate, magnesium aluminometasilicate and the like.

Preferable examples of the lubricant include magnesium stearate, calcium stearate, talc and colloidal silica.

Preferable examples of the binder include gelatinized starch, sucrose, gelatin, gum arabic, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like.

Preferable examples of the disintegrant include lactose, sucrose, starch, carboxymethylcellulose, carboxymethylcellulose calcium, croscarmellose sodium, carboxymethylstarch sodium, light silicic anhydride and low-substituted hydroxypropylcellulose.

Preferable examples of the solvent include water for injection, physiological saline, Ringer's solution, alcohol, propylene glycol, polyethylene glycol, sesame oil, corn oil, olive oil and cottonseed oil.

Preferable examples of the solubilizer include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, laurylaminopropionic acid, lecithin, benzalkonium chloride, benzethonium chloride and glycerol monostearate; hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose; polysorbates, polyoxyethylene-hardened castor oil, and so forth.

Preferable examples of the isotonizing agent include sodium chloride, glycerol, D-mannitol, D-sorbitol and glucose.

Preferable examples of the buffer include buffer solutions of phosphate, acetate, carbonate and citrate.

Preferable examples of the local analgesic include benzyl alcohol and the like.

Preferable examples of the preservative include para-oxybenzoate esters, chlorobutanol, benzyl alcohol, phenethyl alcohol, dehydroacetic acid and sorbic acid.

Preferable examples of the anti-oxidant include sulfite salts and ascorbate salts.

Preferable examples of the coloring agent include water-soluble edible tar colors (e.g., food colors such as Food Color Red No. 2 and No. 3, Food Color Yellow No. 4 and No. 5, Food Color Blue No. 1 and No. 2), water-insoluble lake colors (e.g., the aluminum salt form of the above water-soluble edible tar colors), and natural colors (e.g., β-carotene, chlorophyll, iron oxide red).

Preferred examples of the sweeteners include saccharin sodium, dipotassium glycyrrhizinate, aspartame and stevia.

(9) Mode of Administration

The dosage form of the above-mentioned pharmaceutical composition includes, for example, oral preparations such as tablets, capsules (including soft capsules and microcapsules), granules, powders, syrups, emulsions and suspensions; non-oral preparations such as injections (e.g., subcutaneous injection, intravenous injection, intramuscular injection, intraperitoneal injection), external application forms (e.g., nasal preparations, transdermal preparations, ointments), suppositories (e.g., rectal suppositories, vaginal suppositories), pellets, solutions for instillation, sustained-release preparations (e.g., sustained-release microcapsule) and the like. These can be each safely administered orally or non-orally.

The pharmaceutical composition can be produced according to a method conventionally used in the field of pharmaceutical reparations, such as the method described in Japan Pharmacopoeia and the like. The specific production methods of the pharmaceutical preparation are described in detail in the following. While the content of the compound of the present invention in the pharmaceutical composition varies depending on the dosage form, dose of the compound of the present invention and the like, it is, for example, about 0.1–100 wt %.

For example, an oral agent is produced by adding, to the active ingredient, an excipient (e.g., lactose, sucrose, starch, D-mannitol and the like), a disintegrant (e.g., carboxymethylcellulose calcium and the like), a binder (e.g., gelatinized starch, gum arabic, carboxymethylcellulose, hydroxypropylcellulose, polyvinylpyrrolidone and the like), a lubricant (e.g., talc, magnesium stearate, polyethylene glycol 6000 and the like) and the like, compression-molding the mixture, and where necessary, coating the same using a coating base for masking of taste, enteric property or sustained release according to a method known per se.

Examples of the coating base include a sugar coating base, a water-soluble film coating base, an enteric film coating base, or a sustained-release film coating base and the like.

Useful as the sugar coating base is sucrose and, further, one or more ingredients selected from talc, precipitated calcium carbonate, gelatin, gum arabic, pullulan, carnauba wax and the like may be used in combination.

Examples of the water-soluble film coating base include cellulose polymers such as hydroxypropylcellulose, hydroxypropylmethylcellulose, hydroxyethylcellulose and methylhydroxyethylcellulose; synthetic polymers such as polyvinylacetal diethylaminoacetate, aminoalkyl methacrylate copolymer E [Eudragit E (trademark), Rohm Pharma] and polyvinylpyrrolidone; and polysaccharides such as pullulan and the like; and the like.

Examples of the enteric film coating base include cellulose polymers such as hydroxypropylmethylcellulose phthalate, hydroxypropylmethylcellulose acetate succinate, carboxymethylethylcellulose, and cellulose acetate phthalate; acrylic acid polymers such as methacrylic acid copolymer L [Eudragit L (trademark), Rohm Pharma], methacrylic acid copolymer LD [Eudragit L-30D55 (trademark), Rohm Pharma] and methacrylic acid copolymer S [Eudragit S (trademark), Rohm Pharma]; and natural products such as shellac and the like.

Examples of the sustained-release film coating base include cellulose polymers such as ethylcellulose; acrylic acid polymers such as aminoalkyl methacrylate copolymer RS [Eudragit RS (trademark), Rohm Pharma] and an ethyl acrylate-methyl methacrylate copolymer suspension [Eudragit NE (trademark), Rohm Pharma]; and so forth.

Two or more of the above coating bases may be used in admixture in appropriate proportions. On the occasion of coating, a shading agent such as titanium oxide, red ferric oxide may be used.

Injections are produced by dissolving, suspending or emulsifying the active ingredient in an aqueous solvent (e.g., distilled water, physiological saline, Ringer's solution) or an oleaginous solvent (e.g., vegetable oils such as olive oil, sesame oil, cotton seed oil, corn oil; propylene glycol), together with a dispersant (e.g., polysorbate 80, polyoxyethylene-hardened castor oil 60, polyethylene glycol, carboxymethylcellulose, sodium alginate), a preservative (e.g., methylparaben, propylparaben, benzyl alcohol, chlorobutanol, phenol), an isotonizing agent (e.g., sodium chloride, glycerol, D-mannitol, D-sorbitol, glucose) and the like. If desirable, additives such as a solubilizer (e.g., sodium salicylate, sodium acetate), a stabilizer (e.g., human serum albumin), an analgesic (e.g., benzyl alcohol), may be used.

(10) Target Disease

The compound of the present invention and the pharmaceutical agent of the present invention are useful as agents for prophylaxis or treatment of diabetes (e.g., type 1 diabetes, type 2 diabetes, gestational diabetes and the like); agents for prophylaxis or treatment of hyperlipidemia (e.g., hypertriglyceridemia, hypercholesterolemia, low HDL lipemia, postprandial hyperlipemia and the like); agents for prophylaxis or treatment of arteriosclerosis; agents for prophylaxis or treatment of impaired glucose tolerance [IGT (Impaired Glucose Tolerance)]; an insulin secretagogue; and an agent for suppressing progress of impaired glucose tolerance into diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, a non-fasting blood glucose level (glucose concentration of intravenous plasma) of not less than 200 mg/dl. A condition not falling under the above-mentioned diabetes, and not being "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention and the pharmaceutical agent of the present invention can be also used as agents for prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention and the pharmaceutical agent of the present invention can prevent progress of borderline type, impaired glucose tolerance, IFG (Impaired Fasting Glucose) or IFG (Impaired Fasting Glycemia) into diabetes.

The compound of the present invention and the pharmaceutical agent of the present invention can be also used as agents for prophylaxis or treatment of, for example, diabetic complications [e.g., neuropathy, nephropathy, retinopathy, cataract, macroangiopathy, osteopenia, hyperosmolar diabetic coma, infectious disease (respiratory infection, urinary tract infection, gastrointestinal infection, dermal soft tissue infections, inferior limb infection and the like), diabetic gangrene, xerostomia, hypacusis, cerebrovascular disorder, peripheral blood circulation disorder and the like], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease and the like), muscular dystrophy, myocardial infarction, angina pectoris, cerebrovascular accident (e.g., cerebral infarction, cerebral apoplexy), insulin resistance syndrome, Syndrome X, hyperinsulinemia, hyperinsulinemia-induced sensory disorder, tumor (e.g., leukemia, breast cancer, prostatic cancer, skin cancer and the like), irritable bowel syndrome, acute or chronic diarrhea, inflammatory diseases (e.g., chronic rheumatoid arthritis, spondylitis deformans, arthritis cleformans, lumbar pain, gout, postoperative or traumatic inflammation, remission of tumentia, neuralgia, pharyngolaryngitis, cystitis, hepatitis (inclusive of nonalcoholic steatohepatitis), pneumonia, pancreatitis, inflammatory bowel disease, ulcerative colitis, gastric mucosal injury (inclusive of gastric mucosal injury caused by aspirin) and the like), visceral obesity syndrome and the like.

The compound of the present invention and the pharmaceutical agent of the present invention can be also used for decreasing visceral fat, suppressing visceral fat accumulation, improving glycometabolism, improving lipid metabolism, suppressing production of oxidized LDL, improving lipoprotein metabolism, improving coronary artery metabolism, prophylaxis or treatment of cardiovascular complications, prophylaxis or treatment of heart failure complications, lowering blood remnant, prophylaxis or treatment of anovulation, prophylaxis or treatment of hypertrichosis, prophylaxis or treatment of hyperandrogenemia and the like.

The compound of the present invention and the pharmaceutical agent of the present invention can be also used for secondary prophylaxis or suppression of progression of the above-mentioned various diseases (e.g., cardiovascular event such as myocardial infarction and the like).

Particularly, the compound of the present invention and the pharmaceutical agent of the present invention are useful glucose dependent insulin secretagogues that exhibit a selective insulin secretion promoting action only in the presence of high concentration glucose (e.g., in patients showing fasting blood glucose level of not less than 126 mg/dl or 75 g oral glucose tolerance test (75 g OGTT) 2 h level of not less than 140 mg/dl and the like). Therefore, the compound of the present invention and the pharmaceutical agent of the present invention are particularly useful as safe agents for prophylaxis or treatment of diabetes, which are associated with a low risk of vascular complications, induction of hypoglycemia and the like, which are the negative effects caused by insulin.

While the dose of the compound of the present invention and the pharmaceutical agent of the present invention varies depending on the administration subject, administration route, target disease, condition and the like, the compound of the present invention as an active ingredient is generally given in a single dose of about 0.01–100 mg/kg body weight, preferably 0.05–30 mg/kg body weight, more preferably 0.1–2 mg/kg body weight, in the case of, for example, oral administration to adult diabetic patients. This dose is desirably given 1 to 3 times a day.

(11) Combined Use with Pharmaceutical Agent

The compound of the present invention can be used in combination with therapeutic agents such as a therapeutic agent of diabetes, a therapeutic agent of diabetic complications, an antihyperlipemic agent, a hypotensive agent, an antiobesity agent, a diuretic agent, a chemotherapeutic agent, an immunotherapeutic agent, an antithrombotic agent, a therapeutic agent of osteoporosis, an antidementia agent, an agent for ameliorating erectile dysfunction, a therapeutic agent of incontinentia or pollakiuria and the like (hereinafter to be briefly referred to as a combination drug). In this case, the timing of administration of the compound of the present invention and a combination drug is not limited. These may be simultaneously administered to an administration subject or, administered in a staggered manner. The dose of the combination drug can be determined as appropriate based on the dose clinically employed. The proportion of the compound of the present invention and combination drug can be appropriately determined depending on the administration subject, administration route, target disease, condition, combination and the like. When, for example, the administration subject is human, a combination drug is used in an amount of 0.01–100 parts by weight per 1 part by weight of the compound of the present invention.

Examples of the therapeutic agent of diabetes include insulin preparations (e.g., animal insulin preparations obtained by extraction from the bovine or swine pancreas; human insulin preparations synthesized by a genetic engineering technique using *Escherichia coli* or a yeast; insulin-zinc; protamine-insulin-zinc; fragment or derivative of insulin (e.g., INS-1 and the like)), insulin sensitizers (e.g., pioglitazone hydrochloride, rosiglitazone or its maleate, GI-262570, JTT-501, MCC-555, YM-440, KRP-297, CS-011, FK-614, the compounds described in WO99/58510 such as (E)-4-[4-(5-methyl-2-phenyl-4-oxazolylmethoxy)benzyloxyimino]-4-phenylbutyric acid), NN-622, AR-H-039242, BMS-298585, EML-16336 and the like), α-glucosidase inhibitors (e.g., voglibose, acarbose, miglitol, emiglitate), biguanides (e.g., phenformin, metformin, buformin), insulin secretagogue [sulfonylureas (e.g., tolbutamide, glibenclamide, gliclazide, chlorpropamide, tolazamide, acetohexamide, glyclopyramide, glimepiride, glipizide, glybuzole etc.), repaglinide, senaglinide, nateglinide, mitiglinide or its calcium salt hydrate], GLP-1 receptor agonist [e.g., GLP-1, NN-2211, AC-2993 (exendin-4), BIM-51077, Aib(8,35)hGLP-1(7,37)NH$_2$ etc.], amyrin agonist (e.g., pramlintide), phosphotyrosine phosphatase inhibitors (e.g., vanadic acid), dipeptidylpeptidase IV inhibitors (e.g., NVP-DPP-278, PT-100, P32/98), β3 agonists (e.g., CL-316243, SR-58611-A, UL-TG-307, SB-226552, AJ-9677, BMS-196085, AZ40140), gluconeogenesis inhibitors (e.g., glycogen phosphorylase inhibitors, glucose-6-phosphatse inhibitors, glucagon antagonists), SGLT (sodium-glucose cotransporter) inhibitors (e.g., T-1095), etc.

Examples of the therapeutic agent of diabetic complications include aldose reductase inhibitors (e.g., tolrestat, epalrestat, zenarestat, zopolrestat, minalrestat, fidarestat, SNK-860, CT-112), neurotrophic factors and increasing agents thereof (e.g., NGF, NT-3, BDNF, neurotrophin production secretion promoter such as 4-(4-chlorophenyl)-2-(2-methyl-1-imidazolyl)-5-[3-(2-methylphenoxy)propyl]oxazole etc.,) and the like, neuranagenesis promoters (e.g., Y-128 etc.), PKC inhibitors (e.g., LY-333531 etc.), AGE inhibitors (e.g., ALT-946, pimagedine, pyradoxamine, N-phenacylthiazolium bromide (ALT-766), EXO-226), active oxygen scavengers (e.g., thioctic acid), cerebral vasodilators (e.g., tiapoburide, mexiletine), and the like.

Examples of the antihyperlipemic agent include statin compounds which are cholesterol synthesis inhibitors (e.g., pravastatin, simvastatin, lovastatin, atorvastatin, fluvastatin, cerivastatin, itavastatin or their salts (e.g., sodium salt)), squalene synthase inhibitors (e.g., the compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid etc.) or fibrate compounds (e.g., bezafibrate, clofibrate, simfibrate, clinofibrate) having a triglyceride lowering action, and the like.

Examples of the hypotensive agent include angiotensin converting enzyme inhibitors (e.g., captopril, enalapril, delapril), angiotensin II antagonists (e.g., candesartan cilexetil, losartan, eprosartan, balsartan, telmisartan, irbesartan, tasosartan), calcium antagonist (e.g., manidipine, nifedipine, amlodipine, efonidipine, nicardipine), clonidine, and the like.

Examples of the antiobesity agent include antiobesity drugs acting on the central nervous system (e.g., dexfenfluramine, fenfluramine, phentermine, sibutramine, anfepramon, dexamphetamine, mazindol, phenylpropanolamine, clobenzorex), pancreatic lipase inhibitors (e.g., orlistat), β3 agonists (e.g., CL-316243, SR-58611-A, UL-TG-307, SB-226552, AJ-9677, BMS-196085, AZ40140), anorectic peptides (e.g., leptin, CNTF (Ciliary Neurotrophic Factor)), cholecystokinin agonists (e.g., lintitript, FPL-15849), and the like.

Examples of the diuretic agent include xanthine derivatives (e.g., theobromine and sodium salicylate, theobromine and calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide, and the like.

Examples of the chemotherapeutic agent include alkylating agents (e.g., cyclophosphamide, ifosamide), metabolic antagonists (e.g., methotrexate, 5-fluorouracil), antitumor antibiotics (e.g., mitomycin, adriamycin), plant-derived antitumor agents (e.g., vincristine, vindesine, Taxol), cisplatin, carboplatin, etoposide, and the like. Among these, 5-fluorouracil derivatives such as Furtulon and Neo-Furtulon are preferable.

Examples of the immunotherapeutic agent include microorganism- or bacterium-derived components (e.g., muramyl dipeptide derivatives, Picibanil), immunopotentiator polysaccharides (e.g., lentinan, schizophyllan, krestin), genetically engineered cytokines (e.g., interferons, interleukins (IL)), colony stimulating agents (e.g., granulocyte colony stimulating factor, erythropoietin), and the like. Among these, IL-1, IL-2, IL-12 and the like are preferable.

Examples of the antithrombotic agent include heparin (e.g., heparin sodium, heparin calcium, dalteparin sodium and the like), warfarin (e.g., warfarin potassium and the like), anti-thrombin drugs (e.g., aragatroban and the like), thrombolytic agents (e.g., urokinase, tisokinase, alteplase, nateplase, monteplase, pamiteplase and the like), platelet aggregation inhibitors (e.g., ticlopidine hydrochloride, cilostazol, ethyl icosapentate, beraprost sodium, sarpogrelate hydrochloride and the like) and the like.

Examples of the therapeutic agent of osteoporosis include alfacalcidol, calcitriol, elcatonin, calcitonin salmon, estriol, ipriflavone, pamidronate disodium, alendronate sodium hydrate, incadronate disodium and the like.

Examples of the antidementia agent include tacrine, donepezil, rivastigmine, galantamine and the like.

Examples of the agent for ameliorating erectile dysfunction include apomorphine, sildenafil citrate and the like.

Examples of the therapeutic agent of incontinentia or pollakiuria include flavoxate hydrochloride, oxybutynin hydrochloride, propiverine hydrochloride and the like.

Further, agents whose effects of ameliorating cachexia have been confirmed in animal models or clinically, namely cyclooxygenase inhibitors (e.g., indomethacin) (Cancer Research, vol. 49, pp. 5935–5939, 1989), progesterone derivatives (e.g., megestrol acetate) (Journal of Clinical Oncology, vol. 12, pp. 213–225, 1994), glucocorticoids (e.g., dexamethasone), metoclopramide pharmaceuticals, tetrahydrocannabinol pharmaceuticals (the above references are applied to both), fat metabolism ameliorating agents (e.g., eicosapentanoic acid) (British Journal of Cancer, vol. 68, pp. 314–318, 1993), growth hormones, IGF-1, and antibodies to the cachexia-inducing factor TNF-α, LIF, IL-6 or oncostatin M, can also be used in combination with the preparation of the invention.

The combination drug is preferably an insulin preparation, an insulin sensitizer, an α-glucosidase inhibitor, a biguanide, an insulin secretagogue (preferably a sulfonylurea) or the like.

Two or more of the above-mentioned combination drugs can be used in combination in an appropriate ratio. Preferable combinations in the case of using two or more combination drugs are, for example, as shown in the following.
1) an insulin secretagogue (preferably a sulfonylurea) and an α-glucosidase inhibitor;
2) an insulin secretagogue (preferably a sulfonylurea) and a biguanide;
3) an insulin secretagogue (preferably a sulfonylurea), a biguanide and an α-glucosidase inhibitor;
4) an insulin sensitizer and an α-glucosidase inhibitor;
5) an insulin sensitizer and a biguanide;
6) an insulin sensitizer, a biguanide and an α-glucosidase inhibitor.

When the compound of the present invention or the pharmaceutical agent of the present invention is used in combination with a combination drug, the amount thereof can be reduced within a safe range in consideration of counteraction of these agents. Particularly, the dose of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent of diabetic complications, antihyperlipemic agent and hypotensive agent can be reduced whereby an adverse effect which may be caused by these agents can be prevented effectively.

(12) Production Method

Hereinafter the production methods of the compound of the present invention are explained. Since the compounds (Ia) and (II) are encompassed in compound (I), the production method of compound (I) is explained.

The compound (I) can be produced according to a method known per se, such as Method A to Method I shown in the following, or an analogous method thereto.

The compound (I-2) wherein, in the formula (I), Y is a carboxyl group can be produced by the following Method A.

[Method A]

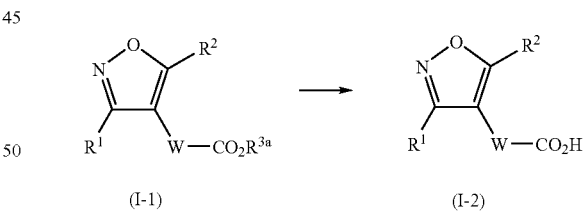

wherein $R^{3a}$ is an optionally substituted hydrocarbon group, an optionally substituted heterocyclic group or an optionally substituted acyl group, and other symbols are as defined above.

As the "optionally substituted hydrocarbon group", "optionally substituted heterocyclic group" and "optionally substituted acyl group" represented by $R^{3a}$, those exemplified for $R^3$ can be used.

According to this method, compound (I-1) is subjected to hydrolysis reaction to give compound (I-2).

The hydrolysis reaction is carried out according to a conventional method in the presence of an acid or a base in a water-containing solvent.

As the acid, for example, hydrochloric acid, sulfuric acid, acetic acid, hydrobromic acid and the like can be used.

As the base, for example, alkaline metal carbonates such as potassium carbonate, sodium carbonate, cesium carbonate and the like; alkaline earth metal carbonates such as barium carbonate, calcium carbonate and the like; alkali metal alkoxides such as sodium methoxide and the like; alkaline metal hydroxides such as potassium hydroxide, sodium hydroxide, lithium hydroxide and the like; alkaline earth metal hydroxides such as barium hydroxide, calcium hydroxide and the like; and the like can be used.

The amount of the acid or base to be used is generally an excess amount relative to compound (I-1). Preferably, the amount of the acid to be used is about 2—about 50 equivalents relative to compound (I-1) and the amount of the base to be used is about 1.2—about 5 equivalents relative to compound (I-1).

Examples of the water-containing solvent include a mixed solvent of one kind of solvent selected from alcohols such as methanol, ethanol and the like; ethers such as tetrahydrofuran, dioxane, diethyl ether and the like; dimethyl sulfoxide and acetone and the like, with water, and the like. When the reaction is carried out under acidic conditions, an excess acid may be used as a solvent.

The reaction temperature is generally from about −20° C. to about 150° C., preferably from about −10° C. to about 100° C.

The reaction time is generally from about 0.1 to about 20 hours.

The compound (I-2) thus obtained can be isolated and purified by a known separation and purification means, such as concentration, concentration under reduced pressure, solvent extraction, crystallization, recrystallization, solvent substitution, chromatography and the like.

The compound (I-1) used as a starting material compound in the above-mentioned Method A can be produced according to the method described in, for example, *Journal of Heterocyclic Chemistry*, vol. 28, p. 453 (1991); *Journal of Organic Chemistry*, vol. 49, p. 4419 (1984); *Tetrahedron Letters*, vol. 34, p. 485 (1993) and the like, or a method analogous thereto.

The compound (I-3) having amidated carboxyl group for Y in the formula (I) is produced by, for example, the following Method B.

[Method B]

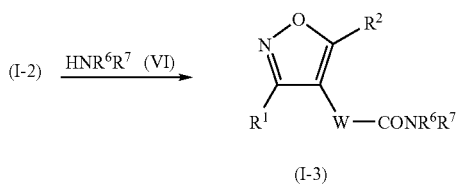

wherein the symbols in the formula are as defined above.

In this method, compound (I-2) is subjected to amidation reaction to give compound (I-3). This reaction is carried out by a method known per se, such as a method comprising direct condensation of compound (I-2) and compound (VI) using a condensing agent, a method comprising appropriate reaction of a reactive derivative of compound (I-2) with compound (VI) and the like. Examples of the condensing agent include condensing agents generally known, such as carbodiimide condensing agents (e.g., dicyclohexylcarbodiimide, diisopropylcarbodiimide, 1-ethyl-3-dimethylaminopropylcarbodiimide, a hydrochloride thereof and the like); phosphoric acid condensing agents (e.g., diethyl cyanophosphate, diphenylphosphoryl azide and the like); carbonyldiimidazole, 2-chloro-1,3-dimethylimidazolium tetrafluoroborate and the like.

The solvent to be used for the reaction using a condensing agent includes amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water and the like. These solvents may be used after mixing at a suitable ratio.

The amount of Compound (VI) to be used is 0.1–10 mol equivalents, preferably 0.3–3 mol equivalents, relative to compound (I-2).

The amount of the condensing agent to be used is 0.1–10 molar equivalents, preferably 0.3–3 molar equivalents, relative to compound (I-2).

When a carbodiimide condensing agent such as dicyclohexylcarbodiimide, diisopropylcarbodiimide, 1-ethyl-3-dimethylaminopropylcarbodiimide and hydrochloride thereof and the like is used as a condensing agent, the reaction efficiency can be increased by using a suitable condensation promoter (e.g., 1-hydroxy-7-azabenzotriazole, 1-hydroxybenzotriazole, N-hydroxysuccinimide, N-hydroxyphthalimide and the like) as necessary. When a phosphoric acid condensing agent such as diethyl cyanophosphate, diphenylphosphoryl azide and the like is used as a condensing agent, the reaction efficiency can be generally increased by adding an organic amine base such as triethylamine and the like.

The amount of the above-mentioned condensation promoter and organic amine base to be used is 0.1–10 molar equivalents, preferably 0.3–3 molar equivalents, relative to compound (I-2).

The reaction temperature is generally from about −30° C. to about 100° C.

The reaction time is generally from 0.5 to 60 hours.

In the method using a reactive derivative of compound (I-2), the reactive derivative of compound (I-2) is exemplified by acid anhydride, acid halide (acid chloride, acid bromide), imidazolide, or a mixed acid anhydride (e.g., anhydride with methyl carbonate, ethyl carbonate, isobutyl carbonate and the like) and the like.

When an acid anhydride or acid halide is used, for example, the reaction is generally carried out in the presence of a base in a solvent inert to the reaction.

As the base, for example, triethylamine, pyridine, N-ethylmorpholine, N,N-dimethylaniline, 4-dimethylaminopyridine, lithium hydroxide, sodium hydroxide, potassium hydroxide, sodium hydrogencarbonate, sodium carbonate, potassium carbonate, cesium carbonate and the like can be used.

The solvent inert to the reaction is exemplified by amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water and the like. These solvents may be used after mixing at a suitable ratio. When the above-mentioned amides are used as a solvent inert to the reaction, the reaction may be carried out in the absence of a base.

The amount of Compound (VI) to be used is 0.1–10 molar equivalents, preferably 0.3–3 molar equivalents, relative to compound (I-2). The amount of the base to be used is 0.1–10 molar equivalents, preferably 0.3–3 molar equivalents, relative to compound (I-2).

The reaction temperature is generally from about −30° C. to about 100° C.

The reaction time is generally from 0.5 to 20 hours.

When a mixed acid anhydride is used, compound (I-2) and chlorocarbonate ester (e.g., methyl chlorocarbonate, ethyl chlorocarbonate, isobutyl chlorocarbonate and the like) are reacted in the presence of a base (e.g., triethylamine, aniline, N-methylmorpholine, N,N-dimethylaniline, 4-dimethylaminopyridine, sodium hydroxide, potassium hydroxide, lithium hydroxide, sodium hydrogencarbonate, sodium carbonate, potassium carbonate, cesium carbonate etc.) and then reacted with compound (VI).

The amount of Compound (VI) to be used is 0.1–10 molar equivalents, preferably 0.3–3 molar equivalents, relative to compound (I-2).

The reaction temperature is generally from −30° C. to 100° C.

The reaction time is generally from 0.5 to 20 hours.

The compound (I-3) thus obtained can be isolated and purified by a known separation and purification means, such as concentration, concentration under reduced pressure, solvent extraction, crystallization, recrystallization, solvent substitution, chromatography and the like.

The compound (I-2) used as a starting material compound in the above-mentioned Method B can be produced by, for example, the above-mentioned Method A.

The compound (VI) used as a starting material compound in the above-mentioned Method B can be produced by a method known per se.

The compound (I-4) having a hydroxy group for Y in the formula (I) can be produced by, for example, the following Method C.

[Method C]

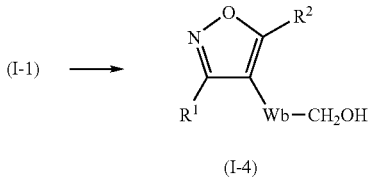

(I-4)

wherein Wb is a bond or a divalent aliphatic hydrocarbon group, and other symbols are as defined above.

The "divalent aliphatic hydrocarbon group" represented by Wb is exemplified by those recited as the aforementioned W.

In this method, compound (I-1) is subjected to a reduction reaction to give compound (I-4).

This reaction is carried out according to a method known per se in the presence of a reducing agent in a solvent inert to the reaction.

Examples of the reducing agent include sodium borohydride, lithium borohydride, lithium aluminum hydride, diisobutylaluminum hydride, sodium dihydrobis(2-methoxyethoxy)aluminate, borane and a complex thereof (e.g., borane-tetrahydrofuran, pyridineborane, borane-dimethylsulfide and the like) and the like.

The amount of the reducing agent to be used is preferably about 0.5—about 10 molar equivalents relative to compound (I-1).

The solvent that does not adversely influence the reaction is exemplified by aromatic hydrocarbons such as benzene, toluene, xylene and the like; halogenated hydrocarbons such as chloroform, dichloromethane and the like; ethers such as tetrahydrofuran, dioxane, diethyl ether and the like; water, alcohols such as methanol, ethanol, isopropanol and the like; and the like. These solvents may be used after mixing at a suitable ratio.

The reaction temperature is generally from about −50° C. to about 150° C., preferably from about −10° C. to about 100° C.

The reaction time is generally from about 0.5 to about 20 hours.

The thus-obtained compound (I-4) can be isolated and purified by a known separation and purification means, such as concentration, concentration under reduced pressure, solvent extraction, crystallization, recrystallization, solvent substitution, chromatography and the like.

The compound (I-5) having a group represented by the formula: —OCOR$^4$ (R$^4$ is as defined above) for Y in the formula (I) is produced by, for example, the following Method D.

[Method D]

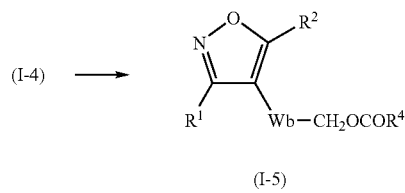

(I-5)

wherein the symbols in the formula are as defined above.

In this method, compound (I-4) is subjected to acylation reaction to give compound (I-5). This reaction can be carried out by a method known per se. Such method is exemplified by a method comprising direct condensation of compound (I-4) with carboxylic acid derivative (R$^4$CO$_2$H) using a condensing agent, a method comprising appropriate reaction of a reactive derivative of carboxylic acid derivative (R$^4$CO$_2$H) with compound (I-4) and the like. Here, the method comprising direct condensation of compound (I-4) with carboxylic acid derivative (R$^4$CO$_2$H) using a condensing agent is performed in the same manner as in the aforementioned "direct condensation of compound (I-2) with compound (VI) using a condensing agent".

In the method using a reactive derivative of the carboxylic acid derivative, the reactive derivative of the carboxylic acid derivative is, for example, acid anhydride, acid halide (acid chloride, acid bromide), imidazolide, a mixed acid anhydride (e.g., anhydride with methyl carbonate, ethyl carbonate, isobutyl carbonate and the like), and the like.

For example, when an acid anhydride or an acid halide is used, the reaction is generally carried out in a solvent inert to the reaction in the presence of a base.

The base is, for example, triethylamine, pyridine, N-methylmorpholine, N,N-dimethylaniline, 4-dimethylaminopyridine, lithium hydroxide, sodium hydroxide, potassium hydroxide, sodium hydrogencarbonate, sodium carbonate, potassium carbonate, cesium carbonate and the like.

The solvent inert to the reaction is exemplified by amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water and the like. These solvents may be used after mixing at a suitable ratio. When the above-mentioned amides are used as the solvent inert to the reaction, the reaction may be carried out in the absence of a base.

The amount of the reactive derivative of carboxylic acid to be used is 0.1–10 molar equivalents, preferably 0.3–3 molar equivalents, relative to compound (I-4). The amount of the base to be used is 0.1–10 molar equivalents, preferably 0.3–3 molar equivalents, relative to compound (I-4).

The reaction temperature is generally from −30° C. to 100° C.

The reaction time is generally from 0.5 to 20 hours.

When a mixed acid anhydride is used, a carboxylic acid derivative ($R^4CO_2H$) and a chlorocarbonate ester (e.g., methyl chlorocarbonate, ethyl chlorocarbonate, isobutyl chlorocarbonate and the like) are reacted in the presence of a base (e.g., triethylamine, aniline, N-methylmorpholine, N,N-dimethylaniline, 4-dimethylaminopyridine, lithium hydroxide, sodium hydroxide, potassium hydroxide, sodium hydrogencarbonate, sodium carbonate, potassium carbonate, cesium carbonate and the like), and then reacted with compound (I-4).

The amount of the carboxylic acid derivative to be used is 0.1–10 molar equivalents, preferably 0.3–3 molar equivalents, relative to compound (I-4).

The reaction temperature is generally from −30° C. to 100° C.

The reaction time is generally from 0.5 to 20 hours.

The thus-obtained compound (I-5) can be isolated and purified by a known separation and purification means, such as concentration, concentration under reduced pressure, solvent extraction, crystallization, recrystallization, solvent substitution, chromatography and the like.

The compound (I-4) used as a starting material compound in the above-mentioned Method D is produced by, for example, the above-mentioned Method C.

The compound (I-6) having a group represented by the formula: —$OR^{3a}$ ($R^{3a}$ is as defined above) for Y in the formula (I) can be produced by, for example, the following Method E and Method F.

[Method E]

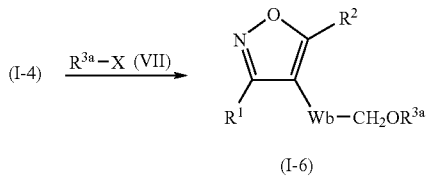

wherein X is a hydroxy group, a halogen atom or a group represented by the formula: —$OSO_2R^8$ ($R^8$ is alkyl having 1 to 4 carbon atoms or aryl group having 6 to 10 carbon atoms optionally substituted by alkyl having 1 to 4 carbon atoms), and other symbols are as defined above.

As used herein, the alkyl having 1 to 4 carbon atoms of the "alkyl having 1 to 4 carbon atoms" and the "aryl group having 6 to 10 carbon atoms optionally substituted by alkyl having 1 to 4 carbon atoms" represented by $R^8$ is exemplified by methyl, ethyl, propyl, isopropyl, butyl, isobutyl, sec-butyl, t-butyl and the like, with preference given to methyl.

The aryl group having 6 to 10 carbon atoms of the "aryl group having 6 to 10 carbon atoms optionally substituted alkyl having 1 to 4 carbon atoms" represented by $R^8$ is exemplified by phenyl, naphthyl and the like, with preference given to phenyl.

In this method, compound (I-6) is produced by the reaction of compound (I-4) with compound (VII).

When X is a hydroxy group, this reaction is carried out by a method known per se, such as a method described in, for example, Synthesis p. 1 (1981), or a method analogous thereto. That is, this reaction is generally carried out in the presence of an organic phosphorus compound and electrophile in a solvent that does not adversely influence the reaction.

The organic phosphorus compound is, for example, triphenylphosphine, tributylphosphine and the like.

The electrophile is, for example, diethyl azodicarboxylate, diisopropyl azodicarboxylate, azodicarbonyldipiperidine and the like.

The amount of the organic phosphorus compound and electrophile to be used is preferably about 1—about 5 molar equivalent, relative to compound (I-4).

The solvent that does not adversely influence the reaction is exemplified by ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like; and the like. These solvents may be used after mixing at a suitable ratio.

The reaction temperature is generally from about −50° C. to about 150° C., preferably from about −10° C. to about 100° C.

The reaction time is generally from about 0.5 to about 20 ours.

When X is a halogen atom or a group represented by the formula: —$OSO_2R^8$ ($R^8$ is as defined above), this reaction is carried out according to a conventional method in the presence of a base in a solvent that does not adversely influence the reaction.

The base is exemplified by alkali metal salts such as lithium hydroxide, potassium hydroxide, sodium hydroxide, sodium hydrogencarbonate, potassium carbonate, cesium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undeca-7-ene and the like; metal hydrides such as potassium hydride, sodium hydride and the like; alkali metal alkoxides such as sodium methoxide, sodium ethoxide, potassium t-butoxide and the like; and the like.

The amount of these bases to be used is preferably about 1—about 5 molar equivalents relative to compound (I-4).

The solvent that does not adversely influence the reaction is exemplified by aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like; and the like. These solvents may be used after mixing at a suitable ratio.

The reaction temperature is generally from about −50° C. to about 150° C., preferably from about −10° C. to about 100° C.

The reaction time is generally from about 0.5 to about 20 hours.

The thus-obtained compound (I-6) can be isolated and purified by a known separation and purification means, such as concentration, concentration under reduced pressure, solvent extraction, crystallization, recrystallization, solvent substitution, chromatography and the like.

[Method F]

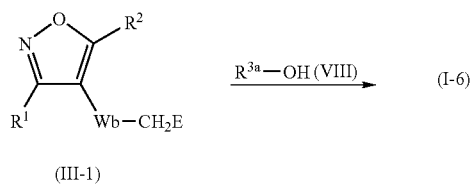

(III-1)

wherein E is a halogen atom or a group represented by the formula: —OSO$_2$R$^8$ (R$^8$ is as defined above), and other symbols are as defined above.

In this method, compound (I-6) is produced by reacting compound (III-1) with compound (VIII).

This reaction is carried out according to a conventional method in the presence of a base in a solvent that does not adversely influence the reaction.

The base is exemplified by alkali metal salts such as lithium hydroxide, potassium hydroxide, sodium hydroxide, sodium hydrogencarbonate, sodium carbonate, potassium carbonate, cesium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undeca-7-ene and the like; metal hydrides such as potassium hydride, sodium hydride and the like; alkali metal alkoxides such as sodium methoxide, sodium ethoxide, potassium t-butoxide and the like; and the like.

The amount of the base to be used is preferably about 1—about 5 molar equivalents relative to compound (III-1).

The solvent that does not adversely influence the reaction is exemplified by aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like; and the like. These solvents may be used after mixing at a suitable ratio.

The reaction temperature is generally from about −50° C. to about 150° C., preferably from about −10° C. to about 100° C.

The reaction time is generally from about 0.5 to about 20 hours.

The thus-obtained compound (I-6) can be isolated and purified by a known separation and purification means, such as concentration, concentration under reduced pressure, solvent extraction, crystallization, recrystallization, solvent substitution, chromatography and the like.

A compound having an esterified carboxyl group for Y, and —CH=CH— or —(CH$_2$)$_2$— for W in the formula (I) [compound (I-9) or (I-10), respectively] is produced by the following Method G.

[Method G]

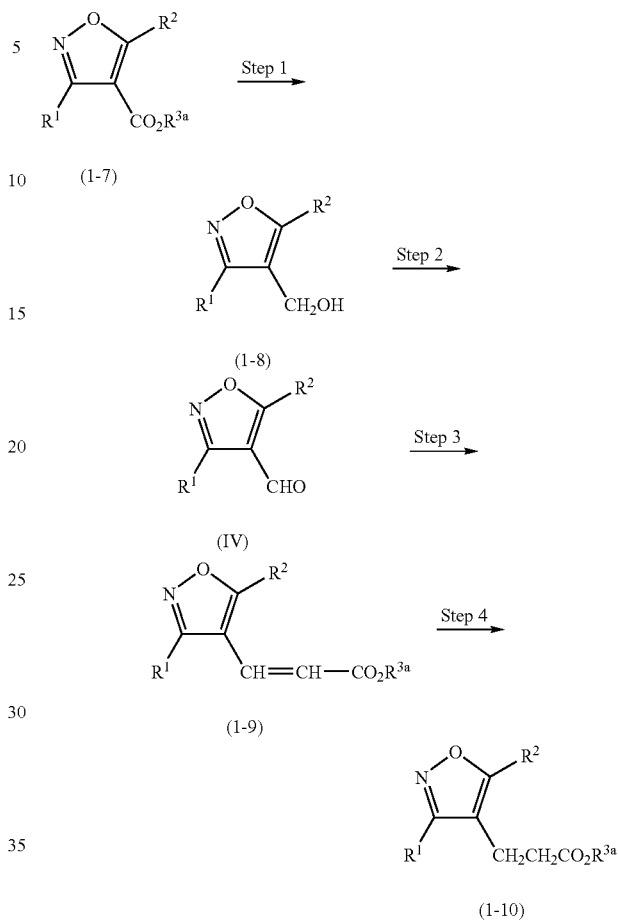

wherein the symbols in the formula are as defined above.

(Step 1) Reduction Reaction

This reaction is carried our according to a conventional method in the presence of a reducing agent in a solvent inert to the reaction.

The reducing agent is, for example, sodium borohydride, lithium borohydride, lithium aluminum hydride, diisobutylaluminum hydride, sodium dihydrobis(2-methoxyethoxy)aluminate, borane and a complex thereof (e.g., borane-tetrahydrofuran, pyridineborane, borane-dimethylsulfide and the like), and the like.

The amount of the reducing agent to be used is preferably about 0.5—about 10 molar equivalents relative to compound (I-7).

The solvent that does not adversely influence the reaction is exemplified by aromatic hydrocarbons such as benzene, toluene, xylene and the like; halogenated hydrocarbons such as chloroform, dichloromethane and the like; ethers such as tetrahydrofuran, dioxane, diethyl ether and the like; water; alcohols such as methanol, ethanol, isopropanol and the like; and the like. These solvents may be used after mixing at a suitable ratio.

The reaction temperature is generally from about −50° C. to about 150° C., preferably from about −10° C. to about 100° C.

The reaction time is generally from about 0.5 to about 20 hours.

The thus-obtained compound (I-8) can be isolated and purified by a known separation and purification means, such as concentration, concentration under reduced pressure, solvent extraction, crystallization, recrystallization, solvent substitution, chromatography and the like.

The compound (I-7) used as a starting material compound in step 1 of the above-mentioned Method G can be produced by the method described in, for example, *Journal of Heterocyclic Chemistry*, vol. 28, p. 453 (1991); *Journal of Organic Chemistry*, vol. 49, p. 4419 (1984); *Tetrahedron Letters*, vol. 34, p. 485 (1993) and the like or a method analogous thereto.

(Step 2) Oxidization Reaction

This reaction is carried out according to a conventional method in the presence of an oxidant in a solvent inert to the reaction.

The oxidant is, for example, a metal oxidant such as manganese dioxide, pyridinium chlorochromate, pyridinium dichromate, ruthenium oxide and the like, and the like.

The amount of the oxidant to be used is preferably about 1—about 10 molar equivalents relative to compound (I-8).

The solvent that does not adversely influence the reaction is exemplified by aromatic hydrocarbons such as benzene, toluene, xylene and the like; ethers such as tetrahydrofuran, dioxane, diethyl ether and the like; halogenated hydrocarbons such as chloroform, dichloromethane and the like; and the like. These solvents may be used after mixing at a suitable ratio.

The reaction temperature is generally from about $-50°$ C. to about $150°$ C., preferably from about $-10°$ C. to about $100°$ C.

The reaction time is generally from about 0.5 to about 20 hours.

The compound (IV) can be also produced by adding a reaction reagent such as a sulfur trioxide-pyridine complex or oxalyl chloride and the like to compound (I-8) in a mixed solvent of sulfoxides such as dimethyl sulfoxide and the like with halogenated hydrocarbons such as chloroform, dichloromethane and the like, and reacting the compound with an organic base such as triethylamine, N-methylmorpholine and the like.

The amount of the reaction reagent to be used is preferably about 1—about 10 molar equivalents relative to compound (I-8).

The amount of the organic base to be used is preferably about 1—about 10 molar equivalents relative to compound (I-8).

The reaction temperature is generally from about $-50°$ C. to about $150°$ C., preferably from about $-10°$ C. to about $100°$ C.

The reaction time is generally from about 0.5 to about 20 hours.

The thus-obtained compound (IV) can be isolated and purified by a known separation and purification means, such as concentration, concentration under reduced pressure, solvent extraction, crystallization, recrystallization, solvent substitution, chromatography and the like.

(Step 3) Carbon-Addition Reaction

In this reaction, compound (I-9) is produced by the reaction of an organic phosphorus reagent with compound (IV) in the presence of a base.

This method is conducted according to a conventional method in the presence of a base in a solvent inert to the reaction.

The organic phosphorus reagent is, for example, methyl dimethylphosphonoacetate, ethyl diethylphosphonoacetate, ethyl dimethylphosphonoacetate and the like.

The amount of the organic phosphorus reagent to be used is preferably about 1—about 10 molar equivalents relative to compound (IV).

The base is exemplified by alkali metal salts such as potassium hydroxide, sodium hydroxide, sodium hydrogencarbonate, potassium carbonate and the like; alkaline earth metal salts such as barium carbonate, calcium carbonate, barium hydroxide, calcium hydroxide and the like; amines such as pyridine, triethylamine, N,N-dimethylaniline, 1,8-diazabicyclo[5.4.0]undeca-7-ene and the like; metal hydrides such as potassium hydride, sodium hydride and the like; alkali metal alkoxides such as sodium methoxide, sodium ethoxide, potassium t-butoxide and the like; and the like.

The amount of the base to be used is preferably about 1—about 5 molar equivalents relative to compound (IV).

The solvent that does not adversely influence the reaction is exemplified by aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; sulfoxides such as dimethyl sulfoxide and the like; and the like. These solvents may be used after mixing at a suitable ratio.

The reaction temperature is generally from about $-50°$ C. to about $150°$ C., preferably from about $-10°$ C. to about $100°$ C.

The reaction time is generally from about 0.5 to about 20 hours.

The thus-obtained compound (I-9) can be isolated and purified by a known separation and purification means, such as concentration, concentration under reduced pressure, solvent extraction, crystallization, recrystallization, solvent substitution, chromatography and the like.

(Step 4) Hydrogenation Reaction

This method is conducted according to a conventional method in a solvent inert to the reaction under a hydrogen atmosphere or in the presence of a hydrogen source such as formic acid and the like and a metal catalyst.

The metal catalyst is exemplified by transition metal catalysts such as palladium-carbon, palladium-barium carbonate, palladium black, platinum oxide, platinum-carbon, Raney nickel, Wilkinson catalyst and the like, and the like.

The amount of these transition metal catalysts to be used is preferably about 0.01—about 10 molar equivalents relative to compound (I-9).

The solvent that does not adversely influence the reaction is exemplified by aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; alcohols such as methanol, ethanol, isopropanol and the like; and the like. These solvents may be used after mixing at a suitable ratio.

The reaction temperature is generally from about $-50°$ C. to about $150°$ C., preferably from about $-10°$ C. to about $100°$ C.

The reaction time is generally from about 0.5 to about 20 hours.

The thus-obtained compound (I-10) can be isolated and purified by a known separation and purification means, such as concentration, concentration under reduced pressure, solvent extraction, crystallization, recrystallization, solvent substitution, chromatography and the like.

The compound (I-11) having a carboxyl group for Y and —(CH₂)₂— for W in the formula (I) can be also produced by the following Method H.

[Method H]

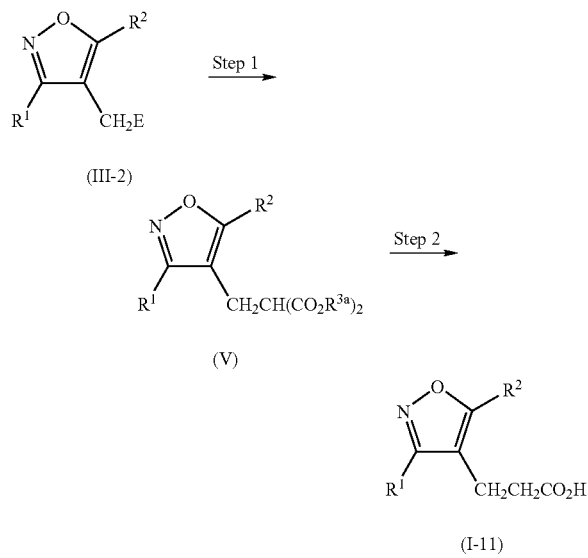

wherein the symbols in the formula are as defined above.

(Step 1) Carbon-Addition Reaction

In this method, compound (V) is produced by subjecting compound (III-2) to 2 carbons-addition reaction using malonic acid diester.

This reaction is conducted according to a conventional method in the presence of malonic acid diester and a base in a solvent that does not adversely influence the reaction.

The base is exemplified by alkali metal salts such as lithium hydroxide, potassium hydroxide, sodium hydroxide, sodium hydrogencarbonate, potassium carbonate, cesium carbonate and the like; alkaline earth metal salts such as barium carbonate, calcium carbonate, barium hydroxide, calcium hydroxide and the like; amine such as pyridine, triethylamine, N,N-dimethylaniline, 1,8-diazabicyclo[5.4.0]undeca-7-ene and the like; metal hydrides such as potassium hydride, sodium hydride and the like; alkali metal alkoxides such as sodium methoxide, sodium ethoxide, potassium t-butoxide and the like; and the like.

The malonic acid diester is, for example, diethyl malonate, dimethyl malonate, dipropyl malonate, dibutyl malonate and the like.

The amount of the base and malonic acid diester to be used is preferably about 1—about 5 molar equivalents relative to compound (III-2).

The solvent that does not adversely influence the reaction is exemplified by aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide, N,N-dimethylacetamide and the like; and the like. These solvents may be used after mixing at a suitable ratio.

The reaction temperature is generally from about −50° C. to about 150° C., preferably from about −10° C. to about 100° C.

The reaction time is generally from about 0.5 to about 20 hours.

The thus-obtained compound (V) can be isolated and purified by a known separation and purification means, such as concentration, concentration under reduced pressure, solvent extraction, crystallization, recrystallization, solvent substitution, chromatography and the like.

(Step 2) Decarbonation Reaction

In this method, compound (I-11) is produced by subjecting compound (V) to a decarbonation reaction.

This decarbonation reaction is carried out according to a conventional method under acidic conditions or basic conditions.

When the reaction is carried out under acidic conditions, this method is conducted according to a conventional method in a solvent inert to the reaction.

The acid is, for example, hydrochloric acid, sulfuric acid, acetic acid, hydrobromic acid and the like.

The amount of the acid to be used is generally an excess amount of compound (V), preferably about 2—about 50 equivalents, relative to compound (V).

The solvent inert to the reaction is, for example, a mixed solvent of water and one or more kinds selected from alcohols such as methanol, ethanol and the like; ketones such as acetone, 2-butanone and the like; and the like. Alternatively, an excess acid may be used as a solvent.

When the reaction is carried out under basic conditions, this method is conducted according to a conventional method comprising hydrolysis to convert compound (V) to dicarboxylic acid, and then pyrolysis to give compound (I-11).

The hydrolysis reaction is carried out according to a conventional method in the presence of a base in a water-containing solvent that does not influence the reaction.

The base is exemplified by alkali metal salts such as lithium hydroxide, sodium hydroxide, potassium hydroxide, potassium carbonate, sodium carbonate, cesium carbonate and the like; alkaline earth metal salts such as barium carbonate, calcium carbonate, barium hydroxide, calcium hydroxide and the like; alkali metal alkoxides such as sodium methoxide and the like; and the like.

The amount of the base to be used is generally an excess amount of compound (V), preferably about 2.5—about 20 equivalent, relative to compound (V).

The water-containing solvent that does not influence the reaction is, for example, a mixed solvent of one or more kinds selected from alcohols such as methanol, ethanol and the like; ethers such as tetrahydrofuran, dioxane, diethyl ether and the like; dimethyl sulfoxide and acetone and the like, with water; and the like.

The reaction temperature is generally from about −20° C. to about 150° C., preferably from about −10° C. to about 100° C.

The reaction time is generally from about 0.1 to about 20 hours.

This pyrolysis reaction is carried out according to a conventional method in a solvent inert to the reaction.

The solvent inert to the reaction is, for example, pyridine, quinoline, collidine and the like.

The reaction temperature is generally from about −20° C. to about 250° C., preferably from about 50° C. to about 200° C.

The reaction time is generally from about 0.1 to about 20 hours.

The thus-obtained compound (I-11) can be isolated and purified by a known separation and purification means, such as concentration, concentration under reduced pressure, solvent extraction, crystallization, recrystallization, solvent substitution, chromatography and the like.

Of the compounds (III-1) used as a starting material compound in Method F, a compound wherein E is a halogen atom or a group represented by the formula: —$OSO_2R^8$ ($R^8$ is as defined above) can be produced by, for example, the following Method I. The compound (III-1) encompasses compound (III-2) used as a starting material compound in Method H.

[Method I]

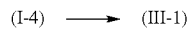

wherein each symbol is as defined above.

The compound (III-1) wherein E is a halogen atom can be produced by, for example, reacting compound (I-4) with a halogenating agent.

This method is conducted according to a conventional method in the presence of a halogenating agent in a solvent inert to the reaction.

The halogenating agent is, for example, thionyl chloride or phosphorus tribromide and the like.

The amount of the halogenating agent to be used is preferably about 1—about 20 molar equivalents relative to compound (I-4).

The solvent that does not adversely influence the reaction is exemplified by aromatic hydrocarbons such as benzene, toluene, xylene and the like; ethers such as tetrahydrofuran, dioxane, diethyl ether and the like; halogenated hydrocarbons such as chloroform, dichloromethane and the like and the like. These solvents may be used after mixing at a suitable ratio. Alternatively, an excess halogenating agent may be used as a solvent.

The reaction temperature is generally from about –20° C. to about 150° C., preferably from about 0° C. to about 100° C.

The reaction time is generally from about 0.1 to about 20 hours.

The compound (III-1) wherein E is a group represented by the formula: —$OSO_2R^8$ ($R^8$ is as defined above) is produced by, for example, reacting compound (I-4) with a sulfonylating agent in the presence of a suitable base.

This method is conducted according to a conventional method in the presence of a sulfonylating agent in a solvent inert to the reaction.

The sulfonylating agent is, for example, mesyl chloride, tosyl chloride or benzenesulfonyl chloride and the like. In this case, compound (I-1) wherein E is mesyloxy, tosyloxy and benzenesulfonyloxy respectively, is produced.

The amount of the sulfonylating agent and base to be used is preferably about 1—about 2 molar equivalents relative to compound (I-4).

The solvent that does not adversely influence the reaction is exemplified by aromatic hydrocarbons such as benzene, toluene, xylene and the like; ethers such as tetrahydrofuran, dioxane, diethyl ether and the like; amides such as N,N-dimethylformamide, N,N-dimethylacetamide and the like; halogenated hydrocarbons such as chloroform, dichloromethane and the like; ethyl acetate, acetone and the like. These solvents may be used after mixing at a suitable ratio.

The reaction temperature is generally from about –20° C. to about 150° C., preferably from about 0° C. to about 100° C.

The reaction time is generally from about 0.1 to about 20 hours.

The thus-obtained compound (III-1) can be isolated and purified by a known separation and purification means, such as concentration, concentration under reduced pressure, solvent extraction, crystallization, recrystallization, solvent substitution, chromatography and the like.

In each of the aforementioned reactions, when the starting material compound has amino, carboxy, hydroxy or carbonyl as a substituent, these groups may have a protecting group introduced therein, such as one generally used in peptide chemistry and the like. The objective compound can be obtained by removing the protecting group as necessary after the reaction.

The amino-protecting group is, for example, formyl, $C_{1-6}$ alkyl-carbonyl (e.g., acetyl, propionyl and the like), $C_{1-6}$ alkoxy-carbonyl (e.g., methoxycarbonyl, ethoxycarbonyl, tert-butoxycarbonyl and the like), benzoyl, $C_{7-13}$ aralkyl-carbonyl (e.g., benzylcarbonyl and the like), $C_{7-13}$ aralkyloxy-carbonyl (e.g., benzyloxycarbonyl, 9-fluorenylmethoxycarbonyl and the like), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups are optionally substituted by 1 to 3 halogen atoms (e.g., fluorine, chlorine, bromine, iodine and the like), $C_{1-6}$ alkoxy (e.g., methoxy, ethoxy, propoxy and the like) or nitro and the like.

The carboxy-protecting group is, for example, $C_{1-6}$ alkyl (e.g., methyl, ethyl, propyl, isopropyl, butyl, tert-butyl and the like), $C_{7-13}$ aralkyl (e.g., benzyl and the like), phenyl, trityl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups are optionally substituted by 1 to 3 halogen atoms (e.g., fluorine, chlorine, bromine, iodine and the like), $C_{1-6}$ alkoxy (e.g., methoxy, ethoxy, propoxy and the like) or nitro and the like.

The hydroxy-protecting group is, for example, $C_{1-6}$ alkyl (e.g., methyl, ethyl, propyl, isopropyl, butyl, tert-butyl and the like), phenyl, trityl, $C_{7-13}$ aralkyl (e.g., benzyl and the like), formyl, $C_{1-6}$ alkyl-carbonyl (e.g., acetyl, propionyl and the like), benzoyl, $C_{7-13}$ aralkyl-carbonyl (e.g., benzylcarbonyl and the like), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like. These groups are optionally substituted by 1 to 3 halogen atoms (e.g., fluorine, chlorine, bromine, iodine and the like), $C_{1-6}$ alkyl (e.g., methyl, ethyl, propyl and the like), $C_{1-6}$ alkoxy (e.g., methoxy, ethoxy, propoxy and the like) or nitro and the like.

The carbonyl-protecting group is, for example, cyclic acetal (e.g., 1,3-dioxane and the like), non-cyclic acetal (e.g., di-$C_{1-6}$ alkyl acetal and the like) and the like.

These protecting groups can be eliminated according to a method known per se, such as a method described in *Protective Groups in Organic Synthesis*, John Wiley and Sons (1980) and the like. For example, employed is a method using acid, base, UV light, hydrazine, phenyl hydrazine, sodium N-methyldithiocarbamate, tetrabutylammonium fluoride, palladium acetate, trialkylsilyl halide (e.g., trimethylsilyl iodide, trimethylsilyl bromide and the like) and the like, reduction and the like.

When the starting material compound can form a salt in each of the aforementioned reactions, the compound in the form of a salt may be used. The salt is, for example, the salt of compound (I) exemplified above.

When compound (I) contains an optical isomer, a stereoisomer, a positional isomer or a rotational isomer, these are also encompassed in compound (I), and can be obtained as a single product according to a synthetic method and separation method known per se. For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method and the like.

1) Fractional Recrystallization Method

A salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine and the like) is formed, which is separated by a fractional recrystallization method, and applied, where desired, to a neutralization step to give a free optical isomer.

2) Chiral Column Method

A racemate or a salt thereof is applied to a column for separation of an optical isomer (chiral column) to allow separation. In the case of a liquid chromatography, for example, a mixture of an optical isomer is applied to a chiral column such as ENANTIO-OVM (manufactured by Tosoh Corporation) or CHIRAL series (manufactured by Daicel Chemical Industries, Ltd.) and the like, and eluted with water, various buffers (e.g., phosphate buffer) and organic solvents (e.g., ethanol, methanol, isopropanol, acetonitrile, trifluoroacetic acid, diethylamine and the like) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A racemic mixture is prepared into a diastereomeric mixture by chemical reaction with an optically active reagent, which is separated into a single material by a typical separation means (e.g., fractional recrystallization, chromatography method and the like) and the like, and subjected to a chemical treatment such as hydrolysis and the like to separate an optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl)phenylacetic acid], (−)-menthoxyacetic acid and the like) and the like are subjected to condensation to give an ester form or amide form diastereomer. When compound (I) has a carboxylic acid group, this compound and an optically active amine reagent or an optically active alcohol reagent are subjected to condensation to give an amide form or ester form diastereomer. The separated diastereomer is converted to an optical isomer of the original compound by acid hydrolysis or base hydrolysis.

The present invention further relates to a glucose-dependent insulin secretagogue containing an isoxazole derivative.

As used herein, the isoxazole derivative is not particularly limited as long as it has an isoxazole skeleton. Examples of the isoxazole derivative include a compound having a group represented by the formula: —W—Y (W and Y are as defined above) at the 4-position of the isoxazole skeleton, and the like.

The isoxazole derivative is preferably compound (I) or a salt thereof or a prodrug thereof, more preferably compound (II) or a salt thereof or a prodrug thereof.

The glucose-dependent insulin secretagogue means a pharmaceutical agent that shows a selective insulin secretion promoting action in the presence of high concentration glucose (e.g., patients showing fasting blood glucose level of not less than 126 mg/dl or 75 g oral glucose tolerance test (75 g OGTT) 2 h level of not less than 140 mg/dl and the like). Therefore, the glucose-dependent insulin secretagogue of the present invention is useful as a safe agent for the prophylaxis or treatment of diabetes, which is associated with a low risk of vascular complications, induction of hypoglycemia and the like, which are the negative effects caused by insulin.

The glucose-dependent insulin secretagogue of the present invention can be produced in the same manner as in the aforementioned pharmaceutical composition and can be used safely for a mammal (e.g., human, mouse, rat, rabbit, dog, cat, bovine, horse, swine, monkey etc.).

The dose and the administration method of the glucose-dependent insulin secretagogue of the present invention are the same as those for the aforementioned compounds of the present invention. Moreover, the glucose-dependent insulin secretagogue of the present invention can be also used in combination with the aforementioned combination drug.

The present invention is explained in detail in the following by referring to Experimental Examples, Reference Examples, Examples and Preparation Examples, which are not to be construed as limitative.

In the following Reference Examples and Examples, "%" means percent by weight unless specifically indicated. In addition, room temperature means a temperature of 1–30° C.

In Examples, HPLC was measured under the following conditions.

measurement tool: LC-10Avp system, Shimadzu Seisakusho
column: CAPSEL PAK C18UG120 S-3 μm, 2.0×50 mm
solvent:
  Solution A; 0.1% trifluoroacetic acid-containing water,
  Solution B; 0.1% trifluoroacetic acid-containing acetonitrile
gradient cycle: 0.00 min (Solution A/Solution B=90/10), 4.00 min (Solution A/Solution B=5/95), 5.50 min (Solution A/Solution B=5/95), 5.51 min (Solution A/Solution B=90/10), 8.00 min (Solution A/Solution B=90/10)
injection amount: 2 μl, flow rate: 0.5 ml/min, detection method: UV 220 nm In Examples, mass spectrum (MS) was measured under the following conditions.

measurement tool: Micromass Ltd., platform II, Waters Corporation ZQ, or Waters Corporation ZMD
ionization method: Atmospheric Pressure Chemical Ionization: APCI or Electron Spray Ionization: ESI
preparative HPLC apparatus: Gilson, Inc., high through-put purification system column: YMC Combiprep ODS-A S-5 μm, 50×20 mm
solvent:
 Solution A; 0.1% trifluoroacetic acid-containing water,
 Solution B; 0.1% trifluoroacetic acid-containing acetonitrile
gradient cycle: 0.00 min (Solution A/Solution B=90/10), 1.20 min (Solution A/Solution B=90/10), 4.75 min (Solution A/Solution B=0/100), 7.30 min (Solution A/Solution B=0/100), 7.40 min (Solution A/Solution B=90/10), 7.50 min (Solution A/Solution B=90/10)
flow rate: 25 ml/min, detection method: UV 220 nm

EXAMPLES

Experimental Example 1

Hypoglycemic Action in Rats

Male SD rats (7 weeks of age, 5 per group) were fasted overnight and blood was drawn from the tail vein to measure the glucose level before administration of the test compound. Then the test compound (30 mg/kg body weight/10 mL (compounds of Examples 8, 16, 66, 68, 79, 94, 123) or 50 mg/kg body weight/10 mL (compounds of Examples 58, 70)) suspended in 0.5% methyl cellulose was orally administered to the rats using a gastric tube. Oral glucose tolerance test (2 g/kg body weight/10 mL) was started 60 min later. Blood was drawn at 30 min after starting the glucose loading, and glucose level was measured. The glucose level was measured using an automatic analyzer (HITACHI 7070). The glucose level of the test compound group is expressed in a value (%) relative to the control group and shown in Table 1.

TABLE 1

| test compound (Example No.) | glucose level (% of control) |
| --- | --- |
| 8 | 85 |
| 16 | 88 |
| 58 | 85 |
| 66 | 80 |
| 68 | 75 |
| 70 | 88 |
| 79 | 77 |
| 94 | 81 |
| 123 | 86 |

As shown above, the compound of the present invention has a superior blood glucose level-lowering effect, and is useful as an agent for the prophylaxis or treatment of diabetes and the like.

Experimental Example 2

Insulin Secretion Promoting Action in Pancreatic Langerhans' Islet of Rats

The pancreas of 8-week-old male SD rat was treated with collagenase and the isolated Langerhans' islet was preincubated for 1 hr in a medium (KRB) containing 2.8 mmol/L glucose in a 24 well incubation plate, which was followed by incubation for 1 hr in KRB containing the test compound (100 μmol/L, see Table 2) and 7.5 mmol/L glucose (control group was free of test compound). The medium was recovered and the amount of the secreted insulin was measured using a radioimmunoassay kit (trademark: SHIONORIA insulin kit (manufactured by Shionogi & Co., Ltd.)). The Langerhans' islet was lysed by ultrasonication and the DNA amount was measured, based on which the insulin level in the medium was amended. The insulin secretion amount of the test compound group is expressed in a value (%) relative to the control group and shown in Table 2.

TABLE 2

| Test compound (Example No.) | insulin secretion promoting action (%) |
| --- | --- |
| 8 | 256 |
| 64 | 273 |
| 70 | 235 |
| 77 | 201 |
| 92 | 156 |

As shown above, the compound of the present invention has a superior insulin secretion promoting action, and is useful as an agent for the prophylaxis or treatment of diabetes and the like.

Reference Example 1

A mixture of 4'-trifluoromethoxyacetophenone (6.30 g), sodium hydride (60%, oil, 1.22 g) and diethyl carbonate (70 ml) was stirred at 80° C. for 1 hr. Water was added to the reaction mixture, and the aqueous layer was neutralized with dilute hydrochloric acid. Then, the mixture was stirred at room temperature for 30 min, and extracted with ethyl acetate. The ethyl acetate layer was washed with saturated brine, dried ($MgSO_4$) and concentrated. A mixture of the residue and N,N-dimethylformamide dimethylacetal (5.54 g) was refluxed for 1.5 hr. The reaction mixture was concentrated, and the residue was dissolved in ethanol (120 ml). To the obtained solution was added hydroxylamine hydrochloride (4.29 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and ethyl 5-(4-trifluoromethoxyphenyl)isoxazole-4-carboxylate (6.60 g, yield 71%) was obtained as a yellow oil from a fraction eluted with ethyl acetate-hexane (1:2, volume ratio). NMR ($CDCl_3$) δ: 1.38 (3H, t, J=7.0 Hz), 4.36 (2H, q, J=7.0 Hz), 7.35 (2H, d, J=8.8 Hz), 8.22 (2H, d, J=8.8 Hz), 8.64 (1H, s).

Ref rence Example 2

To a solution of ethyl 5-(4-trifluoromethoxyphenyl)isoxazole-4-carboxylate (6.60 g) in tetrahydrofuran (80 ml) was gently added diisobutylaluminum hydride (1.0 M tetrahydrofuran solution, 55 ml) at 0° C. The mixture was stirred at room temperature for 30 min. The reaction mixture was poured into dilute hydrochloric acid and the mixture was extracted with ethyl acetate. The ethyl acetate layer was washed with saturated brine, dried ($MgSO_4$) and concentrated to give 5-(4-trifluoromethoxyphenyl)-4-isoxazolylmethanol (5.70 g, yield 99%) as colorless crystals. The crystals were recrystallized from ethyl acetate-hexane. melting point: 45–46° C.

Reference Example 3

A mixture of 4'-trifluoromethylacetophenone (10.0 g), sodium hydride (60%, oil, 2.13 g) and diethyl carbonate (80 ml) was stirred at 80° C. for 90 min. Water was added to the reaction mixture, and the mixture was neutralized with dilute hydrochloric acid and extracted with ethyl acetate. The ethyl acetate layer was washed with saturated brine, dried ($MgSO_4$) and concentrated. The residue was subjected to silica gel column chromatography, and ethyl 3-oxo-3-(4-trifluoromethylphenyl)propionate was obtained as an oil from a fraction eluted with ethyl acetate-hexane (1:9, volume ratio). A mixture of this oil and N,N-dimethylformamide dimethylacetal (9.50 g) was refluxed for 1 hr. The reaction mixture was concentrated, and the residue was dissolved in ethanol (80 ml). To the obtained solution was added hydroxylamine hydrochloride (7.39 g), and the mixture was refluxed for 2 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, the crystals obtained from a fraction eluted with ethyl acetate-hexane (1:9, volume ratio) were recrystallized from hexane to give ethyl 5-(4-trifluoromethylphenyl)isoxazole-4-carboxylate (8.42 g, yield 56%) as a colorless prism. melting point: 53–54° C.

Reference Example 4

A mixture of N-methoxy-N-methylamine hydrochloride (9.28 g), triethylamine (14 ml) and N,N-dimethylformamide (500 ml) was stirred at room temperature for 30 min. 5-Phenylisoxazole-4-carboxylic acid (14.95 g), 1-hydroxy-1H-1,2,3-benzotriazole hydrate (14.08 g) and 1-ethyl-3-(3-dimethylaminopropyl)carbodiimide hydrochloride (18.00 g) were added and the mixture was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-methoxy-N-methyl-(5-phenyl-4-isoxazolyl)carbamide (13.95 g, yield 76%) was obtained as a colorless oil from a fraction eluted with ethyl acetate-hexane (1:4, volume ratio). NMR ($CDCl_3$) δ: 3.36 (3H, s), 3.57 (3H, s), 7.44–7.56 (3H, m), 7.86–7.98 (2H, m), 8.52 (1H, s).

Reference Example 5

To a solution of N-methoxy-N-methyl-(5-phenyl-4-isoxazolyl)carbamide (13.01 g) in tetrahydrofuran (200 ml) was gently added diisobutylaluminum hydride (1.0 M tetrahydrofuran solution, 120 ml) at 0° C. and the mixture was stirred at room temperature for 30 min. The reaction mixture was poured into dilute hydrochloric acid and the mixture was extracted with ethyl acetate. The ethyl acetate layer was washed with saturated brine, dried ($MgSO_4$) and concentrated. The residue was subjected to silica gel column chromatography, and 5-phenylisoxazole-4-carbaldehyde (8.54 g, yield 88%) was obtained as a colorless oil from a fraction eluted with ethyl acetate-hexane (1:4, volume ratio). NMR ($CDCl_3$) δ: 7.53–7.66 (3H, m), 7.87–7.96 (2H, m), 8.72 (1H, s), 10.10 (1H, s).

Reference Example 6

A mixture of methyl 4'-fluorobenzoylacetate (10.02 g) and N,N-dimethylformamide dimethylacetal (8.63 g) was refluxed for 1.5 hr. The reaction mixture was concentrated, and the residue was dissolved in ethanol (150 ml). To the obtained solution was added hydroxylamine hydrochloride (6.75 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and methyl 5-(4-fluorophenyl)isoxazole-4-carboxylate (9.75 g, yield 91%) was obtained as colorless crystals from a fraction eluted with ethyl acetate-hexane (1:4, volume ratio). The crystals were recrystallized from ethyl acetate-hexane. melting point: 92–93° C.

Reference Example 7

To a solution of methyl 5-(4-fluorophenyl)isoxazole-4-carboxylate (7.06 g) in tetrahydrofuran (50 ml) was gently added diisobutylaluminum hydride (1.0 M tetrahydrofuran solution, 80 ml) at 0° C. and the mixture was stirred at room temperature for 30 min. The reaction mixture was poured into dilute hydrochloric acid and the mixture was extracted with ethyl acetate. The ethyl acetate layer was washed with saturated brine, dried ($MgSO_4$) and concentrated to give 5-(4-fluorophenyl)-4-isoxazolylmethanol (6.35 g, yield 90%) as colorless crystals. The crystals were recrystallized from ethyl acetate-hexane. melting point: 41–42° C.

Ref rence Example 8

A mixture of 3',4'-difluoroacetophenone (10.27 g), sodium hydride (60%, oil, 2.60 g) and diethyl carbonate (150 ml) was stirred at 80° C. for 1 hr. Water was added to the reaction mixture, and the aqueous layer was neutralized with dilute hydrochloric acid. The mixture was stirred at room temperature for 30 min and extracted with ethyl acetate. The ethyl acetate layer was washed with saturated brine, dried ($MgSO_4$) and concentrated. A mixture of the residue and N,N-dimethylformamide dimethylacetal (11.80 g) was refluxed for 1.5 hr. The reaction mixture was concentrated, and the residue was dissolved in ethanol (200 ml). To the obtained solution was added hydroxylamine hydrochloride (9.18 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and ethyl 5-(3,4-difluorophenyl)isoxazole-4-carboxylate (11.60 g, yield 70%) was obtained as colorless crystals from a fraction eluted with ethyl acetate-hexane (1:9, volume ratio). The crystals were recrystallized from ethyl acetate-hexane. melting point: 64–65° C.

Reference Example 9

To a solution of ethyl 5-(3,4-difluorophenyl)isoxazole-4-carboxylate (6.68 g) in tetrahydrofuran (100 ml) was gently added diisobutylaluminum hydride (1.0 M tetrahydrofuran solution, 75 ml) at 0° C. The mixture was stirred at room temperature for 30 min. The reaction mixture was poured into dilute hydrochloric acid and the mixture was extracted with ethyl acetate. The ethyl acetate layer was washed with saturated brine, dried ($MgSO_4$) and concentrated to give 5-(3,4-difluorophenyl)-4-isoxazolylmethanol (6.68 g, yield 92%) as colorless crystals. The crystals were recrystallized from ethyl acetate-hexane. melting point: 72–73° C.

Reference Example 10

A mixture of 4'-bromoacetophenone (9.00 g), sodium hydride (60%, oil, 1.80 g) and diethyl carbonate (100 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried ($MgSO_4$) and concentrated. A mixture of the residue and N,N-dimethylformamide dimethylacetal (8.10 g) was refluxed for 1.5 hr. The reaction mixture was concentrated, and the residue was dissolved in ethanol (150 ml). To the obtained solution was added hydroxylamine hydrochloride (6.33 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and ethyl 5-(4-bromophenyl) isoxazole-4-carboxylate (10.17 g, yield 76%) was obtained as colorless crystals from a fraction eluted with ethyl acetate-hexane (1:9, volume ratio). The crystals were recrystallized from ethyl acetate-hexane. melting point: 47–48° C.

Reference Example 11

To a solution of ethyl 5-(4-bromophenyl)isoxazole-4-carboxylate (9.50 g) in tetrahydrofuran (70 ml) was gently added diisobutylaluminum hydride (1.0 M tetrahydrofuran solution, 70 ml) at 0° C. The mixture was stirred at room temperature for 30 min. The reaction mixture was poured into dilute hydrochloric acid and the mixture was extracted with ethyl acetate. The ethyl acetate layer was washed with saturated brine, dried ($MgSO_4$) and concentrated to give 5-(4-bromophenyl)-4-isoxazolylmethanol (8.03 g, yield 98%) as colorless crystals. The crystals were recrystallized from ethyl acetate-hexane. melting point: 104–105° C.

Reference Example 12

A mixture of ethyl 4'-nitrobenzoylacetate (10.61 g) and N,N-dimethylformamide dimethylacetal (8.06 g) was refluxed for 1.5 hr. The reaction mixture was concentrated, and the residue was dissolved in ethanol (200 ml). To the obtained solution was added hydroxylamine hydrochloride (6.33 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and ethyl 5-(4-nitrophenyl)isoxazole-4-carboxylate (9.78 g, yield 83%) was obtained as colorless crystals from a fraction eluted with ethyl acetate-hexane (1:4, volume ratio). The crystals were recrystallized from ethyl acetate-hexane. melting point: 78–79° C.

Reference Example 13

To a solution of ethyl 5-(4-nitrophenyl)isoxazole-4-carboxylate (9.06 g) in tetrahydrofuran (50 ml) was gently added diisobutylaluminum hydride (1.0 M tetrahydrofuran solution, 80 ml) at 0° C. and the mixture was stirred at room temperature for 30 min. The reaction mixture was poured into dilute hydrochloric acid and the mixture was extracted with ethyl acetate. The ethyl acetate layer was washed with saturated brine, dried ($MgSO_4$) and concentrated to give 5-(4-nitrophenyl)-4-isoxazolylmethanol (7.16 g, yield 94%) as colorless crystals. The crystals were recrystallized from ethyl acetate-hexane. melting point: 170–171° C.

Reference Example 14

A mixture of 3'-chloroacetophenone (7.00 g), sodium hydride (60%, oil, 1.80 g) and diethyl carbonate (100 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried ($MgSO_4$) and concentrated. A mixture of the residue and N,N-dimethylformamide dimethylacetal (8.15 g) was refluxed for 1.5 hr. The reaction mixture was concentrated and the residue was dissolved in ethanol (100 ml). To the obtained solution was added hydroxylamine hydrochloride (6.30 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and ethyl 5-(3-chlorophenyl)isoxazole-4-carboxylate (9.13 g, yield 80%) was obtained as colorless crystals from a fraction eluted with ethyl acetate-hexane (1:9, volume ratio). The crystals were recrystallized from ethyl acetate-hexane. melting point: 77–78° C.

Reference Example 15

To a solution of ethyl 5-(3-chlorophenyl)isoxazole-4-carboxylate (8.50 g) in tetrahydrofuran (80 ml) was gently added diisobutylaluminum hydride (1.0 M tetrahydrofuran solution, 80 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried ($MgSO_4$) and concentrated to give 5-(3-chlorophenyl)-4-isoxazolylmethanol (6.87 g, yield 97%) as colorless crystals. The crystals were recrystallized from ethyl acetate-hexane. melting point: 80–81° C.

Reference Example 16

A mixture of 5-acetyl-1,3-benzodioxole (7.45 g), sodium hydride (60%, oil, 1.80 g) and diethyl carbonate (100 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried ($MgSO_4$) and concentrated. A mixture of the residue and N,N-dimethylformamide dimethylacetal (8.30 g) was refluxed for 1.5 hr. The reaction mixture was concentrated, and the residue was dissolved in ethanol (100 ml). To the obtained solution was added hydroxylamine hydrochloride (6.33 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and ethyl 5-(1,3-benzodioxol-5-yl)isoxazole-4-carboxylate (9.49 g, yield 80%) was obtained as colorless crystals from a fraction eluted with ethyl acetate-hexane (1:9, volume ratio). The crystals were recrystallized from ethyl acetate-hexane. melting point: 73–74° C.

Reference Example 17

To a solution of ethyl 5-(1,3-benzodioxol-5-yl)isoxazole-4-carboxylate (8.56 g) in tetrahydrofuran (70 ml) was gently added diisobutylaluminum hydride (1.0 M tetrahydrofuran solution, 70 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-(1,3-benzodioxol-5-yl)-4-isoxazolylmethanol (6.97 g, yield 97%) as colorless crystals. The crystals were recrystallized from ethyl acetate-hexane. melting point: 92–93° C.

Reference Example 18

A mixture of 3'-chloro-4'-fluoroacetophenone (9.54 g), sodium hydride (60%, oil, 2.15 g) and diethyl carbonate (100 ml) was stirred at 800 for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried (MgSO$_4$) and concentrated. A mixture of the residue and N,N-dimethylformamide dimethylacetal (9.63 g) was refluxed for 1.5 hr. The reaction mixture was concentrated, and the residue was dissolved in ethanol (100 ml). To the obtained solution was added hydroxylamine hydrochloride (7.47 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried (MgSO$_4$) and concentrated. The residue was subjected to silica gel column chromatography, and ethyl 5-(3-chloro-4-fluorophenyl)isoxazole-4-carboxylate (10.33 g, yield 71%) was obtained as colorless crystals from a fraction eluted with ethyl acetate-hexane (1:9, volume ratio). The crystals were recrystallized from ethyl acetate-hexane. melting point: 106–107° C.

Reference Example 19

To a solution of ethyl 5-(3-chloro-4-fluorophenyl)isoxazole-4-carboxylate (9.50 g) in tetrahydrofuran (75 ml) was gently added diisobutylaluminum hydride (1.0 M tetrahydrofuran solution, 75 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-(3-chloro-4-fluorophenyl)-4-isoxazolylmethanol (7.58 g, yield 95%) as colorless crystals. The crystals were recrystallized from ethyl acetate-hexane. melting point: 106–107° C.

Reference Example 20

A mixture of 3',4'-dimethoxyacetophenone (9.20 g), sodium hydride (60%, oil, 1.99 g) and diethyl carbonate (100 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried (MgSO$_4$) and concentrated. A mixture of the residue and N,N-dimethylformamide dimethylacetal (8.95 g) was refluxed for 1.5 hr. The reaction mixture was concentrated, and the residue was dissolved in ethanol (100 ml). To the obtained solution was added hydroxylamine hydrochloride (6.98 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried (MgSO$_4$) and concentrated. The residue was subjected to silica gel column chromatography, and ethyl 5-(3,4-dimethoxyphenyl)isoxazole-4-carboxylate (10.81 g, yield 78%) was obtained as colorless crystals from a fraction eluted with ethyl acetate-hexane (1:9, volume ratio). The crystals were recrystallized from ethyl acetate-hexane. melting point: 113–114° C.

Reference Example 21

To a solution of ethyl 5-(3,4-dimethoxyphenyl)isoxazole-4-carboxylate (8.40 g) in tetrahydrofuran (100 ml) was gently added diisobutylaluminum hydride (1.0 M tetrahydrofuran solution, 65 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-(3,4-dimethoxyphenyl)-4-isoxazolylmethanol (6.85 g, yield 96%) as colorless crystals. The crystals were recrystallized from ethyl acetate-hexane. melting point: 83–84° C.

Reference Example 22

A mixture of 4'-chloro-3'-fluoroacetophenone (12.50 g), sodium hydride (60%, oil, 2.88 g) and diethyl carbonate (150 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried (MgSO$_4$) and concentrated. A mixture of the residue and N,N-dimethylformamide dimethylacetal (12.99 g) was refluxed for 1.5 hr. The reaction mixture was concentrated, and the residue was dissolved in ethanol (150 ml). To the obtained solution was added hydroxylamine hydrochloride (10.10 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried (MgSO$_4$) and concentrated. The residue was subjected to silica gel column chromatography, and ethyl 5-(4-chloro-3-fluorophenyl)isoxazole-4-carboxylate (14.86 g, yield 76%) was obtained as colorless crystals from a fraction eluted with ethyl acetate-hexane (1:9, volume ratio). The crystals were recrystallized from ethyl acetate-hexane. melting point: 76–77° C.

Refer nce Example 23

To a solution of ethyl 5-(4-chloro-3-fluorophenyl)isoxazole-4-carboxylate (12.00 g) in tetrahydrofuran (100 ml) was gently added diisobutylaluminum hydride (1.0 M tetrahydrofuran solution, 100 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-(4-chloro-3-fluorophenyl)-4-isoxazolylmethanol (9.73 g, yield 96%) as colorless crystals. The crystals were recrystallized from ethyl acetate-hexane. melting point: 87–88° C.

Reference Example 24

A mixture of 4'-methoxyacetophenone (7.52 g), sodium hydride (60%, oil, 2.00 g) and diethyl carbonate (100 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried (MgSO$_4$) and concentrated. A mixture of the residue and N,N-dimethylformamide dimethylacetal (8.93 g) was refluxed for 1.5 hr. The reaction mixture was concentrated, and the residue was dissolved in ethanol (100 ml). To the obtained solution was added hydroxylamine hydrochloride (6.97 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried (MgSO$_4$) and concentrated. The residue was subjected to silica gel column chromatography, and ethyl 5-(4-methoxyphenyl)isoxazole-4-carboxylate (9.48 g, yield 77%) was obtained as colorless crystals from a fraction eluted with ethyl acetate-hexane (1:9, volume ratio). The crystals were recrystallized from ethyl acetate-hexane. melting point: 54–55° C.

Reference Example 25

To a solution of ethyl 5-(4-methoxyphenyl)isoxazole-4-carboxylate (8.56 g) in tetrahydrofuran (100 ml) was gently added diisobutylaluminum hydride (1.0 M tetrahydrofuran solution, 80 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-(4-methoxyphenyl)-4-isoxazolylmethanol (6.87 g, yield 97%) as colorless crystals. The crystals were recrystallized from ethyl acetate-hexane. melting point: 57–58° C.

Reference Example 26

A mixture of 3'-bromo-4'-fluoroacetophenone (12.46 g), sodium hydride (60%, oil, 2.30 g) and diethyl carbonate (100 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried (MgSO$_4$) and concentrated. A mixture of the residue and N,N-dimethylformamide dimethylacetal (10.29 g) was refluxed for 1.5 hr. The reaction mixture was concentrated, and the residue was dissolved in ethanol (150 ml). To the obtained solution was added hydroxylamine hydrochloride (12.06 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried (MgSO$_4$) and concentrated. The residue was subjected to silica gel column chromatography, and ethyl 5-(3-bromo-4-fluorophenyl)isoxazole-4-carboxylate (13.55 g, yield 75%) was obtained as colorless crystals from a fraction eluted with ethyl acetate-hexane (1:9, volume ratio). The crystals were recrystallized from ethyl acetate-hexane. melting point: 111–112° C.

Reference Example 27

To a solution of ethyl 5-(3-bromo-4-fluorophenyl)isoxazole-4-carboxylate (10.01 g) in tetrahydrofuran (70 ml) was gently added diisobutylaluminum hydride (1.0 M tetrahydrofuran solution, 70 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-(3-bromo-4-fluorophenyl)-4-isoxazolylmethanol (8.26 g, yield 95%) as colorless crystals. The crystals were recrystallized from ethyl acetate-hexane. melting point: 134–135° C.

Reference Example 28

A mixture of 3'-bromo-4'-chloroacetophenone (6.27 g), sodium hydride (60%, oil, 1.06 g) and diethyl carbonate (90 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried (MgSO$_4$) and concentrated. A mixture of the residue and N,N-dimethylformamide dimethylacetal (4.84 g) was refluxed for 1.5 hr. The reaction mixture was concentrated, and the residue was dissolved in ethanol (100 ml). To the obtained solution was added hydroxylamine hydrochloride (3.75 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried (MgSO$_4$) and concentrated. The residue was subjected to silica gel column chromatography, and ethyl 5-(3-bromo-4-chlorophenyl)isoxazole-4-carboxylate (6.25 g, yield 70%) was obtained as colorless crystals from a fraction eluted with ethyl acetate-hexane (1:9, volume ratio). The crystals were recrystallized from diethyl ether-hexane. melting point: 109–110° C.

Reference Example 29

To a solution of ethyl 5-(3-bromo-4-chlorophenyl)isoxazole-4-carboxylate (6.19 g) in tetrahydrofuran (100 ml) was gently added diisobutylaluminum hydride (1.0 M tetrahydrofuran solution, 40 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-(3-bromo-4-chlorophenyl)-4-isoxazolylmethanol (5.10 g, yield 94%) as a colorless oil. NMR (CDCl$_3$) δ: 4.73 (2H, d, J=4.8 Hz), 7.59 (1H, d, J=8.4 Hz), 7.72 (1H, dd, J=2.2, 8.4 Hz), 8.10 (1H, d, J=2.2 Hz), 8.37 (1H, s).

Reference Example 30

To a solution of 3-(5-phenyl-4-isoxazolyl)propan-1-ol (15.00 g) and triethylamine (21.0 ml) in ethyl acetate (500 ml) was gently added methanesulfonyl chloride (9.0 ml) at 0° C., and the mixture was stirred at room temperature overnight. The reaction mixture was poured into dilute hydrochloric acid, and the mixture was extracted with ethyl acetate. The ethyl acetate layer was washed with saturated brine, dried ($MgSO_4$) and concentrated. A mixture of the residue, sodium cyanide (7.33 g), sodium iodide (13.48 g) and N,N-dimethylformamide (150 ml) was stirred at 70° C. for 5 hr. The reaction mixture was poured into water and the mixture was extracted with ethyl acetate. The ethyl acetate layer was washed with saturated brine, dried ($MgSO_4$) and concentrated. The residue was subjected to silica gel column chromatography, and 4-(5-phenyl-4-isoxazolyl)butyronitrile (13.47 g, yield 86%) was obtained as a colorless oil from a fraction eluted with ethyl acetate-hexane (1:2, volume ratio). NMR ($CDCl_3$) δ: 1.91–2.09 (2H, m), 2.36–2.46 (2H, m), 2.78–2.94 (2H, m), 7.44–7.58 (3H, m), 7.64–7.74 (2H, m), 8.22 (1H, s).

Reference Example 31

A mixture of 2',4'-dichloroacetophenone (17.01 g), sodium hydride (60%, oil, 3.58 g) and diethyl carbonate (200 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried ($MgSO_4$) and concentrated. A mixture of the residue and N,N-dimethylformamide dimethylacetal (16.23 g) was refluxed for 1.5 hr. The reaction mixture was concentrated, and the residue was dissolved in ethanol (200 ml). To the obtained solution was added hydroxylamine hydrochloride (12.53 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and ethyl 5-(2,4-dichlorophenyl)isoxazole-4-carboxylate (17.51 g, yield 68%) was obtained as a pale yellow oil from a fraction eluted with ethyl acetate-hexane (1:9, volume ratio). NMR ($CDCl_3$) δ: 1.24 (3H, t, J=7.0 Hz), 4.25 (2H, q, J=7.0 Hz), 7.39 (1H, dd, J=1.8, 8.4 Hz), 7.46 (1H, d, J=8.4 Hz), 7.56 (1H, d, J=1.8 Hz), 8.67 (1H, s).

Reference Example 32

To a solution of ethyl 5-(2,4-dichlorophenyl)isoxazole-4-carboxylate (8.60 g) in tetrahydrofuran (50 ml) was gently added diisobutylaluminum hydride (1.0 M tetrahydrofuran solution, 65 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried ($MgSO_4$) and concentrated to give 5-(2,4-dichlorophenyl)-4-isoxazolylmethanol (7.09 g, yield 96%) as colorless crystals. The crystals were recrystallized from ethyl acetate-hexane. melting point: 76–77° C.

Reference Example 33

A mixture of 3',4'-dichloroacetophenone (8.64 g), sodium hydride (60%, oil, 1.83 g) and diethyl carbonate (100 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried ($MgSO_4$) and concentrated. A mixture of the residue and N,N-dimethylformamide dimethylacetal (8.15 g) was refluxed for 1.5 hr. The reaction mixture was concentrated, and the residue was dissolved in ethanol (100 ml). To the obtained solution was added hydroxylamine hydrochloride (6.51 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and ethyl 5-(3,4-dichlorophenyl)isoxazole-4-carboxylate (10.33 g, yield 79%) was obtained as colorless crystals from a fraction eluted with ethyl acetate-hexane (1:9, volume ratio). The crystals were recrystallized from ethyl acetate-hexane. melting point: 117–118° C.

Reference Example 34

To a solution of ethyl 5-(3,4-dichlorophenyl)isoxazole-4-carboxylate (8.60 g) in tetrahydrofuran (50 ml) was gently added diisobutylaluminum hydride (1.0 M tetrahydrofuran solution, 65 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried ($MgSO_4$) and concentrated to give 5-(3,4-dichlorophenyl)-4-isoxazolylmethanol (6.97 g, yield 95%) as colorless crystals. The crystals were recrystallized from ethyl acetate-hexane. melting point: 101–102° C.

Reference Example 35

A mixture of 3',5'-dichloroacetophenone (12.80 g), sodium hydride (60%, oil, 2.71 g) and diethyl carbonate (150 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried ($MgSO_4$) and concentrated. A mixture of the residue and N,N-dimethylformamide dimethylacetal (12.18 g) was refluxed for 1.5 hr. The reaction mixture was concentrated, and the residue was dissolved in ethanol (200 ml). To the obtained solution was added hydroxylamine hydrochloride (9.49 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and ethyl 5-(3,5-dichlorophenyl)isoxazole-4-carboxylate (12.48 g, yield 64%) was obtained as colorless crystals from a fraction eluted with ethyl acetate-hexane (1:9, volume ratio). The crystals were recrystallized from ethyl acetate-hexane. melting point: 50–51° C.

Reference Example 36

To a solution of ethyl 5-(3,5-dichlorophenyl)isoxazole-4-carboxylate (10.82 g) in tetrahydrofuran (100 ml) was gently added diisobutylaluminum hydride (1.0 M tetrahydrofuran solution, 100 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-(3,5-dichlorophenyl)-4-isoxazolylmethanol (10.28 g, yield 94%) as colorless crystals. The crystals were recrystallized from ethyl acetate-hexane. melting point: 104–105° C.

Reference Example 37

A mixture of 4'-phenylacetophenone (10.00 g), sodium hydride (60%, oil, 1.96 g) and diethyl carbonate (150 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried (MgSO$_4$) and concentrated. A mixture of the residue and N,N-dimethylformamide dimethylacetal (8.89 g) was refluxed for 1.5 hr. The reaction mixture was concentrated, and the residue was dissolved in ethanol (200 ml). To the obtained solution was added hydroxylamine hydrochloride (6.88 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried (MgSO$_4$) and concentrated. The residue was subjected to silica gel column chromatography, and ethyl 5-(4-phenylphenyl)isoxazole-4-carboxylate (10.98 g, yield 76%) was obtained as colorless crystals from a fraction eluted with ethyl acetate-hexane (1:9, volume ratio). The crystals were recrystallized from ethyl acetate-hexane. melting point: 73–75° C.

Reference Example 38

To a solution of ethyl 5-(4-phenylphenyl)isoxazole-4-carboxylate (10.68 g) in tetrahydrofuran (100 ml) was gently added diisobutylaluminum hydride (1.0 M tetrahydrofuran solution, 83.7 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-(4-phenylphenyl)-4-isoxazolylmethanol (7.55 g, yield 83%) as colorless crystals. The crystals were recrystallized from ethyl acetate-hexane. melting point: 108–110° C.

Reference Example 39

To a solution of ethyl propiolate (7.50 g) in tetrahydrofuran (50 ml) was gently added a solution of pyrrolidine (6.4 ml) in tetrahydrofuran (5 ml) at 0° C. and the mixture was stirred at 0° C. for 30 min. To the obtained mixture was added a solution of 3,4-dichloro-N-hydroxybenzenecarboxyimidoyl chloride (11.40 g) in tetrahydrofuran (100 ml) at 0° C., and a solution of triethylamine (15 ml) in tetrahydrofuran (10 ml) was gently added at 0° C. The mixture was stirred at room temperature overnight and the reaction mixture was poured into dilute hydrochloric acid. The mixture was extracted with ethyl acetate and the ethyl acetate layer was washed with saturated brine, dried (MgSO$_4$) and concentrated. The residue was subjected to silica gel column chromatography, and ethyl 3-(3,4-dichlorophenyl)isoxazole-4-carboxylate (12.26 g, yield 84%) was obtained as colorless crystals from a fraction eluted with ethyl acetate-hexane (1:9, volume ratio). The crystals were recrystallized from ethyl acetate-hexane. melting point: 129–130° C.

Reference Example 40

To a solution of ethyl 3-(3,4-dichlorophenyl)isoxazole-4-carboxylate (7.80 g) in tetrahydrofuran (60 ml) was gently added diisobutylaluminum hydride (1.0 M tetrahydrofuran solution, 60 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 3-(3,4-dichlorophenyl)-4-isoxazolylmethanol (6.43 g, yield 96%) as colorless crystals. The crystals were recrystallized from ethyl acetate-hexane. melting point: 103–104° C.

Reference Example 41

To a solution of ethyl propiolate (7.51 g) in tetrahydrofuran (50 ml) was gently added a solution of pyrrolidine (6.4 ml) in tetrahydrofuran (5 ml) at 0° C. and the mixture was stirred at 0° C. for 30 min. To the obtained mixture was added a solution of 3-chloro-4-fluoro-N-hydroxybenzenecarboxyimidoyl chloride (10.20 g) in tetrahydrofuran (100 ml) at 0° C. and then a solution of triethylamine (15 ml) in tetrahydrofuran (10 ml) was gently added at 0° C. The mixture was stirred at room temperature overnight, the reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and ethyl 3-(3-chloro-4-fluorophenyl)isoxazole-4-carboxylate (10.93 g, yield 83%) was obtained as colorless crystals from a fraction eluted with ethyl acetate-hexane (1:9, volume ratio). The crystals were recrystallized from ethyl acetate-hexane. melting point: 108–1090° C.

Reference Example 42

To a solution of ethyl 3-(3-chloro-4-fluorophenyl)isoxazole-4-carboxylate (9.70 g) in tetrahydrofuran (50 ml) was gently added diisobutylaluminum hydride (1.0 M tetrahydrofuran solution, 80 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 3-(3-chloro-4-fluorophenyl)-4-isoxazolylmethanol (7.91 g, yield 97%) as colorless crystals. The crystals were recrystallized from ethyl acetate-hexane. melting point: 87–88° C.

Reference Example 43

To a solution of ethyl propiolate (8.61 g) in tetrahydrofuran (50 ml) was gently added a solution of pyrrolidine (7.4 ml) in tetrahydrofuran (5 ml) at 0° C. and the mixture was stirred at 0° C. for 30 min. To the obtained mixture was added a solution of 4-chloro-3-fluoro-N-hydroxybenzenecarboxyimidoyl chloride (11.70 g) in tetrahydrofuran (100 ml) at 0° C. and then a solution of triethylamine (16 ml) in tetrahydrofuran (10 ml) was gently added at 0° C. The mixture was stirred at room temperature overnight, the reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and ethyl 3-(4-chloro-3-fluorophenyl)isoxazole-4-carboxylate (12.63 g, yield 83%) was obtained as colorless crystals from a fraction eluted with ethyl acetate-hexane (1:9, volume ratio). The crystals were recrystallized from ethyl acetate-hexane. melting point: 77–78° C.

Reference Example 44

To a solution of ethyl 3-(4-chloro-3-fluorophenyl)isoxazole-4-carboxylate (12.00 g) in tetrahydrofuran (100 ml) was gently added diisobutylaluminum hydride (1.0 M tetrahydrofuran solution, 100 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 3-(4-chloro-3-fluorophenyl)-4-isoxazolylmethanol (9.75 g, yield 96%) as colorless crystals. The crystals were recrystallized from ethyl acetate-hexane. melting point: 124–125° C.

Reference Example 45

To a solution of ethyl propiolate (6.13 g) in tetrahydrofuran (40 ml) was gently added a solution of pyrrolidine (5.2 ml) in tetrahydrofuran (5 ml) at 0° C. and the mixture was stirred at 0° C. for 30 min. To the obtained mixture was added a solution of 3-bromo-4-fluoro-N-hydroxybenzenecarboxyimidoyl chloride (10.10 g) in tetrahydrofuran (100 ml) at 0° C. and then a solution of triethylamine (11.5 ml) in tetrahydrofuran (10 ml) was gently added at 0° C. The mixture was stirred at room temperature overnight, the reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and ethyl 3-(3-bromo-4-fluorophenyl)isoxazole-4-carboxylate (13.96 g, yield 71%) was obtained as colorless crystals from a fraction eluted with ethyl acetate-hexane (1:9, volume ratio). The crystals were recrystallized from ethyl acetate-hexane. melting point: 96–97° C.

Reference Example 46

To a solution of ethyl 3-(3-bromo-4-fluorophenyl)isoxazole-4-carboxylate (10.47 g) in tetrahydrofuran (100 ml) was gently added diisobutylaluminum hydride (1.0 M tetrahydrofuran solution, 75 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 3-(3-bromo-4-fluorophenyl)-4-isoxazolylmethanol (9.75 g, yield 96%) as colorless crystals. The crystals were recrystallized from ethyl acetate-hexane. melting point: 93–94° C.

Reference Example 47

A mixture of N-methoxy-N-methylamine hydrochloride (4.53 g), triethylamine (7.0 ml) and N,N-dimethylformamide (15 ml) was stirred at room temperature for 30 min and 3-methyl-5-phenylisoxazole-4-carboxylic acid (8.26 g), 1-hydroxy-1H-1,2,3-benzotriazole hydrate (6.58 g) and 1-ethyl-3-(3-dimethylaminopropyl)carbodiimide hydrochloride (8.33 g) were added. The mixture was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-methoxy-N-methyl-(3-methyl-5-phenyl-4 -isoxazolyl)carbamide (13.95 g, yield 76%) was obtained as a pale yellow oil from a fraction eluted with ethyl acetate-hexane (1:4, volume ratio). NMR (CDCl$_3$) δ: 2.36 (3H, s), 3.20–3.60 (6H, m), 7.42–7.52 (3H, m), 7.72–7.84 (2H, m).

Reference Example 48

To a solution of N-methoxy-N-methyl-(3-methyl-5-phenyl-4-isoxazolyl)carbamide (7.51 g) in tetrahydrofuran (150 ml) was gently added diisobutylaluminum hydride (1.0 M tetrahydrofuran solution, 70 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-methyl-5-phenylisoxazole-4-carbaldehyde (5.39 g, yield 94%) was obtained as colorless crystals from a fraction eluted with ethyl acetate-hexane (1:4, volume ratio). The crystals were recrystallized from ethyl acetate-hexane. melting point: 87–88° C.

Reference Example 49

To a solution of ethyl propiolate (5.01 g) in tetrahydrofuran (50 ml) was gently added a solution of pyrrolidine (4.3 ml) in tetrahydrofuran (5 ml) at 0° C. and the mixture was stirred at 0° C. for 30 min. To the obtained mixture was added a solution of 4-phenyl-N-hydroxybenzenecarboxyimidoyl chloride (9.28 g) in tetrahydrofuran (100 ml) at 0° C. and then a solution of triethylamine (12.0 ml) in tetrahydrofuran (10 ml) was gently added at 0° C. The mixture was stirred at room temperature overnight, the reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and ethyl 3 -(4-phenylphenyl)isoxazole-4-carboxylate (13.04 g, yield 87%) was obtained as colorless crystals from a fraction eluted with ethyl acetate-hexane (1:9, volume ratio). The crystals were recrystallized from ethyl acetate-hexane. melting point: 81–82° C.

Reference Example 50

To a solution of ethyl 3-(4-phenylphenyl)isoxazole-4-carboxylate (10.00 g) in tetrahydrofuran (100 ml) was gently added diisobutylaluminum hydride (1.0 M tetrahydrofuran solution, 80 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 3-(4-phenylphenyl)-4-isoxazolylmethanol (8.32 g, yield 97%) as colorless crystals. The crystals were recrystallized from ethyl acetate-hexane. melting point: 138–139° C.

Reference Example 51

A mixture of 3-(4-phenylphenyl)-4-isoxazolylmethanol (4.16 g) and thionyl chloride (10.0 ml) was stirred at 0° C. for 30 min. The reaction mixture was concentrated, and saturated aqueous sodium hydrogencarbonate was added to the residue. The mixture was extracted with ethyl acetate and the ethyl acetate layer was washed with saturated brine, dried (MgSO$_4$) and concentrated. The obtained colorless crystals were filtrated to give 4-chloromethyl-3-(4-phenylphenyl)isoxazole (3.84 g, yield 92%). The crystals were recrystallized from ethyl acetate-hexane. melting point: 102–103° C.

Reference Example 52

To a solution of ethyl propiolate (5.00 g) in tetrahydrofuran (50 ml) was gently added a solution of pyrrolidine (4.3 ml) in tetrahydrofuran (5 ml) at 0° C. and the mixture was stirred at 0° C. for 30 min. To the obtained mixture was added a solution of 4-trifluoromethyl-N-hydroxybenzenecarboxyimidoyl chloride (7.50 g) in tetrahydrofuran (100 ml) at 0° C. and a solution of triethylamine (10.0 ml) in tetrahydrofuran (10 ml) was gently added at 0° C. The mixture was stirred at room temperature overnight, after which the reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and ethyl 3-(4-trifluoromethylphenyl)isoxazole-4-carboxylate (8.09 g, yield 85%) was obtained as a colorless oil from a fraction eluted with ethyl acetate-hexane (1:9, volume ratio). NMR (CDCl$_3$) δ: 1.32 (3H, t, J=7.0 Hz), 4.32 (2H, q, J=7.0 Hz), 7.70–7.78 (2H, m), 7.88–7.97 (2H, m), 9.05 (1H, s).

Reference Example 53

To a solution of ethyl 3-(4-trifluoromethylphenyl)isoxazole-4-carboxylate (8.00 g) in tetrahydrofuran (150 ml) was gently added diisobutylaluminum hydride (1.0 M tetrahydrofuran solution, 60 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 3-(4-trifluoromethylphenyl)-4-isoxazolylmethanol (6.46 g, yield 95%) as colorless crystals. The crystals were recrystallized from ethyl acetate-hexane. melting point: 70–71° C.

Reference Example 54

A mixture of 3-(4-trifluoromethylphenyl)-4-isoxazolylmethanol (6.00 g) and thionyl chloride (10.0 ml) was stirred at 0° C. for 30 min. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The obtained colorless crystals were filtrated to give 4-chloromethyl-3-(4-trifluoromethylphenyl)isoxazole (6.16 g, yield 95%). The crystals were recrystallized from ethyl acetate-hexane. melting point: 84–85° C.

Reference Example 55

To a solution of methyl acetoacetate (8.88 g) and 4-chloro-N-hydroxybenzenecarboxyimidoyl chloride (9.65 g) in tetrahydrofuran (100 ml) was gently added a solution of triethylamine (15 ml) in tetrahydrofuran (10 ml) at 0° C. The mixture was stirred at room temperature overnight, the reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:9, volume ratio). To a solution of the obtained colorless oil in tetrahydrofuran (100 ml) was gently added diisobutylaluminum hydride (1.0 M tetrahydrofuran solution, 110 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 3-(4-chlorophenyl)-5-methyl-4-isoxazolylmethanol (7.69 g, yield 68%) as colorless crystals. The crystals were recrystallized from ethanol. melting point: 94–95° C.

Reference Example 56

A mixture of 3-(4-chlorophenyl)-5-methyl-4-isoxazolylmethanol (2.23 g) and thionyl chloride (5.0 ml) was stirred at 0° C. for 30 min. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The obtained colorless crystals were filtrated to give 4-chloromethyl-3-(4-chlorophenyl)-5-methylisoxazole (2.20 g, yield 91%). The crystals were recrystallized from diisopropyl ether. melting point: 91–92° C.

Reference Example 57

To a solution of methyl acetoacetate (8.88 g) and 4-trifluoromethyl-N-hydroxybenzenecarboxyimidoyl chloride (11.35 g) in tetrahydrofuran (100 ml) was gently added a solution of triethylamine (15 ml) in tetrahydrofuran (10 ml) at 0° C. and the mixture was stirred at room temperature overnight. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:9, volume ratio). To a solution of the obtained colorless oil in tetrahydrofuran (100 ml) was gently added diisobutylaluminum hydride (1.0 M tetrahydrofuran solution, 110 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give 5-methyl-3-(4-trifluoromethylphenyl)-4-isoxazolylmethanol (7.86 g, yield 60%) as colorless crystals. The crystals were recrystallized from diisopropyl ether-hexane. melting point: 72–73° C.

Reference Example 58

A mixture of 5-methyl-3-(4-trifluoromethylphenyl)-4-isoxazolylmethanol (1.75 g) and thionyl chloride (5.0 ml) was stirred at 0° C. for 30 min. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The obtained colorless crystals were filtrated to give 4-chloromethyl-5-methyl-3-(4-trifluoromethylphenyl)isoxazole (1.50 g, yield 80%). The crystals were recrystallized from diisopropyl ether. melting point: 91–92° C.

Reference Example 59

To a solution of ethyl 5-(4-trifluoromethylphenyl)isoxazole-4-carboxylate (7.63 g) in tetrahydrofuran (100 ml) was gently added diisobutylaluminum hydride (1.0 M hexane solution, 59 ml) at 0° C. and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated to give 5-(4-trifluoromethylphenyl)-4-isoxazolylmethanol (6.29 g, yield 97%) as colorless crystals. The crystals were recrystallized from ethyl acetate-hexane to give a colorless prism. melting point: 106–107° C.

Reference Example 60

To a mixture of 5-(4-trifluoromethylphenyl)-4-isoxazolylmethanol (5.65 g), tetrahydrofuran (20 ml) and toluene (80 ml) was added dropwise thionyl chloride (4.15 g) at 0° C. and the mixture was stirred at room temperature for 1 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The obtained colorless crystals were filtrated and recrystallized from ethyl acetate-hexane to give 4-chloromethyl-5-(4-trifluoromethylphenyl)isoxazole (4.70 g, yield 77%) as a colorless prism. melting point: 99–100° C.

Reference Example 61

A mixture of 2',4'-difluoroacetophenone (9.50 g), sodium hydride (60%, oil, 2.44 g) and diethyl carbonate (80 ml) was stirred for 1.5 hr at 80° C. Water was added to the reaction mixture, and the mixture was neutralized with dilute hydrochloric acid and extracted with ethyl acetate. The ethyl acetate layer was washed with saturated brine, dried (MgSO$_4$) and concentrated. A mixture of the residue and N,N-dimethylformamide dimethylacetal (7.25 g) was refluxed for 1 hr. The reaction mixture was concentrated, and the residue was dissolved in ethanol (60 ml). To the obtained solution was added hydroxylamine hydrochloride (6.34 g) and the mixture was refluxed for 2 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and ethyl 5-(2,4-difluorophenyl)isoxazole-4-carboxylate (3.85 g, yield 35%) was obtained as an oil from a fraction eluted with ethyl acetate-hexane (1:9, volume ratio). NMR (CDCl$_3$) δ: 1.29 (3H, t, J=7.0 Hz), 4.29 (2H, q, J=7.0 Hz), 6.9–7.1 (2H, m), 7.6–7.75 (1H, m), 8.66 (1H, s).

Reference Example 62

To a solution of ethyl 5-(2,4-difluorophenyl)isoxazole-4-carboxylate (3.85 g) in tetrahydrofuran (60 ml) was gently added diisobutylaluminum hydride (1.0 M hexane solution, 33 ml) at 0° C. and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 5-(2,4-difluorophenyl)-4-isoxazolylmethanol (2.70 g, yield 84%) was obtained as colorless crystals from a fraction eluted with ethyl acetate-hexane (1:1, volume ratio). The crystals were recrystallized from ethyl acetate-hexane to give a colorless prism. melting point: 60–61° C.

Reference Example 63

To a solution of 5-(2,4-difluorophenyl)-4-isoxazolylmethanol (2.50 g) in toluene (50 ml) was added dropwise thionyl chloride (2.11 g) at 0° C., and the mixture was stirred at room temperature for 1 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was subjected to silica gel column chromatography, and 4-chloromethyl-5-(2,4-difluorophenyl)isoxazole (2.20 g, yield 81%) was obtained as an oil from a fraction eluted with ethyl acetate-hexane (1:5, volume ratio). NMR (CDCl$_3$) δ: 4.53 (2H, s), 6.95–7.15 (2H, m), 7.6–7.75 (1H, m), 8.43 (1H, s).

Reference Example 64

A mixture of 2-acetyl-5-chlorothiophene (10.0 g), sodium hydride (60%, oil, 2.49 g) and diethyl carbonate (80 ml) was stirred at 80° C. for 30 min. Water was added to the reaction mixture, and the mixture was neutralized with dilute hydrochloric acid and extracted with ethyl acetate. The ethyl acetate layer was washed with saturated brine, dried (MgSO$_4$) and concentrated. The residue was subjected to silica gel column chromatography, and ethyl 3-(5-chloro-2-thienyl)-3-oxopropionate was obtained as an oil from a fraction eluted with ethyl acetate-hexane (1:5, volume ratio). A mixture of this oil and N,N-dimethylformamide dimethylacetal (11.1 g) was refluxed for 1 hr. The reaction mixture was concentrated, and the residue was dissolved in ethanol (80 ml). To the obtained solution was added hydroxylamine hydrochloride (8.65 g), and the mixture was refluxed for 2 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and the crystals obtained from a fraction eluted with ethyl acetate-hexane (1:5, volume ratio) were recrystallized from ethyl acetate-hexane to give ethyl 5-(5-chloro-2-thienyl)isoxazole-4-carboxylate (9.34 g, yield 58%) as a colorless prism. melting point: 74–75° C.

Reference Example 65

To a solution of ethyl 5-(5-chloro-2-thienyl)isoxazole-4-carboxylate (9.00 g) in tetrahydrofuran (100 ml) was gently added diisobutylaluminum hydride (1.5 M toluene solution, 52 ml) at 0° C. and the mixture was stirred at room temperature for 1.5 hr. The reaction mixture was poured into dilute hydrochloric acid, and the precipitated 5-(5-chloro-2-thienyl)-4-isoxazolylmethanol (7.00 g, yield 93%) was filtrated and recrystallized from ethyl acetate-hexane to give a colorless needle. melting point: 80–81° C.

Reference Example 66

To a mixture of 5-(5-chloro-2-thienyl)-4-isoxazolylmethanol (6.54 g), tetrahydrofuran (20 ml) and toluene (100 ml) was added dropwise thionyl chloride (5.41 g) at 0° C., and the mixture was stirred at room temperature for 1 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was subjected to silica gel column chromatography, and crystals of 4-chloromethyl-5-(5-chloro-2-thienyl)isoxazole (6.98 g, yield 98%) were obtained from a fraction eluted with ethyl acetate-hexane (1:5, volume ratio) and recrystallized from ethyl acetate-hexane to give a colorless prism. melting point: 70–71° C.

Reference Example 67

A mixture of 4'-chloro-3'-methylacetophenone (10.0 g), sodium hydride (60%, oil, 2.38 g) and diethyl carbonate (80 ml) was stirred for 90 min at 80° C. Water was added to the reaction mixture, and the mixture was neutralized with dilute hydrochloric acid and extracted with ethyl acetate. The ethyl acetate layer was washed with saturated brine, dried ($MgSO_4$) and concentrated. The residue was subjected to silica gel column chromatography, and ethyl 3-(4-chloro-3-methylphenyl)-3-oxopropionate was obtained as an oil from a fraction eluted with ethyl acetate-hexane (1:9, volume ratio). A mixture of this oil and N,N-dimethylformamide dimethylacetal (10.6 g) was refluxed for 1 hr. The reaction mixture was concentrated, and the residue was dissolved in ethanol (80 ml). To the obtained solution was added hydroxylamine hydrochloride (8.24 g), and the mixture was refluxed for 2 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and crystals of ethyl 5-(4-chloro-3-methylphenyl)isoxazole-4-carboxylate (9.26 g, yield 59%) were obtained from a fraction eluted with ethyl acetate-hexane (1:5, volume ratio) and recrystallized from hexane to give a colorless prism. melting point: 50–51° C.

Reference Example 68

To a solution of ethyl 5-(4-chloro-3-methylphenyl)isoxazole-4-carboxylate (8.50 g) in tetrahydrofuran (100 ml) was gently added diisobutylaluminum hydride (1.5 M toluene solution, 47 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated to give 5-(4-chloro-3-methylphenyl)-4-isoxazolylmethanol (6.13 g, yield 86%) as colorless crystals, which were recrystallized from ethyl acetate-hexane to give a colorless needle. melting point: 92–93° C.

Reference Example 69

To a mixture of 5-(4-chloro-3-methylphenyl)-4-isoxazolylmethanol (5.80 g), tetrahydrofuran (20 ml) and toluene (80 ml) was added dropwise thionyl chloride (4.63 g) at 0° C. and the mixture was stirred at room temperature for 2 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The obtained colorless crystals were filtrated and recrystallized from ethyl acetate-hexane to give 4-chloromethyl-5-(4-chloro-3-methylphenyl) isoxazole (5.47 g, yield 87%) as a colorless prism. melting point: 84–85° C.

Reference Example 70

A mixture of 2',5'-dichloroacetophenone (10.0 g), sodium hydride (60%, oil, 2.12 g) and diethyl carbonate (80 ml) was stirred at 80° C. for 20 min. Water was added to the reaction mixture, and the mixture was neutralized with dilute hydrochloric acid and extracted with ethyl acetate. The ethyl acetate layer was washed with saturated brine, dried ($MgSO_4$) and concentrated. The residue was subjected to silica gel column chromatography, and ethyl 3-(2,5-dichlorophenyl)-3-oxopropionate was obtained as an oil from a fraction eluted with ethyl acetate-hexane (1:9, volume ratio). A mixture of this oil and N,N-dimethylformamide dimethylacetal (9.46 g) was refluxed for 1 hr. The reaction mixture was concentrated, and the residue was dissolved in ethanol (80 ml). To the obtained solution was added hydroxylamine hydrochloride (7.35 g), and the mixture was refluxed for 2 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and ethyl 5-(2,5-dichlorophenyl)isoxazole-4-carboxylate (6.40 g, yield 42%) was obtained as an oil from a fraction eluted with ethyl acetate-hexane (1:5, volume ratio). NMR ($CDCl_3$) δ: 1.23 (3H, t, J=7 Hz), 4.25 (2H, q, J=7 Hz), 7.4–7.6 (3H, m), 8.68 (1H, s).

Reference Example 71

To a solution of ethyl 5-(2,5-dichlorophenyl)isoxazole-4-carboxylate (6.40 g) in tetrahydrofuran (100 ml) was gently added diisobutylaluminum hydride (1.5 M toluene solution, 33 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 5-(2,5-dichlorophenyl)-4-isoxazolylmethanol (3.86, yield 71%) was obtained as colorless crystals from a fraction eluted with ethyl acetate-hexane (1:1, volume ratio) and recrystallized from isopropyl ether-hexane to give a colorless prism. melting point: 51–52° C.

Reference Example 72

To a solution of 5-(2,5-dichlorophenyl)-4-isoxazolyl-methanol (3.80 g) in toluene (60 ml) was added dropwise thionyl chloride (2.78 g) at 0° C. and the mixture was stirred at room temperature for 2 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was subjected to silica gel column chromatography, and 4-chloromethyl-5-(2,5-dichlorophenyl)isoxazole (2.15 g, yield 53%) was obtained as an oil from a fraction eluted with ethyl acetate-hexane (1:9, volume ratio). NMR ($CDCl_3$) δ: 4.45 (2H, s), 7.4–7.55 (3H, m), 8.48 (1H, s).

Reference Example 73

A mixture of 4'-methylthioacetophenone (20.0 g), sodium hydride (60%, oil, 4.81 g) and diethyl carbonate (120 ml) was stirred at 80° C. for 1.5 hr. Water was added to the reaction mixture, and the mixture was neutralized with dilute hydrochloric acid and extracted with ethyl acetate. The ethyl acetate layer was washed with saturated brine, dried ($MgSO_4$) and concentrated. The residue was subjected to silica gel column chromatography, and ethyl 3-(4-methylthiophenyl)-3-oxopropionate was obtained as an oil from a fraction eluted with ethyl acetate-hexane (1:9, volume ratio). A mixture of this oil and N,N-dimethylformamide dimethylacetal (21.5 g) was refluxed for 1 hr. The reaction mixture was concentrated, and the residue was dissolved in ethanol (80 ml). To the obtained solution was added hydroxylamine hydrochloride (16.7 g), and the mixture was refluxed for 2 hr. The reaction mixture was concentrated, water was added to the residue and the mixture as extracted with ethyl acetate. The ethyl acetate layer was washed with saturated brine, dried ($MgSO_4$) and concentrated. the residue was subjected to silica gel column chromatography, and the crystals obtained from a fraction eluted with ethyl acetate-hexane (1:5, volume ratio) were recrystallized from ethyl acetate-hexane to give crystals of ethyl 5-(4-methylthiophenyl)isoxazole-4-carboxylate (18.9 g, yield 60%). melting point: 59–60° C.

Reference Example 74

To a solution of ethyl 5-(4-methylthiophenyl)isoxazole-4-carboxylate (10.0 g) in tetrahydrofuran (100 ml) was gently added diisobutylaluminum hydride (0.95 M hexane solution, 92 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The obtained crystals were recrystallized from ethyl acetate-isopropyl ether to give 5-(4-methylthiophenyl)-4-isoxazolylmethanol (7.50 g, yield 89%) as a colorless prism. melting point: 102–103° C.

Reference Example 75

To a mixture of 5-(4-methylthiophenyl)-4-isoxazolyl-methanol (7.35 g), tetrahydrofuran (20 ml) and toluene (80 ml) was added dropwise thionyl chloride (5.93 g) at 0° C. and the mixture was stirred at room temperature for 2 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was subjected to silica gel column chromatography, and 4-chloromethyl-5-(4-methylthiophenyl)isoxazole (7.70 g, yield 97%) was obtained as crystals from a fraction eluted with ethyl acetate-hexane (1:3, volume ratio) and recrystallized from diethyl ether-hexane to give a colorless prism. melting point: 73–74° C.

Reference Example 76

A mixture of 4'-methylacetophenone (15.4 g), sodium hydride (60%, oil, 4.59 g) and diethyl carbonate (80 ml) was stirred at 80° C. for 30 min. Water was added to the reaction mixture, and the mixture was neutralized with dilute hydrochloric acid and extracted with ethyl acetate. The ethyl acetate layer was washed with saturated brine, dried ($MgSO_4$) and concentrated. A mixture of the residue and N,N-dimethylformamide dimethylacetal (20.5 g) was refluxed for 1 hr. The reaction mixture was concentrated, and the residue was dissolved in ethanol (120 ml). To the obtained solution was added hydroxylamine hydrochloride (16.0 g), and the mixture was refluxed for 2 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and ethyl 5-(4-methylphenyl)isoxazole-4-carboxylate (17.2 g, yield 65%) was obtained as colorless crystals from a fraction eluted with ethyl acetate-hexane (1:9, volume ratio) and recrystallized from hexane to give a colorless prism. melting point: 45–46° C.

Reference Example 77

To a solution of ethyl 5-(4-methylphenyl)isoxazole-4-carboxylate (7.70 g) in tetrahydrofuran (100 ml) was gently added diisobutylaluminum hydride (1.0 M toluene solution, 83 ml) at 0° C. and the mixture was stirred at room temperature for 2 hr. The reaction mixture was poured into dilute hydrochloric acid, and the mixture was extracted with ethyl acetate. The ethyl acetate layer was washed with saturated brine, dried ($MgSO_4$) and concentrated. The residue was dissolved in toluene (100 ml) and thionyl chloride (5.94 g) was added dropwise at 0° C., after which the mixture was stirred at room temperature for 1 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was subjected to silica gel column chromatography, and 4-chloromethyl-5-(4-methylphenyl)isoxazole (6.49 g, yield 94%) was obtained as an oil from a fraction eluted with ethyl acetate-hexane (1:9, volume ratio). NMR ($CDCl_3$) δ: 2.44 (3H, s), 4.62 (2H, s), 7.34 (2H, d, J=8 Hz), 7.67 (2H, d, J=8 Hz), 8.35 (1H, s).

Reference Example 78

A mixture of 2-acetyl-4,5-dichlorothiophene (6.10 g), sodium hydride (60%, oil, 1.25 g) and diethyl carbonate (60 ml) was stirred at 80° C. for 30 min. Water was added to the reaction mixture, and the mixture was neutralized with dilute hydrochloric acid and extracted with ethyl acetate. The ethyl acetate layer was washed with saturated brine, dried ($MgSO_4$) and concentrated. The residue was subjected to silica gel column chromatography, and an oil was obtained from a fraction eluted with ethyl acetate-hexane (1:9, volume ratio). A mixture of the oil and N,N-dimethylformamide dimethylacetal (5.60 g) was refluxed for 1 hr. The reaction mixture was concentrated, and the residue was dissolved in ethanol (80 ml). To the obtained solution was added hydroxylamine hydrochloride (4.35 g) and the mixture was refluxed for 1.5 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and ethyl 5-(4,5-dichloro-2-thienyl)isoxazole-4-carboxylate (3.42 g, yield 37%) was obtained as colorless crystals from a fraction eluted with ethyl acetate-hexane (1:9, volume ratio) and recrystallized from ethyl acetate to give a pale-yellow prism. melting point: 120–121° C.

Referenc Exampl 79

To a solution of ethyl 5-(4,5-dichloro-2-thienyl)isoxazole-4-carboxylate (3.30 g) in tetrahydrofuran (60 ml) was gently added diisobutylaluminum hydride (0.95 M hexane solution, 29.7 ml) at 0° C. and the mixture was stirred at room temperature for 2 hr. The reaction mixture was poured into dilute hydrochloric acid, and the mixture was extracted with ethyl acetate. The ethyl acetate layer was washed with saturated brine, dried ($MgSO_4$) and concentrated. The residue was dissolved in toluene (60 ml), thionyl chloride (2.02 g) was added dropwise at 0° C., and the mixture was stirred at room temperature for 1 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was subjected to silica gel column chromatography, and 4-chloromethyl-5-(4,5-dichloro-2-thienyl)isoxazole (2.41 g, yield 79%) was obtained as crystals from a fraction eluted with ethyl acetate-hexane (1:9, volume ratio) and recrystallized from hexane to give a colorless prism. melting point: 60–61° C.

Reference Example 80

A mixture of 4-nitrobenzylbromide (15.0 g) and triisopropyl phosphite (15.9 g) was stirred for 3 hr while heating under reflux. The reaction mixture was subjected to silica gel column chromatography, and diisopropyl 4-nitrobenzylphosphonate (19.5 g) was obtained as an oil from a fraction eluted with ethyl acetate-chloroform (1:1, volume ratio). A mixture of this oil, 5% palladium-carbon (2.3 g) and ethanol (130 ml) was stirred at room temperature for 6 hr under a hydrogen atmosphere. The catalyst was filtered off and the filtrate (ethanol solution) was concentrated to give diisopropyl 4-aminobenzylphosphonate (17.2 g, yield 98%) as a yellow oil.

NMR ($CDCl_3$) δ: 1.17 (6H, d, J=7 Hz), 1.27 (6H, d, J=7 Hz), 2.92 (2H, brs), 3.25 (2H, d, J=22 Hz), 4.55–4.65 (2H, m), 6.64 (2H, d, J=8 Hz), 7.09 (2H, dd, J=3/9 Hz).

In the same manner as in Reference Example 1, the following compounds were synthesized.

Reference Example 81

Dibutyl 4-aminobenzylphosphonate
yield 98% (yellow oil)
NMR ($CDCl_3$) δ: 0.90 (6H, t, J=7 Hz), 1.25–1.45 (4H, m), 1.5–1.65 (4H, m), 2.87 (2H brs), 3.04 (2H, d, J=22 Hz), 3.9–4.05 (4H, m), 6.66 (2H, d, J=8 Hz), 7.08 (2H, dd, J=3/9 Hz).

Reference Example 82

Diethyl 4-amino-3-methylbenzylphosphonate
yield 97% (yellow oil)
NMR ($CDCl_3$) δ: 1.25 (6H, t, J=7 Hz), 2.16 (3H, s), 3.03 (2H, d, J=21 Hz), 3.18 (2H, s), 3.95–4.05 (4H, m), 6.66 (2H, d, J=8 Hz), 6.95–7.0 (2H, m).

Reference Example 83

To a mixture of titanium tetrachloride (20.0 g) and tetrahydrofuran (100 ml) were added 4-nitrobenzaldehyde (8.00 g) and ethyl diethylphosphonoacetate (11.9 g) under ice-cooling, and N-methylmorpholine (21.4 g) was added. The mixture was stirred at room temperature for 1 hr. The reaction mixture was poured into water and the mixture was extracted with ethyl acetate. The ethyl acetate layer was concentrated to give crystals of 4-[(E)-2-(diethylphosphono)-2-ethoxycarbonylethenyl]nitrobenzene (15.7 g, yield 83%), which were recrystallized from dichloromethane-isopropyl ether to give a colorless prism (14.0 g). melting point: 60–61° C. A mixture of this compound (5.00 g), iron (3.13 g), conc. hydrochloric acid (7 ml) and ethanol (30 ml) was stirred at room temperature for 30 min. The reaction mixture was poured into water and the mixture was extracted with ethyl acetate. The ethyl acetate layer was concentrated, and the residue was subjected to silica gel column chromatography to give crystals of 4-[(E)-2-(diethylphosphono)-2-ethoxycarbonylethenyl]aniline (2.40 g, yield 52%) from a fraction eluted with ethyl acetate-hexane (2:1, v/v), which were recrystallized from acetone-isopropyl ether to give a pale yellow needle (1.75 g). melting point: 79–80° C.

Elemental analysis: Calculated ($C_{15}H_{22}NO_5P$) C, 55.04; H, 6.77; N, 4.29. Found C, 55.07; H, 6.92; N, 4.25.

Example 1

To a solution of 5-(4-trifluoromethoxyphenyl)-4-isoxazolylmethanol (5.60 g) in toluene (100 ml) was added dropwise thionyl chloride (2.36 ml) at 0° C. and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was dissolved in tetrahydrofuran (100 ml) and added to a mixture of diethyl malonate (6.92 g), sodium hydride (60%, oil, 1.72 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (70 ml) and acetic acid (70 ml) was refluxed for 5 hr. The reaction mixture was concentrated, and water was added to the residue. The obtained colorless crystals were filtrated to give 3-[5-(4-trifluoromethoxyphenyl)-4-isoxazolyl]propionic acid (3.77 g, yield 58%). The crystals were recrystallized from acetone-hexane. melting point: 116–118° C.

Example 2

A mixture of 3-[5-(4-trifluoromethoxyphenyl)-4-isoxazolyl]propionic acid (3.30 g), conc. sulfuric acid (0.2 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(4-trifluoromethoxyphenyl)-4-isoxazolyl]propionate (2.80 g, yield 81%) was obtained as a colorless oil from a fraction eluted with ethyl acetate-hexane (1:3, volume ratio). NMR (CDCl$_3$) δ: 2.66 (2H, t, J=7.4 Hz), 2.99 (2H, q, J=7.4 Hz), 3.69 (3H, s), 7.35 (2H, dd, J=1.0, 9.2 Hz), 7.76 (2H, d, J=9.2 Hz), 8.24 (1H, s).

Example 3

To a solution of methyl 3-[5-(4-trifluoromethoxyphenyl)-4-isoxazolyl]propionate (1.63 g) in tetrahydrofuran (25 ml) was gently added diisobutylaluminum hydride (1.0 M hexane solution, 13.2 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(4-trifluoromethoxyphenyl)-4-isoxazolyl]propan-1-ol (1.36 g, yield 92%) was obtained as colorless crystals from a fraction eluted with ethyl acetate-hexane (2:1, volume ratio). The crystals were recrystallized from ethyl acetate-hexane. melting point: 50–51° C.

Example 4

A mixture of 3-[5-(4-bromophenyl)-4-isoxazolyl]propan-1-ol (1.10 g), copper cyanide (1.41 g), tris(dibenzylideneacetone)dipalladium (130 mg), 1,1'-bis(diphenylphosphino)ferrocene (314 mg), tetraethylammonium cyanide (553 mg) and 1,4-dioxane (20 ml) was refluxed for 3.5 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography, and 3-[5-(4-cyanophenyl)-4-isoxazolyl]propan-1-ol (418 mg, yield 52%) was obtained as pale yellow crystals from a fraction eluted with ethyl acetate-hexane (1:3, volume ratio). The crystals were recrystallized from ethyl acetate-hexane. melting point: 82–83° C.

Example 5

To a solution of ethyl propiolate (6.13 g) in tetrahydrofuran (40 ml) was gently added a solution of pyrrolidine (5.2 ml) in tetrahydrofuran (5 ml) at 0° C. and the mixture was stirred at 0° C. for 30 min. To the obtained mixture was added a solution of 4-chloro-N-hydroxybenzenecarboxyimidoyl chloride (7.60 g) in tetrahydrofuran (100 ml) at 0° C., and a solution of triethylamine (11.5 ml) in tetrahydrofuran (10 ml) was gently added at 0° C. The mixture was stirred at room temperature overnight, poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:9, volume ratio). To a solution of the obtained colorless oil in tetrahydrofuran (100 ml) was gently added diisobutylaluminum hydride (1.0 M hexane solution, 85 ml) at 1° C. and the mixture was stirred at room temperature for 30 min. The reaction mixture was poured into dilute hydrochloric acid, and the mixture was extracted with ethyl acetate. The ethyl acetate layer was washed with saturated brine, dried (MgSO$_4$) and concentrated to give a colorless oil. To a solution of the obtained colorless oil in toluene (100 ml) was added dropwise thionyl chloride (4.50 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml), and added to a mixture of diethyl malonate (12.81 g), sodium hydride (60%, oil, 3.20 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[3-(4-chlorophenyl)-4-isoxazolyl]propionic acid (4.93 g, yield 49%). The crystals were recrystallized from isopropyl ether. melting point: 149–150° C.

Example 6

To a solution of 5-(3-bromo-4-chlorophenyl)-4-isoxazolylmethanol (5.09 g) in toluene (100 ml) was added dropwise thionyl chloride (1.93 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (50 ml), and added to a mixture of diethyl malonate (5.64 g), sodium hydride (60%, oil, 1.41 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(3-bromo-4-chlorophenyl)-4-isoxazolyl]propionic acid (3.24 g, yield 56%). The crystals were recrystallized from diethyl ether-hexane. melting point: 177–180° C.

Example 7

A mixture of ethyl benzoylacetate (12.65 g) and N,N-dimethylformamide dimethylacetal (11.80 g) was refluxed for 1.5 hr. The reaction mixture was concentrated, and the residue was dissolved in ethanol (200 ml). To the obtained solution was added hydroxylamine hydrochloride (9.18 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and a yellow oil was obtained from a fraction eluted with ethyl acetate-hexane (1:2, volume ratio). To a solution of the obtained yellow oil in tetrahydrofuran (100 ml) was gently added diisobutylaluminum hydride (1.0 M hexane solution, 100 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried ($MgSO_4$) and concentrated. To a solution of the residue in toluene (100 ml) was added dropwise thionyl chloride (5.0 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was dissolved in tetrahydrofuran (100 ml) and added to a mixture of diethyl malonate (13.50 g), sodium hydride (60%, oil, 3.33 g) and tetrahydrofuran (30 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-(5-phenyl-4-isoxazolyl)propionic acid (9.14 g, yield 64%). The crystals were recrystallized from isopropyl ether. melting point: 90–91° C.

Example 8

A mixture of 4'-chloroacetophenone (10.47 g), sodium hydride (60%, oil, 2.71 g) and diethyl carbonate (150 ml) was stirred at 80° C. for 1 hr. Water was added to the reaction mixture, and the aqueous layer was neutralized with dilute hydrochloric acid. The mixture was stirred at room temperature for 30 min, and then extracted with ethyl acetate. The ethyl acetate layer was washed with saturated brine, dried ($MgSO_4$) and concentrated. A mixture of the residue and N,N-dimethylformamide dimethylacetal (12.18 g) was refluxed for 1.5 hr. The reaction mixture was concentrated, and the residue was dissolved in ethanol (200 ml). To the obtained solution was added hydroxylamine hydrochloride (9.49 g) and the mixture was refluxed for 5 hr. The reaction mixture was concentrated, dilute hydrochloric acid was added to the residue, and the mixture was extracted with ethyl acetate. The ethyl acetate layer was washed with saturated brine, dried ($MgSO_4$) and concentrated. The residue was subjected to silica gel column chromatography, and a yellow oil was obtained from a fraction eluted with ethyl acetate-hexane (1:2, volume ratio). To a solution of the obtained yellow oil in tetrahydrofuran (100 ml) was gently added diisobutylaluminum hydride (1.0 M hexane solution, 100 ml) at 0° C., and the mixture was stirred at room temperature for 30 min. The reaction mixture was poured into dilute hydrochloric acid, and the mixture was extracted with ethyl acetate. The ethyl acetate layer was washed with saturated brine, dried ($MgSO_4$) and concentrated. To a solution of the residue in toluene (100 ml) was added dropwise thionyl chloride (2.7 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was dissolved in tetrahydrofuran (100 ml) and added to a mixture of diethyl malonate (7.96 g), sodium hydride (60%, oil, 1.95 g) and tetrahydrofuran (30 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(4-chlorophenyl)-4-isoxazolyl]propionic acid (7.84 g, yield 46%). The crystals were recrystallized from isopropyl ether. melting point: 155–154° C.

Example 9

To a solution of methyl 3-[5-(3-bromo-4-chlorophenyl)-4-isoxazolyl]propionate (1.00 g) in tetrahydrofuran (30 ml) was gently added diisobutylaluminum hydride (1.0 M hexane solution, 6.5 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[5-(3-bromo-4-chlorophenyl)-4-isoxazolyl]propan-1-ol (0.85 g, yield 92%) was obtained as colorless crystals from a fraction eluted with ethyl acetate-hexane (2:1, volume ratio). The crystals were recrystallized from ethyl acetate-hexane. melting point: 75–76° C.

Example 10

To a solution of diethyl malonate (4.71 g) in tetrahydrofuran (40 ml) was gradually added sodium hydride (60%, oil, 1.07 g) at 0° C. The mixture was stirred for 10 min and a solution of 4-chloromethyl-5-(4-trifluoromethylphenyl)isoxazole (3.50 g) in tetrahydrofuran (40 ml) was added dropwise at 0° C. The mixture was stirred at room temperature for 15 hr. The reaction mixture was poured into water, acidified with 2N hydrochloric acid and extracted with ethyl acetate. The ethyl acetate layer was washed with saturated brine, dried ($MgSO_4$) and concentrated. The residue was dissolved in a mixture of 6N hydrochloric acid (40 ml) and acetic acid (60 ml) and heated under reflux for 8 hr. The reaction mixture was concentrated, and water was added to the residue. The obtained colorless crystals were filtrated, dried and recrystallized from ethyl acetate to give a colorless prism (3.00 g, yield 79%) of 3-[5-(4-trifluoromethylphenyl)-4-isoxazolyl]propionic acid. melting point: 171–172° C.

Example 11

To a solution of 5-(4-fluorophenyl)-4-isoxazolylmethanol (5.84 g) in toluene (50 ml) was added dropwise thionyl chloride (3 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was dissolved in tetrahydrofuran (100 ml) and added to a mixture of diethyl malonate (6.92 g), sodium hydride (60%, oil, 1.70 g) and tetrahydrofuran (50 ml) t 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (30 ml) and acetic acid (50 ml) was refluxed for 5 hr. The reaction mixture was concentrated, and water was added to the residue. The obtained colorless crystals were filtrated to give 3-[5-(4-fluorophenyl)-4-isoxazolyl]propionic acid (4.53 g, yield 78%). The crystals were recrystallized from isopropyl ether. melting point: 126–127° C.

Example 12

To a solution of diethyl malonate (11.0 g) in tetrahydrofuran (60 ml) was gradually added sodium hydride (60%, oil, 2.50 g) at 0° C. The mixture was stirred for 10 min and a solution of 4-chloromethyl-5-(4-methylphenyl)isoxazole (6.48 g) in tetrahydrofuran (80 ml) was added dropwise at 0° C. The mixture was stirred at room temperature for 15 hr. The reaction mixture was poured into 2N hydrochloric acid and the mixture was extracted with ethyl acetate. The ethyl acetate layer was concentrated and the residue was dissolved in a mixture of 6N hydrochloric acid (80 ml) and acetic acid (120 ml). The mixture was heated under reflux for 8 hr. The reaction mixture was concentrated, and water was added to the residue. The obtained colorless crystals were filtrated, dried and recrystallized from ethyl acetate-hexane to give a colorless prism (5.03 g, yield 70%) of 3-[5-(4-methylphenyl)-4-isoxazolyl]propionic acid. melting point: 121–122° C.

Example 13

To a solution of 5-(4-methoxyphenyl)-4-isoxazolylmethanol (6.09 g) in toluene (100 ml) was added dropwise thionyl chloride (3.3 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was dissolved in tetrahydrofuran (100 ml) and added to a mixture of diethyl malonate (9.51 g), sodium hydride (60%, oil, 2.32 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(4-methoxyphenyl)-4-isoxazolyl]propionic acid (5.16 g, yield 70%). The crystals were recrystallized from isopropyl ether-diethyl ether. melting point: 101–102° C.

Example 14

A mixture of diethyl 4-aminobenzylphosphonate (0.37 g), 3-[5-(4-chlorophenyl)-4-isoxazolyl]propionic acid (0.35 g), 1-hydroxy-1H-1,2,3-benzotriazole hydrate (0.25 g), 1-ethyl-3-(3-dimethylaminopropyl)carbodiimide hydrochloride (0.33 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-(4-diethylphosphonomethylphenyl)-3-[5-(4-chlorophenyl)-4-isoxazolyl]propionamide (0.61 g, yield 92%) was obtained as colorless crystals from a fraction eluted with ethyl acetate-hexane (1:1, volume ratio). The crystals were recrystallized from ethyl acetate-hexane. melting point: 138–139° C.

Example 15

A mixture of 3-[5-(4-chlorophenyl)-4-isoxazolyl]propionic acid (6.57 g), conc. sulfuric acid (0.5 ml) and methanol (100 ml) was refluxed for 4 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and methyl 3-[5-(4-chlorophenyl)-4-isoxazolyl]propionate (6.51 g, yield 94%) was obtained as colorless crystals from a fraction eluted with ethyl acetate-hexane (1:3, volume ratio). The crystals were recrystallized from ethyl acetate-hexane. melting point: 51–52° C.

Example 16

To a solution of methyl 3-[5-(4-chlorophenyl)-4-isoxazolyl]propionate (6.00 g) in tetrahydrofuran (100 ml) was gently added diisobutylaluminum hydride (1.0 M hexane solution, 50 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[5-(4-chlorophenyl)-4-isoxazolyl]propan-1-ol (4.89 g, yield 91%) was obtained as colorless crystals from a fraction eluted with ethyl acetate-hexane (2:1, volume ratio). The crystals were recrystallized from ethyl acetate-hexane. melting point: 58–59° C.

Example 17

A mixture of diethyl 4-aminobenzylphosphonate (0.76 g), 3-[3-(4-chlorophenyl)-4-isoxazolyl]propionic acid (0.66 g), 1-hydroxy-1H-1,2,3-benzotriazole hydrate (0.49 g), 1-ethyl-3-(3-dimethylaminopropyl)carbodiimide hydrochloride (1.41 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-(4-diethylphosphonomethylphenyl)-3-[3-(4-chlorophenyl)-4-isoxazolyl]propionamide (1.14 g, yield 91%) was obtained as colorless crystals from a fraction eluted with ethyl acetate-hexane (1:1, volume ratio). The crystals were recrystallized from ethyl acetate-hexane. melting point: 88–90° C.

Example 18

To a mixture of 3-[3-(4-chlorophenyl)-4-isoxazolyl]propionic acid (1.28 g), triethylamine (1.1 ml) and tetrahydrofuran (100 ml) was added ethyl chlorocarbonate (0.6 ml) at −30° C. and the mixture was stirred at −20° C. for 1 hr. To the obtained mixture was added aqueous ammonia (15 ml) and the mixture was stirred at room temperature for 1 hr. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated to give 3-[3-(4-chlorophenyl)-4-isoxazolyl]propionamide (0.91 g, yield 71%) as colorless crystals. The crystals were recrystallized from acetone-hexane. melting point: 158–159° C.

Example 19

A mixture of 3-[3-(4-chlorophenyl)-4-isoxazolyl]propionic acid (4.05 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and methyl 3-[3-(4-chlorophenyl)-4-isoxazolyl]propionate (3.93 g, yield 92%) was obtained as colorless crystals from a fraction eluted with ethyl acetate-hexane (1:3, volume ratio). The crystals were recrystallized from ethyl acetate-hexane. melting point: 56–57° C.

Example 20

A mixture of 3-trifluoromethylbenzylamine (0.75 ml), 3-[3-(4-chlorophenyl)-4-isoxazolyl]propionic acid (0.90 g), 1-hydroxy-1H-1,2,3-benzotriazole hydrate (0.82 g), 1-ethyl-3-(3-dimethylaminopropyl)carbodiimide hydrochloride (1.03 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-(3-trifluoromethylbenzyl)-3-[3-(4-chlorophenyl)-4-isoxazolyl]propionamide (1.27 g, yield 87%) was obtained as colorless crystals from a fraction eluted with ethyl acetate-hexane (1:1, volume ratio). The crystals were recrystallized from isopropyl ether-hexane. melting point: 80–81° C.

Example 21

A mixture of diethyl 4-aminobenzylphosphonate (1.25 g), 3-(5-phenyl-4-isoxazolyl)propionic acid (1.00 g), 1-hydroxy-1H-1,2,3-benzotriazole hydrate (0.80 g), 1-ethyl-3-(3-dimethylaminopropyl)carbodiimide hydrochloride (1.08 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-(4-diethylphosphonomethylphenyl)-3-(5-phenyl-4-isoxazolyl)propionamide (1.89 g, yield 93%) was obtained as colorless crystals from a fraction eluted with ethyl acetate-hexane (1:1, volume ratio). The crystals were recrystallized from ethyl acetate-hexane. melting point: 139–140° C.

Example 22

To a mixture of 3-(5-phenyl-4-isoxazolyl)propionic acid (1.08 g), triethylamine (1.1 ml) and tetrahydrofuran (100 ml) was added ethyl chlorocarbonate (0.6 ml) at −30° C. and the mixture was stirred at −20° C. for 1 hr. To the obtained mixture was added aqueous ammonia (20 ml), and the mixture was stirred at room temperature for 1 hr. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated to give 3-(5-phenyl-4-isoxazolyl)propionamide (0.82 g, yield 78%) as colorless crystals. The crystals were recrystallized from ethyl acetate-hexane. melting point: 151–152° C.

Example 23

To a mixture of 3-(5-phenyl-4-isoxazolyl)propionic acid (1.00 g), triethylamine (1.0 ml) and tetrahydrofuran (50 ml) was added ethyl chlorocarbonate (0.5 ml) at −30° C. and the mixture was stirred at −20° C. for 1 hr. To the obtained mixture was added aqueous ethylamine solution (10 ml), and the mixture was stirred at room temperature for 1 hr. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated to give N-ethyl-3-(5-phenyl-4-isoxazolyl)propionamide (0.93 g, yield 83%) as colorless crystals. The crystals were recrystallized from ethyl acetate-hexane. melting point: 75–76° C.

Example 24

A mixture of ethyl (E)-3-(5-phenyl-4-isoxazolyl)propenoate (4.89 g), 2N hydrochloric acid (50 ml) and acetic acid (50 ml) was refluxed for 3 hr. The reaction mixture was concentrated, and water was added to the residue. The obtained colorless crystals were filtrated to give (E)-3-(5-phenyl-4-isoxazolyl)propenoic acid (4.02 g, yield 93%). The crystals were recrystallized from acetone-hexane. melting point: 197–199° C.

Example 25

To a mixture of (E)-3-(5-phenyl-4-isoxazolyl)propenoic acid (0.97 g), triethylamine (1 ml) and tetrahydrofuran (60 ml) was added ethyl chlorocarbonate (0.5 ml) at −30° C. and the mixture was stirred at −20° C. for 1 hr. To the obtained mixture was added aqueous ammonia (1 ml), and the mixture was stirred at room temperature for 1 hr. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated to give (E)-3-(5-phenyl-4-isoxazolyl)propenamide (0.86 g, yield 89%) as colorless crystals. The crystals were recrystallized from acetone-hexane. melting point: 194–196° C.

Example 26

A mixture of diethyl 4-aminobenzylphosphonate (0.83 g), (E)-3-(5-phenyl-4-isoxazolyl)propenoic acid (0.69 g), 1-hydroxy-1H-1,2,3-benzotriazole hydrate (0.54 g), 1-ethyl-3-(3-dimethylaminopropyl)carbodiimide hydrochloride (0.65 g) and N,N-dimethylformamide (30 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and (E)-N-(4-diethylphosphonomethylphenyl)-3-(5-phenyl-4-isoxazolyl)propenamide (0.86 g, yield 61%) was obtained as colorless crystals from a fraction eluted with ethyl acetate-hexane (1:1, volume ratio). The crystals were recrystallized from ethyl acetate-hexane. melting point: 173–174° C.

Example 27

To a mixture of (E)-3-(5-phenyl-4-isoxazolyl)propenoic acid (0.76 g), triethylamine (0.8 ml) and tetrahydrofuran (50 ml) was added ethyl chlorocarbonate (0.4 ml) at −30° C. and the mixture was stirred at −20° C. for 1 hr. To the obtained mixture was added aqueous ethylamine solution (1 ml), and the mixture was stirred at room temperature for 1 hr. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated to give (E)-N-ethyl-3-(5-phenyl-4-isoxazolyl)propenamide (0.78 g, yield 91%) as colorless crystals. The crystals were recrystallized from acetone-hexane. melting point: 156–157° C.

Example 28

To a mixture of 3-(3-methyl-5-phenyl-4-isoxazolyl)propionic acid (0.95 g), triethylamine (1.0 ml) and tetrahydrofuran (50 ml) was added ethyl chlorocarbonate (0.5 ml) at −30° C. and the mixture was stirred at −20° C. for 1 hr. To the obtained mixture was added aqueous ammonia (5 ml), and the mixture was stirred at room temperature for 1 hr. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated to give 3-(3-methyl-5-phenyl-4-isoxazolyl)propionamide (0.86 g, yield 91%) as colorless crystals. The crystals were recrystallized from ethyl acetate-hexane. melting point: 149–151° C.

Example 29

A mixture of methyl 4-aminobenzoate (0.47 g), 3-(3-methyl-5-phenyl-4-isoxazolyl)propionic acid (0.60 g), 1-hydroxy-1H-1,2,3-benzotriazole hydrate (0.50 g), 1-ethyl-3-(3-dimethylaminopropyl)carbodiimide hydrochloride (0.61 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-(4-methoxycarbonylphenyl)-3-(3-methyl-5-phenyl-4-isoxazolyl)propionamide (0.75 g, yield 79%) was obtained as colorless crystals from a fraction eluted with ethyl acetate-hexane (1:1, volume ratio). The crystals were recrystallized from ethyl acetate-hexane. melting point: 140–141° C.

Example 30

A mixture of N-diphenylmethylpiperazine (0.85 g), 3-(5-phenyl-4-isoxazolyl)propionic acid (0.70 g), 1-hydroxy-1H-1,2,3-benzotriazole hydrate (0.55 g), 1-ethyl-3-(3-dimethylaminopropyl)carbodiimide hydrochloride (0.69 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-diphenylmethyl-N'-[3-(5-phenyl-4-isoxazolyl)propionyl]piperazine (1.35 g, yield 93%) was obtained as a colorless oil from a fraction eluted with ethyl acetate-hexane (1:1, volume ratio). NMR (CDCl$_3$) δ: 2.26–2.42 (4H, m), 2.50–2.64 (2H, m), 2.94–3.08 (2H, m), 3.32–3.44 (2H, m), 3.56–3.68 (2H, m), 4.22 (1H, s), 7.12–7.54 (13H, m), 7.66–7.86 (2H, m), 8.21 (1H, s).

Example 31

A mixture of 2-amino-4-(4-chlorophenyl)thiazole (0.75 g), 3-(5-phenyl-4-isoxazolyl)propionic acid (0.72 g), 1-hydroxy-1H-1,2,3-benzotriazole hydrate (0.55 g), 1-ethyl-3-(3-dimethylaminopropyl)carbodiimide hydrochloride (0.70 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-[4-(4-chlorophenyl)-2-thiazolyl]-3-(5-phenyl-4-isoxazolyl)propionamide (0.58 g, yield 43%) was obtained as colorless crystals from a fraction eluted with ethyl acetate-hexane (1:1, volume ratio). The crystals were recrystallized from ethyl acetate-hexane. melting point: 172–173° C.

Example 32

A mixture of methyl 4-aminobenzoate (0.46 g), 3-(5-phenyl-4-isoxazolyl)propionic acid (0.60 g), 1-hydroxy-1H-1,2,3-benzotriazole hydrate (0.48 g), 1-ethyl-3-(3-dimethylaminopropyl)carbodiimide hydrochloride (0.61 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-(4-methoxycarbonylphenyl)-3-(5-phenyl-4-isoxazolyl)propionamide (0.86 g, yield 89%) was obtained as colorless crystals from a fraction eluted with ethyl acetate-hexane (1:1, volume ratio). The crystals were recrystallized from ethyl acetate-hexane. melting point: 111–112° C.

Example 33

A mixture of 2-amino-5-methyl-4-phenylthiazole (0.95 g), 3-(5-phenyl-4-isoxazolyl)propionic acid (1.01 g), 1-hydroxy-1H-1,2,3-benzotriazole hydrate (0.78 g), 1-ethyl-3-(3-dimethylaminopropyl)carbodiimide hydrochloride (0.97 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-(5-methyl-4-phenyl-2-thiazolyl)-3-(5-phenyl-4-isoxazolyl)propionamide (1.74 g, yield 96%) was obtained as colorless crystals from a fraction eluted with ethyl acetate-hexane (1:1, volume ratio). The crystals were recrystallized from ethyl acetate-hexane. melting point: 150–151° C.

Example 34

A mixture of 2-aminoquinoline (0.55 g), 3-(5-phenyl-4-isoxazolyl)propionic acid (0.82 g), 1-hydroxy-1H-1,2,3-benzotriazole hydrate (0.68 g), 1-ethyl-3-(3-dimethylaminopropyl)carbodiimide hydrochloride (0.91 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-(2-quinolyl)-3-(5-phenyl-4-isoxazolyl)propionamide (1.09 g, yield 84%) was obtained as colorless crystals from a fraction eluted with ethyl acetate-hexane (1:1, volume ratio). The crystals were recrystallized from ethyl acetate-hexane. melting point: 112–113° C.

Example 35

A mixture of 4-aminobenzamide (0.55 g), 3-(5-phenyl-4-isoxazolyl)propionic acid (0.87 g), 1-hydroxy-1H-1,2,3-benzotriazole hydrate (0.68 g), 1-ethyl-3-(3-dimethylaminopropyl)carbodiimide hydrochloride (0.88 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-(4-carbamoylphenyl)-3-(5-phenyl-4-isoxazolyl)propionamide (0.95 g, yield 71%) was obtained as colorless crystals from a fraction eluted with ethyl acetate-hexane (1:1, volume ratio). The crystals were recrystallized from tetrahydrofuran-hexane. melting point: 250–251° C.

Example 36

A mixture of 3-(2-aminoethyl)indole hydrochloride (0.46 g), triethylamine (0.6 ml) and N,N-dimethylformamide (20 ml) was stirred at room temperature for 1 hr. To the obtained mixture was added 3-(5-phenyl-4-isoxazolyl)propionic acid (0.42 g), 1-hydroxy-1H-1,2,3-benzotriazole hydrate (0.37 g) and 1-ethyl-3-(3-dimethylaminopropyl)carbodiimide hydrochloride (0.45 g), and the mixture was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-[2-(3-indolyl)ethyl]-3-(5-phenyl-4-isoxazolyl)propionamide (0.63 g, yield 91%) was obtained as a colorless oil from a fraction eluted with ethyl acetate-hexane (1:1, volume ratio). NMR (CDCl$_3$) δ: 2.32–2.44 (2H, m), 2.88–3.04 (4H, m), 3.54–3.66 (2H, m), 5.45 (1H, br s), 6.93 (1H, d, J=2.2 Hz), 7.04–7.28 (2H, m), 7.32–7.62 (5H, m), 7.64–7.74 (2H, m), 8.05 (1H, br s), 8.17 (1H, s).

Example 37

A mixture of diethyl 4-aminobenzylphosphonate (1.20 g), 5-phenyl-4-isoxazolylacetic acid (0.84 g), 1-hydroxy-1H-1,2,3-benzotriazole hydrate (0.75 g), 1-ethyl-3-(3-dimethylaminopropyl)carbodiimide hydrochloride (0.97 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-(4-diethylphosphonomethylphenyl)-5-phenyl-4-isoxazolylacetamide (1.58 g, yield 89%) was obtained as colorless crystals from a fraction eluted with ethyl acetate-hexane (1:1, volume ratio). The crystals were recrystallized from ethyl acetate-hexane. melting point: 132–133° C.

Example 38

A mixture of 2-amino-4-(4-chlorophenyl)thiazole (0.65 g), 5-phenyl-4-isoxazolylacetic acid (0.60 g), 1-hydroxy-1H-1,2,3-benzotriazole hydrate (0.51 g), 1-ethyl-3-(3-dimethylaminopropyl)carbodiimide hydrochloride (0.59 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-[4-(4-chlorophenyl)-2-thiazolyl]-5-phenyl-4-isoxazolylacetamide (0.92 g, yield 79%) was obtained as colorless crystals from a fraction eluted with ethyl acetate-hexane (1:1, volume ratio). The crystals were recrystallized from ethyl acetate-hexane. melting point: 210–211° C.

Example 39

A mixture of ethyl 4-aminophenylacetate (0.32 g), 3-[5-(4-chlorophenyl)-4-isoxazolyl]propionic acid (0.37 g), 1-hydroxy-1H-1,2,3-benzotriazole hydrate (0.28 g), 1-ethyl-3-(3-dimethylaminopropyl)carbodiimide hydrochloride (0.35 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-(4-ethoxycarbonylmethylphenyl)-3-[5-(4-chlorophenyl)-4-isoxazolyl]propionamide (0.56 g, yield 93%) was obtained as colorless crystals from a fraction eluted with ethyl acetate-hexane (1:1, volume ratio). The crystals were recrystallized from ethyl acetate-hexane. melting point: 117–118° C.

Example 40

A mixture of 3-aminopyridine (0.18 g), 3-[5-(4-chlorophenyl)-4-isoxazolyl]propionic acid (0.50 g), 1-hydroxy-1H-1,2,3-benzotriazole hydrate (0.35 g), 1-ethyl-3-(3-dimethylaminopropyl)carbodiimide hydrochloride (0.45 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-(3-pyridyl)-3-[5-(4-chlorophenyl)-4-isoxazolyl]propionamide (0.60 g, yield 96%) was obtained as colorless crystals from a fraction eluted with ethyl acetate-hexane (1:1, volume ratio). The crystals were recrystallized from acetone-hexane. melting point: 197–198° C.

Example 41

A mixture of 5-amino-2-(2-methyl-1-imidazolyl)pyridine (0.40 g), 3-[5-(4-chlorophenyl)-4-isoxazolyl]propionic acid (0.58 g), 1-hydroxy-1H-1,2,3-benzotriazole hydrate (0.45 g), 1-ethyl-3-(3-dimethylaminopropyl)carbodiimide hydrochloride (0.54 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-[6-(2-methyl-1-imidazolyl)-3-pyridyl]-3-[5-(4-chlorophenyl)-4-isoxazolyl]propionamide (0.59 g, yield 63%) was obtained as colorless crystals from a fraction eluted with ethyl acetate-hexane (1:1, volume ratio). The crystals were recrystallized from acetone-hexane. melting point: 193–194° C.

Example 42

A mixture of 1-(3-methoxyphenyl)ethylamine (0.32 g), 3-[5-(4-chlorophenyl)-4-isoxazolyl]propionic acid (0.45 g), 1-hydroxy-1H-1,2,3-benzotriazole hydrate (0.33 g), 1-ethyl-3-(3-dimethylaminopropyl)carbodiimide hydrochloride (0.40 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-[1-(3-methoxyphenyl)ethyl]-3-[5-(4-chlorophenyl)-4-isoxazolyl]propionamide (0.61 g, yield 88%) was obtained as colorless crystals from a fraction eluted with ethyl acetate-hexane (1:1, volume ratio). The crystals were recrystallized from ethyl acetate-hexane. melting point: 89–90° C.

Example 43

A mixture of 2-aminomethyl-5-methylpyrazine (0.25 ml), 3-[5-(4-chlorophenyl)-4-isoxazolyl]propionic acid (0.45 g), 1-hydroxy-1H-1,2,3-benzotriazole hydrate (0.35 g), 1-ethyl-3-(3 -dimethylaminopropyl)carbodiimide hydrochloride (0.40 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-(5-methyl-2-pyrazinylmethyl)-3-[5-(4-chlorophenyl)-4-isoxazolyl]propionamide (0.58 g, yield 90%) was obtained as colorless crystals from a fraction eluted with ethyl acetate-hexane (1:1, volume ratio). The crystals were recrystallized from ethyl acetate-hexane. melting point: 124–125° C.

Example 44

A mixture of 4-(1-imidazolyl)aniline (0.51 g), 3-(5-phenyl-4-isoxazolyl)propionic acid (0.70 g), 1-hydroxy-1H-1,2,3-benzotriazole hydrate (0.60 g), 1-ethyl-3-(3-dimethylaminopropyl)carbodiimide hydrochloride (0.75 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-[4-(1-imidazolyl)phenyl]-3-(5-phenyl-4-isoxazolyl)propionamide (0.95 g, yield 83%) was obtained as colorless crystals from a fraction eluted with ethyl acetate-hexane (1:1, volume ratio). The crystals were recrystallized from ethyl acetate-hexane. melting point: 176–177° C.

Example 45

A mixture of 6-aminoquinoline (0.38 g), 3-(5-phenyl-4-isoxazolyl)propionic acid (0.56 g), 1-hydroxy-1H-1,2,3-benzotriazole hydrate (0.46 g), 1-ethyl-3-(3-dimethylaminopropyl)carbodiimide hydrochloride (0.60 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried ($MgSO_4$) and concentrated. The residue was subjected to silica gel column chromatography, and N-(6-quinolyl)-3-(5-phenyl-4-isoxazolyl)propionamide (0.79 g, yield 89%) was obtained as colorless crystals from a fraction eluted with ethyl acetate-hexane (1:1, volume ratio). The crystals were recrystallized from ethyl acetate-hexane. melting point: 170–171° C.

Example 46

A mixture of 2-aminopyrazine (0.26 g), 3-(5-phenyl-4-isoxazolyl)propionic acid (0.58 g), 1-hydroxy-1H-1,2,3-benzotriazole hydrate (0.46 g), 1-ethyl-3-(3-dimethylaminopropyl)carbodiimide hydrochloride (0.60 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-(2-pyrazinyl)-3-(5-phenyl-4-isoxazolyl)propionamide (0.46 g, yield 58%) was obtained as colorless crystals from a fraction eluted with ethyl acetate-hexane (1:1, volume ratio). The crystals were recrystallized from ethyl acetate-hexane. melting point: 163–164° C.

Example 47

A mixture of 4-(1-morpholino)aniline (0.90 g), 3-(5-phenyl-4-isoxazolyl)propionic acid (1.07 g), 1-hydroxy-1H-1,2,3-benzotriazole hydrate (0.90 g), 1-ethyl-3-(3-dimethylaminopropyl)carbodiimide hydrochloride (1.15 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-[4-(1-morpholino)phenyl]-3-(5-phenyl-4-isoxazolyl)propionamide (1.23 g, yield 66%) was obtained as colorless crystals from a fraction eluted with ethyl acetate-hexane (1:1, volume ratio). The crystals were recrystallized from acetone-hexane. melting point: 197–198° C.

Example 48

A mixture of 5-amino-2-(1-morpholino)pyridine (0.85 g), 3-(5-phenyl-4-isoxazolyl)propionic acid (1.01 g), 1-hydroxy-1H-1,2,3-benzotriazole hydrate (0.85 g), 1-ethyl-3-(3-dimethylaminopropyl)carbodiimide hydrochloride (1.09 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-[6-(1-morpholino)-3-pyridyl]-3-(5-phenyl-4-isoxazolyl)propionamide (0.86 g, yield 49%) was obtained as colorless crystals from a fraction eluted with ethyl acetate-hexane (1:1, volume ratio). The crystals were recrystallized from ethyl acetate-hexane. melting point: 146–147° C.

Example 49

A mixture of 4-(1-imidazolyl)aniline (0.85 g), 4-(5-phenyl-4-isoxazolyl)butanoic acid (1.21 g), 1-hydroxy-1H-1,2,3-benzotriazole hydrate (0.95 g), 1-ethyl-3-(3-dimethylaminopropyl)carbodiimide hydrochloride (1.20 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-[4-(1-imidazolyl)phenyl]-4-(5-phenyl-4-isoxazolyl)butaneamide (1.68 g, yield 86%) was obtained as colorless crystals from a fraction eluted with ethyl acetate-hexane (1:1, volume ratio). The crystals were recrystallized from ethyl acetate-hexane. melting point: 132–133° C.

Example 50

A mixture of 3-(5-phenyl-4-isoxazolyl)propionic acid (18.62 g), conc. sulfuric acid (0.2 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-(5-phenyl-4-isoxazolyl)propionate (19.03 g, yield 96%) was obtained as a colorless oil from a fraction eluted with ethyl acetate-hexane (1:3, volume ratio). NMR (CDCl$_3$) δ: 2.59–2.71 (2H, m), 2.95–3.06 (2H, m), 3.68 (3H, s), 7.42–7.56 (3H, m), 7.64–7.74 (2H, m), 8.22 (1H, s).

Example 51

To a solution of methyl 3-(5-phenyl-4-isoxazolyl)propionate (18.13 g) in tetrahydrofuran (300 ml) was gently added diisobutylaluminum hydride (1.0 M hexane solution, 160 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-(5-phenyl-4-isoxazolyl)propan-1-ol (15.72 g, yield 99%) was obtained as a colorless oil from a fraction eluted with ethyl acetate-hexane (2:1, volume ratio). NMR (CDCl$_3$) δ: 1.82–2.00 (2H, m), 2.72–2.88 (2H, m), 3.66–3.78 (2H, m), 7.41–7.56 (3H, m), 7.68–7.78 (2H, m), 8.21 (1H, s).

Example 52

A mixture of 4-(5-phenyl-4-isoxazolyl)butyronitrile (12.83 g) and conc. hydrochloric acid (100 ml) was refluxed overnight. The reaction mixture was extracted with ethyl acetate. The ethyl acetate layer was washed with saturated brine, dried (MgSO$_4$) and concentrated. The residue was subjected to silica gel column chromatography, and 4-(5-phenyl-4-isoxazolyl)butanoic acid (13.03 g, yield 93%) was obtained as colorless crystals from a fraction eluted with ethyl acetate-hexane (1:1, volume ratio). The crystals were recrystallized from ethyl acetate-hexane. melting point: 67–68° C.

Example 53

A mixture of diethyl 4-aminobenzylphosphonate (1.74 g), 4-(5-phenyl-4-isoxazolyl)butanoic acid (1.38 g), 1-hydroxy-1H-1,2,3-benzotriazole hydrate (1.08 g), 1-ethyl-3-(3-dimethylaminopropyl)carbodiimide hydrochloride (1.38 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-(4-diethylphosphonomethylphenyl)-4-(5-phenyl-4-isoxazolyl)butaneamide (2.56 g, yield 94%) was obtained as colorless crystals from a fraction eluted with ethyl acetate-hexane (1:1, volume ratio). The crystals were recrystallized from ethyl acetate-hexane. melting point: 128–129° C.

Example 54

A mixture of 4-[2-(3-ethyl-4H-triazol-4-yl)ethoxy]aniline (1.12 g), 3-(5-phenyl-4-isoxazolyl)propionic acid (1.04 g), 1-hydroxy-1H-1,2,3-benzotriazole hydrate (0.89 g), 1-ethyl-3-(3-dimethylaminopropyl)carbodiimide hydrochloride (1.11 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-[4-[2-(3-ethyl-4H-triazol-4-yl)ethoxy]phenyl]-3-(5-phenyl-4-isoxazolyl)propionamide (1.58 g, yield 76%) was obtained as colorless crystals from a fraction eluted with ethyl acetate-hexane (1:1, volume ratio). The crystals were recrystallized from acetone-hexane. melting point: 167–168° C.

Example 55

A mixture of 4-[2-(3-ethyl-4H-triazol-4-yl)ethoxy]aniline (0.51 g), 4-(5-phenyl-4-isoxazolyl)butanoic acid (0.51 g), 1-hydroxy-1H-1,2,3-benzotriazole hydrate (0.40 g), 1-ethyl-3-(3-dimethylaminopropyl)carbodiimide hydrochloride (0.50 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-[4-[2-(3-ethyl-4H-triazol-4-yl)ethoxy]phenyl]-4-(5-phenyl-4-isoxazolyl)butaneamide (0.83 g, yield 84%) was obtained as colorless crystals from a fraction eluted with ethyl acetate-hexane (1:1, volume ratio). The crystals were recrystallized from acetone-hexane. melting point: 125–126° C.

Example 56

To a mixture of 5-phenylisoxazole-4-carbaldehyde (7.18 g), ethyl diethylphosphonoacetate (9.35 g) and N,N-dimethylformamide (150 ml) was added sodium hydride (60%, oil, 1.65 g) at 0° C., and the mixture was stirred at room temperature for 3 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and ethyl (E)-3-(5-phenyl-4-isoxazolyl)propenoate (8.88 g, yield 88%) was obtained as a yellow oil from a fraction eluted with ethyl acetate-hexane (1:4, volume ratio). NMR (CDCl$_3$) δ: 1.33 (3H, t, J=7.2 Hz), 4.27 (2H, q, J=7.2 Hz), 6.34 (1H, d, J=15.4 Hz), 7.48–7.82 (6H, m), 8.52 (1H, s).

Example 57

A solution of 4-chloromethyl-3-(4-phenylphenyl)isoxazole (3.20 g) in tetrahydrofuran (100 ml) was added to a mixture of diethyl malonate (5.70 g), sodium hydride (60%, oil, 1.40 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (30 ml) and acetic acid (30 ml) was refluxed for 5 hr. The reaction mixture was concentrated, and water was added to the residue. The obtained colorless crystals were filtrated to give 3-[3-(4-phenylphenyl)-4-isoxazolyl]propionic acid (2.89 g, yield 83%). The crystals were recrystallized from acetone-hexane. melting point: 169–170° C.

Example 58

To a solution of methyl 3-[5-(4-fluorophenyl)-4-isoxazolyl]propionate (3.21 g) in tetrahydrofuran (30 ml) was gently added diisobutylaluminum hydride (1.0 M hexane solution, 30 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(4-fluorophenyl)-4-isoxazolyl]propan-1-ol (2.48 g, yield 87%) was obtained as a pale yellow oil from a fraction eluted with ethyl acetate-hexane (1:1, volume ratio). NMR (CDCl$_3$) δ: 1.38 (1H, br s), 1.82–2.02 (2H, m), 2.70–2.84 (2H, m), 3.64–3.80 (2H, m), 7.10–7.26 (2H, m), 7.64–7.80 (2H, m), 8.21 (1H, s).

Example 59

To a solution of diethyl malonate (3.38 g) in tetrahydrofuran (40 ml) was gradually added sodium hydride (60%, oil, 770 mg) at 0° C. The mixture was stirred for 10 min and a solution of 4-chloromethyl-5-(2,4-difluorophenyl)isoxazole (2.20 g) in tetrahydrofuran (40 ml) was added dropwise at 0° C. The mixture was stirred at room temperature for 15 hr. The reaction mixture was acidified by pouring into 2N hydrochloric acid and extracted with ethyl acetate. The ethyl acetate layer was concentrated, and the residue was dissolved in a mixture of 6N hydrochloric acid (40 ml) and acetic acid (60 ml) and heated under reflux for 8 hr. The reaction mixture was concentrated, and water was added to the residue. The obtained colorless crystals were filtrated, dried and recrystallized from ethyl acetate-hexane to give a colorless prism (2.10 g, yield 87%) of 3-[5-(2,4-difluorophenyl)-4-isoxazolyl]propionic acid. melting point: 125–126° C.

Example 60

To a solution of 3-[5-(4-trifluoromethylphenyl)-4-isoxazolyl]propionic acid (2.20 g) in methanol (50 ml) was added conc. sulfuric acid (1 ml) and the mixture was heated under reflux for 1 hr. The reaction mixture was concentrated, and iced water was poured into the residue. The precipitated crystals (1.70 g, yield 74%) of methyl 3-[5-(4-trifluoromethylphenyl)-4-isoxazolyl]propionate were collected by filtration. The crystals were recrystallized from ethyl acetate-hexane to give a colorless prism. melting point: 68–69° C.

Example 61

To a solution of 3-[5-(2,4-difluorophenyl)-4-isoxazolyl]propionic acid (1.25 g) in methanol (40 ml) was added conc. sulfuric acid (1 ml) and the mixture was heated under reflux for 1 hr. The reaction mixture was concentrated, and iced water was poured into the residue. The precipitated crystals were collected by filtration. The crystals were subjected to silica gel column chromatography, and the crystals obtained from a fraction eluted with ethyl acetate-hexane (1:1, volume ratio) were recrystallized from ethyl acetate-hexane to give a colorless prism (1.15 g, yield 87%) of methyl 3-[5-(2,4 -difluorophenyl)-4-isoxazolyl]propionate. melting point: 40–41° C.

Example 62

To a solution of methyl 3-[5-(4-trifluoromethylphenyl)-4-isoxazolyl]propionate (1.40 g) in tetrahydrofuran (80 ml) was gently added diisobutylaluminum hydride (1.0 M hexane solution, 10.3 ml) at 0° C., and the mixture was stirred at room temperature for 1 hr. The reaction mixture was poured into 2N hydrochloric acid, concentrated and the precipitated crystals were collected by filtration and recrystallized from ethyl acetate-hexane to give 3-[5-(4-trifluoromethylphenyl)-4-isoxazolyl]propan-1-ol (970 mg, yield 76%) as a colorless needle. melting point: 85–86° C.

Example 63

To a solution of methyl 3-[5-(2,4-difluorophenyl)-4-isoxazolyl]propionate (1.05 g) in tetrahydrofuran (30 ml) was gently added diisobutylaluminum hydride (1.0 M hexane solution, 8.7 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[5-(2,4-difluorophenyl)-4-isoxazolyl]propan-1-ol (640 mg, yield 68%) was obtained as a colorless oil from a fraction eluted with ethyl acetate-hexane (1:1, volume ratio). NMR ($CDCl_3$) δ: 1.29 (1H, br s), 1.75–1.95 (2H, m), 2.55–2.65 (2H, m), 3.6–3.75 (2H, m), 6.9–7.1 (2H, m), 7.5–7.65 (1H, m), 8.25 (1H, s).

Example 64

To a solution of diethyl malonate (10.1 g) in tetrahydrofuran (60 ml) was gradually added sodium hydride (60%, oil, 2.29 g) at 0° C. The mixture was stirred for 10 min and a solution of 4-chloromethyl-5-(5-chloro-2-thienyl)isoxazole (6.70 g) in tetrahydrofuran (60 ml) was added dropwise at 0° C. The mixture was stirred at room temperature for 15 hr. The reaction mixture was acidified by pouring into 2N hydrochloric acid and extracted with ethyl acetate. The ethyl acetate layer was concentrated and the residue was dissolved in a mixture of 6N hydrochloric acid (80 ml) and acetic acid (120 ml). The mixture was heated under reflux for 8 hr. The reaction mixture was concentrated, and water was added to the residue. The obtained colorless crystals were filtrated, dried and recrystallized from ethyl acetate to give a colorless prism (4.95 g, yield 67%) of 3-[5-(5-chloro-2-thienyl)-4-isoxazolyl]propionic acid. melting point: 138–139° C.

Example 65

To a solution of 3-[5-(5-chloro-2-thienyl)-4-isoxazolyl]propionic acid (2.20 g) in methanol (50 ml) was added conc. sulfuric acid (1 ml) and the mixture was heated under reflux for 1 hr. The reaction mixture was concentrated, iced water was poured on the residue and the mixture was extracted with ethyl acetate. The ethyl acetate layer was washed with water, dried ($MgSO_4$) and concentrated. The residue was subjected to silica gel column chromatography, and crystals (3.80 g, yield 86%) of methyl 3-[5-(5-chloro-2-thienyl)-4-isoxazolyl]propionate were obtained from a fraction eluted with ethyl acetate-hexane (1:3, volume ratio). The crystals were recrystallized from diethyl ether-isopropyl ether to give a colorless prism. melting point: 34–35° C.

Example 66

To a solution of methyl 3-[5-(5-chloro-2-thienyl)-4-isoxazolyl]propionate (3.10 g) in tetrahydrofuran (80 ml) was gently added diisobutylaluminum hydride (1.5 M toluene solution, 17 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[5-(5-chloro-2-thienyl)-4-isoxazolyl]propan-1-ol (2.02 g, yield 73%) was obtained as a colorless oil from a fraction eluted with ethyl acetate-hexane (1:1, volume ratio). NMR ($CDCl_3$) δ: 1.41 (1H, br t, J=5 Hz), 1.8–2.0 (2H, m), 2.73 (2H, t, J=8 Hz), 3.73 (2H, td, J=6, 5 Hz), 6.98 (1H, d, J=4 Hz), 7.29 (1H, d, J=4 Hz), 8.17 (1H, s).

Example 67

To a solution of methyl 3-[5-(2,4-dichlorophenyl)-4-isoxazolyl]propionate (2.00 g) in tetrahydrofuran (30 ml) was gently added diisobutylaluminum hydride (1.0 M hexane solution, 15 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[5-(2,4-dichlorophenyl)-4-isoxazolyl]propan-1-ol (1.67 g, yield 92%) was obtained as a colorless oil from a fraction eluted with ethyl acetate-hexane (2:1, volume ratio). NMR ($CDCl_3$) δ: 1.20–1.32 (1H, br t), 1.70–1.88 (2H, m), 2.44–2.60 (2H, m), 3.56–3.70 (2H, m), 7.35–7.39 (2H, m), 7.53–7.57 (1H, m), 8.27 (1H, s).

Example 68

To a solution of methyl 3-[5-(3,4-dichlorophenyl)-4-isoxazolyl]propionate (1.63 g) in tetrahydrofuran (25 ml) was gently added diisobutylaluminum hydride (1.0 M hexane solution, 13 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(3,4-dichlorophenyl)-4-isoxazolyl]propan-1-ol (1.53 g, yield 97%) was obtained as colorless crystals from a fraction eluted with ethyl acetate-hexane (2:1, volume ratio). The crystals were recrystallized from ethyl acetate-hexane. melting point: 66–67° C.

Example 69

To a solution of 5-(2,4-dichlorophenyl)-4-isoxazolyl-methanol (5.15 g) in toluene (100 ml) was added dropwise thionyl chloride (2.00 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (5.89 g), sodium hydride (60%, oil, 1.45 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid.(50 ml) and acetic acid (50 ml) was refluxed for 5 hr. The reaction mixture was concentrated, and water was added to the residue. The obtained colorless crystals were filtrated to give 3-[5-(2,4-dichlorophenyl)-4-isoxazolyl]propionic acid (3.85 g, yield 72%). The crystals were recrystallized from acetone-hexane. melting point: 106–107° C.

Exampl 70

To a solution of 5-(3,4-dichlorophenyl)-4-isoxazolyl-methanol (6.50 g) in toluene (100 ml) was added dropwise thionyl chloride (3.0 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (8.53 g), sodium hydride (60%, oil, 2.01 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(3,4-dichlorophenyl)-4-isoxazolyl]propionic acid (5.96 g, yield 78%). The crystals were recrystallized from acetone-hexane. melting point: 171–172° C.

Example 71

A mixture of 3-[5-(4-fluorophenyl)-4-isoxazolyl]propionic acid (3.68 g), conc. sulfuric acid (0.05 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(4-fluorophenyl)-4-isoxazolyl]propionate (3.50 g, yield 90%) was obtained as a pale yellow oil from a fraction eluted with ethyl acetate-hexane (1:4, volume ratio). NMR (CDCl$_3$) δ: 2.65 (2H, t, J=7.4 Hz), 2.98 (2H, t, J=7.4 Hz), 3.69 (3H, s), 7.12–7.28 (2H, m), 7.64–7.78 (2H, m), 8.22 (1H, s).

Example 72

A mixture of 3-[5-(2,4-dichlorophenyl)-4-isoxazolyl]propionic acid (3.00 g), conc. sulfuric acid (0.1 ml) and methanol (50 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(2,4-dichlorophenyl)-4-isoxazolyl]propionate (2.96 g, yield 94%) was obtained as a colorless oil from a fraction eluted with ethyl acetate-hexane (1:4, volume ratio). NMR (CDCl$_3$) δ: 2.46–2.58 (2H, m), 2.71–2.81 (2H, m), 3.66 (3H, s), 7.35–7.42 (2H, m), 7.54–7.58 (1H, m), 8.28 (1H, s).

Example 73

A mixture of 3-[5-(3,4-dichlorophenyl)-4-isoxazolyl]propionic acid (3.20 g), conc. sulfuric acid (0.1 ml) and methanol (50 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(3,4-dichlorophenyl)-4-soxazolyl]propionate (3.26 g, yield 97%) was obtained as colorless crystals from a fraction eluted with ethyl acetate-hexane (1:4, volume ratio). The crystals were recrystallized from ethyl acetate-hexane. melting point: 74–75° C.

Example 74

To a solution of 5-(3,5-dichlorophenyl)-4-isoxazolyl-methanol (6.06 g) in toluene (100 ml) was added dropwise thionyl chloride (2.7 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (7.96 g), sodium hydride (60%, oil, 1.95 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(3,5-dichlorophenyl)-4-isoxazolyl]propionic acid (5.96 g, yield 84%). The crystals were recrystallized from acetone-hexane. melting point: 143–144° C.

Example 75

A mixture of 3-[5-(3,5-dichlorophenyl)-4-isoxazolyl]propionic acid (3.50 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(3,5-dichlorophenyl)-4-isoxazolyl]propionate (3.49 g, yield 99%) was obtained as a pale yellow oil from a fraction eluted with ethyl acetate-hexane (1:3, volume ratio). NMR (CDCl$_3$) δ: 2.62–2.72 (2H, m), 2.92–3.02 (2H, m), 3.70 (3H, s), 7.45 (1H, t, J=1.8 Hz), 7.60 (1H, d, J=1.8 Hz), 8.24 (1H, s).

Example 76

To a solution of methyl 3-[5-(3,5-dichlorophenyl)-4-isoxazolyl]propionate (2.25 g) in tetrahydrofuran (30 ml) was gently added diisobutylaluminum hydride (1.0 M hexane solution, 20 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(3,5-dichlorophenyl)-4-isoxazolyl]propan-1-ol (1.65 g, yield 81%) was obtained as a colorless oil from a fraction eluted with ethyl acetate-hexane (2:1, volume ratio). NMR (CDCl$_3$) δ: 1.83–2.00 (2H, m), 2.72–2.86 (2H, m), 3.68–3.80 (2H, m), 7.43 (1H, t, J=1.8 Hz), 7.64 (2H, d, J=1.8 Hz), 8.24 (1H, s).

Example 77

To a solution of 5-(3,4-difluorophenyl)-4-isoxazolylmethanol (4.80 g) in toluene (100 ml) was added dropwise thionyl chloride (2.5 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (7.26 g), sodium hydride (60%, oil, 1.79 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(3,4-difluorophenyl)-4-isoxazolyl]propionic acid (4.98 g, yield 87%). The crystals were recrystallized from ethyl acetate-hexane. melting point: 102–103° C.

Example 78

A mixture of 3-[5-(3,4-difluorophenyl)-4-isoxazolyl]propionic acid (3.45 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(3,4-difluorophenyl)-4-isoxazolyl]propionate (3.56 g, yield 98%) was obtained as a pale yellow oil from a fraction eluted with ethyl acetate-hexane (1:3, volume ratio). NMR (CDCl$_3$) δ: 2.60–2.71 (2H, m), 2.92–3.03 (2H, m), 3.69 (3H, s), 7.22–7.65 (3H, m), 8.23 (1H, s).

Exampl 79

To a solution of methyl 3-[5-(3,4-difluorophenyl)-4-isoxazolyl]propionate (2.20 g) in tetrahydrofuran (30 ml) was gently added diisobutylaluminum hydride (1.0 M hexane solution, 20 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(3,4-difluorophenyl)-4-isoxazolyl]propan-1-ol (1.88 g, yield 95%) was obtained as a colorless oil from a fraction eluted with ethyl acetate-hexane (2:1, volume ratio). NMR (CDCl$_3$) δ: 1.38 (1H, br s), 1.82–2.00 (2H, m), 2.72–2.84 (2H, m), 3.66–3.82 (2H, m), 7.21–7.38 (1H, m), 7.44–7.66 (2H, m), 8.22 (1H, s).

Example 80

To a solution of 5-(4-nitrophenyl)-4-isoxazolylmethanol (6.56 g) in toluene (100 ml) was added dropwise thionyl chloride (3.3 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (9.56 g), sodium hydride (60%, oil, 2.35 g) and tetrahydrofuran (50 ml) at 0° C. The mixture was stirred at 0° C. for 1 hr and at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(4-nitrophenyl)-4-isoxazolyl]propionic acid (6.19 g, yield 79%). The crystals were recrystallized from acetone-hexane. melting point: 204–205° C.

Example 81

A mixture of 3-[5-(4-nitrophenyl)-4-isoxazolyl]propionic acid (5.28 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(4-nitrophenyl)-4-isoxazolyl]propionate (5.45 g, yield 98%) was obtained as colorless crystals from a fraction eluted with ethyl acetate-hexane (1:3, volume ratio). The crystals were recrystallized from ethyl acetate-hexane. melting point: 118–119° C.

Example 82

To a solution of methyl 3-[5-(4-nitrophenyl)-4-isoxazolyl]propionate (1.60 g) in tetrahydrofuran (20 ml) was gently added diisobutylaluminum hydride (1.0 M hexane solution, 20 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(4-nitrophenyl)-4-isoxazolyl]propan-1-ol (1.36 g, yield 95%) was obtained as colorless crystals from a fraction eluted with ethyl acetate-hexane (2:1, volume ratio). The crystals were recrystallized from ethyl acetate-hexane. melting point: 132–133° C.

Example 83

To a solution of 5-(4-bromophenyl)-4-isoxazolylmethanol (7.55 g) in toluene (50 ml) was added dropwise thionyl chloride (3.3 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (9.58 g), sodium hydride (60%, oil, 2.36 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(4-bromophenyl)-4-isoxazolyl]propionic acid (6.18 g, yield 70%). The crystals were recrystallized from ethyl acetate-hexane. melting point: 164–165° C.

Example 84

A mixture of 3-[5-(4-bromophenyl)-4-isoxazolyl]propionic acid (5.00 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(4-bromophenyl)-4-isoxazolyl]propionate (5.03 g, yield 96%) was obtained as colorless crystals from a fraction eluted with ethyl acetate-hexane (1:3, volume ratio). The crystals were recrystallized from ethyl acetate-hexane. melting point: 58–59° C.

Example 85

To a solution of methyl 3-[5-(4-bromophenyl)-4-isoxazolyl]propionate (4.06 g) in tetrahydrofuran (30 ml) was gently added diisobutylaluminum hydride (1.0 M hexane solution, 30 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(4-bromophenyl)-4-isoxazolyl]propan-1-ol (3.58 g, yield 97%) was obtained as colorless crystals from a fraction eluted with ethyl acetate-hexane (2:1, volume ratio). The crystals were recrystallized from ethyl acetate-hexane. melting point: 72–73° C.

Example 86

To a solution of 5-(3-chlorophenyl)-4-isoxazolylmethanol (6.80 g) in toluene (100 ml) was added dropwise thionyl chloride (3.6 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml), and added to a mixture of diethyl malonate (10.38 g), sodium hydride (60%, oil, 2.56 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(3-chlorophenyl)-4-isoxazolyl]propionic acid (5.95 g, yield 73%). The crystals were recrystallized from acetone-hexane. melting point: 110–111° C.

Example 87

A mixture of 3-[5-(3-chlorophenyl)-4-isoxazolyl]propionic acid (3.10 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(3-chlorophenyl)-4-isoxazolyl]propionate (3.06 g, yield 93%) was obtained as a colorless oil from a fraction eluted with ethyl acetate-hexane (1:4, volume ratio). NMR (CDCl$_3$) δ: 2.59–2.71 (2H, m), 2.93–3.05 (2H, m), 3.69 (3H, s), 7.36–7.50 (2H, m), 7.54–7.65 (1H, m), 7.69–7.73 (1H, m), 8.23 (1H, s).

Example 88

To a solution of methyl 3-[5-(3-chlorophenyl)-4-isoxazolyl]propionate (2.50 g) in tetrahydrofuran (30 ml) was gently added diisobutylaluminum hydride (1.0 M hexane solution, 25 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(3-chlorophenyl)-4-isoxazolyl]propan-1-ol (2.38 g, yield 95%) was obtained as a colorless oil from a fraction eluted with ethyl acetate-hexane (2:1, volume ratio). NMR (CDCl$_3$) δ: 1.39 (1H, br s), 1.84–2.00 (2H, m), 2.72–2.86 (2H, m), 3.66–3.80 (2H, m), 7.38–7.49 (2H, m), 7.56–7.68 (1H, m), 7.70–7.77 (1H, m), 8.23 (1H, s).

Example 89

To a solution of 5-(1,3-benzodioxol-5-yl)-4-isoxazolylmethanol (7.90 g) in toluene (150 ml) was added dropwise thionyl chloride (4.0 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (200 ml) and added to a mixture of diethyl malonate (11.55 g), sodium hydride (60%, oil, 2.85 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. the residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(1,3-benzodioxol-5-yl)-4-isoxazolyl]propionic acid (7.36 g, yield 78%). The crystals were recrystallized from acetone-hexane. melting point: 150–151° C.

Example 90

A mixture of 3-[5-(1,3-benzodioxol-5-yl)-4-isoxazolyl]propionic acid (4.19 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(1,3-benzodioxol-5-yl)-4-isoxazolyl]propionate (4.26 g, yield 97%) was obtained as colorless crystals from a fraction eluted with ethyl acetate-hexane (1:3, volume ratio). The crystals were recrystallized from ethyl acetate-hexane. melting point: 84–85° C.

Example 91

To a solution of methyl 3-[5-(1,3-benzodioxol-5-yl)-4-isoxazolyl]propionate (2.70 g) in tetrahydrofuran (30 ml) was gently added diisobutylaluminum hydride (1.0 M hexane solution, 25 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(1,3-benzodioxol-5-yl)-4-isoxazolyl]propan-1-ol (2.33 g, yield 96%) was obtained as colorless crystals from a fraction eluted with ethyl acetate-hexane (2:1, volume ratio). The crystals were recrystallized from ethyl acetate-hexane. melting point: 45–46° C.

Example 92

To a solution of 5-(3-chloro-4-fluorophenyl)-4-isoxazolylmethanol (7.01 g) in toluene (100 ml) was added dropwise thionyl chloride (3.5 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (9.89 g), sodium hydride (60%, oil, 2.43 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(3-chloro-4-fluorophenyl)-4-isoxazolyl]propionic acid (6.68 g, yield 80%). The crystals were recrystallized from acetone-hexane. melting point: 118–119° C.

Example 93

A mixture of 3-[5-(3-chloro-4-fluorophenyl)-4-isoxazolyl]propionic acid (3.10 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(3-chloro-4-fluorophenyl)-4-isoxazolyl]propionate (3.18 g, yield 97%) was obtained as a pale yellow oil from a fraction eluted with ethyl acetate-hexane (1:3, volume ratio). NMR (CDCl$_3$) δ: 2.60–2.72 (2H, m), 2.91–3.03 (2H, m), 3.69 (3H, s), 7.22–7.33 (1H, m), 7.52–7.66 (1H, m), 7.74–7.82 (1H, m), 8.23 (1H, s).

Example 94

To a solution of methyl 3-[5-(3-chloro-4-fluorophenyl)-4-isoxazolyl]propionate (3.00 g) in tetrahydrofuran (25 ml) was gently added diisobutylaluminum hydride (1.0 M hexane solution, 25 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(3-chloro-4-fluorophenyl)-4-isoxazolyl]propan-1-ol (2.59 g, yield 95%) was obtained as a pale yellow oil from a fraction eluted with ethyl acetate-hexane (2:1, volume ratio). NMR (CDCl$_3$) δ: 1.40 (1H, br s), 1.82–2.00 (2H, m), 2.70–2.84 (2H, m), 3.66–3.78 (2H, m), 7.20–7.32 (1H, m), 7.55–7.67 (1H, m), 7.76–7.84 (1H, m), 8.22 (1H, s).

Example 95

To a solution of diethyl malonate (5.82 g) in tetrahydrofuran (40 ml) was gradually added sodium hydride (60%, oil, 1.32 g) at 0° C. The mixture was stirred for 10 min and a solution of 4-chloromethyl-5-(4-chloro-3-methylphenyl)isoxazole (4.00 g) in tetrahydrofuran (40 ml) was added dropwise at 0° C. and the mixture was stirred at room temperature for 15 hr. The reaction mixture was poured into water, acidified with 2N hydrochloric acid and extracted with ethyl acetate. The ethyl acetate layer was washed with saturated brine, dried (MgSO$_4$) and concentrated. The residue was dissolved in a mixture of 6N hydrochloric acid (40 ml) and acetic acid (60 ml) and heated under reflux for 8 hr. The reaction mixture was concentrated, and water was added to the residue. The obtained colorless crystals were filtrated, dried and recrystallized from ethyl acetate to give a colorless prism (2.56 g, yield 58%) of 3-[5-(4-chloro-3-methylphenyl)-4-isoxazolyl]propionic acid. melting point: 158–159° C.

Example 96

To a solution of 3-[5-(4-chloro-3-methylphenyl)-4-isoxazolyl]propionic acid (1.80 g) in methanol (50 ml) was added conc. sulfuric acid (1 ml) and the mixture was heated under reflux for 1 hr. The reaction mixture was concentrated, and iced water was poured on the residue. The precipitated crystals of methyl 3-[5-(4-chloro-3-methylphenyl)-4-isoxazolyl]propionate were filtrated and recrystallized from ethyl acetate-hexane to give a colorless needle (1.72 g, yield 91%). melting point: 60–61° C.

Example 97

To a solution of methyl 3-[5-(4-chloro-3-methylphenyl)-4-isoxazolyl]propionate (1.20 g) in tetrahydrofuran (40 ml) was gently added diisobutylaluminum hydride (1.0 M toluene solution, 9.5 ml) at 0° C., and the mixture was stirred at room temperature for 3 hr. Water was carefully added to the reaction mixture, acidified with dilute hydrochloric acid and extracted with ethyl acetate. The ethyl acetate layer was washed with saturated brine, dried (MgSO$_4$) and concentrated. The residue was subjected to silica gel column chromatography and the crystals obtained from a fraction eluted with ethyl acetate-hexane (1:1, volume ratio) were recrystallized from ethyl acetate-hexane to give a colorless needle of 3-[5-(4-chloro-3-methylphenyl)-4-isoxazolyl]propan-1-ol (780 mg, yield 72%). melting point: 50–51° C.

Example 98

To a solution of diethyl malonate (2.89 g) in tetrahydrofuran (40 ml) was gradually added sodium hydride (60%, oil, 655 mg) at 0° C. The mixture was stirred for 10 min and a solution of 4-chloromethyl-5-(2,5-dichlorophenyl)isoxazole (2.15 g) in tetrahydrofuran (40 ml) was added dropwise at 0° C. The mixture was stirred at room temperature for 15 hr. The reaction mixture was poured into water, acidified with 2N hydrochloric acid and extracted with ethyl acetate. The ethyl acetate layer was washed with saturated brine, dried (MgSO$_4$) and concentrated. The residue was dissolved in a mixture of 6N hydrochloric acid (40 ml) and acetic acid (60 ml) and heated under reflux for 8 hr. The reaction mixture was concentrated, and water was added to the residue. The obtained colorless crystals were filtrated, dried and recrystallized from ethyl acetate to give a colorless prism (1.35 g, yield 58%) of 3-[5-(2,5-dichlorophenyl)-4-isoxazolyl]propionic acid. melting point: 103–104° C.

Example 99

To a solution of 3-[5-(2,5-dichlorophenyl)-4-isoxazolyl]propionic acid (800 mg) in methanol (30 ml) was added conc. sulfuric acid (1 ml) and the mixture was heated under reflux for 1 hr. The reaction mixture was concentrated, iced water was poured on the residue and the mixture was extracted with ethyl acetate. The ethyl acetate layer was washed with saturated brine, dried (MgSO$_4$) and concentrated. The residue was subjected to silica gel column chromatography, and methyl 3-[5-(2,5-dichlorophenyl)-4-isoxazolyl]propionate as obtained as a colorless oil (500 mg, yield 60%) from a fraction eluted with ethyl acetate-hexane (1:9, volume ratio).

NMR (CDCl$_3$) δ: 2.5–2.85 (4H, m), 3.66 (3H, s), 7.35–7.5 (3H, m), 8.28 (1H, s).

Example 100

To a solution of 5-(3,4-dimethoxyphenyl)-4-isoxazolyl-methanol (6.65 g) in toluene (100 ml) was added dropwise thionyl chloride (3.1 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (9.10 g), sodium hydride (60%, oil, 2.25 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(3,4-dimethoxyphenyl)-4-isoxazolyl]propionic acid (7.36 g, yield 78%). The crystals were recrystallized from acetone-hexane. melting point: 169–170° C.

Example 101

A mixture of 3-[5-(3,4-dimethoxyphenyl)-4-isoxazolyl]propionic acid (2.53 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(3,4-dimethoxyphenyl)-4-isoxazolyl]propionate (2.58 g, yield 97%) was obtained as colorless crystals from a fraction eluted with ethyl acetate-hexane (1:3, volume ratio). The crystals were recrystallized from ethyl acetate-hexane. melting point: 68–69° C.

Example 102

To a solution of methyl 3-[5-(3,4-dimethoxyphenyl)-4-isoxazolyl]propionate (1.70 g) in tetrahydrofuran (20 ml) was gently added diisobutylaluminum hydride (1.0 M hexane solution, 15 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(3,4-dimethoxyphenyl)-4-isoxazolyl]propan-1-ol (1.26 g, yield 82%) was obtained as colorless crystals from a fraction eluted with ethyl acetate-hexane (2:1, volume ratio). The crystals were recrystallized from ethyl acetate-hexane. melting point: 55–56° C.

Example 103

To a solution of diethyl malonate (10.3 g) in tetrahydrofuran (80 ml) was gradually added sodium hydride (60%, oil, 2.34 g) at 0° C. The mixture was stirred for 10 min and a solution of 4-chloromethyl-5-(4-methylthiophenyl)isoxazole (7.00 g) in tetrahydrofuran (70 ml) was added dropwise at 0° C. The mixture was stirred at room temperature for 8 hr. The reaction mixture was poured into water, acidified with 2N hydrochloric acid and extracted with ethyl acetate. The ethyl acetate layer was washed with saturated brine, dried (MgSO$_4$) and concentrated. The residue was dissolved in a mixture of 6N hydrochloric acid (50 ml) and acetic acid (100 ml), and heated under reflux for 5 hr. The reaction mixture was concentrated, and water was added to the residue to give colorless crystals (4.68 g, yield 61%) of 3-[5-(4-methylthiophenyl)-4-isoxazolyl]propionic acid. The crystals were recrystallized from ethyl acetate-isopropyl ether to give a colorless prism. melting point: 124–125° C.

Example 104

To a solution of 3-[5-(4-methylthiophenyl)-4-isoxazolyl]propionic acid (3.70 g) in methanol (100 ml) was added conc. sulfuric acid (1 ml) and the mixture was heated under reflux for 1 hr. The reaction mixture was concentrated, iced water was poured on the residue and the precipitated crystals of methyl 3-[5-(4-methylthiophenyl)-4-isoxazolyl]propionate were filtrated, which were recrystallized from ethyl acetate-isopropyl ether to give a colorless prism (3.60 g, yield 92%). melting point: 57–58° C.

Example 105

To a solution of methyl 3-[5-(4-methylthiophenyl)-4-isoxazolyl]propionate (1.60 g) in tetrahydrofuran (60 ml) was gently added diisobutylaluminum hydride (0.95 M toluene solution, 15.2 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and the crystals obtained from a fraction eluted with acetone-hexane (1:1, volume ratio) were recrystallized from ethyl acetate-hexane to give 3-[5-(4-methylthiophenyl)-4-isoxazolyl]propan-1-ol as a colorless prism crystal (1.36 g, yield 95%). melting point: 54–55° C.

Example 106

To a solution of 3-[5-(4-methylthiophenyl)-4-isoxazolyl]propan-1-ol (500 mg) in tetrahydrofuran (30 ml) was gradually added m-chloroperbenzoic acid (870 mg) at 0° C., and the mixture was stirred at room temperature for 1 hr. The reaction mixture was poured into iced water, and extracted with ethyl acetate. The ethyl acetate layer was washed with saturated brine, dried (MgSO$_4$) and concentrated. The residue was subjected to silica gel column chromatography to give crystals (480 mg, yield 85%) of 3-[5-(4-methylsulfonylphenyl)-4-isoxazolyl]propan-1-ol from a fraction eluted with acetone-hexane (1:1, volume ratio). The crystals were recrystallized from ethyl acetate-isopropyl ether to give a colorless needle. melting point: 125–126° C.

Example 107

To a solution of 3-[5-(4-methylthiophenyl)-4-isoxazolyl]propan-1-ol (900 mg) in acetonitrile (20 ml) was gradually added m-chloroperbenzoic acid (750 mg) at 0° C., and the mixture was stirred at room temperature for 1 hr. The reaction mixture was poured into iced water and extracted with ethyl acetate. The ethyl acetate layer was washed with saturated brine, dried (MgSO$_4$) and concentrated. The residue was subjected to silica gel column chromatography, and crystals (390 mg, yield 41%) of 3-[5-(4-methylsulfinylphenyl)-4-isoxazolyl]propan-1-ol were obtained from a fraction eluted with acetone-hexane (2:1, volume ratio). The crystals were recrystallized from ethyl acetate-diethyl ether to give a colorless prism. melting point: 73–74° C.

Example 108

To a solution of 5-(4-chloro-3-fluorophenyl)-4-isoxazolylmethanol (7.80 g) in toluene (150 ml) was added dropwise thionyl chloride (4.0 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (150 ml) and added to a mixture of diethyl malonate (10.98 g), sodium hydride (60%, oil, 2.71 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(4-chloro-3-fluorophenyl)-4-isoxazolyl]propionic acid (7.20 g, yield 78%). The crystals were recrystallized from acetone-hexane. melting point: 139–140° C.

Example 109

A mixture of 3-[5-(4-chloro-3-fluorophenyl)-4-isoxazolyl]propionic acid (5.08 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and methyl 3-[5-(4-chloro-3-fluorophenyl)-4-isoxazolyl]propionate (5.25 g, yield 98%) was obtained as colorless crystals from a fraction eluted with ethyl acetate-hexane (1:3, volume ratio). The crystals were recrystallized from ethyl acetate-hexane. melting point: 53–54° C.

Example 110

To a solution of methyl 3-[5-(4-chloro-3-fluorophenyl)-4-isoxazolyl]propionate (3.30 g) in tetrahydrofuran (30 ml) was gently added diisobutylaluminum hydride (1.0 M hexane solution, 25 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[5-(4-chloro-3-fluorophenyl)-4-isoxazolyl]propan-1-ol (2.79 g, yield 94%) was obtained as colorless crystals from a fraction eluted with ethyl acetate-hexane (2:1, volume ratio). The crystals were recrystallized from ethyl acetate-hexane. melting point: 51–52° C.

Example 111

To a solution of 3-(3,4-dichlorophenyl)-4-isoxazolylmethanol (5.50 g) in toluene (50 ml) was added dropwise thionyl chloride (2.5 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was dissolved in tetrahydrofuran (100 ml) and added to a mixture of diethyl malonate (7.21 g), sodium hydride (60%, oil, 1.79 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[3-(3,4-dichlorophenyl)-4-isoxazolyl]propionic acid (5.09 g, yield 79%). The crystals were recrystallized from acetone-hexane. melting point: 181–182° C.

Example 112

A mixture of 3-[3-(3,4-dichlorophenyl)-4-isoxazolyl]propionic acid (3.03 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and methyl 3-[3-(3,4-dichlorophenyl)-4-isoxazolyl]propionate (3.15 g, yield 99%) was obtained as colorless crystals from a fraction eluted with ethyl acetate-hexane (1:3, volume ratio). The crystals were recrystallized from ethyl acetate-hexane. melting point: 87–88° C.

Example 113

To a solution of methyl 3-[3-(3,4-dichlorophenyl)-4-isoxazolyl]propionate (2.40 g) in tetrahydrofuran (30 ml) was gently added diisobutylaluminum hydride (1.0 M hexane solution, 20 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[3-(3,4 -dichlorophenyl)-4-isoxazolyl]propan-1-ol (2.06 g, yield 95%) was obtained as colorless crystals from a fraction eluted with ethyl acetate-hexane (2:1, volume ratio). The crystals were recrystallized from ethyl acetate-hexane. melting point: 62–63° C.

Example 114

To a solution of 3-(3-chloro-4-fluorophenyl)-4-isoxazolylmethanol (6.60 g) in toluene (75 ml) was added dropwise thionyl chloride (3.5 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was dissolved in tetrahydrofuran (100 ml), and added to a mixture of diethyl malonate (9.31 g), sodium hydride (60%, oil, 2.30 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[3-(3-chloro-4-fluorophenyl)-4-isoxazolyl]propionic acid (5.71 g, yield 73%). The crystals were recrystallized from acetone-hexane. melting point: 140–141° C.

Example 115

A mixture of 3-[3-(3-chloro-4-fluorophenyl)-4-isoxazolyl]propionic acid (4.34 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and methyl 3-[3-(3-chloro-4-fluorophenyl)-4-isoxazolyl]propionate (4.39 g, yield 96%) was obtained as colorless crystals from a fraction eluted with ethyl acetate-hexane (1:3, volume ratio). The crystals were recrystallized from ethyl acetate-hexane. melting point: 39–40° C.

Example 116

To a solution of methyl 3-[3-(3-chloro-4-fluorophenyl)-4-isoxazolyl]propionate (3.50 g) in tetrahydrofuran (50 ml) was gently added diisobutylaluminum hydride (1.0 M hexane solution, 30 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[3-(3-chloro-4-fluorophenyl)-4-isoxazolyl]propan-1-ol (2.89 g, yield 92%) was obtained as a colorless oil from a fraction eluted with ethyl acetate-hexane (2:1, volume ratio). NMR ($CDCl_3$) δ: 1.30 (1H, t, J=5.2 Hz), 1.74–1.94 (2H, m), 2.62–2.74 (2H, m), 3.64–3.76 (2H, m), 7.18–7.31 (1H, m), 7.50–7.60 (1H, m), 7.74 (1H, dd, J=2.2, 7.0 Hz), 8.29 (1H, s).

Example 117

To a solution of 3-(4-chloro-3-fluorophenyl)-4-isoxazolylmethanol (9.04 g) in toluene (100 ml) was added dropwise thionyl chloride (4.5 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. The residue was dissolved in tetrahydrofuran (100 ml), and added to a mixture of diethyl malonate (12.75 g), sodium hydride (60%, oil, 3.15 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[3-(4-chloro-3-fluorophenyl)-4-isoxazolyl]propionic acid (7.72 g, yield 72%). The crystals were recrystallized from acetone-hexane. melting point: 148–149° C.

Example 118

A mixture of 3-[3-(4-chloro-3-fluorophenyl)-4-isoxazolyl]propionic acid (5.00 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and methyl 3-[3-(4-chloro-3-fluorophenyl)-4-isoxazolyl]propionate (5.01 g, yield 96%) was obtained as colorless crystals from a fraction eluted with ethyl acetate-hexane (1:3, volume ratio). The crystals were recrystallized from ethyl acetate-hexane. melting point: 57–58° C.

Example 119

To a solution of methyl 3-[3-(4-chloro-3-fluorophenyl)-4-isoxazolyl]propionate (3.69 g) in tetrahydrofuran (30 ml) was gently added diisobutylaluminum hydride (1.0 M hexane solution, 30 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[3-(4-chloro-3-fluorophenyl)-4-isoxazolyl]propan-1-ol (3.06 g, yield 92%) was obtained as colorless crystals from a fraction eluted with ethyl acetate-hexane (2:1, volume ratio). The crystals were recrystallized from ethyl acetate-hexane. melting point: 54–55° C.

Example 120

A mixture of 3-[5-(4-methoxyphenyl)-4-isoxazolyl]propionic acid (2.75 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried ($MgSO_4$) and concentrated. The residue was subjected to silica gel column chromatography, and methyl 3-[5-(4-methoxyphenyl)-4-isoxazolyl]propionate (2.76 g, yield 95%) was obtained as a colorless oil from a fraction eluted with ethyl acetate-hexane (1:3, volume ratio). NMR ($CDCl_3$) δ: 2.58–2.70 (2H, m), 2.92–3.04 (2H, m), 3.68 (3H, s), 3.87 (3H, s), 6.96–7.06 (2H, m), 7.59–7.69 (2H, m), 8.18 (1H, s).

Example 121

To a solution of methyl 3-[5-(4-methoxyphenyl)-4-isoxazolyl]propionate (2.50 g) in tetrahydrofuran (20 ml) was gently added diisobutylaluminum hydride (1.0 M hexane solution, 20 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[5-(4-methoxyphenyl)-4-isoxazolyl]propan-1-ol (2.03 g, yield 91%) was obtained as a colorless oil from a fraction eluted with ethyl acetate-hexane (2:1, volume ratio). NMR ($CDCl_3$) δ: 1.82–1.98 (2H, m), 2.70–2.82 (2H, m), 3.66–3.78 (2H, m), 3.86 (3H, s), 6.95–7.06 (2H, m), 7.62–7.73 (2H, m), 8.18 (1H, s).

Example 122

A mixture of 3-[5-(4-methylphenyl)-4-isoxazolyl]propionic acid (4.00 g), conc. sulfuric acid (2 ml) and methanol (80 ml) was refluxed for 1 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(4-methylphenyl)-4-isoxazolyl]propionate (3.35 g, yield 79%) was obtained as a colorless oil from a fraction eluted with ethyl acetate-hexane (1:7, volume ratio). NMR (CDCl$_3$) δ: 2.41 (3H, s), 2.63 (2H, t, J=7.5 Hz), 2.99 (2H, t, J=7.5 Hz), 3.68 (3H, s), 7.30 (2H, d, J=8 Hz), 7.59 (2H, d, J=8 Hz), 8.20 (1H, s).

Example 123

To a solution of diethyl malonate (3.55 g) in tetrahydrofuran (50 ml) was gradually added sodium hydride (60%, oil, 710 mg) at 0° C. The mixture was stirred for 10 min and a solution of 4-chloromethyl-5-(4,5-dichloro-2-thienyl)isoxazole (2.38 g) in tetrahydrofuran (50 ml) was added dropwise at 0° C. The mixture was stirred at room temperature for 15 hr. The reaction mixture was poured into water, acidified with 2N hydrochloric acid and extracted with ethyl acetate. The ethyl acetate layer was washed with saturated brine, dried (MgSO$_4$) and concentrated. The residue was dissolved in a mixture of 6N hydrochloric acid (60 ml) and acetic acid (90 ml), and the solution was heated under reflux for 8 hr. The reaction mixture was concentrated, and water was added to the residue to give colorless crystals (2.04 g, yield 79%) of 3-[5-(4,5-dichloro-2-thienyl)-4-isoxazolyl]propionic acid. The crystals were recrystallized from ethyl acetate-hexane to give a colorless prism. melting point: 142–143° C.

Example 124

To a solution of 3-[5-(4,5-dichloro-2-thienyl)-4-isoxazolyl]propionic acid (1.60 g) in methanol (30 ml) was added conc. sulfuric acid (1 ml) and the mixture was heated under reflux for 1 hr. The reaction mixture was concentrated, iced water was poured on the residue and the mixture was extracted with ethyl acetate. The ethyl acetate layer was washed with saturated brine, dried (MgSO$_4$) and concentrated. The residue was subjected to silica gel column chromatography, and crystals (1.34 g, yield 80%) of methyl 3-[5-(4,5-dichloro-2-thienyl)-4-isoxazolyl]propionate was obtained from a fraction eluted with ethyl acetate-hexane (1:7, volume ratio). The crystals were recrystallized from diethyl ether-hexane to give a colorless needle. melting point: 49–50° C.

Example 125

To a solution of 3-(3-bromo-4-fluorophenyl)-4-isoxazolylmethanol (6.79 g) in toluene (50 ml) was added dropwise thionyl chloride (3.0 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (8.11 g), sodium hydride (60%, oil, 2.00 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[3-(3-bromo-4-fluorophenyl)-4-isoxazolyl]propionic acid (6.33 g, yield 81%). The crystals were recrystallized from acetone-hexane. melting point: 151–152° C.

Example 126

A mixture of 3-[3-(3-bromo-4-fluorophenyl)-4-isoxazolyl]propionic acid (3.15 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[3-(3-bromo-4-fluorophenyl)-4-isoxazolyl]propionate (3.11 g, yield 95%) was obtained as colorless crystals from a fraction eluted with ethyl acetate-hexane (1:3, volume ratio). The crystals were recrystallized from ethyl acetate-hexane. melting point: 57–58° C.

Example 127

To a solution of methyl 3-[3-(3-bromo-4-fluorophenyl)-4-isoxazolyl]propionate (1.68 g) in tetrahydrofuran (20 ml) was gently added diisobutylaluminum hydride (1.0 M hexane solution, 15 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[3-(3-bromo-4-fluorophenyl)-4-isoxazolyl]propan-1-ol (1.49 g, yield 97%) was obtained as colorless crystals from a fraction eluted with ethyl acetate-hexane (2:1, volume ratio). The crystals were recrystallized from ethyl acetate-hexane. melting point: 40–41° C.

Example 128

To a solution of 5-(3-bromo-4-fluorophenyl)-4-isoxazolylmethanol (6.49 g) in toluene (100 ml) was added dropwise thionyl chloride (2.6 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml) and added to a mixture of diethyl malonate (7.65 g), sodium hydride (60%, oil, 1.87 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-(3-bromo-4-fluorophenyl)-4-isoxazolyl]propionic acid (5.06 g, yield 67%). The crystals were recrystallized from acetone-hexane. melting point: 136–137° C.

Example 129

A mixture of 3-[5-(3-bromo-4-fluorophenyl)-4-isoxazolyl]propionic acid (2.38 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(3-bromo-4-fluorophenyl)-4-isoxazolyl]propionate (2.39 g, yield 96%) was obtained as a colorless oil from a fraction eluted with ethyl acetate-hexane (1:3, volume ratio). NMR (CDCl$_3$) δ: 2.60–2.71 (2H, m), 2.91–3.03 (2H, m), 3.69 (3H, s), 7.18–7.32 (1H, m), 7.60–7.70 (1H, m), 7.94 (1H, dd, J=2.2, 6.2 Hz), 8.23 (1H, s).

Example 130

To a solution of methyl 3-[5-(3-bromo-4-fluorophenyl)-4-isoxazolyl]propionate (1.43 g) in tetrahydrofuran (20 ml) was gently added diisobutylaluminum hydride (1.0 M hexane solution, 10 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(3-bromo-4-fluorophenyl)-4-isoxazolyl]propan-1-ol (1.11 g, yield 85%) was obtained as colorless crystals from a fraction eluted with ethyl acetate-hexane (2:1, volume ratio). The crystals were recrystallized from ethyl acetate-hexane. melting point: 57–58° C.

Example 131

To a solution of 5-(4-phenylphenyl)-4-isoxazolylmethanol (7.11 g) in toluene (200 ml) was added dropwise thionyl chloride (3.10 ml) at 0° C., and the mixture was stirred at room temperature for 3 hr. The reaction mixture was concentrated, saturated aqueous sodium hydrogencarbonate was added to the residue, and the mixture was extracted with ethyl acetate. The ethyl acetate layer was washed with saturated brine, dried (MgSO$_4$) and concentrated. The residue was dissolved in tetrahydrofuran (100 ml), and added to a mixture of diethyl malonate (9.07 g), sodium hydride (60%, oil, 2.22 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (70 ml) and acetic acid (70 ml) was refluxed for 5 hr. The reaction mixture was concentrated, and water was added to the residue. The obtained colorless crystals were filtrated to give 3-[5-(4-phenylphenyl)-4-isoxazolyl]propionic acid (6.30 g, yield 76%). the crystals were recrystallized from ethyl acetate-hexane. melting point: 94–95° C.

Example 132

A mixture of 3-[5-(4-phenylphenyl)-4-isoxazolyl]propionic acid (6.00 g), conc. sulfuric acid (0.1 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(4-phenylphenyl)-4-isoxazolyl]propionate (5.91 g, yield 94%) was obtained as colorless crystals from a fraction eluted with ethyl acetate-hexane (1:3, volume ratio). The crystals were recrystallized from ethyl acetate-hexane. melting point: 103–104° C.

Example 133

To a solution of methyl 3-[5-(4-phenylphenyl)-4-isoxazolyl]propionate (1.00 g) in tetrahydrofuran (25 ml) was gently added diisobutylaluminum hydride (1.0 M hexane solution, 8.0 ml) at 0° C., and the mixture was stirred at room temperature for 1 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and 3-[5-(4-phenylphenyl)-4-isoxazolyl]propan-1-ol (0.656 g, yield 72%) was obtained as colorless crystals from a fraction eluted with ethyl acetate-hexane (2:1, volume ratio). The crystals were recrystallized from ethyl acetate-hexane. melting point: 94–95° C.

Example 134

A mixture of 3-[5-(3-bromo-4-chlorophenyl)-4-isoxazolyl]propionic acid (2.74 g), conc. sulfuric acid (0.2 ml) and methanol (100 ml) was refluxed for 4 hr. The reaction mixture was concentrated, water was added to the residue and the mixture was extracted with ethyl acetate. The ethyl acetate layer was washed with saturated brine, dried (MgSO$_4$) and concentrated. The residue was subjected to silica gel column chromatography, and methyl 3-[5-(3-bromo-4-chlorophenyl)-4-isoxazolyl]propionate (2.22 g, yield 78%) was obtained as colorless crystals from a fraction eluted with ethyl acetate-hexane (1:3, volume ratio). The crystals were recrystallized from ethyl acetate-hexane. melting point: 54–55° C.

Example 135

A mixture of diethyl 4-aminobenzylphosphonate (0.58 g), 3-(3-methyl-5-phenyl-4-isoxazolyl)propionic acid (0.50 g), 1-hydroxy-1H-1,2,3-benzotriazole hydrate (0.37 g), 1-ethyl-3-(3-dimethylaminopropyl)carbodiimide hydrochloride (0.46 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and N-(4-diethylphosphonomethylphenyl)-3-(3-methyl-5-phenyl-4-isoxazolyl)propionamide (0.87 g, yield 88%) was obtained as colorless crystals from

Example 136

To a mixture of 3-methyl-5-phenylisoxazole-4-carbaldehyde (4.94 g), ethyl diethylphosphonoacetate (6.53 g) and N,N-dimethylformamide (70 ml) was added sodium hydride (60%, oil, 1.13 g) at 0° C., and the mixture was stirred at room temperature for 3 hr. The reaction mixture was poured into dilute hydrochloric acid, and the mixture was extracted with ethyl acetate. The ethyl acetate layer was washed with saturated brine, dried (MgSO$_4$) and concentrated. The residue was subjected to silica gel column chromatography, and a yellow oil was obtained from a fraction eluted with ethyl acetate-hexane (1:4, volume ratio). A mixture of the obtained yellow oil, 2N hydrochloric acid (50 ml) and acetic acid (50 ml) was refluxed for 3 hr. The reaction mixture was concentrated, and water was added to the residue. The obtained colorless crystals were filtrated to give (E)-3-(3-methyl-5-phenyl-4-isoxazolyl)propenoic acid (4.02 g, yield 93%). The crystals were recrystallized from ethyl acetate-hexane. melting point: 173–174° C.

Example 137

A mixture of methyl 4-aminobenzoate (0.30 g), (E)-3-(3-methyl-5-phenyl-4-isoxazolyl)propenoic acid (0.35 g), 1-hydroxy-1H-1,2,3-benzotriazole hydrate (0.27 g), 1-ethyl-3-(3-dimethylaminopropyl)carbodiimide hydrochloride (0.35 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and (E)-N-(4-methoxycarbonylphenyl)-3-(3-methyl-5-phenyl-4-isoxazolyl)propenamide (0.51 g, yield 92%) was obtained as colorless crystals from a fraction eluted with ethyl acetate-hexane (1:1, volume ratio). The crystals were recrystallized from ethyl acetate-hexane. melting point: 174–175° C.

Example 138

A mixture of ethyl 4-aminophenylacetate (1.11 g), (E)-3-(3-methyl-5-phenyl-4-isoxazolyl)propenoic acid (0.95 g), 1-hydroxy-1H-1,2,3-benzotriazole hydrate (0.75 g), 1-ethyl-3-(3 -dimethylaminopropyl)carbodiimide hydrochloride (0.91 g) and N,N-dimethylformamide (20 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and (E)-N-(4-ethoxycarbonylmethylphenyl)-3-(3-methyl-5-phenyl-4-isoxazolyl)propenamide (1.82 g, yield 97%) was obtained as colorless crystals from a fraction eluted with ethyl acetate-hexane (1:1, volume ratio). The crystals were recrystallized from ethyl acetate-hexane. melting point: 164–165° C.

a fraction eluted with ethyl acetate-hexane (1:1, volume ratio). The crystals were recrystallized from ethyl acetate-hexane. melting point: 114–115° C.

Example 139

A mixture of diethyl 4-aminobenzylphosphonate (0.43 g), (E)-3-(3-methyl-5-phenyl-4-isoxazolyl)propenoic acid (0.50 g), 1-hydroxy-1H-1,2,3-benzotriazole hydrate (0.38 g), 1-ethyl-3-(3-dimethylaminopropyl)carbodiimide hydrochloride (0.45 g) and N,N-dimethylformamide (15 ml) was stirred at room temperature overnight. The reaction mixture was poured into water and the mixture was extracted with ethyl acetate. The ethyl acetate layer was washed with dilute hydrochloric acid, saturated aqueous sodium hydrogencarbonate and then saturated brine, dried (MgSO$_4$) and concentrated. The residue was subjected to silica gel column chromatography, and (E)-N-(4-diethylphosphonomethylphenyl)-3-(3-methyl-5-phenyl-4-isoxazolyl)propenamide (0.71 g, yield 83%) was obtained as colorless crystals from a fraction eluted with ethyl acetate-hexane (1:1, volume ratio). The crystals were recrystallized from ethyl acetate-hexane. melting point: 155–156° C.

Example 140

A solution of 4-chloromethyl-3-(4-trifluoromethylphenyl)isoxazole (2.90 g) in tetrahydrofuran (100 ml) was added to a mixture of diethyl malonate (5.35 g), sodium hydride (60%, oil, 1.30 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (30 ml) and acetic acid (30 ml) was refluxed for 5 hr. The reaction mixture was concentrated, and water was added to the residue. The obtained colorless crystals were filtrated to give 3-[3-(4-trifluoromethylphenyl)-4-isoxazolyl]propionic acid (2.49 g, yield 79%). The crystals were recrystallized from ethyl acetate-hexane. melting point: 173–174° C.

Example 141

4-Chloromethyl-3-(4-chlorophenyl)-5-methylisoxazole (1.21 g) was dissolved in tetrahydrofuran (50 ml) and added to a mixture of diethyl malonate (1.20 g), sodium hydride (60%, oil, 0.21 g) and tetrahydrofuran (20 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried (MgSO$_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (30 ml) and acetic acid (30 ml) was refluxed for 5 hr. The reaction mixture was concentrated, and water was added to the residue. The obtained colorless crystals were filtrated to give 3-[3-(4-chlorophenyl)-5-methyl-4-isoxazolyl]propionic acid (1.20 g, yield 90%). The crystals were recrystallized from ethanol. melting point: 187–188° C.

Example 142

To a solution of methyl propionylacetate (9.95 g) and 4-chloro-N-hydroxybenzenecarboxyimidoyl chloride (9.65 g) in tetrahydrofuran (100 ml) was gently added a solution of triethylamine (15 ml) in tetrahydrofuran (10 ml) at 0° C. The mixture was stirred at room temperature overnight, the reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:9, volume ratio). To a solution of the obtained colorless oil in tetrahydrofuran (100 ml) was gently added diisobutylaluminum hydride (1.0 M hexane solution, 110 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried ($MgSO_4$) and concentrated to give a colorless oil. A mixture of the obtained colorless oil and thionyl chloride (10.0 ml) was stirred at 0° C. for 30 min. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated to give a colorless oil. The obtained colorless oil was dissolved in tetrahydrofuran (100 ml) and added to a mixture of diethyl malonate (2.40 g), sodium hydride (60%, oil, 0.42 g) and tetrahydrofuran (20 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (30 ml) and acetic acid (30 ml) was refluxed for 5 hr. The reaction mixture was concentrated, and water was added to the residue. The obtained colorless crystals were filtrated to give 3-[3-(4-chlorophenyl)-5-ethyl-4-isoxazolyl]propionic acid (4.33 g, yield 30%). The crystals were recrystallized from ethanol. melting point: 164–165° C.

Example 143

To a solution of ethyl benzoylacetate (5.76 g) and sodium hydride (60%, oil, 0.12 g) in tetrahydrofuran (60 ml) was gently added methyl acrylate (3.2 ml) at room temperature and the mixture was stirred at room temperature overnight. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:9, volume ratio). A mixture of the obtained colorless oil, hydroxylamine hydrochloride (1.68 g) and isopropyl alcohol (65 ml) was refluxed for 16 hr. The reaction mixture was poured into dilute hydrochloric acid, and the mixture was extracted with ethyl acetate. The ethyl acetate layer was washed with saturated brine, dried ($MgSO_4$) and concentrated to give a colorless oil. A mixture of the obtained colorless oil, 2N sodium hydroxide (20 ml) and methanol (30 ml) was stirred at room temperature for 1 hr. The reaction mixture was acidified with dilute hydrochloric acid and extracted with ethyl acetate. The ethyl acetate layer was washed with saturated brine, dried ($MgSO_4$) and concentrated. The obtained colorless crystals were filtrated to give 3-[5-hydroxy-3-phenyl-4-isoxazolyl]propionic acid (2.49 g, yield 36%). The crystals were recrystallized from ethanol. melting point: 183–184° C.

Example 144

A solution of 4-chloromethyl-5-methyl-3-(4-trifluoromethylphenyl)isoxazole (1.37 g) in tetrahydrofuran (50 ml) was added to a mixture of diethyl malonate (1.20 g), sodium hydride (60%, oil, 0.21 g) and tetrahydrofuran (20 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (30 ml) and acetic acid (30 ml) was refluxed for 5 hr. The reaction mixture was concentrated, and water was added to the residue. The obtained colorless crystals were filtrated to give 3-[5-methyl-3-(4-trifluoromethylphenyl)-4-isoxazolyl]propionic acid (1.25 g, yield 84%). The crystals were recrystallized from ethanol-hexane. melting point: 138–139° C.

Example 145

To a solution of methyl acetoacetate (8.88 g) and 3-trifluoromethyl-N-hydroxybenzenecarboxyimidoyl chloride (11.35 g) in tetrahydrofuran (100 ml) was gently added triethylamine (15 ml) in tetrahydrofuran (10 ml) at 0° C. and the mixture was stirred at room temperature overnight. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:9, volume ratio). To a solution of the obtained colorless oil in tetrahydrofuran (100 ml) was gently added diisobutylaluminum hydride (1.0 M hexane solution, 110 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried ($MgSO_4$) and concentrated to give a colorless oil. A mixture of the obtained colorless oil and thionyl chloride (5.0 ml) was stirred at 0° C. for 30 min. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. A solution of the obtained colorless oil in tetrahydrofuran (100 ml) and added to a mixture of diethyl malonate (12.20 g), sodium hydride (60%, oil, 3.05 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[5-methyl-3-(3-trifluoromethylphenyl)-4-isoxazolyl] propionic acid (6.54 g, yield 43%). The crystals were recrystallized from ethanol-water. melting point: 63–64° C.

Example 146

A mixture of dibenzoylmethane (4.48 g), methyl acrylate (1.8 ml), potassium t-butoxide (0.23 g) and N,N-dimethylformamide (40 ml) was stirred at room temperature overnight. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:9, volume ratio). A mixture of the obtained colorless oil, hydroxylamine hydrochloride (1.00 g) and isopropyl alcohol (50 ml) was refluxed for 6 hr. The reaction mixture was poured into dilute hydrochloric acid, and the mixture was extracted with ethyl acetate. The ethyl acetate layer was washed with saturated brine, dried ($MgSO_4$) and concentrated to give a colorless oil. A mixture of the obtained colorless oil, 2N sodium hydroxide (20 ml) and methanol (30 ml) was stirred at room temperature for 2 hr. The reaction mixture was acidified with dilute hydrochloric acid and extracted with ethyl acetate. The ethyl acetate layer was washed with saturated brine, dried ($MgSO_4$) and concentrated. The obtained colorless crystals were filtrated to give 3-[3,5-diphenyl-4-isoxazolyl]propionic acid (1.91 g, yield 33%). The crystals were recrystallized from ethanol. melting point: 152–153° C.

Example 147

To a solution of methyl acetoacetate (8.88 g) and 2-chloro-N-hydroxybenzenecarboxyimidoyl chloride (9.65 g) in tetrahydrofuran (100 ml) was gently added a solution of triethylamine (15 ml) in tetrahydrofuran (10 ml) at 0° C. The mixture was stirred at room temperature overnight, the reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:9, volume ratio). To a solution of the obtained colorless oil in tetrahydrofuran (100 ml) was gently added diisobutylaluminum hydride (1.0 M hexane solution, 110 ml) at 0° C. and the mixture was stirred at room temperature for 30 min. The reaction mixture was poured into dilute hydrochloric acid, and the mixture was extracted with ethyl acetate. The ethyl acetate layer was washed with saturated brine, dried ($MgSO_4$) and concentrated to give a colorless oil. A mixture of the obtained colorless oil and thionyl chloride (5.0 ml) was stirred at 0° C. for 30 min. The reaction mixture was concentrated, saturated aqueous sodium hydrogencarbonate was added to the residue, and the mixture was extracted with ethyl acetate. The ethyl acetate layer was washed with saturated brine, dried ($MgSO_4$) and concentrated. A solution of the obtained colorless oil in tetrahydrofuran (100 ml) was added to a mixture of diethyl malonate (12.20 g), sodium hydride (60%, oil, 3.05 g) and tetrahydrofuran (50 ml) at 0° C. The mixture was stirred at 0° C. for 1 hr and then at room temperature overnight. The reaction mixture was acidified with dilute hydrochloric acid and extracted with ethyl acetate. The ethyl acetate layer was washed with saturated brine, dried ($MgSO_4$) and concentrated. The residue was subjected to silica gel column chromatography, and a colorless oil was obtained from a fraction eluted with ethyl acetate-hexane (1:3, volume ratio). A mixture of the obtained colorless oil, 6N hydrochloric acid (50 ml) and acetic acid (50 ml) was refluxed for 5 hr. The reaction mixture was concentrated, and water was added to the residue. The obtained colorless crystals were filtrated to give 3-[3-(2-chlorophenyl)-5-methyl-4-isoxazolyl]propionic acid (5.40 g, yield 40%). The crystals were recrystallized from ethyl acetate-hexane. melting point: 79–81° C.

Example 148

To a solution of methyl 3-[5-(4-methylphenyl)-4-isoxazolyl]propionate (2.00 g) in tetrahydrofuran (50 ml) was gently added diisobutylaluminum hydride (0.95 M hexane solution, 21.5 ml) at 0° C., and the mixture was stirred at room temperature for 1 hr. Sodium sulfate 10 hydrate (6.57 g) was added to the reaction mixture and the mixture was stirred for 2 hr, after which an insoluble material was filtered off. The filtrate was concentrated and the residue was subjected to silica gel column chromatography, and 3-[5-(4-methylphenyl)-4-isoxazolyl]propan-1-ol (1.53 g, yield 86%) was obtained as a colorless oil from a fraction eluted with ethyl acetate-hexane (1:1, volume ratio). NMR ($CDCl_3$) δ: 1.25–1.35 (1H, m), 1.8–2.0 (2H, m), 2.41 (3H, s), 2.7–2.85 (2H, m), 3.65–3.8 (2H, m), 7.29 (2H, d, J=8 Hz), 7.62 (2H, d, J=8 Hz), 8.19 (1H, s).

Example 149

To a solution of methyl 3-[5-(4,5-dichloro-2-thienyl)-4-isoxazolyl]propionate (1.30 g) in tetrahydrofuran (40 ml) was gently added diisobutylaluminum hydride (0.95 M hexane solution, 11.2 ml) at room temperature, and the mixture was stirred for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[5-(4,5-dichloro-2-thienyl)-4-isoxazolyl]propan-1-ol (1.05 g, yield 89%) was obtained as a colorless oil from a fraction eluted with ethyl acetate-hexane (1:1, volume ratio). NMR ($CDCl_3$) δ: 1.35–1.5 (1H, m), 1.8–2.0 (2H, m), 2.65–2.8 (2H, m), 3.65–4.0 (2H, m), 7.29 (1H, s), 8.19 (1H, s).

Example 150

To a solution of methyl 3-[5-(2,5-dichlorophenyl)-4-isoxazolyl]propionate (500 mg) in tetrahydrofuran (30 ml) was gently added diisobutylaluminum hydride (1.0 M toluene solution, 4.2 ml) and the mixture was stirred at room temperature for 1 hr. The reaction mixture was poured into dilute hydrochloric acid, and the mixture was extracted with ethyl acetate. The ethyl acetate layer was washed with saturated brine, dried ($MgSO_4$) and concentrated. The residue was subjected to silica gel column chromatography, and 3-[5-(2,5-dichlorophenyl)-4-isoxazolyl]propan-1-ol (420 mg, yield 93%) was obtained as a colorless oil from a fraction eluted with ethyl acetate-hexane (1:1, volume ratio). NMR ($CDCl_3$) δ: 1.28 (1H, t, J=5 Hz), 1.7–1.9 (2H, m), 2.5–2.6 (2H, m), 3.65 (2H, td, J=6, 5 Hz), 7.35–7.5 (3H, m), 8.27 (1H, s).

Example 151

A mixture of diethyl 4-aminobenzylphosphonate (0.73 g), 3-[5-(4-fluorophenyl)-4-isoxazolyl]propionic acid (0.49 g), 1-hydroxy-7-aza-1H-1,2,3-benzotriazole (HOAT) (0.40 g), 1-ethyl-3-(3-dimethylaminopropyl)carbodiimide (WSCI) (0.45 g) and N,N-dimethylformamide (5 ml) was stirred at room temperature overnight. The reaction mixture was poured into a 1N aqueous hydrochloric acid solution and extracted with ethyl acetate. The ethyl acetate layer was washed with 10% aqueous potassium carbonate solution, and then with saturated brine, dried (MgSO$_4$) and concentrated. The obtained solid was recrystallized from ethyl acetate-hexane to give N-[4-(diethylphosphonomethyl)phenyl]-3-[5-(4-fluorophenyl)-4-isoxazolyl]propionamide (0.67 g, yield 70%) as a colorless prism. melting point: 134–135° C.

Elemental Analysis:
Calculated (C$_{23}$H$_{26}$FN$_2$O$_5$P) C, 60.00; H, 5.69; N, 6.08. Found C, 59.83; H, 5.52; N, 6.03.
HPLC analysis: purity 100% (retention time: 3.735 min)
MS (ESI+): 461 (M+H)
NMR (CDCl$_3$) δ: 1.23 (6H, t, J=7 Hz), 2.69 (2H, t, J=7 Hz), 3.0–3.2 (4H, m), 3.9–4.1 (4H, m), 7.1–7.3 (4H, m), 7.38 (2H, d, J=8.5 Hz), 7.7–7.8 (2H, m), 8.13 (1H, br s), 8.26 (1H, s).

Example 152

A mixture of diethyl 4-aminobenzylphosphonate (72.9 mg), 3-[5-(4-trifluoromethylphenyl)-4-isoxazolyl]propionic acid (57 mg), 1-hydroxy-7-aza-1H-1,2,3-benzotriazole (40 mg), 1-ethyl-3-(3-dimethylaminopropyl)carbodiimide (45 mg) and N,N-dimethylformamide (0.3 ml) was stirred at room temperature overnight. The reaction mixture was directly introduced into preparative HPLC and purified to give N-[4-(diethylphosphonomethyl)phenyl]-3-[5-(4-trifluoromethylphenyl)-4-isoxazolyl]propionamide.

yield: 40 mg (yield 71%)
HPLC analysis: purity 100% (retention time: 3.858 min)
MS (ESI+): 511 (M+H)

In the same manner as in Example 152, the following compounds were synthesized.

Example 153

N-[4-(diethylphosphonomethyl)phenyl]-3-[5-(4-methylthiophenyl)-4-isoxazolyl]propionamide yield: 80 mg (yield: 82%)
HPLC analysis: purity 100% (retention time: 3.713 min)
MS (ESI+): 489 (M+H)
NMR (CDCl$_3$) δ: 1.23 (6H, t, J=7 Hz), 2.53 (3H, s), 2.68 (2H, t, J=7 Hz), 3.0–3.1 (4H, m), 3.9–4.05 (4H, m), 7.1–7.2 (2H, m), 7.3–7.4 (4H, m), 7.66 (2H, d, J=8.5 Hz), 8.08 (1H, br s), 8.24 (1H, s).

Example 154

N-[4-(diethylphosphonomethyl)phenyl]-3-[5-(2,4-difluorophenyl)-4-isoxazolyl]propionamide yield: 35 mg (yield: 74%)
HPLC analysis: purity 100% (retention time: 3.554 min)
MS (ESI+): 479 (M+H)

Example 155

N-[4-(diethylphosphonomethyl)phenyl]-3-[5-(5-chloro-2-thienyl)-4-isoxazolyl]propionamide yield: 71 mg (yield: 73%)
HPLC analysis: purity 100% (retention time: 3.779 min)
MS (ESI+): 483 (M+H)

Example 156

N-[4-(diethylphosphonomethyl)phenyl]-3-[5-(4-trifluoromethoxyphenyl)-4-isoxazolyl]propionamide yield: 82 mg (yield: 78%)
HPLC analysis: purity 100% (retention time: 3.914 min)
MS (ESI+): 527 (M+H)
NMR (CDCl$_3$) δ: 1.23 (6H, t, J=7 Hz), 2.71 (2H, t, J=7 Hz), 3.0–3.1 (4H, m), 3.9–4.05 (4H, m), 7.1–7.2 (2H, m), 7.3–7.4 (4H, m), 7.79 (2H, d, J=8.5 Hz), 8.29 (1H, s).

Example 157

N-[4-(diethylphosphonomethyl)phenyl]-3-[5-(3-bromo-4-chlorophenyl)-4-isoxazolyl]propionamide yield: 53 mg (yield: 48%)
HPLC analysis: purity 99.6% (retention time: 3.985 min)
MS (ESI+): 555 (M+H), 557

Example 158

A mixture of N-[4-(diethylphosphonomethyl)phenyl]-3-[5-(4-methylthiophenyl)-4-isoxazolyl]propionamide (98 mg), m-chloroperbenzoic acid (60 mg) and tetrahydrofuran (5 ml) was stirred at room temperature for 4 hr. 10% aqueous sodium sulfite solution was added to the reaction mixture and the mixture was extracted with ethyl acetate. The ethyl acetate layer was washed with 10% aqueous potassium carbonate solution, and then with saturated brine, dried (MgSO$_4$) and concentrated. The residue was purified by preparative HPLC to give N-[4-(diethylphosphonomethyl)phenyl]-3-[5-(4-methylsulfinylphenyl)-4-isoxazolyl]propionamide.

yield: 16 mg (yield: 16%)
HPLC analysis: purity 95.1% (retention time: 2.903 min)
MS (ESI+): 505 (M+H)

Example 159

N-[4-(Diethylphosphonomethyl)phenyl]-3-[5-(4-methylsulfonylphenyl)-4-isoxazolyl]propionamide was obtained from a fraction that later eluted by preparative HPLC in the experiment of Example 158.

yield: 14 mg (yield: 13%)
HPLC analysis: purity 93.0% (retention time: 3.163 min)
MS (ESI+): 521 (M+H)

Example 160

A mixture of 4-hydroxypiperidine (10 mg), 3-[5-(3-chlorophenyl)-4-isoxazolyl]propionic acid (25 mg), PS-carbodiimide (100 mg, manufactured by Argonaut Technologies) and dichloromethane (1 ml) was shaken at room temperature overnight. The reaction mixture was filtrated and the filtrate was concentrated. The obtained residue was purified by preparative HPLC to give 1-{3-[5-(3-chlorophenyl)-4-isoxazolyl]propanoyl}-4-piperidinol.

yield: 15 mg (yield: 46%)
HPLC analysis: purity 98.1% (retention time: 3.084 min)
MS (APCI+): 335 (M+H)

In the same manner as in Example 160, the following compounds were synthesized.

Example 161

3-[5-(3-chlorophenyl)-4-isoxazolyl]-N-methyl-N-(1-methyl-4-piperidinyl)propionamide trifluoroacetate yield: 36 mg (yield: 75%)
HPLC analysis: purity 98.9% (retention time: 2.697 min)
MS (APCI+): 362 (M+H)

Example 162

N-((3S)-1-{3-[5-(3-chlorophenyl)-4-isoxazolyl]propanoyl}pyrrolidin-3-yl)-2,2,2-trifluoroacetamide yield: 22 mg (yield: 53%)
HPLC analysis: purity 97.5% (retention time: 3.572 min)
MS (APCI+): 416 (M+H)

Example 163 tert-butyl (3S)-1-{3-[5-(3-chlorophenyl)-4-isoxazolyl]propanoyl}pyrrolidin-3-ylcarbamate yield: 37 mg (yield: 89%)
HPLC analysis: purity 96.7% (retention time: 3.771 min)
MS (APCI−): 418 (M−H)

Example 164

4-{3-[5-(3-chlorophenyl)-4-isoxazolyl]propanoyl}thiomorpholine 1,1'-dioxide yield: 2 mg (yield: 7%)
HPLC analysis: purity 95.8% (retention time: 3.308 min)
MS (APCI+): 369 (M+H)

Example 165

A mixture of diethyl 4-aminobenzylphosphonate (36 mg), 3-[5-(3-chloro-4-fluorophenyl)-4-isoxazolyl]propionic acid (27 g), 1-hydroxy-7-aza-1H-1,2,3-benzotriazole (20 mg), 1-ethyl-3-(3-dimethylaminopropyl)carbodiimide (30 mg) and N,N-dimethylformamide (0.5 ml) was stirred at room temperature overnight. The reaction mixture was poured into 1N aqueous hydrochloric acid solution and the mixture was extracted with ethyl acetate. The ethyl acetate layer was concentrated, and the obtained solid was purified by preparative HPLC to give 3-[5-(3-chloro-4-fluorophenyl)-4-isoxazolyl]-N-[4-(diethylphosphonomethyl)phenyl]propionamide.

yield: 39 mg (yield: 79%)
HPLC analysis: purity 99.5% (retention time: 3.875 min)
MS (ESI+): 495 (M+H)

In the same manner as in Example 165, the following compounds were synthesized.

Example 166

3-[5-(4-bromophenyl)-4-isoxazolyl]-N-[4-(diethylphosphonomethyl)phenyl]propionamide yield: 36 mg (yield: 69%)
HPLC analysis: purity 99.6% (retention time: 3.897 min)
MS (ESI+): 521 (M+H), 523

Example 167

N-((3S)-1-{3-[5-(3-chloro-4-fluorophenyl)-4-isoxazolyl]propanoyl}pyrrolidin-3-yl)-2,2,2-trifluoroacetamide yield: 26 mg (yield: 60%)
HPLC analysis: purity 99.8% (retention time: 3.764 min)
MS (ESI+): 434 (M+H)

Example 168

N-((3S)-1-{3-[5-(4-bromophenyl)-4-isoxazolyl]propanoyl}pyrrolidin-3-yl)-2,2,2-trifluoroacetamide yield: 33 mg (yield: 72%)
HPLC analysis: purity 93.6% (retention time: 3.768 min)
MS (ESI+): 460 (M+H), 462

Example 169

N-((3S)-1-{3-[5-(4-fluorophenyl)-4-isoxazolyl]propanoyl}pyrrolidin-3-yl)-2,2,2-trifluoroacetamide yield: 25 mg (yield: 74%)
HPLC analysis: purity 98.3% (retention time: 3.480 min)
MS (ESI+): 400 (M+H)

Exampl 170

3-[5-(3-chloro-4-fluorophenyl)-4-isoxazolyl]-N-methyl-N-(1-methyl-4-piperidinyl)propionamide trifluoroacetate yield: 36 mg (yield: 69%)
HPLC analysis: purity 99.7% (retention time: 2.910 min)
MS (ESI+): 380 (M+H)

Example 171

3-[5-(4-bromophenyl)-4-isoxazolyl]-N-methyl-N-(1-methyl-4-piperidinyl)propionamide trifluoroacetate yield: 20 mg (yield: 38%)
HPLC analysis: purity 99.2% (retention time: 2.925 min)
MS (ESI+): 406 (M+H), 408

Example 172

3-[5-(4-fluorophenyl)-4-isoxazolyl]-N-methyl-N-(1-methyl-4-piperidinyl)propionamide trifluoroacetate yield: 23 mg (yield: 49%)
HPLC analysis: purity 97.5% (retention time: 2.654 min)
MS (ESI+): 346 (M+H)

Example 173

1-(3-[5-(3-chloro-4-fluorophenyl)-4-isoxazolyl]propanoyl)-4-piperidinol yield: 34 mg (yield: 96%)
HPLC analysis: purity 95.5% (retention time: 3.255 min)
MS (ESI+): 353 (M+H)

Example 174

1-{3-[5-(4-bromophenyl)-4-isoxazolyl]propanoyl}-4-piperidinol yield: 11 mg (yield: 28%)
HPLC analysis: purity 98.5% (retention time: 3.264 min)
MS (ESI+): 379 (M+H), 381

Example 175

1-(3-[5-(4-fluorophenyl)-4-isoxazolyl]propanoyl}-4-piperidinol yield: 22 mg (yield: 68%)
HPLC analysis: purity 89.5% (retention time: 2.952 min)
MS (ESI+): 319 (M+H)

Example 176

1-{3-[5-(3-chloro-4-fluorophenyl)-4-isoxazolyl]propanoyl}-4-(2-furoyl)piperazine yield: 32 mg (yield: 75%)
HPLC analysis: purity 95.9% (retention time: 3.634 min)
MS (ESI+): 432 (M+H)

Example 177

1-{3-[5-(4-bromophenyl)-4-isoxazolyl]propanoyl}-4-(2-furoyl)piperazine yield: 41 mg (yield: 89%)
HPLC analysis: purity 96.1% (retention time: 3.637 min)
MS (ESI+): 458 (M+H), 460

Example 178

1-{3-[5-(4-fluorophenyl)-4-isoxazolyl]propanoyl}-4-(2-furoyl)piperazine yield: 20 mg (yield: 50%)
HPLC analysis: purity 98.9% (retention time: 3.352 min)
MS (ESI+): 398 (M+H)

Example 179

1-{3-[5-(3-chloro-4-fluorophenyl)-4-isoxazolyl]propanoyl}-4-methylpiperazine trifluoroacetate yield: 40 mg (yield: 85%)
HPLC analysis: purity 96.6% (retention time: 2.857 min)
MS (ESI+): 352 (M+H)

Example 180

1-{3-[5-(4-bromophenyl)-4-isoxazolyl]propanoyl}-4-methylpiperazine trifluoroacetate yield: 43 mg (yield: 87%)
HPLC analysis: purity 95.7% (retention time: 2.852 min)
MS (ESI+): 378 (M+H), 380

Example 181

1-{3-[5-(4-fluorophenyl)-4-isoxazolyl]propanoyl}-4-methylpiperazine trifluoroacetate yield: 32 mg (yield: 74%)
HPLC analysis: purity 93.4% (retention time: 2.574 min)
MS (ESI+): 318 (M+H)

Example 182

A mixture of N'-benzyl-N,N-dimethylethylenediamine (27 mg), 3-[5-(4-fluorophenyl)-4-isoxazolyl]propionic acid (24 mg), 1-hydroxy-7-aza-1H-1,2,3-benzotriazole (20 mg), 1-ethyl-3-(3-dimethylaminopropyl)carbodiimide (23 mg) and N,N-dimethylformamide (0.3 ml) was stirred at room temperature overnight. The reaction mixture was directly introduced into preparative HPLC and purified to give N-benzyl-N-[2-(dimethylamino)ethyl]-3-[5-(4-fluorophenyl)-4-isoxazolyl]propionamide trifluoroacetate.

yield: 47 mg (yield 92%)
HPLC analysis: purity 93.8% (retention time: 2.481 min)
MS (APCI+): 396 (M+H)

In the same manner as in Example 182, the following compounds were synthesized.

Example 183

N-butyl-3-[5-(4-fluorophenyl)-4-isoxazolyl]propionamide yield: 21 mg (yield 71%)
HPLC analysis: purity 97.9% (retention time: 3.463 min)
MS (APCI+): 291 (M+H)

Example 184

N-(cyclohexylmethyl)-3-[5-(4-fluorophenyl)-4-isoxazolyl]propionamide yield: 23 mg (yield 71%)
HPLC analysis: purity 95.2% (retention time: 3.870 min)
MS (APCI+): 331 (M+H)
NMR (CDCl$_3$)δ: 0.8–1.8 (11H, m), 2.46 (2H, t, J=7 Hz), 2.95–3.1 (4H, m), 5.40 (1H, br s), 7.15–7.25 (2H, m), 7.7–7.8 (2H, m), 8.21 (1H, s).

Example 185

N-cyclopropyl-3-[5-(4-fluorophenyl)-4-isoxazolyl]propionamide yield: 20 mg (yield 73%)
HPLC analysis: purity 97.0% (retention time: 3.031 min)
MS (APCI+): 275 (M+H)

Example 186

N-benzyl-3-[5-(4-fluorophenyl)-4-isoxazolyl]propionamide yield: 23 mg (yield 71%)
HPLC analysis: purity 95.4% (retention time: 3.566 min)
MS (APCI+): 325 (M+H)

Example 187

N-(1,3-benzodioxol-5-ylmethyl)-3-[5-(4-fluorophenyl)-4-isoxazolyl]propionamide yield: 27 mg (yield 73%)
HPLC analysis: purity 97.2% (retention time: 3.507 min)
MS (APCI+): 369 (M+H)

Example 188

3-[5-(4-fluorophenyl)-4-isoxazolyl]-N-(2-phenylethyl)propionamide yield: 25 mg (yield 74%)
HPLC analysis: purity 98.4% (retention time: 3.680 min)
MS (APCI+): 339 (M+H)

Example 189

3-[5-(4-fluorophenyl)-4-isoxazolyl]-N-(3-phenylpropyl)propionamide yield: 25 mg (yield 71%)
HPLC analysis: purity 98.9% (retention time: 3.822 min)
MS (APCI+): 353 (M+H)

Example 190

N-benzhydryl-3-[5-(4-fluorophenyl)-4-isoxazolyl]propionamide yield: 23 mg (yield 57%)
HPLC analysis: purity 98.4% (retention time: 4.051 min)
MS (APCI+): 401 (M+H)

Example 191

3-[5-(4-fluorophenyl)-4-isoxazolyl]-N-(2-methoxyethyl)propionamide yield: 21 mg (yield 72%)
HPLC analysis: purity 99.4% (retention time: 2.904 min)
MS (APCI+): 293 (M+H)

Example 192

3-[5-(4-fluorophenyl)-4-isoxazolyl]-N-[3-(methylsulfanyl)propyl]propionamide yield: 23 mg (yield 70%)
HPLC analysis: purity 97.9% (retention time: 3.345 min)
MS (APCI+): 323 (M+H)

Example 193

3-[5-(4-fluorophenyl)-4-isoxazolyl]-N-(tetrahydro-2-furanylmethyl)propionamide yield: 21 mg (yield 65%)
HPLC analysis: purity 98.1% (retention time: 3.057 min)
MS (APCI+): 319 (M+H)

Example 194

3-[5-(4-fluorophenyl)-4-isoxazolyl]-N-[2-(1H-indol-3-yl)ethyl]propionamide yield: 34 mg (yield 89%)
HPLC analysis: purity 99.7% (retention time: 3.657 min)
MS (APCI+): 378 (M+H)

Example 195

N-(2-ethylpropyl)-3-[5-(4-fluorophenyl)-4-isoxazolyl]propionamide yield: 22 mg (yield 71%)
HPLC analysis: purity 98.8% (retention time: 3.566 min)
MS (APCI+): 305 (M+H)

Example 196

N-(tert-butyl)-3-[5-(4-fluorophenyl)-4-isoxazolyl]propionamide yield: 23 mg (yield 80%)
HPLC analysis: purity 98.7% (retention time: 3.548 min)
MS (APCI+): 291 (M+H)

Example 197

N-cyclohexyl-3-[5-(4-fluorophenyl)-4-isoxazolyl]propionamide yield: 24 mg (yield 76%)
HPLC analysis: purity 96.8% (retention time: 3.672 min)
MS (APCI+): 317 (M+H)

Example 198

3-[5-(4-fluorophenyl)-4-isoxazolyl]-N-(2-propynyl)propionamide yield: 20 mg (yield 72%)
HPLC analysis: purity 99.2% (retention time: 3.092 min)
MS (APCI+): 273 (M+H)

Example 199

3-[5-(4-fluorophenyl)-4-isoxazolyl]-N-[4-(trifluoromethyl)benzyl]propionamide yield: 28 mg (yield 73%)
HPLC analysis: purity 99.2% (retention time: 3.913 min)
MS (APCI+): 393 (M+H)
NMR (CDCl$_3$) δ: 2.54 (2H, t, J=7 Hz), 3.04 (2H, t, J=7 Hz), 4.47 (2H, d, J=7 Hz), 5.82 (1H, br s), 7.1–7.4 (4H, m), 7.57 (2H, d, J=8 Hz), 7.65–7.8 (2H, m), 8.20 (1H, s).

Example 200

N-[2-(3,4-dimethoxyphenyl)ethyl]-3-[5-(4-fluorophenyl)-4-isoxazolyl]propionamide yield: 29 mg (yield 73%)
HPLC analysis: purity 99.1% (retention time: 3.454 min)
MS (APCI+): 399 (M+H)

Example 201

N-(3,3-diphenylpropyl)-3-[5-(4-fluorophenyl)-4-isoxazolyl]propionamide yield: 30 mg (yield 70%)
HPLC analysis: purity 99.4% (retention time: 4.173 min)
MS (APCI+): 429 (M+H)

Example 202

N-(2,3-dihydro-1H-inden-2-yl)-3-[5-(4-fluorophenyl)-4-isoxazolyl]propionamide yield: 26 mg (yield 75%)
HPLC analysis: purity 98.9% (retention time: 3.763 min)
MS (APCI+): 351 (M+H)

Example 203

3-[5-(4-fluorophenyl)-4-isoxazolyl]-N-(3-isopropoxypropyl)propionamide yield: 24 mg (yield 71%)
HPLC analysis: purity 99.4% (retention time: 3.375 min)
MS (APCI+): 333 (M−H)

Example 204

3-[5-(4-fluorophenyl)-4-isoxazolyl]-N-(2-oxo-3-azepanyl)propionamide yield: 25 mg (yield 72%)
HPLC analysis: purity 97.5% (retention time: 2.953 min)
MS (APCI+): 346 (M+H)

Example 205

3-[5-(4-fluorophenyl)-4-isoxazolyl]-N-(2-furylmethyl)propionamide yield: 23 mg (yield 73%)
HPLC analysis: purity 99.4% (retention time: 3.364 min)
MS (APCI−): 313 (M−H)

Example 206

3-[5-(4-fluorophenyl)-4-isoxazolyl]-N-[3-(2-oxo-1-pyrrolidinyl)propyl]propionamide yield: 29 mg (yield 80%)
HPLC analysis: purity 99.5% (retention time: 2.847 min)
MS (APCI+): 360 (M+H)

Example 207

3-[5-(4-fluorophenyl)-4-isoxazolyl]-N-methyl-N-(1-naphthylmethyl)propionamide yield: 24 mg (yield 62%)
HPLC analysis: purity 99.8% (retention time: 4.165 min)
MS (APCI+): 389 (M+H)

Example 208

N-[2-(3,4-dimethoxyphenyl)ethyl]-3-[5-(4-fluorophenyl)-4-isoxazolyl]-N-methylpropionamide yield: 25 mg (yield 61%)
HPLC analysis: purity 98.1% (retention time: 3.626 min)
MS (ESI+): 413 (M+H)

Example 209

3-[5-(4-fluorophenyl)-4-isoxazolyl]-N,N-bis(2-methoxyethyl)propionamide yield: 23 mg (yield 66%)
HPLC analysis: purity 99.6% (retention time: 3.353 min)
MS (ESI+): 351 (M+H)

Example 210

1-{3-[5-(4-fluorophenyl)-4-isoxazolyl]propanoyl}piperidine yield: 29 mg (yield 96%)
HPLC analysis: purity 99.6% (retention time: 3.566 min)
MS (APCI+): 303 (M+H)

Exampl 211

4-{3-[5-(4-fluorophenyl)-4-isoxazolyl]propanoyl}-2,6-dimethylmorpholine yield: 31 mg (yield 93%)
HPLC analysis: purity 99.7% (retention time: 3.423 min)
MS (APCI+): 333 (M+H)
NMR (CDCl$_3$) δ: 1.18 (6H, t, J=7 Hz), 2.25–2.4 (1H, m), 2.5–2.8 (3H, m), 3.02 (2H, t, J=7 Hz), 3.4–3.6 (3H, m), 4.4–4.5 (1H, m), 7.15–7.25 (2H, m), 7.7–7.8 (2H, m), 8.24 (1H, s).

Example 212

2-{3-[5-(4-fluorophenyl)-4-isoxazolyl]propanoyl}-1,2,3,4-tetrahydroisoquinoline yield: 26 mg (yield 75%)
HPLC analysis: purity 99.0% (retention time: 3.902 min)
MS (APCI+): 351 (M+H)

Example 213

1-{3-[5-(4-fluorophenyl)-4-isoxazolyl]propanoyl}-4-piperidinecarboxyamide yield: 39 mg (yield 90%)
HPLC analysis: purity 99.5% (retention time: 2.792 min)
MS (APCI+): 346 (M+H)

Example 214

2-(1-{3-[5-(4-fluorophenyl)-4-isoxazolyl]propanoyl}-4-piperidinyl)ethanol yield: 27 mg (yield 77%)
HPLC analysis: purity 96.2% (retention time: 3.086 min)
MS (APCI+): 347 (M+H)

Example 215

4-{3-[5-(4-fluorophenyl)-4-isoxazolyl]propanoyl}thiomorpholine yield: 23 mg (yield 72%)
HPLC analysis: purity 99.4% (retention time: 3.496 min)
MS (APCI+): 321 (M+H)

Example 216

4-benzyl-1-{3-[5-(4-fluorophenyl)-4-isoxazolyl]propanoyl}piperidine yield: 8 mg (yield 21%)
HPLC analysis: purity 99.8% (retention time: 4.273 min)
MS (APCI+): 393 (M+H)

Example 217

3-acetamide-1-{3-[5-(4-fluorophenyl)-4-isoxazolyl]propanoyl}pyrrolidine yield: 28 mg (yield 80%)
HPLC analysis: purity 99.7% (retention time: 2.779 min)
MS (APCI+): 346 (M+H)

Example 218

N-cyclohexyl-3-[5-(4-fluorophenyl)-4-isoxazolyl]-N-methylpropionamide yield: 19 mg (yield 58%)
HPLC analysis: purity 99.5% (retention time: 3.966 min)
MS (APCI+): 331 (M+H)

Example 219

N-benzyl-3-[5-(4-fluorophenyl)-4-isoxazolyl]-N-methylpropionamide yield: 28 mg (yield 83%)
HPLC analysis: purity 99.5% (retention time: 3.837 min)
MS (APCI+): 339 (M+H)

Example 220

N-benzyl-N-[2-(ethoxycarbonyl)ethyl]-3-[5-(4-fluorophenyl)-4-isoxazolyl]propionamide yield: 25 mg (yield 60%)
HPLC analysis: purity 98.8% (retention time: 4.068 min)
MS (APCI+): 425 (M+H)

Example 221

N-ethyl-3-[5-(4-fluorophenyl)-4-isoxazolyl]-N-(2-methoxyethyl)propionamide yield: 34 mg (yield 90%)
HPLC analysis: purity 99.5% (retention time: 3.410 min)
MS (APCI−): 319 (M−H)

Example 222

1-{3-[5-(4-fluorophenyl)-4-isoxazolyl]propanoyl}morpholine yield: 47 mg (yield 90%)
HPLC analysis: purity 97.0% (retention time: 3.070 min)
MS (APCI+): 305 (M+H)
NMR (CDCl$_3$) δ: 2.60 (2H, t, J=7 Hz), 3.03 (2H, t, J=7 Hz), 3.35–3.45 (2H, m), 3.55–3.7 (6H, m), 7.15–7.25 (2H, m), 7.7–7.8 (2H, m), 8.23 (1H, s).

Example 223

1-{3-[5-(4-fluorophenyl)-4-isoxazolyl]propanoyl)-3,5-dimethylpiperidine yield: 44 mg (yield 90%)
HPLC analysis: purity 99.5% (retention time: 4.029 min).
MS (APCI+): 331 (M+H)
NMR (CDCl$_3$) δ: 0.7–0.9 (6H, m), 1.3–1.5 (1H, m), 1.7–2.0 (2H, m), 2.35–2.65 (3H, m), 2.9–3.1 (3H, m), 3.3–3.8 (2H, m), 4.5–4.7 (1H, m), 7.1–7.25 (2H, m), 7.65–7.8 (2H, m), 8.23 (1H, s).

Example 224

2-{3-[5-(4-fluorophenyl)-4-isoxazolyl]propanoyl}decahydroisoquinoline yield: 28 mg (yield 78%)
HPLC analysis: purity 90.1% (retention time: 2.861 min)
MS (APCI+): 357 (M+H)

Example 225

4-(ethoxycarbonyl)-1-{3-[5-(4-fluorophenyl)-4-isoxazolyl]propanoyl}piperidine yield: 33 mg (yield 88%)
HPLC analysis: purity 99.1% (retention time: 3.614 min)
MS (APCI+): 375 (M+H)

Example 226

N-(2,6-dimethylphenyl)-N-[((2S)-1-(3-[5-(4-fluorophenyl)-4-isoxazolyl]propanoyl}pyrrolidinyl)methyl]amine yield: 7 mg (yield 18%)
HPLC analysis: purity 97.8% (retention time: 3.186 min)
MS (APCI+): 422 (M+H)

Example 227

4-(4-chlorophenyl)-1-{3-[5-(4-fluorophenyl)-4-isoxazolyl]propanoyl}-4-piperidinol yield: 9 mg (yield 21%)
HPLC analysis: purity 99.7% (retention time: 3.817 min)
MS (APCI–): 427 (M–H)

Example 228

3-(N-acetyl-N-ethylamino)-1-{3-[5-(4-fluorophenyl)-4-isoxazolyl]propanoyl}pyrrolidine yield: 14 mg (yield 36%)
HPLC analysis: purity 97.0% (retention time: 3.055 min)
MS (APCI+): 374 (M+H)

Example 229

N-[2-(dimethylamino)ethyl]-3-[5-(4-fluorophenyl)-4-isoxazolyl]-N-methylpropionamide trifluoroacetate yield: 39 mg (yield 89%)
HPLC analysis: purity 99.8% (retention time: 2.481 min)
MS (APCI–): 318 (M–H)

Example 230

N-(1-benzyl-3-pyrrolidinyl)-3-[5-(4-fluorophenyl)-4-isoxazolyl]-N-methylpropionamide trifluoroacetate yield: 49 mg (yield 93%)
HPLC analysis: purity 94.5% (retention time: 2.980 min)
MS (APCI+): 408 (M+H)

Example 231

N-ethyl-3-[5-(4-fluorophenyl)-4-isoxazolyl]-N-(4-pyridinylmethyl)propionamide trifluoroacetate yield: 43 mg (yield 91%)
HPLC analysis: purity 99.5% (retention time: 2.637 min)
MS (APCI+): 354 (M+H)

Example 232

3-[5-(4-fluorophenyl)-4-isoxazolyl]-N,N-bis(3-pyridinylmethyl)propionamide 2-trifluoroacetate yield: 57 mg (yield 90%)
HPLC analysis: purity 99.7% (retention time: 2.193 min)
MS (APCI+): 417 (M+H)

Example 233

1-ethyl-4-{3-[5-(4-fluorophenyl)-4-isoxazolyl]propanoyl}piperazine trifluoroacetate yield: 42 mg (yield 93%)
HPLC analysis: purity 99.6% (retention time: 2.473 min)
MS (APCI+): 332 (M+H)

Example 234

1-(ethoxycarbonylmethyl)-4-{3-[5-(4-fluorophenyl)-4-isoxazolyl]propanoyl}piperazine trifluoroacetate yield: 43 mg (yield 86%)
HPLC analysis: purity 99.7% (retention time: 2.627 min)
MS (APCI+): 390 (M+H)

Example 235

1-benzyl-4-{3-[5-(4-fluorophenyl)-4-isoxazolyl]propanoyl}piperazine trifluoroacetate yield: 41 mg (yield 80%)
HPLC analysis: purity 98.6% (retention time: 2.834 min)
MS (APCI+): 394 (M+H)

Example 236

1-{3-[5-(4-fluorophenyl)-4-isoxazolyl]propanoyl}-4-(2-pyridinyl)piperazine trifluoroacetate yield: 47 mg (yield 96%)
HPLC analysis: purity 99.6% (retention time: 2.598 min)
MS (APCI+): 381 (M+H)

Example 237

1-benzhydryl-4-{3-[5-(4-fluorophenyl)-4-isoxazolyl]propanoyl piperazine trifluoroacetate yield: 59 mg (yield 96%)
HPLC analysis: purity 99.2% (retention time: 3.202 min)
MS (APCI–): 468 (M–H)

Example 238

1-{3-[5-(4-fluorophenyl)-4-isoxazolyl]propanoyl}-4-phenylpiperazine trifluoroacetate yield: 40 mg (yield 81%)
HPLC analysis: purity 98.5% (retention time: 3.456 min)
MS (APCI+): 380 (M+H)

Example 239

1-{3-[5-(4-fluorophenyl)-4-isoxazolyl]propanoyl}-4-(2-methoxyphenyl)piperazine trifluoroacetate yield: 47 mg (yield 89%)
HPLC analysis: purity 99.5% (retention time: 3.140 min)
MS (APCI+): 410 (M+H)

Example 240

1-{3-[5-(4-fluorophenyl)-4-isoxazolyl]propanoyl}-4-(1-piperidinyl)piperidine trifluoroacetate yield: 48 mg (yield 96%)
HPLC analysis: purity 99.2% (retention time: 2.578 min)
MS (APCI+): 386 (M+H)

Example 241

3-[5-(4-fluorophenyl)-4-isoxazolyl]-N-methyl-N-(1-methyl-3-pyrrolidinyl)propionamide trifluoroacetate yield: 40 mg (yield 90%)
HPLC analysis: purity 99.4% (retention time: 2.494 min)
MS (APCI+): 332 (M+H)

Example 242

N-benzyl-N-(1-benzyl-3-pyrrolidinyl)-3-[5-(4-fluorophenyl)-4-isoxazolyl]propionamide trifluoroacetate yield: 54 mg (yield 90%)
HPLC analysis: purity 97.0% (retention time: 3.378 min)
MS (APCI+): 484 (M+H)

Example 243

3-[5-(4-fluorophenyl)-4-isoxazolyl]-N,N-bis(2-pyridinylmethyl)propionamide 2-trifluoroacetate yield: 48 mg (yield 80%)
HPLC analysis: purity 99.0% (retention time: 2.606 min)
MS (APCI+): 417 (M+H)

Example 244

1-{3-[5-(4-fluorophenyl)-4-isoxazolyl]propanoyl}-4-(2-hydroxyethyl)piperazine trifluoroacetate yield: 36 mg (yield 79%)
HPLC analysis: purity 99.6% (retention time: 2.390 min)
MS (APCI+): 348 (M+H)

Example 245

1-{3-benzodioxol-5-ylmethyl)-4-{3-[5-(4-fluorophenyl)-4-isoxazolyl]propanoyl}piperazine trifluoroacetate yield: 58 mg (yield 95%)
HPLC analysis: purity 98.4% (retention time: 2.864 min)
MS (APCI+): 438 (M+H)

Example 246

1-{3-[5-(4-fluorophenyl)-4-isoxazolyl]propanoyl}-4-(2-pyrimidinyl)piperazine trifluoroacetate yield: 43 mg (yield 86%)
HPLC analysis: purity 99.1% (retention time: 3.054 min)
MS (APCI+): 382 (M+H)

Example 247

1-{3-[5-(4-fluorophenyl)-4-isoxazolyl]propanoyl}-4-[(E)-3-phenyl-2-propenyl]piperazine trifluoroacetate yield: 48 mg (yield 91%)
HPLC analysis: purity 96.9% (retention time: 3.064 min)
MS (APCI+): 420 (M+H)

Example 248

(2S)-1-{3-[5-(4-fluorophenyl)-4-isoxazolyl]propanoyl}-2-(1-pyrrolidinylmethyl)pyrrolidine trifluoroacetate yield: 44 mg (yield 91%)
HPLC analysis: purity 99.5% (retention time: 2.701 min)
MS (APCI+): 372 (M+H)

Example 249

1-{3-[5-(4-fluorophenyl)-4-isoxazolyl]propanoyl}-4-(1-pyrrolidinyl)piperidine trifluoroacetate yield: 44 mg (yield 91%)
HPLC analysis: purity 99.4% (retention time: 2.530 min)
MS (APCI+): 372 (M+H)

Example 250

1-{3-[5-(4-fluorophenyl)-4-isoxazolyl]propanoyl)-4-[3-(trifluoromethyl)phenyl]piperazine trifluoroacetate yield: 34 mg (yield 61%)
HPLC analysis: purity 99.6% (retention time: 4.229 min)
MS (APCI+): 448 (M+H)

Example 251

1-(4-acetylphenyl)-4-{3-[5-(4-fluorophenyl)-4-isoxazolyl]propanoyl}piperazine trifluoroacetate yield: 35 mg (yield 65%)
HPLC analysis: purity 100% (retention time: 3.619 min)
MS (APCI+): 422. (M+H)

Example 252

1-(2-chlorophenyl)-4-{3-[5-(4-fluorophenyl)-4-isoxazolyl]propanoyl}piperazine trifluoroacetate yield: 37 mg (yield 71%)
HPLC analysis: purity 99.1% (retention time: 4.176 min)
MS (APCI+): 414 (M+H)

Example 253

1-{3-[5-(4-fluorophenyl)-4-isoxazolyl]propanoyl}-4-(3-methoxyphenyl)piperazine trifluoroacetate yield: 52 mg (yield 98%)
HPLC analysis: purity 99.6% (retention time: 3.625 min)
MS (APCI+): 410 (M+H)

Example 254

1-(3-chlorophenyl)-4-{3-[5-(4-fluorophenyl)-4-isoxazolyl]propanoyl}piperazine trifluoroacetate yield: 27 mg (yield 51%)
HPLC analysis: purity 98.8% (retention time: 4.149 min)
MS (APCI+): 414 (M+H)

Example 255

1-(3-[5-(4-fluorophenyl)-4-isoxazolyl]propanoyl}-4-(2-methylphenyl)piperazine trifluoroacetate yield: 11 mg (yield 22%)
HPLC analysis: purity 97.7% (retention time: 4.004 min)
MS (APCI+): 394 (M+H)

Example 256

1-(2-ethoxyphenyl)-4-{3-[5-(4-fluorophenyl)-4-isoxazolyl]propanoyl}piperazine trifluoroacetate yield: 40 mg (yield 75%)
HPLC analysis: purity 99.2% (retention time: 3.336 min)
MS (APCI+): 424 (M+H)

Example 257

1-(2-fluorophenyl)-4-{3-[5-(4-fluorophenyl)-4-isoxazolyl]propanoyl}piperazine trifluoroacetate yield: 34 mg (yield 67%)
HPLC analysis: purity 99.4% (retention time: 3.956 min)
MS (APCI+): 398 (M+H)

Example 258

1-(4-chlorophenyl)-4-{3-[5-(4-fluorophenyl)-4-isoxazolyl]propanoyl}piperazine trifluoroacetate yield: 28 mg (yield 53%)
HPLC analysis: purity 99.5% (retention time: 4.084 min)
MS (APCI+): 414 (M+H)

Example 259

1-{3-[5-(4-fluorophenyl)-4-isoxazolyl]propanoyl}-4-(4-methoxyphenyl)piperazine trifluoroacetate yield: 24 mg (yield 45%)
HPLC analysis: purity 99.2% (retention time: 3.085 min)
MS (APCI+): 410 (M+H)

Example 260

1-(4-fluorophenyl)-4-{3-[5-(4-fluorophenyl)-4-isoxazolyl]propanoyl}piperazine trifluoroacetate yield: 30 mg (yield 58%)
HPLC analysis: purity 99.0% (retention time: 3.643 min)
MS (APCI+): 398 (M+H)
NMR (CDCl$_3$) δ: 2.66 (2H, t, J=7 Hz), 3.0–3.1 (6H, m), 3.57 (2H, m, J=5 Hz), 3.79 (2H, m, J=5 Hz), 6.85–7.0 (4H, m), 7.15–7.25 (2H, m), 7.7–7.8 (2H, m), 8.25 (1H, s).

Example 261

1-{3-[5-(4-fluorophenyl)-4-isoxazolyl]propanoyl}-4-(3-methylphenyl)piperazine trifluoroacetate yield: 32 mg (yield 63%)
HPLC analysis: purity 89.6% (retention time: 3.545 min)
MS (APCI+): 394 (M+H)

Example 262

2-ethyl-1-{3-[5-(4-fluorophenyl)-4-isoxazolyl]propanoyl}piperidine yield: 27 mg (yield 80%)
HPLC analysis: purity 98.9% (retention time: 3.916 min)
MS (APCI+): 331 (M+H)

Example 263

1-{3-[5-(4-fluorophenyl)-4-isoxazolyl]propanoyl}-3-piperidinecarboxyamide yield: 30 mg (yield 86%)
HPLC analysis: purity 99.1% (retention time: 2.860 min)
MS (APCI+): 346 (M+H)

Example 264

1-(3-[5-(4-fluorophenyl)-4-isoxazolyl]propanoyl)-4-phenyl-4-piperidinol yield: 32 mg (yield 82%)
HPLC analysis: purity 99.3% (retention time: 3.541 min)
MS (APCI–): 393 (M–H)

Example 265

4-(4-bromophenyl)-1-{3-[5-(4-fluorophenyl)-4-isoxazolyl]propanoyl}-4-piperidinol yield: 37 mg (yield 79%)
HPLC analysis: purity 99.2% (retention time: 3.867 min)
MS (APCI–): 471 (M–H), 473

Example 266

1-{3-[5-(4-fluorophenyl)-4-isoxazolyl]propanoyl}azepane yield: 25 mg (yield 79%)
HPLC analysis: purity 99.0% (retention time: 3.709 min)
MS (APCI+): 317 (M+H)

Example 267

1-{3-[5-(4-fluorophenyl)-4-isoxazolyl]propanoyl}azocane yield: 27 mg (yield 81%)
HPLC analysis: purity 99.2% (retention time: 3.881 min)
MS (APCI+): 331 (M+H)

Example 268

1-{3-[5-(4-fluorophenyl)-4-isoxazolyl]propanoyl}decahydroquinoline yield: 30 mg (yield 84%)
HPLC analysis: purity 98.9% (retention time: 4.166 min)
MS (APCI+): 357 (M+H)

Example 269

1-{3-[5-(4-fluorophenyl)-4-isoxazolyl]propanoyl}-4-phenyl-4-piperidinecarbonitrile yield: 35 mg (yield 86%)
HPLC analysis: purity 98.9% (retention time: 3.929 min)
MS (APCI+): 404 (M+H)

Example 270

4-acetyl-1-{3-[5-(4-fluorophenyl)-4-isoxazolyl]propanoyl}-4-phenylpiperidine yield: 17 mg (yield 41%)
HPLC analysis: purity 99.0% (retention time: 3.898 min)
MS (APCI+): 421 (M+H)

Example 271

2-ethoxycarbonyl-1-{3-[5-(4-fluorophenyl)-4-isoxazolyl]propanoyl}piperidine yield: 23 mg (yield 64%)
HPLC analysis: purity 98.3% (retention time: 3.693 min)
MS (APCI+): 361 (M+H)

Example 272

N-[2-(dimethylamino)ethyl]-3-[5-(4-fluorophenyl)-4-isoxazolyl]propionamide trifluoroacetate yield: 20 mg (yield 47%)
HPLC analysis: purity 99.9% (retention time: 2.516 min)
MS (ESI+): 306 (M+H)

Example 273

N-[3-(diethylamino)propyl]-3-[5-(4-fluorophenyl)-4-isoxazolyl]propionamide trifluoroacetate yield: 34 mg (yield 75%)
HPLC analysis: purity 99.8% (retention time: 2.567 min)
MS (ESI+): 348 (M+H)

Example 274

3-[5-(4-fluorophenyl)-4-isoxazolyl]-N-[2-(1-piperidinyl)ethyl]propionamide trifluoroacetate yield: 34 mg (yield 73%)
HPLC analysis: purity 99.8% (retention time: 2.621 min)
MS (ESI+): 346 (M+H)

Example 275

3-[5-(4-fluorophenyl)-4-isoxazolyl]-N-[2-(4-morpholinyl)ethyl]propionamide trifluoroacetate yield: 33 mg (yield 71%)
HPLC analysis: purity 99.7% (retention time: 2.499 min)
MS (ESI+): 348 (M+H)

Example 276

3-[5-(4-fluorophenyl)-4-isoxazolyl]-N-[3-(4-methyl-1-piperazinyl)propyl]propionamide 2-trifluoroacetate yield: 27 mg (yield 45%)
HPLC analysis: purity 99.7% (retention time: 2.282 min)
MS (ESI+): 375 (M+H)
NMR (CDCl$_3$) δ: 1.6–1.75 (2H, m), 2.45 (2H, t, J=7 Hz), 2.79 (3H, s), 2.8–2.9 (4H, m), 3.0–3.1 (4H, m), 7.35–7.45 (2H, m), 7.75–7.85 (2H, m), 8.02 (1H, br s), 8.52 (1H, s).

Example 277

3-[5-(4-fluorophenyl)-4-isoxazolyl]-N-[3-(methylanilino)propyl]propionamide trifluoroacetate yield: 39 mg (yield 78%)
HPLC analysis: purity 99.8% (retention time: 2.842 min)
MS (ESI+): 382 (M+H)

Example 278

N-(1-benzyl-4-piperazinyl)-3-[5-(4-fluorophenyl)-4-isoxazolyl]propionamide trifluoroacetate yield: 39 mg (yield 74%)
HPLC analysis: purity 99.9% (retention time: 2.863 min)
MS (ESI+): 408 (M+H)

Example 279

3-[5-(4-fluorophenyl)-4-isoxazolyl]-N-(2,2,6,6-tetramethyl-4-piperidinyl)propionamide trifluoroacetate yield: 23 mg (yield 48%)
HPLC analysis: purity 100% (retention time: 2.661 min)
MS (ESI+): 374 (M+H)
NMR (CDCl$_3$) δ: 1.25–1.4 (12H, m), 1.7–1.9 (2H, m), 2.43 (2H, t, J=7 Hz), 2.86 (2H, t, J=7 Hz), 3.55–3.65 (2H, m), 4.0–4.1 (1H, m), 7.35–7.45 (2H, m), 7.7–7.8 (1H, m), 7.75–7.85 (2H, m), 7.95–8.05 (1H, m), 8.51 (1H, s), 8.5–8.6 (1H, m).

Example 280

N-(2-anilinoethyl)-3-[5-(4-fluorophenyl)-4-isoxazolyl]propionamide trifluoroacetate yield: 35 mg (yield 76%)
HPLC analysis: purity 99.7% (retention time: 3.002 min)
MS (ESI+): 354 (M+H)

Example 281

3-[5-(4-fluorophenyl)-4-isoxazolyl]-N-(2-pyridinylmethyl)propionamide trifluoroacetate yield: 27 mg (yield 62%)
HPLC analysis: purity 99.9% (retention time: 2.497 min)
MS (ESI+): 326 (M+H)

Example 282

3-[5-(4-fluorophenyl)-4-isoxazolyl]-N-[2-(4-pyridinyl)ethyl]propionamide trifluoroacetate yield: 32 mg (yield 72%)
HPLC analysis: purity 99.9% (retention time: 2.454 min)
MS (ESI+): 340 (M+H)

Example 283

3-[5-(4-fluorophenyl)-4-isoxazolyl]-N-[3-(1-imidazolyl)propyl]propionamide trifluoroacetate yield: 31 mg (yield 68%)
HPLC analysis: purity 99.9% (retention time: 2.496 min)
MS (ESI+): 343 (M+H)

Example 284

N-[2-(diisopropylamino)ethyl]-3-[5-(4-fluorophenyl)-4-isoxazolyl]propionamide trifluoroacetate yield: 33 mg (yield 69%)
HPLC analysis: purity 99.8% (retention time: 2.733 min)
MS (ESI+): 362 (M+H)

Example 285

N-[3-(dimethylamino)-2,2-dimethylpropyl]-3-[5-(4-fluorophenyl)-4-isoxazolyl]propionamide trifluoroacetate yield: 32.1 mg (yield 70%)
HPLC analysis: purity 99.9% (retention time: 2.570 min)
MS (ESI+): 348 (M+H)

Example 286

3-[5-(4-fluorophenyl)-4-isoxazolyl]-N-[3-(2-methyl-1-piperidinyl)propyl]propionamide trifluoroacetate yield: 35 mg (yield 71%)
HPLC analysis: purity 100% (retention time: 2.696 min)
MS (ESI+): 374 (M+H)

Example 287

3-[5-(4-fluorophenyl)-4-isoxazolyl]-N-[3-(4-morpholinyl)propyl]propionamide trifluoroacetate yield: 35 mg (yield 74%)
HPLC analysis: purity 100% (retention time: 2.512 min)
MS (ESI+): 362 (M+H)

Example 288

3-[5-(4-fluorophenyl)-4-isoxazolyl]-N-[2-(1-pyrrolidinyl)ethyl]propionamide trifluoroacetate yield: 31 mg (yield 69%)
HPLC analysis: purity 99.9% (retention time: 2.542 min)
MS (ESI+): 332 (M+H)

Example 289

N-[2-(ethyl-3-methylanilino)ethyl]-3-[5-(4-fluorophenyl)-4-isoxazolyl]propionamide trifluoroacetate yield: 39 mg (yield 77%)
HPLC analysis: purity 99.5% (retention time: 3.054 min)
MS (ESI+): 396 (M+H)

Example 290

N-(1-benzyl-3-pyrrolidinyl)-3-[5-(4-fluorophenyl)-4-isoxazolyl]propionamide trifluoroacetate yield: 38 mg (yield 74%)
HPLC analysis: purity 99.7% (retention time: 2.922 min)
MS (ESI+): 394 (M+H)

Example 291

N-{3-[bis(2-hydroxyethyl)amino]propyl}-3-[5-(4-fluorophenyl)-4-isoxazolyl]propionamide trifluoroacetate yield: 34 mg (yield 68%)
HPLC analysis: purity 99.9% (retention time: 2.417 min)
MS (ESI+): 380 (M+H)

Example 292

3-[5-(4-fluorophenyl)-4-isoxazolyl]-N-(4-pyridinylmethyl)propionamide trifluoroacetate yield: 46 mg (yield 95%)
HPLC analysis: purity 100% (retention time: 2.466 min)
MS (ESI+): 326 (M+H)

Example 293

3-[5-(4-fluorophenyl)-4-isoxazolyl]-N-(3-pyridinylmethyl)propionamide trifluoroacetate yield: 31 mg (yield 71%)
HPLC analysis: purity 99.9% (retention time: 2.456 min)
MS (ESI+): 326 (M+H)

Example 294

3-[5-(4-fluorophenyl)-4-isoxazolyl]-N-[2-(3-pyridinyl)ethyl]propionamide trifluoroacetate yield: 35 mg (yield 78%)
HPLC analysis: purity 100% (retention time: 2.489 min)
MS (ESI+): 340 (M+H)

Example 295

N-[2-(dimethylamino)ethyl]-3-{5-[4-(trifluoromethyl)phenyl]-4-isoxazolyl}propionamide trifluoroacetate yield: 5 mg (yield 20%)
HPLC analysis: purity 100% (retention time: 2.931 min)
MS (ESI+): 356 (M+H)

Example 296

N-[3-(methylanilino)propyl]-3-{5-[4-(trifluoromethyl)phenyl]-4-isoxazolyl)propionamide trifluoroacetate yield: 3 mg (yield 10%)
HPLC analysis: purity 92.9% (retention time: 3.212 min)
MS (ESI+): 432 (M+H)

Example 297

N-(1-benzyl-4-piperidinyl)-3-{5-[4-(trifluoromethyl)phenyl]-4-isoxazolyl}propionamide trifluoroacetate yield: 11 mg (yield 39%)
HPLC analysis: purity 100% (retention time: 3.213 min)
MS (ESI+): 458 (M+H)

Example 298

N-(2,2,6,6-tetramethyl-4-piperidinyl)-3-{5-[4-(trifluoromethyl)phenyl]-4-isoxazolyl}propionamide trifluoroacetate yield: 8 mg (yield 28%)
HPLC analysis: purity 100% (retention time: 3.069 min)
MS (ESI+): 424 (M+H)

Example 299

N-(2-anilinoethyl)-3-{5-[4-(trifluoromethyl)phenyl]-4-isoxazolyl}propionamide trifluoroacetate yield: 7 mg (yield 13%)
HPLC analysis: purity 92.2% (retention time: 3.387 min)
MS (ESI+): 404 (M+H)

Exampl 300

N-(2-pyridinylmethyl)-3-{5-[4-(trifluoromethyl)phenyl]-4-isoxazolyl}propionamide trifluoroacetate yield: 11 mg (yield 48%)
HPLC analysis: purity 99.9% (retention time: 2.949 min)
MS (ESI+): 376 (M+H)

Example 301

N-[2-(4-pyridinyl)ethyl]-3-{5-[4-(trifluoromethyl)phenyl]-4-isoxazolyl}propionamide trifluoroacetate yield: 10 mg (yield 41%)
HPLC analysis: purity 100% (retention time: 2.899 min)
MS (ESI+): 390 (M+H)

Example 302

N-[3-(1-imidazolyl)propyl]-3-{5-[4-(trifluoromethyl)phenyl]-4-isoxazolyl}propionamide trifluoroacetate yield: 13 mg (yield 50%)
HPLC analysis: purity 100% (retention time: 2.928 min)
MS (ESI+): 393 (M+H)

Example 303

N-[3-(dimethylamino)-2,2-dimethylpropyl]-3-{5-[4-(trifluoromethyl)phenyl]-4-isoxazolyl}propionamide trifluoroacetate yield: 12 mg (yield 45%)
HPLC analysis: purity 100% (retention time: 3.020 min)
MS (ESI+): 398 (M+H)

Example 304

N-[3-(2-methyl-1-piperidinyl)propyl]-3-{5-[4-(trifluoromethyl)phenyl]-4-isoxazolyl}propionamide trifluoroacetate yield: 5 mg (yield 20%)
HPLC analysis: purity 100% (retention time: 3.088 min)
MS (ESI+): 424 (M+H)

Example 305

N-[2-(ethyl-3-methylanilino)ethyl]-3-{5-[4-(trifluoromethyl)phenyl]-4-isoxazolyl}propionamide trifluoroacetate yield: 4 mg (yield 14%)
HPLC analysis: purity 98.9% (retention time: 3.411 min)
MS (ESI+): 446 (M+H)

Example 306

N-(1-benzyl-3-pyrrolidinyl)-3-{5-[4-(trifluoromethyl)phenyl]-4-isoxazolyl}propionamide trifluoroacetate yield: 10 mg (yield 34%)
HPLC analysis: purity 100% (retention time: 3.275 min)
MS (ESI+): 444 (M+H)

Example 307

N-{3-[bis(2-hydroxyethyl)amino]propyl}-3-{5-[4-(trifluoromethyl)phenyl]-4-isoxazolyl}propionamide trifluoroacetate yield: 7 mg (yield 25%)
HPLC analysis: purity 100% (retention time: 2.854 min)
MS (ESI+): 430 (M+H)

Example 308

N-{2-[(5-nitro-2-pyridinyl)amino]ethyl}-3-{5-[4-(trifluoromethyl)phenyl]-4-isoxazolyl}propionamide trifluoroacetate yield: 15 mg (yield 52%)
HPLC analysis: purity 98.1% (retention time: 3.732 min)
MS (ESI+): 450 (M+H)

Example 309

N-(4-pyridinylmethyl)-3-{5-[4-(trifluoromethyl)phenyl]-4-isoxazolyl}propionamide trifluoroacetate yield: 8 mg (yield 31%)
HPLC analysis: purity 100% (retention time: 2.907 min)
MS (ESI+): 376 (M+H)

Example 310

N-(3-pyridinylmethyl)-3-{5-[4-(trifluoromethyl)phenyl]-4-isoxazolyl}propionamide trifluoroacetate yield: 13 mg (yield 51%)
HPLC analysis: purity 100% (retention time: 2.901 min)
MS (ESI+): 376 (M+H)

Example 311

N-[2-(3-pyridinyl)ethyl]-3-{5-[4-(trifluoromethyl)phenyl]-4-isoxazolyl}propionamide trifluoroacetate yield: 13 mg (yield 53%)
HPLC analysis: purity 100% (retention time: 2.916 min)
MS (ESI+): 390 (M+H)

Example 312

3-[5-(4-fluorophenyl)-4-isoxazolyl]-N-phenylpropionamide yield: 25 mg (yield 79%)
HPLC analysis: purity 100% (retention time: 3.728 min)
MS (ESI+): 311 (M+H)

Example 313

N-(2,3-dihydro-5-indenyl)-3-[5-(4-fluorophenyl)-4-isoxazolyl]propionamide yield: 27 mg (yield 78%)
HPLC analysis: purity 99.1% (retention time: 4.100 min)
MS (ESI+): 351 (M+H)

Example 314

N-(3,5-dimethoxyphenyl)-3-[5-(4-fluorophenyl)-4-isoxazolyl]propionamide yield: 31 mg (yield 84%)
HPLC analysis: purity 99.5% (retention time: 3.784 min)
MS (ESI+): 371 (M+H)

Example 315

N-(4-benzylphenyl)-3-[5-(4-fluorophenyl)-4-isoxazolyl]propionamide yield: 17 mg (yield 43%)
HPLC analysis: purity 99.6% (retention time: 4.307 min)
MS (ESI+): 401 (M+H)

Example 316

N-(1,1'-biphenyl-3-yl)-3-[5-(4-fluorophenyl)-4-isoxazolyl]propionamide yield: 34 mg (yield 87%)
HPLC analysis: purity 97.7% (retention time: 4.300 min)
MS (ESI+): 387 (M+H)

Example 317

3-[5-(4-fluorophenyl)-4-isoxazolyl]-N-(2-thiazolyl)propionamide yield: 34 mg (yield 90%)
HPLC analysis: purity 97.2% (retention time: 3.346 min)
MS (ESI+): 318 (M+H)

Example 318

3-[5-(4-fluorophenyl)-4-isoxazolyl]-N-(4-pyridinyl)propionamide trifluoroacetate yield: 27 mg (yield 63%)
HPLC analysis: purity 98.8% (retention time: 2.646 min)
MS (ESI+): 312 (M+H)

Example 319

N-(5,6-dimethyl-1,2,4-triazine-3-yl)-3-[5-(4-fluorophenyl)-4-isoxazolyl]propionamide yield: 20 mg (yield 59%)
HPLC analysis: purity 98.4% (retention time: 3.081 min)
MS (ESI+): 342 (M+H)

Example 320

3-[5-(4-fluorophenyl)-4-isoxazolyl]-N-(6-quinolinyl)propionamide trifluoroacetate yield: 40 mg (yield 80%)
HPLC analysis: purity 99.7% (retention time: 2.756 min)
MS (ESI+): 362 (M+H)

Example 321

N-(2-benzothiazolyl)-3-[5-(4-fluorophenyl)-4-isoxazolyl]propionamide yield: 22 mg (yield 61%)
HPLC analysis: purity 98.7% (retention time: 3.908 min)
MS (ESI+): 368 (M+H)

Example 322

N-(2-fluorophenyl)-3-[5-(4-fluorophenyl)-4-isoxazolyl]propionamide yield: 26 mg (yield 78%)
HPLC analysis: purity 99.5% (retention time: 3.735 min)
MS (ESI+): 329 (M+H)

Example 323

N-(2,3-dihydro-1,4-benzodioxyn-6-yl)-3-[5-(4-fluorophenyl)-4-isoxazolyl]propionamide yield: 30 mg (yield 80%)
HPLC analysis: purity 100% (retention time: 3.608 min)
MS (ESI+): 369 (M+H)

Example 324

3-[5-(4-fluorophenyl)-4-isoxazolyl]-N-[4-(trifluoromethyl)phenyl]propionamide yield: 33 mg (yield 84%)
HPLC analysis: purity 100% (retention time: 4.170 min)
MS (ESI+): 395 (M+H)

Example 325

3-[5-(4-fluorophenyl)-4-isoxazolyl]-N-(2-phenoxyphenyl)propionamide yield: 38 mg (yield 93%)
HPLC analysis: purity 99.1% (retention time: 4.258 min)
MS (ESI+): 403 (M+H)

Example 326

3-[5-(4-fluorophenyl)-4-isoxazolyl]-N-(1-phenyl-5-pyrazolyl)propionamide yield: 19 mg (yield 51%)
HPLC analysis: purity 99.5% (retention time: 3.490 min)
MS (ESI+): 377 (M+H)

Example 327

3-[5-(4-fluorophenyl)-4-isoxazolyl]-N-(5-methyl-3-isoxazolyl)propionamide yield: 10 mg (yield 33%)
HPLC analysis: purity 99.5% (retention time: 3.427 min)
MS (ESI+): 316 (M+H)

Example 328

3-[5-(4-fluorophenyl)-4-isoxazolyl]-N-(3-quinolinyl)propionamide trifluoroacetate yield: 44 mg (yield 85%)
HPLC analysis: purity 100% (retention time: 2.959 min)
MS (ESI+): 362 (M+H)

Example 329

N-phenyl-3-{5-[4-(trifluoromethyl)phenyl]-4-isoxazolyl}propionamide yield: 6 mg (yield 35%)
HPLC analysis: purity 98.5% (retention time: 4.174 min)
MS (ESI+): 361 (M+H)

Example 330

N-(2,3-dihydro-5-indenyl)-3-{5-[4-(trifluoromethyl)phenyl]-4-isoxazolyl}propionamide yield: 7 mg (yield 34%)
HPLC analysis: purity 98.3% (retention time: 4.511 min)
MS (ESI+): 401 (M+H)

Example 331

N-(3,4-dichlorophenyl)-3-{5-[4-(trifluoromethyl)phenyl]-4-isoxazolyl}propionamide yield: 12 mg (yield 55%)
HPLC analysis: purity 99.5% (retention time: 4.672 min)
MS (ESI+): 429 (M+H)

Example 332

N-(3,5-dimethoxyphenyl)-3-{5-[4-(trifluoromethyl)phenyl]-4-isoxazolyl}propionamide yield: 12 mg (yield 55%)
HPLC analysis: purity 99.5% (retention time: 4.195 min)
MS (ESI+): 421 (M+H)

Example 333

N-(4-benzylphenyl)-3-{5-[4-(trifluoromethyl)phenyl]-4-isoxazolyl}propionamide yield: 12 mg (yield 55%)
HPLC analysis: purity 96.7% (retention time: 4.698 min)
MS (ESI+): 451 (M+H)

Example 334

N-(1,1'-biphenyl-3-yl)-3-{5-[4-(trifluoromethyl)phenyl]-4-isoxazolyl}propionamide yield: 10 mg (yield 46%)
HPLC analysis: purity 98.2% (retention time: 4.660 min)
MS (ESI+): 437 (M+H)

Example 335

N-(2-thiazolyl)-3-{5-[4-(trifluoromethyl)phenyl]-4-isoxazolyl}propionamide yield: 3 mg (yield 14%)
HPLC analysis: purity 97.5% (retention time: 3.816 min)
MS (ESI+): 368 (M+H)

Example 336

N-(4-pyridinyl)-3-{5-[4-(trifluoromethyl)phenyl]-4-isoxazolyl}propionamide trifluoroacetate yield: 12 mg (yield 52%)
HPLC analysis: purity 80.0% (retention time: 3.114 min)
MS (ESI+): 362 (M+H)

Example 337

N-(5,6-dimethyl-1,2,4-triazin-3-yl)-3-{5-[4-(trifluoromethyl)phenyl]-4-isoxazolyl}propionamide yield: 5 mg (yield 24%)
HPLC analysis: purity 97.4% (retention time: 3.634 min)
MS (ESI+): 392 (M+H)

Example 338

N-(6-quinolinyl)-3-{5-[4-(trifluoromethyl)phenyl]-4-isoxazolyl}propionamide trifluoroacetate yield: 12 mg (yield 60%)
HPLC analysis: purity 98.9% (retention time: 3.189 min)
MS (ESI+): 412 (M+H)

Example 339

N-(2-benzothiazolyl)-3-{5-[4-(trifluoromethyl)phenyl]-4-isoxazolyl}propionamide yield: 6 mg (yield 28%)
HPLC analysis: purity 99.1% (retention time: 4.316 min)
MS (ESI+): 418 (M+H)

Example 340

N-(2-fluorophenyl)-3-{5-[4-(trifluoromethyl)phenyl]-4-isoxazolyl}propionamide yield: 8 mg (yield 44%)
HPLC analysis: purity 99.4% (retention time: 4.200 min)
MS (ESI+): 379 (M+H)

Example 341

N-(2,3-dihydro-1,4-benzodioxyn-6-yl)-3-{5-[4-(trifluoromethyl)phenyl]-4-isoxazolyl}propionamide yield: 10 mg (yield 47%)
HPLC analysis: purity 100% (retention time: 4.056 min)
MS (ESI+): 419 (M+H)

Example 342

N-[3,5-bis(trifluoromethyl)phenyl]-3-{5-[4-(trifluoromethyl)phenyl]-4-isoxazolyl}propionamide yield: 13 mg (yield 52%)
HPLC analysis: purity 99.1% (retention time: 4.859 min)
MS (ESI+): 497 (M+H)

Example 343

N-[4-(trifluoromethoxy)phenyl]-3-{5-[4-(trifluoromethyl)phenyl]-4-isoxazolyl}propionamide yield: 9 mg (yield 41%)
HPLC analysis: purity 99.2% (retention time: 4.566 min)
MS (ESI+): 445 (M+H)

Example 344

N-(2-phenoxyphenyl)-3-{5-[4-(trifluoromethyl)phenyl]-4-isoxazolyl}propionamide yield: 11 mg (yield 48%)
HPLC analysis: purity 99.3% (retention time: 4.680 min)
MS (ESI+): 453 (M+H)

Example 345

N-(1-phenyl-5-pyrazolyl)-3-{5-[4-(trifluoromethyl)phenyl]-4-isoxazolyl}propionamide yield: 11 mg (yield 52%)
HPLC analysis: purity 100% (retention time: 3.952 min)
MS (ESI+): 427 (M+H)

Example 346

N-(5-methyl-3-isoxazolyl)-3-{5-[4-(trifluoromethyl)phenyl]-4-isoxazolyl}propionamide yield: 7 mg (yield 40%)
HPLC analysis: purity 99.5% (retention time: 3.921 min)
MS (ESI+): 366 (M+H)

Example 347

N-(3-pyridinyl)-3-{5-[4-(trifluoromethyl)phenyl]-4-isoxazolyl}propionamide trifluoroacetate yield: 10 mg (yield 41%)
HPLC analysis: purity 86.0% (retention time: 3.046 min)
MS (ESI+): 362 (M+H)

Example 348

N-(2-pyrazinyl)-3-{5-[4-(trifluoromethyl)phenyl]-4-isoxazolyl}propionamide yield: 7 mg (yield 36%)
HPLC analysis: purity 99.0% (retention time: 3.650 min)
MS (ESI+): 363 (M+H)

Example 349

N-(3-quinolinyl)-3-{5-[4-(trifluoromethyl)phenyl]-4-isoxazolyl}propionamide yield: 14 mg (yield 68%)
HPLC analysis: purity 99.2% (retention time: 3.395 min)
MS (ESI+): 412 (M+H)

Example 350

N-(2,1,3-benzothiadiazol-4-yl)-3-{5-[4-(trifluoromethyl)phenyl]-4-isoxazolyl}propionamide yield: 11 mg (yield 52%)
HPLC analysis: purity 100% (retention time: 4.334 min)
MS (ESI+): 419 (M+H)

Example 351

N-[4-(diethylphosphono)phenyl]-3-(5-phenyl-4-isoxazolyl)propionamide yield: 36 mg (yield 84%)
HPLC analysis: purity 99.6% (retention time: 4.208 min)
MS (ESI+): 429 (M+H)

Example 352

N-[4-(diethylphosphono)phenyl]-3-[5-(4-chlorophenyl)-4-isoxazolyl]propionamide yield: 38 mg (yield 83%)
HPLC analysis: purity 100% (retention time: 4.431 min)
MS (ESI+): 463 (M+H)

Example 353

N-[4-(diethylphosphono)phenyl]-2-(5-phenyl-4-isoxazolyl)acetamide yield: 38 mg (yield 91%)
HPLC analysis: purity 94.1% (retention time: 4.136 min)
MS (ESI+): 415 (M+H)

Example 354

N-[4-(diethylphosphono)phenyl]-4-(5-phenyl-4-isoxazolyl)butanamide yield: 34 mg (yield 77%)
HPLC analysis: purity 100% (retention time: 4.258 min)
MS (ESI+): 443 (M+H)

Example 355

N-{4-[(2-oxide-1,3,2-dioxaphosphinan-2-yl)methyl]phenyl}-3-(5-phenyl-4-isoxazolyl)propionamide yield: 35 mg (yield 82%)
HPLC analysis: purity 100% (retention time: 3.796 min)
MS (ESI+): 427 (M+H)

Example 356

3-[5-(4-chlorophenyl)-4-isoxazolyl]-N-{4-[(2-oxide-1,3,2-dioxaphosphinan-2-yl)methyl]phenyl}propionamide yield: 17 mg (yield 36%)
HPLC analysis: purity 100% (retention time: 4.035 min)
MS (ESI+): 461 (M+H)

Example 357

N-{4-[(2-oxide-1,3,2-dioxaphosphinan-2-yl)methyl]phenyl}-2-(5-phenyl-4-isoxazolyl)acetamide yield: 23 mg (yield 55%)
HPLC analysis: purity 100% (retention time: 3.718 min)
MS (ESI+): 413 (M+H)

Example 358

N-{4-[(2-oxide-1,3,2-dioxaphosphinan-2-yl)methyl]phenyl}-4-(5-phenyl-4-isoxazolyl)butanamide yield: 40 mg (yield 92%)
HPLC analysis: purity 99.1% (retention time: 3.862 min)
MS (ESI+): 441 (M+H)

Exampl 359

N-[4-(dimethylphosphonomethyl)phenyl]-3-(5-phenyl-4-isoxazolyl)propionamide yield: 26 mg (yield 63%)
HPLC analysis: purity 100% (retention time: 3.897 min)
MS (ESI+): 415 (M+H)

Example 360

N-[4-(dimethylphosphonomethyl)phenyl]-3-[5-(4-chlorophenyl)-4-isoxazolyl]propionamide yield: 27 mg (yield 59%)
HPLC analysis: purity 100% (retention time: 4.135 min)
MS (ESI+): 449 (M+H)

Example 361

N-[4-(dimethylphosphonomethyl)phenyl]-2-(5-phenyl-4-isoxazolyl)acetamide yield: 26 mg (yield 64%)
HPLC analysis: purity 100% (retention time: 3.826 min)
MS (ESI+): 401 (M+H)

Example 362

N-[4-(dimethylphosphonomethyl)phenyl]-4-(5-phenyl-4-isoxazolyl)butanamide yield: 26 mg (yield 61%)
HPLC analysis: purity 100% (retention time: 3.960 min)
MS (ESI+): 429 (M+H)

Example 363

N-[4-(dimethylphosphonomethyl)phenyl]-3-(3,5-diphenyl-4-isoxazolyl)propionamide yield: 31 mg (yield 64%)
HPLC analysis: purity 99.9% (retention time: 4.417 min)
MS (ESI+): 491 (M+H)

Example 364

N-[4-(dimethylphosphonomethyl)phenyl]-3-[5-(4-methylphenyl)-4-isoxazolyl]propionamide yield: 30 mg (yield 70%)
HPLC analysis: purity 100% (retention time: 4.074 min)
MS (ESI+): 429 (M+H)

Example 365

N-[4-(dimethylphosphonomethyl)phenyl]-3-(3-methyl-5-phenyl-4-isoxazolyl)propionamide yield: 35 mg (yield 82%)
HPLC analysis: purity 100% (retention time: 3.934 min)
MS (ESI+): 429 (M+H)

Example 366

N-[4-(dimethylphosphonomethyl)phenyl]-3-[5-(4-methoxyphenyl)-4-isoxazolyl]propionamide yield: 32 mg (yield 73%)
HPLC analysis: purity 100% (retention time: 3.914 min)
MS (ESI+): 445 (M+H)

Example 367

N-[4-(dimethylphosphonomethyl)phenyl]-3-{5-[4-(trifluoromethyl)phenyl]-4-isoxazolyl}propionamide yield: 30 mg (yield 63%)
HPLC analysis: purity 99.9% (retention time: 4.293 min)
MS (ESI+): 483 (M+H)

Example 368

3-[5-(4-fluorophenyl)-4-isoxazolyl]-N-{4-[(2-oxide-1,3,2-dioxaphosphinan-2-yl)methyl]phenyl}propionamide yield: 27 mg (yield 44%)
HPLC analysis: purity 97.0% (retention time: 3.274 min)
MS (ESI+): 445 (M+H)
NMR (CDCl$_3$) δ: 1.8–2.0 (2H, m), 2.70 (2H, t, J=7 Hz), 3.07 (2H, t, J=7 Hz), 3.19 (2H, d, J=21 Hz), 4.1–4.2 (2H, m), 4.3–4.5 (2H, m), 7.1–7.25 (4H, m), 7.35–7.45 (2H, m), 7.7–7.8 (2H, m), 8.11 (1H, br s), 8.23 (1H, s).

Example 369

N-[4-(diethylphosphonomethyl)phenyl]-3-[5-(4-nitrophenyl)-4-isoxazolyl]propionamide yield: 44 mg (yield 71%)
HPLC analysis: purity 99.4% (retention time: 3.730 min)
MS (ESI+): 488 (M+H)
NMR (CDCl$_3$) δ: 1.24 (6H, t, J=7 Hz), 2.75 (2H, t, J=7 Hz), 3.09 (2H, d, J=22 Hz), 3.15 (2H, d, J=7 Hz), 3.9–4.05 (4H, m), 7.1–7.2 (2H, m), 7.36 (2H, d, J=8.5 Hz), 7.97 (2H, d, J=8.5 Hz), 8.22 (1H, br s), 8.35–8.4 (3H, m).

Example 370

N-[4-(diethylphosphonomethyl)phenyl]-3-[5-(3,4-dimethoxyphenyl)-4-isoxazolyl]propionamide yield: 57 mg (yield 90%)
HPLC analysis: purity 99.9% (retention time: 3.502 min)
MS (ESI+): 503 (M+H)

Example 371

3-[5-(3-bromo-4-fluorophenyl)-4-isoxazolyl]-N-[4-(diethylphosphonomethyl)phenyl]propionamide yield: 51 mg (yield 75%)
HPLC analysis: purity 99.9% (retention time: 3.979 min)
MS (ESI+): 539 (M+H), 541

Example 372

3-[5-(4-chloro-3-fluorophenyl)-4-isoxazolyl]-N-[4-(diethylphosphonomethyl)phenyl]propionamide yield: 48 mg (yield 77%)
HPLC analysis: purity 100% (retention time: 3.990 min)
MS (ESI+): 495 (M+H)

Example 373

3-[5-(3,5-dichlorophenyl)-4-isoxazolyl]-N-[4-(diethylphosphonomethyl)phenyl]propionamide yield: 53 mg (yield 82%)
HPLC analysis: purity 99.6% (retention time: 4.180 min)
MS (ESI+): 511 (M+H)

Example 374

N-[4-(diethylphosphonomethyl)phenyl]-3-[5-(3,4-difluorophenyl)-4-isoxazolyl]propionamide yield: 37 mg (yield 63%)
HPLC analysis: purity 100% (retention time: 3.822 min)
MS (ESI+): 479 (M+H)

Example 375

N-[4-(dimethylphosphonomethyl)phenyl]-3-[5-(4-nitrophenyl)-4-isoxazolyl]propionamide yield: 10 mg (yield 17%)
HPLC analysis: purity 98.7% (retention time: 3.476 min)
MS (ESI+): 460 (M+H)

Example 376

3-[5-(3,4-dimethoxyphenyl)-4-isoxazolyl]-N-[4-(dimethylphosphonomethyl)phenyl]propionamide yield: 43 mg (yield 72%)
HPLC analysis: purity 99.8% (retention time: 3.237 min)
MS (ESI+): 475 (M+H)
NMR (CDCl$_3$) δ: 2.67 (2H, t, J=7 Hz), 3.11 (2H, t, J=7 Hz), 3.14 (2H, d, J=22 Hz), 3.64 (3H, s), 3.69 (3H, s), 3.94 (3H, s), 3.95 (3H, s), 6.97 (1H, d, J=9 Hz), 7.35–7.55 (4H, m), 7.42 (2H, d, J=8.5 Hz), 7.56 (1H, br s), 8.24 (1H, s).

Example 377

3-[5-(3-bromo-4-fluorophenyl)-4-isoxazolyl]-N-[4-(dimethylphosphonomethyl)phenyl]propionamide yield: 34 mg (yield 53%)
HPLC analysis: purity 100% (retention time: 3.732 min)
MS (ESI+): 511 (M+H), 513

Example 378

3-[5-(4-chloro-3-fluorophenyl)-4-isoxazolyl]-N-[4-(dimethylphosphonomethyl)phenyl]propionamide yield: 37 mg (yield 63%)
HPLC analysis: purity 100% (retention time: 3.739 min)
MS (ESI+): 467 (M+H)

Example 379

3-[5-(3,5-dichlorophenyl)-4-isoxazolyl]-N-[4-(dimethylphosphonomethyl)phenyl]propionamide yield: 38 mg (yield 64%)
HPLC analysis: purity 99.8% (retention time: 3.909 min)
MS (ESI+): 483 (M+H)

Example 380

N-[4-(diethylphosphono)phenyl]-3-[5-(4-fluorophenyl)-4-isoxazolyl]propionamide yield: 40 mg (yield 64%)
HPLC analysis: purity 99.6% (retention time: 3.680 min)
MS (ESI+): 447 (M+H)

Example 381

3-[5-(3,4-difluorophenyl)-4-isoxazolyl]-N-[4-(dimethylphosphonomethyl)phenyl]propionamide yield: 31 mg (yield 56%)
HPLC analysis: purity 99.8% (retention time: 3.565 min)
MS (ESI+): 451 (M+H)

Example 382

N-[4-(diethylphosphono)phenyl]-3-[5-(4-nitrophenyl)-4-isoxazolyl]propionamide yield: 49 mg (yield 83%)
HPLC analysis: purity 100% (retention time: 3.746 min)
MS (ESI+): 474 (M+H)

Example 383

N-[4-(diethylphosphono)phenyl]-3-[5-(3,4-dimethoxyphenyl)-4-isoxazolyl]propionamide yield: 51 mg (yield 83%)
HPLC analysis: purity 99.8% (retention time: 3.528 min)
MS (ESI+): 489 (M+H)

Example 384

3-[5-(3-bromo-4-fluorophenyl)-4-isoxazolyl]-N-[4-(diethylphosphono)phenyl]propionamide yield: 52 mg (yield 79%)
HPLC analysis: purity 99.7% (retention time: 4.011 min)
MS (ESI+): 525 (M+H), 527

Example 385

3-[5-(4-chloro-3-fluorophenyl)-4-isoxazolyl]-N-[4-(diethylphosphono)phenyl]propionamide yield: 51 mg (yield 84%)
HPLC analysis: purity 99.9% (retention time: 4.019 min)
MS (ESI+): 481 (M+H)
NMR (CDCl$_3$) δ: 1.32 (6H, t, J=7 Hz), 2.73 (2H, t, J=7 Hz), 3.10 (2H, t, J=7 Hz), 4.0–4.2 (4H, m), 7.5–7.8 (8H, m), 8.27 (1H, s).

Example 386

3-[5-(3,5-dichlorophenyl)-4-isoxazolyl]-N-[4-(diethylphosphono)phenyl]propionamide yield: 53 mg (yield 85%)
HPLC analysis: purity 99.8% (retention time: 4.215 min)
MS (ESI+): 497 (M+H)

Example 387

N-[4-(dimethylphosphonomethyl)phenyl]-3-[5-(4-fluorophenyl)-4-isoxazolyl]propionamide yield: 25 mg (yield 42%)
HPLC analysis: purity 97.9% (retention time: 3.375 min)
MS (ESI+): 433 (M+H)
NMR (CDCl$_3$) δ: 2.69 (2H, t, J=7 Hz), 3.08 (2H, t, J=7 Hz), 3.10 (2H, d, J=21 Hz), 3.62 (3H, s), 3.66 (3H, s), 7.1–7.2 (4H, m), 7.38 (2H, d, J=8.5 Hz), 7.7–7.75 (2H, m), 8.01 (1H, br s), 8.26 (1H, s).

Example 388

N-[4-(diethylphosphono)phenyl]-3-[5-(3,4-difluorophenyl)-4-isoxazolyl]propionamide yield: 36 mg (yield 62%)
HPLC analysis: purity 100% (retention time: 3.849 min)
MS (ESI+): 465 (M+H)

Example 389

3-[5-(4-nitrophenyl)-4-isoxazolyl]-N-{4-[(2-oxide-1,3,2-dioxaphosphinan-2-yl)methyl]phenyl}propionamide yield: 19 mg (yield 33%)
HPLC analysis: purity 100% (retention time: 3.375 min)
MS (ESI+): 472 (M+H)

Example 390

3-[5-(3,4-dimethoxyphenyl)-4-isoxazolyl]-N-{4-[(2-oxide-1,3,2-dioxaphosphinan-2-yl)methyl]phenyl}propionamide yield: 24 mg (yield 40%)
HPLC analysis: purity 100% (retention time: 3.136 min)
MS (ESI+): 487 (M+H)

Example 391

3-[5-(3-bromo-4-fluorophenyl)-4-isoxazolyl]-N-{4-[(2-oxide-1,3,2-dioxaphosphinan-2-yl)methyl]phenyl}propionamide yield: 24 mg (yield 37%)
HPLC analysis: purity 99.9% (retention time: 3.637 min)
MS (ESI+): 523 (M+H), 525

Example 392

3-[5-(4-chloro-3-fluorophenyl)-4-isoxazolyl]-N-{4-[(2-oxide-1,3,2-dioxaphosphinan-2-yl)methyl]phenyl}propionamide yield: 22 mg (yield 37%)
HPLC analysis: purity 100% (retention time: 3.634 min)
MS (ESI+): 479 (M+H)

Example 393

3-[5-(3,5-dichlorophenyl)-4-isoxazolyl]-N-{4-[(2-oxide-1,3,2-dioxaphosphinan-2-yl)methyl]phenyl}propionamide yield: 28 mg (yield 44%)
HPLC analysis: purity 100% (retention time: 3.809 min)
MS (ESI+): 495 (M+H)

Example 394

N-benzyl-N-[2-(diethylamino)ethyl]-3-[5-(4-fluorophenyl)-4-isoxazolyl]propionamide yield: 33 mg (yield 57%)
HPLC analysis: purity 98.3% (retention time: 3.184 min)
MS (ESI+): 424 (M+H)

Example 395

3-[5-(3,4-difluorophenyl)-4-isoxazolyl]-N-{4-[(2-oxide-1,3,2-dioxaphosphinan-2-yl)methyl]phenyl}propionamide yield: 20 mg (yield 35%)
HPLC analysis: purity 100% (retention time: 3.462 min)
MS (ESI+): 463 (M+H)

Example 396

3-[5-(4-fluorophenyl)-4-isoxazolyl]-N-{4-[(5-methyl-2-oxide-1,3,2-dioxaphosphinan-2-yl)methyl]phenyl}propionamide yield: 33 mg (yield 52%)
HPLC analysis: purity 97.6% (retention time: 3.419 min)
MS (ESI+): 459 (M+H)
NMR (CDCl$_3$) δ: 0.84 (3H, t, J=7 Hz), 2.0–2.4 (1H, m), 2.68 (2H, t, J=7 Hz), 3.08 (2H, t, J=7 Hz), 3.1–3.25 (2H, m), 3.75–3.85 (1H, m), 4.0–4.2 (2H, m), 4.25–4.4 (1H, m), 7.1–7.2 (4H, m), 7.35–7.45 (2H, m), 7.7–7.8 (2H, m), 7.95 (1H, br s), 8.27 (1H, s).

Example 397

N-{4-[(5,5-dimethyl-2-oxide-1,3,2-dioxaphosphinan-2-yl)methyl]phenyl}-3-[5-(4-fluorophenyl)-4-isoxazolyl]propionamide yield: 33 mg (yield 50%)
HPLC analysis: purity 95.8% (retention time: 3.546 min)
MS (ESI+): 473 (M+H)
NMR (CDCl$_3$) δ: 1.23 (6H, t, J=7 Hz), 2.69 (2H, t, J=7 Hz), 3.0–3.2 (4H, m), 4.3–4.8 (4H, m), 7.1–7.25 (4H, m), 7.3–7.4 (2H, m), 7.7–7.8 (2H, m), 7.8–7.9 (1H, m), 8.28 (1H, s).

Example 398

N-{4-[(5,5-diethyl-2-oxide-1,3,2-dioxaphosphinan-2-yl)methyl]phenyl}-3-[5-(4-fluorophenyl)-4-isoxazolyl]propionamide yield: 35 mg (yield 50%)
HPLC analysis: purity 100% (retention time: 3.805 min)
MS (ESI+): 501 (M+H)

Example 399

N-{4-[(4,6-dimethyl-2-oxide-1,3,2-dioxaphosphinan-2-yl)methyl]phenyl}-3-[5-(4-fluorophenyl)-4-isoxazolyl]propionamide yield: 34 mg (yield 52%)
HPLC analysis: purity 97.6% (retention time: 3.505 min)
MS (ESI+): 473 (M+H)

Example 400

N-{4-[(5-butyl-5-ethyl-2-oxide-1,3,2-dioxaphosphinan-2-yl)methyl]phenyl}-3-[5-(4-fluorophenyl)-4-isoxazolyl]propionamide yield: 32 mg (yield 44%)
HPLC analysis: purity 98.9% (retention time: 4.130 min)
MS (ESI+): 529 (M+H)
NMR (CDCl$_3$) δ: 0.7–0.95 (6H, m), 1.0–1.4 (8H, m), 2.68 (2H, t, J=7 Hz), 3.07 (2H, t, J=7 Hz), 3.18 (2H, d, J=21 Hz), 3.75–3.9 (2H, m), 4.05–4.2 (2H, m), 7.1–7.25 (4H, m), 7.35–7.45 (2H, m), 7.7–7.8 (2H, m), 7.9–8.0 (1H, m), 8.27 (1H, s).

Example 401

N-{4-[2,2-bis(diethylphosphono)ethenyl]phenyl}-3-[5-(4-fluorophenyl)-4-isoxazolyl]propionamide yield: 31 mg (yield 37%)
HPLC analysis: purity 100% (retention time: 3.730 min)
MS (ESI+): 609 (M+H)

Example 402

N-(4-{[bis(ethylamino)phosphoryl]methyl}phenyl)-3-[5-(4-fluorophenyl)-4-isoxazolyl]propionamide yield: 13 mg (yield 21%)
HPLC analysis: purity 97.3% (retention time: 3.362 min)
MS (ESI+): 459 (M+H)

Example 403

N-[4-(diethylphosphonomethyl)-2-methylphenyl]-3-[5-(4-fluorophenyl)-4-isoxazolyl]propionamide yield: 37 mg (yield 56%)
HPLC analysis: purity 98.1% (retention time: 3.615 min)
MS (ESI+): 475 (M+H)

Example 404

N-[3-(diethylphosphonomethyl)phenyl]-3-[5-(4-fluorophenyl)-4-isoxazolyl]propionamide yield: 34 mg (yield 53%)
HPLC analysis: purity 99.7% (retention time: 3.668 min)
MS (ESI+): 461 (M+H)

Example 405

N-[2-(diethylphosphonomethyl)phenyl]-3-[5-(4-fluorophenyl)-4-isoxazolyl]propionamide yield: 44 mg (yield 69%)
HPLC analysis: purity 96.4% (retention time: 3.789 min)
MS (ESI+): 461 (M+H)

Example 406

N-{4-[(5-ethyl-5-methyl-2-oxide-1,3,2-dioxaphosphinan-2-yl)methyl]phenyl}-3-[5-(4-fluorophenyl)-4-isoxazolyl]propionamide yield: 30 mg (yield 44%)
HPLC analysis: purity 98.4% (retention time: 3.672 min)
MS (ESI+): 487 (M+H)

Exampl 407

N-[4-(dibutylphosphonomethyl)phenyl]-3-[5-(4-fluorophenyl)-4-isoxazolyl]propionamide yield: 44 mg (yield 61%)
HPLC analysis: purity 100% (retention time: 4.299 min)
MS (ESI+): 517 (M+H)

Example 408

N-[4-(diisopropylphosphonomethyl)phenyl]-3-[5-(4-fluorophenyl)-4-isoxazolyl]propionamide yield: 48 mg (yield 70%)
HPLC analysis: purity 100% (retention time: 3.906 min)
MS (ESI+): 489 (M+H)

Example 409

N-{4-[2-(diethylphosphono)ethyl]phenyl}-3-[5-(4-fluorophenyl)-4-isoxazolyl]propionamide yield: 37 mg (yield 57%)
HPLC analysis: purity 100% (retention time: 3.725 min)
MS (ESI+): 475 (M+H)

Example 410

N-{4-[(E)-2-(diethylphosphono)-2-(ethoxycarbonyl)ethenyl]phenyl}-3-[5-(4-fluorophenyl)-4-isoxazolyl]propionamide yield: 9 mg (yield 12%)
HPLC analysis: purity 80.0% (retention time: 3.972 min)
MS (ESI+): 545 (M+H)

Example 411

N-[2-(diethylphosphono)ethyl]-3-[5-(4-fluorophenyl)-4-isoxazolyl]propionamide yield: 1.2 mg (yield 10%)
HPLC analysis: purity 91.6% (retention time: 3.211 min)
MS (ESI+): 399 (M+H)

Example 412

3-[5-(4-fluorophenyl)-4-isoxazolyl]-N-[3-(diethylphosphono)propyl]propionamide yield: 10 mg (yield 18%)
HPLC analysis: purity 97.4% (retention time: 3.182 min)
MS (ESI+): 413 (M+H)

Example 413

A mixture of N-[4-(diethylphosphonomethyl)phenyl]-3-(5-phenyl-4-isoxazolyl)propionamide (221 mg), trimethylsilyl bromide (0.17 ml) and acetonitrile (10 ml) was stirred at room temperature for 16 hr. The reaction mixture was purified by preparative HPLC to give N-[4-(ethylphosphonomethyl)phenyl]-3-(5-phenyl-4-isoxazolyl)propionamide (139 mg, 67%). melting point: 80–82° C.

NMR (CDCl$_3$) δ: 1.27 (3H, t, J=7 Hz), 2.64 (2H, t, J=7 Hz), 3.0–3.2 (4H, m), 3.9–4.1 (2H, m), 7.1–7.2 (3H, m), 7.3–7.4 (2H, m), 7.4–7.6 (4H, m), 7.6–7.7 (2H, m), 8.21 (1H, s).

MS (ESI+): 415 (M+H)

3-(5-Phenyl-4-isoxazolyl)-N-[4-(phosphonomethyl)phenyl]propionamide was obtained as a byproduct of the preparative HPLC.

yield: 39 mg (yield 20%)
melting point: 162–164° C.
NMR (DMSO) δ: 2.67 (2H, t, J=7 Hz), 2.88 (2H, t, J=21 Hz), 2.96 (2H, t, J=7 Hz), 7.15 (2H, dd, J=8.5/2 Hz), 7.45 (2H, d, J=8.5 Hz), 7.5–7.65 (3H, m), 7.76 (2H, dd, J=8.5/2 Hz), 8.56 (1H, s), 9.90 (1H, s).
MS (ESI+): 387 (M+H)

Preparation Example 1

Production of Capsules

| | | |
|---|---|---|
| 1) Compound of Example 68 | | 30 mg |
| 2) Finely divided cellulose | | 10 mg |
| 3) Lactose | | 19 mg |
| 4) Magnesium stearate | | 1 mg |
| Total | | 60 mg |

Preparation Example 2

Production of Tablets

| 1) Compound of Example 68 | 30 g |
|---|---|
| 2) Lactose | 50 g |
| 3) Corn starch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded together with water and the mixture, after vacuum drying, is granulated. The granular mixture is admixed with 14 g of 4) and 1 g of 5) and the resulting mixture is tableted using a tableting machine to give 1000 tablets each containing 30 mg of compound of Example 68.

INDUSTRIAL APPLICABILITY

Since compounds (I), (Ia) and (II) of the present invention have superior insulin secretion promoting action and hypoglycemic action and show low toxicity, they can be used as agents for the prophylaxis or treatment of diabetes and the like.

In addition, the isoxazole derivative of the present invention can be used as a glucose-dependent insulin secretagogue that exhibits selective insulin secretion promoting action only in the presence of high concentration glucose. Therefore, the isoxazole derivative is useful as a safe agent for the prophylaxis or treatment of diabetes, which is associated with a low risk of vascular complications, induction of hypoglycemia and the like, which are the negative effects caused by insulin.

This application is based on a patent application No. 2000-350869 filed in Japan, the contents of which are hereby incorporated by reference.

What is claimed is:

1. A pharmaceutical composition for the treatment of diabetic complications, which comprises a compound represented by the formula (I)

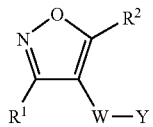

wherein one of $R^1$ and $R^2$ is a hydrogen atom, halogen atom or an alkyl group and the other is an optionally substituted cyclic group;
W is a bond or a divalent aliphatic hydrocarbon group selected from $C_{1-8}$ alkylene or $C_{2-6}$ alkenylene;
Y is a group of the formula: —$OR^3$,
wherein $R^3$ is a hydrogen atom, an optionally substituted aliphatic hydrocarbon group, an optionally substituted alicyclic hydrocarbon group, an optionally substituted aromatic hydrocarbon group, an optionally substituted aromatic aliphatic hydrocarbon group or an optionally substituted acyl group, or Y is an optionally esterified or amidated carboxyl group,
wherein $R^1$, $R^2$, $R^3$ and Y independently do not comprise heterocylce or heteroaryl,
or a salt thereof or a prodrug thereof.

2. The composition of claim 1, wherein the diabetic complication is neuropathy.

3. A compound represented by the formula (II)

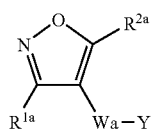

wherein one of $R^{1a}$ and $R^{2a}$ is a hydrogen atom and the other is an optionally substituted cyclic group;
Wa ia a divalent aliphatic hydrocarbon group selected from $C_{1-8}$ alkylene or $C_{2-6}$ alkenylene;
Y is a group of the formula: —$OR^3$,
wherein $R^3$ is a hydrogen atom, an optionally substituted aliphatic hydrocarbon group, an optionally substituted alicyclic hydrocarbon group, an optionally substituted aromatic hydrocarbon group, an optionally substituted aromatic aliphatic hydrocarbon group or an optionally substituted acyl group, or Y is an optionally esterified or amidated carboxyl group,
wherein $R^{1a}$, $R^{2a}$, $R^3$ and Y independently do not comprise heterocylce or heteroaryl,
provided that when Wa is $C_{1-3}$ alkylene and Y is a group of the formula: —$OR^3$, wherein $R^3$ is as defined above, or an optionally methylesterified carboxyl group, $R^{1a}$ should be a hydrogen atom and $R^{2a}$ should be an optionally substituted cyclic group, except 5-phenyl-4-isoxazolylmethanol and 5-phenyl-4-isoxazolylacetic acid, or a salt thereof.

4. The compound of claim 3, wherein the optionally substituted cyclic group represented by $R^{1a}$ or $R^{2a}$ is an optionally substituted aromatic group.

5. The compound of claim 3, wherein $R^{1a}$ is a hydrogen atom and $R^{2a}$ is an optionally substituted cyclic group.

6. The compound of claim 5, wherein $R^{2a}$ is an optionally substituted aromatic group.

7. The compound of claim 3, wherein Wa is a divalent aliphatic hydrocarbon group having 1 to 4 carbon atoms.

8. The compound of claim 3, wherein Y is an optionally amidated carboxyl group.

9. A prodrug of the compound of claim 3.

10. The compound of claim 3, which is
3-[5-(3,4dichlorophenyl)-4-isoxazolyl]propan-1-ol;
3-[5-(3,4dichlorophenyl)-4-isoxazolyl]propionic acid or a salt thereof;
3-[5-(chlorophenyl)-4-isoxazolyl]propan-1-ol;
3-[5-(chlorophenyl)-4-isoxazolyl]propionic acid or a salt thereof;
3-[5-(3,4-difluorophenyl)-4-isoxcazolyl]propan-1-ol;
3-[5-(3,4-difluorophenyl)-4-isoxcazolyl]propionic acid or a salt thereof;
N-[4-(diethylphosphonomethyl)phenyl]-3-(5-phenyl-4-isoxazolyl)propionamide;
N-[4-(diethylphosphonomethyl)phenyl]-3-[5-(4-fluorophenyl)-4-isoxazolyl]propionamide;
N-[4-(dimethylphosphonomethyl)phenyl]-3-(5-phenyl-4-isoxazolyl)propionamide; or N-benzyl-N-[2-(dimethylamino)ethyl]-3-[5-(4-fluorophenyl)-4-isoxazolyl]propionamide.

11. A pharmaceutical composition comprising the compound of claim 3 or a prodrug thereof.

12. A method for the treatment of diabetic complication in a mammal, which comprises administering to said mammal an effective amount of a compound represented by the formula (I)

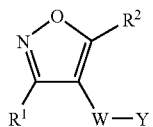

wherein one of $R^1$ and $R^2$ is a hydrogen atom, halogen atom or an alkyl group and the other is an optionally substituted cyclic group;
  W is a bond or a divalent aliphatic hydrocarbon group selected from $C_{1-8}$ alkylene or $C_{2-8}$ alkenylene;
  Y is a group of the formula: —$OR^3$,
  wherein $R^3$ is a hydrogen atom, an optionally substituted aliphatic hydrocarbon group, an optionally substituted alicyclic hydrocarbon group, an optionally substituted aromatic hydrocarbon group, an optionally substituted aromatic aliphatic hydrocarbon group or an optionally substituted acyl group, or Y is an optionally esterified or amidated carboxyl group,
  wherein $R^1$, $R^2$, $R^3$ and Y independently do not comprise heterocylce or heteroaryl,
  or a salt thereof or a prodrug thereof.

13. A method for making a pharmaceutical composition for treating diabetic complications, said method comprising combining a compound represented by the formula (I)

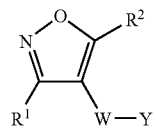

wherein one of $R^1$ and $R^2$ is a hydrogen atom, halogen atom or an alkly group and the other is an optionally substituted cyclic group;
  W is a bond or a divalent aliphatic hydrocarbon group selected from $C_{1-8}$ alkylene or $C_{2-8}$ alkenylene)
  Y is a group of the formula: —$OR^3$,
  wherein $R^3$ is a hydrogen atom, an optionally substituted aliphatic hydrocarbon group, an optionally substituted alicyclic hydrocarbon group, an optionally substituted aromatic hydrocarbon group, an optionally substituted aromatic aliphatic hydrocarbon group or an optionally substituted acyl group, or Y is an optionally esterified or amidated carboxyl group,
  wherein $R^1$, $R^2$, $R^3$ and Y independently do not comprise heterocylce or heteroaryl,
  or a salt thereof or a prodrug thereof with a pharmaceutically acceptable carriers, excipient or diluent.

14. A commercial package comprising the pharmaceutical composition for the treatment of diabetic complications according to claim 1 and written matter associated therewith, the written matter stating that the composition can or should be used for the treatment of diabetic complications.

* * * * *

UNITED STATES PATENT AND TRADEMARK OFFICE
CERTIFICATE OF CORRECTION

PATENT NO. : 7,022,725 B2
APPLICATION NO. : 10/416658
DATED : April 4, 2006
INVENTOR(S) : Yu Momose et al.

It is certified that error appears in the above-identified patent and that said Letters Patent is hereby corrected as shown below:

Col. 161, line 61, in Claim 1, please delete

"selected from $C_{1-8}$ alkylene or $C_{2-6}$ alkenylene;" and insert -- selected from $C_{1-8}$ alkylene or $C_{2-8}$ alkenylene;--

Col. 162, line 21, in Claim 3, please delete

"from $C_{1-8}$ alkylene or $C_{2-6}$ alkenylene" and insert -- from $C_{1-8}$ alkylene or $C_{2-8}$ alkenylene;--

Col. 162, lines 52-59, in Claim 10, please delete

"3-[5-(3,4dichlorophenyl)-4-isoxazolyl]propan-1-ol;
3-[5-(3,4dichlorophenyl)-4-isoxazolyl]propionic acid or a salt thereof;
3-[5-(chlorophenyl)-4-isoxazolyl]propan-1-ol;
3-[5-(chlorophenyl)-4-isoxazolyl]propionic acid or a salt thereof;
3-[5-(3,4-difluorophenyl)-4-isoxcazolyl]propan-1-ol;
3-[5-(3,4-difluorophenyl)-4-isoxcazolyl]propionic acid or a salt thereof;"
and insert --3-[5-(3,4-dichlorophenyl)-4-isoxazolyl]propan-1-ol;
3-[5-(3,4-dichlorophenyl)-4-isoxazolyl]propionic acid or a salt thereof;
3-[5-(4-chlorophenyl)-4-isoxazolyl]propan-1-ol;
3-[5-(4-chlorophenyl)-4-isoxazolyl]propionic acid or a salt thereof;
3-[5-(3,4-difluorophenyl)-4-isoxazolyl]propan-1-ol;
3-[5-(3,4-difluorophenyl)-4-isoxazolyl]propionic acid or a salt thereof;--

Col. 163, line 33, in Claim 13, please delete

"A method for making a phermaceutical composition" and insert --A method for making a pharmaceutical composition--

Col. 164, lines 11-12, in Claim 13, please delete

"or an alkly group and the other is an optionally substituted cyclic group;" and insert --or an alkyl group and the other is an optionally substituted cyclic group;--

UNITED STATES PATENT AND TRADEMARK OFFICE
CERTIFICATE OF CORRECTION

PATENT NO. : 7,022,725 B2  
APPLICATION NO. : 10/416658  
DATED : April 4, 2006  
INVENTOR(S) : Yu Momose et al.

It is certified that error appears in the above-identified patent and that said Letters Patent is hereby corrected as shown below:

Col. 164, line 14, in Claim 13, please delete

"selected from $C_{1-8}$ alkylene or $C_{2-8}$ alkenylene)" and insert -- selected from $C_{1-8}$ alkylene or $C_{2-8}$ alkenylene;--

Col. 164, lines 27- 28, in Claim 13, please delete

"or a salt thereof or a prodrug thereof with a pharmaceutically acceptable carriers, excipient or diluent." and insert -- or a salt thereof or a prodrug thereof with a pharmaceutically acceptable carrier, excipient or diluent. --

Signed and Sealed this

Twelfth Day of December, 2006

JON W. DUDAS  
*Director of the United States Patent and Trademark Office*